United States Patent
Dorok et al.

(10) Patent No.: US 11,495,746 B2
(45) Date of Patent: Nov. 8, 2022

(54) INDANE DERIVATIVES AND THEIR USE IN ORGANIC ELECTRONICS

(71) Applicant: DOTTIKON ES HOLDING AG, Dottikon (CH)

(72) Inventors: Sascha Dorok, Rheinfelden (DE); Marcus Papmeyer, Reinach (CH); Carsten Fleck, Waldshut-Tiengen (DE)

(73) Assignee: Dottikon ES Holding AG, Dottikon (CH)

( * ) Notice: Subject to any disclaimer, the term of this patent is extended or adjusted under 35 U.S.C. 154(b) by 503 days.

(21) Appl. No.: 16/612,825

(22) PCT Filed: May 11, 2018

(86) PCT No.: PCT/EP2018/062212
§ 371 (c)(1),
(2) Date: Jan. 28, 2020

(87) PCT Pub. No.: WO2018/206769
PCT Pub. Date: Nov. 15, 2018

(65) Prior Publication Data
US 2020/0075862 A1 Mar. 5, 2020

(30) Foreign Application Priority Data

May 12, 2017 (EP) .................................... 17170778
Feb. 28, 2018 (EP) .................................... 18159081

(51) Int. Cl.
| | |
|---|---|
| *C07C 209/02* | (2006.01) |
| *H01L 51/00* | (2006.01) |
| *C07C 211/60* | (2006.01) |
| *C07C 211/61* | (2006.01) |
| *C07D 209/86* | (2006.01) |
| *C07D 307/91* | (2006.01) |
| *H01L 51/05* | (2006.01) |
| *H01L 51/50* | (2006.01) |

(52) U.S. Cl.
CPC .......... *H01L 51/006* (2013.01); *C07C 209/02* (2013.01); *C07C 211/60* (2013.01); *C07C 211/61* (2013.01); *C07D 209/86* (2013.01); *C07D 307/91* (2013.01); *H01L 51/0061* (2013.01); *H01L 51/0072* (2013.01); *C07C 2602/08* (2017.05); *C07C 2603/18* (2017.05); *H01L 51/0058* (2013.01); *H01L 51/0073* (2013.01); *H01L 51/0558* (2013.01); *H01L 51/0566* (2013.01); *H01L 51/5012* (2013.01); *H01L 51/5016* (2013.01); *H01L 51/5056* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 3,856,752 | A | 12/1974 | Bateman et al. |
| 3,897,253 | A | 7/1975 | Wilson |
| | | (Continued) | |

FOREIGN PATENT DOCUMENTS

| | | | | |
|---|---|---|---|---|
| CN | 108218721 | * | 6/2018 | ........... C07D 209/86 |
| CN | 108218763 | A | 6/2018 | |
| | | (Continued) | | |

OTHER PUBLICATIONS

John J. Fitzgerald, et al., Synthesis and Characterization of a fluorinated poly(imide-siloxane) copolymer: a study of physical properties and morphology, Polymer, Elsevier, May 1, 1993, pp. 1823-1832, vol. 34, No. 9, Research Laboratories, Eastman Kodak Company, Rochester, New York, USA.

(Continued)

*Primary Examiner* — Robert S Loewe
(74) *Attorney, Agent, or Firm* — Dinsmore & Shohl LLP; Weston R. Gould

(57) ABSTRACT

The present invention relates to indane derivatives of the formula (I) and mixtures thereof, wherein X is selected from groups of the formula -A-(NAr$_2$), wherein A is a chemical bond or phenylene which is unsubstituted or substituted by 1, 2 or 3 substituents selected from $C_1$-$C_6$-alkyl and $C_1$-$C_6$-alkoxy; Ar is unsubstituted or substituted aryl, wherein two groups Ar bound to the same nitrogen atom may together with the nitrogen atom also form a fused ring system having 3 or more than 3 unsubstituted or substituted rings; and the variables Y, n, m, k and l are as defined in the claims and the description. The invention further relates to methods for preparing such compounds and their use in organic electronics, in particular as hole transport material or electron blocking material.

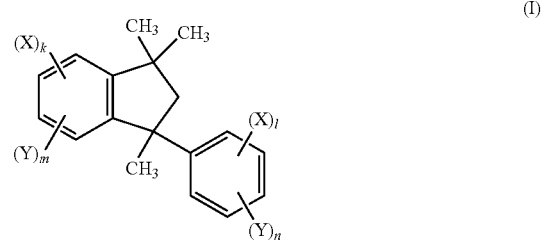

21 Claims, 2 Drawing Sheets

(56) References Cited

U.S. PATENT DOCUMENTS

| | | | | |
|---|---|---|---|---|
| 4,948,216 A | * | 8/1990 | Brazas, Jr. | G02B 6/122 |
| | | | | 430/128 |
| 2006/0270815 A1 | * | 11/2006 | Ittel | C08F 212/34 |
| | | | | 526/172 |
| 2013/0207046 A1 | | 8/2013 | Pflumm et al. | |
| 2015/0380663 A1 | * | 12/2015 | Kim | H01L 51/0071 |
| | | | | 548/417 |
| 2016/0190447 A1 | | 6/2016 | Pflumm et al. | |

FOREIGN PATENT DOCUMENTS

| | | | | |
|---|---|---|---|---|
| DE | 4241258 A1 | * | 6/1994 | C07C 317/22 |
| EP | 1707206 A1 | | 10/2006 | |
| EP | 3085693 A1 | | 10/2016 | |
| JP | S50-062300 A | | 5/1975 | |
| JP | H08-259936 A | | 10/1996 | |
| WO | 1990/05925 A1 | | 5/1990 | |
| WO | 2003/066055 A1 | | 8/2003 | |
| WO | 2005/121133 A1 | | 12/2005 | |
| WO | 2017/025166 A1 | | 2/2017 | |
| WO | 2017036573 A1 | | 3/2017 | |

OTHER PUBLICATIONS

PubChem CID 3095058, downloaded from https://p bchem.ncbi.nlm.nih.gov/compo nd/3095058 on Apr. 9, 2021.

Sun, H. et al., An efficient and selective hydroarylation of Styrenes with Electron-Rich Arenes, Catalyzed by Bismuth (III) Chloride and Affording Markovnikov Adducts, Eur. J. Org. Chem., 18: 4231-4236, 2006.

* cited by examiner

INDANE DERIVATIVES AND THEIR USE IN ORGANIC ELECTRONICS

SUBJECT MATTER OF THE INVENTION

The present invention relates to a new class of indane derivatives, methods for their preparation and the use thereof in organic electronics, in particular as hole transport material (HTM) or electron blocking material (EBM).

BACKGROUND OF THE INVENTION

"Organic electronics" is concerned principally with the development, characterization and application of new materials and manufacturing processes for the production of electronic components based on organic small molecules or polymers with desirable electronic properties. These include in particular organic field-effect transistors (OFETs), like organic thin-film transistors (OTFTs), organic electroluminescent devices, like organic light-emitting diodes (OLEDs), organic solar cells (OSCs), e.g. excitonic solar cells, dye sensitized solar cells (DSSCs) or Perovskite solar cells, electrophotography, in particular photoconductive materials in an organic photoconductor (OPC), organic optical detectors, organic photoreceptors, organic field-quench devices (OFQDs), light-emitting electrochemical cells (LECs) and organic laser diodes. In many cases, organic semiconductors have advantages over classical inorganic semiconductors, for example a better substrate compatibility and a better processability of the semiconductor components based on them. They allow inter alia processing on flexible substrates and enable their interface orbital energies to be adjusted to the particular application sector. Great potential for development is ascribed to organic field-effect transistors, for example in memory elements and integrated optoelectronic devices. Organic light-emitting diodes (OLEDs) exploit the property of materials of emitting light when they are excited by electrical current. Even today, OLEDs are particularly of interest as alternatives to liquid-crystal displays for producing flat visual display units. Owing to the very compact design and the intrinsically lower power consumption, devices which comprise OLEDs are suitable especially for mobile applications, for example for applications in cellphones, laptops, etc.

"Organic photovoltaics" denotes the direct conversion of radiative energy, principally solar energy, to electrical energy using organic components. In contrast to inorganic solar cells, the light does not directly generate free charge carriers in organic solar cells, but rather excitons are formed first, i.e. electrically neutral excited states in the form of electron-hole pairs. These excitons can be separated at suitable photoactive interfaces (organic donor-acceptor interfaces or interfaces to an inorganic semiconductor). For this purpose, it is necessary that excitons which have been generated in the volume of the organic material can diffuse to this photoactive interface. The diffusion of excitons to the active interface thus plays a critical role in organic solar cells. There is a great demand for the development of materials which have maximum transport widths and high mobilities for light-induced excited states (high exciton diffusion lengths) and which are thus advantageously suitable for use as an active material in so-called excitonic solar cells.

In recent years, also dye-sensitized solar cells (DSSCs) have attracted much attention. DSSCs have several advantages compared to silicon-based solar cells such as lower production and material costs because an inexpensive metal oxide semiconductor such as titanium dioxide can be used without the necessity of a high degree of purity. Other advantages include their flexibility, transparency and light weight. The construction of a DSSC is generally based on a transparent substrate (e.g. glass), which is coated with a transparent conductive layer, the working electrode. An n-conductive metal oxide is generally applied to this electrode or in the vicinity thereof, for example a nanoporous $TiO_2$ layer. On the surface thereof, in turn, a monolayer of a light-sensitive dye, for example a ruthenium complex or an organic dye, is typically adsorbed, which can be converted to an excited state by light absorption. The function of the DSSC is based on the fact that light is absorbed by the dye, and electrons are transferred from the excited dye to the n-semiconductive metal oxide semiconductor and migrate thereon to the anode. Although dye-sensitized solar cells are one of the most efficient alternative solar cell technologies at present, there is an ongoing need for further improvement. In liquid DSSCs the area between the two electrodes is filled with a redox electrolyte, for example a solution of iodine ($I_2$) and lithium iodide (LiI), which ensures that a photocurrent can be collected at the front and back contacts of the solar cell. Nevertheless, in many cases liquid DSSCs suffer from durability problems, such as electrode corrosion and electrolyte leakage. Therefore, suitable replacements that can be used for hole conduction in lieu of a liquid electrolyte have been searched for.

Another approach in solar cell technology is the use of organometallic Perovskites as light harvesting compounds. These solar cells are called Perovskite-sensitized solar cells (PSCs). Actual PSCs based on lead iodide allow an energy conversion efficiency exceeding 9%. A variant of the PSCs are hybrid solar cells based on methylammonium lead iodide chloride as crystalline Perovskite absorber material. In those cells mesoporous alumina is used instead of titanium dioxide. The $Al_2O_3$ does not act as n-type oxide but as a meso-scale "scaffold" upon which the device is structured.

Photoconductivity is an optical and electrical phenomenon in which a material becomes electrically conductive due to the absorption of electromagnetic radiation such as visible light, ultraviolet light, infrared light, or gamma radiation. An organic photoconductor (OPC) is one of the components in an electrophotographic (EP) printer. A latent image, which is a surface charge pattern, is created on the OPC prior to contact with a development system containing charged marking particles. This is accomplished by uniformly charging the OPC surface, followed by selective illumination that locally generates opposite charges which then move to the surface and locally neutralize deposited charges. The OPC frequently has two layers: an inner layer for generating charges (charge generation layer—CGL) and an outer layer containing molecular moieties for facilitating charge movement (charge transport layer—CTL).

There is an ongoing demand for new compounds with advantageous properties in the afore-mentioned applications. They should be available by effective and economic routes of synthesis.

It is generally known that certain triarylamines are suitable for the use in organic electronic applications.

WO 2012/034627 describes compounds of the formula (A)

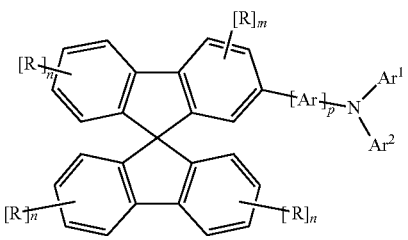

wherein
Ar is an aromatic ring system;
Ar$^1$, Ar$^2$ are an aromatic or heteroaromatic ring system having 6 to 60 C atoms;
R are selected from the group consisting of H, D, F, Cl, Br, I, CN, Si(R$^2$)$_3$, a straight-chain alkyl, alkoxy or thioalkyl group having 1 to 40 C atoms or a branched or cyclic alkyl, alkoxy or thioalkyl group having 3 to 40 C atoms, an aromatic or heteroaromatic ring system having 6 to 60 C atoms or an aralkyl group having 5 to 60 aromatic ring atoms,
m is 0, 1, 2 or 3;
n is on each occurrence, identically or differently, 0, 1, 2, 3 or 4;
p is 0, 1 or 2.

The compounds are used in an electronic device, preferably selected from organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes and organic plasmon emitting devices, in particular in an organic electroluminescent device.

There is an ongoing demand for new organic compounds with good electronic application properties. They should be prepared from readily available educts by effective and economic preparation methods.

It has now been found that, surprisingly, the indane derivatives of the invention are advantageously suitable as hole conductors (p-semiconductors, electron donors) in organic photovoltaics. They are especially suitable as hole transport material (HTM) or electron blocking material (EBM).

SUMMARY OF INVENTION

Therefore, in a first aspect the present invention relates to a compound of the general formula (I)

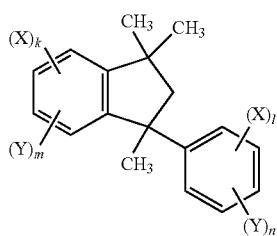

and mixtures thereof, wherein
X is independently on each occurrence selected from groups of the formula -A-(NAr$_2$), wherein
  A is independently on each occurrence a chemical bond or phenylene which is unsubstituted or substituted by 1, 2 or 3 substituents independently selected from the group consisting of C$_1$-C$_6$ alkyl and C$_1$-C$_6$-alkoxy;
  Ar is independently on each occurrence selected from in each case unsubstituted or substituted aryl, wherein two groups Ar bound to the same nitrogen atom may together with the nitrogen atom also form a fused ring system having 3 or more than 3 unsubstituted or substituted rings;
Y is independently on each occurrence selected from hydrogen, C$_1$-C$_6$-alkyl, C$_1$-C$_6$-alkoxy, C$_3$-C$_8$-cycloalkyl, C$_3$-C$_8$-cycloalkoxy, phenyl and phenyloxy, wherein each of the cyclic rings in the four last-mentioned groups are unsubstituted or substituted by 1, 2 or 3 C$_1$-C$_6$-alkyl groups and wherein the phenyl ring bound by a single bond to the phenylindane moiety bears at least one Y group in one of the ortho-positions on the phenyl ring relative to the phenylindane moiety that is hydrogen;
k is 1 or 2;
l is 1 or 2;
m is 2 or 3, wherein 0, 1, 2 or 3 of the m Y groups are different from hydrogen;
n is 3 or 4, wherein 0, 1, 2 or 3 of the n Y groups are different from hydrogen;
the sum of k and m is 4 and the sum of l and n is 5.

Another aspect relates to a mixture of compounds of formula (I), wherein k and l, are each 1, namely to a mixture of compounds of formulae (I.A.a) and (I.B.a)

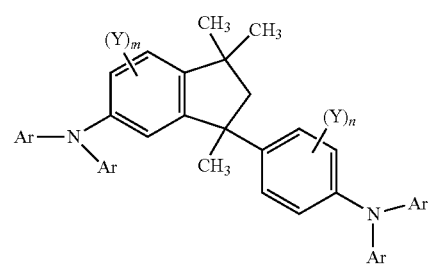

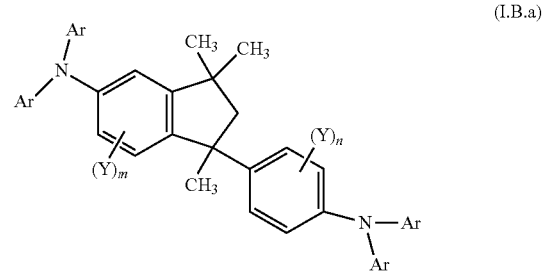

wherein
each Y is independently defined as above in the Summary and below in the Detailed Description;
each Ar is independently defined as above in the Summary and below in the Detailed Description;
m is 3, wherein 0, 1, 2 or 3 of the m Y groups are different from hydrogen; and
n is 4, wherein 0, 1, 2 or 3 of the n Y groups are different from hydrogen;
and to a process for preparing said mixture.

Another aspect relates to a mixture of compounds of formula (I), wherein k and l are each 1, namely to a mixture of compounds of formulae (I.C.a) and (I.D.a)

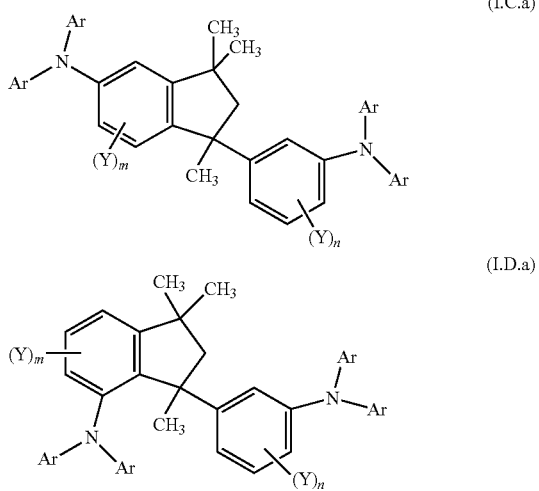

wherein
each Y is independently defined as above in the Summary and below in the Detailed Description;
each Ar is independently defined as above in the Summary and below in the Detailed Description;
m is 3, wherein 0, 1, 2 or 3 of the m Y groups are different from hydrogen; and
n is 4, wherein 0, 1, 2 or 3 of the n Y groups are different from hydrogen.
and to a process for preparing said mixture.

Another aspect relates to processes for preparing compounds of formula (I).

Another aspect of the invention relates to use of the compounds of the invention or a composition (mixture) comprising at least two different compounds of the invention as defined above in the Summary and below in the Detailed Description as a hole transport material (HTM) in organic electronics, as an electron blocking material (EBM) in organic electronics, as a semiconductor material in organic field-effect transistors (OFETs), in particular in thin-film transistors (TFTs), in organic solar cells (OSCs), solid-state dye sensitized solar cells (DSSCs) or Perovskite solar cells, in particular as a hole transport material in organic solar cells, as replacement of the liquid electrolyte in dye sensitized solar cells, as a hole transport material in Perovskite solar cells, in organic light-emitting diodes (OLEDs), in particular for displays on electronic devices and lighting, for electrophotography, in particular as photoconductive material in an organic photoconductor (OPC), for organic optical detectors, organic photoreceptors, organic field-quench devices (O-FQDs), light-emitting electrochemical cells (LECs) and organic laser diodes.

Yet another aspect of the invention relates to an organic field-effect transistor comprising a substrate having at least one gate structure, a source electrode and a drain electrode and at least one compound of the formula (I) as defined above in the Summary and below in the Detailed Description as a semiconductor material.

Yet another aspect of the invention relates to a substrate comprising a plurality of organic field-effect transistors, at least some of the field-effect transistors comprising at least one compound of the formula (I) as defined above in the Summary and below in the Detailed Description.

Yet another aspect of the invention relates to a semiconductor unit comprising a substrate as defined above.

Yet another aspect of the invention relates to an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined as defined above in the Summary and below in the Detailed Description.

Yet another aspect of the invention relates to two processes for preparing compounds of formula (V)

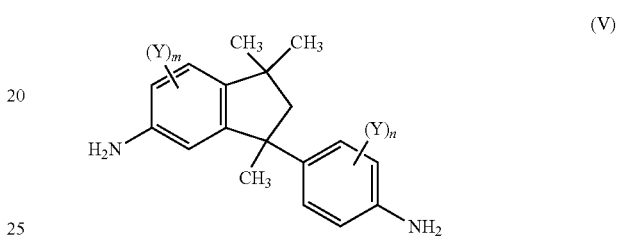

in which
each Y is independently defined as above in the Summary and below in the Detailed Description;
m is 3, wherein 0, 1, 2 or 3 of the m Y groups are different from hydrogen; and
n is 4, wherein 0, 1, 2 or 3 of the n Y groups are different from hydrogen.

The compounds of the formula (V) are valuable intermediates of the compounds according to the invention and for chemical synthesis in general.

Yet another aspect of the invention relates to intermediate compound 6-amino-1-(4'-aminophenyl)-1,3,3-trimethylindane

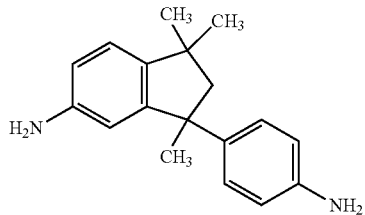 [SMILES: CC1(C)CC(C)(c2ccc(N)cc2)c2cc(N)ccc21]

obtainable by a process, in which
a2.1) an isopropenylbenzene compound (II.1)

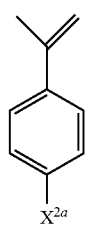

is provided, wherein $X^{2a}$ is selected from F, Cl, Br, I, O-benzyl, $CH_3SO_3$ and $CF_3SO_3$;

b2.1) the isopropenylbenzene compound of the formula (II.1) is subjected to a dimerization in the presence of an acidic catalyst resulting in the compound of the formula (III.1)

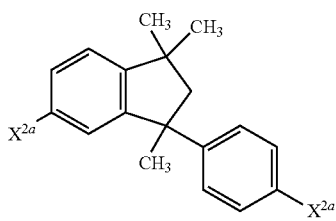

(III.1)

c2.1) the compound of formula (III.1) is subjected to an amination reaction with an alkali bis(trialkylsilyl) amide in the presence of a palladium complex catalyst followed by removal of the trialkylmethylsilyl protecting group to give 6-amino-1-(4'-aminophenyl)-1,3,3-trimethylindane;

or a7.1) a halogenated 1,3,3-trimethylindane compound of the formula XXI.1 is provided,

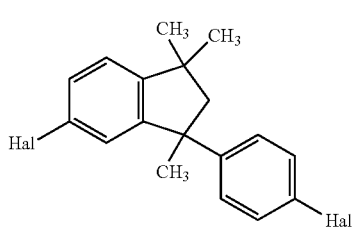

(XXI.1)

in which

Hal is chlorine, bromine or iodine;

b7.1) the compound of formula (XXI.1) is subjected to a copper promoted amidation with an amide of the formula XXII,

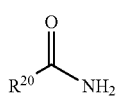

(XXII)

in which $R^{20}$ is hydrogen, $C_1$-$C_{10}$-alkyl, $C_3$-$C_8$-cycloalkyl or $CH_2$—($C_6$-$C_{10}$-aryl);

to give a diamide of the formula (XXIII.1)

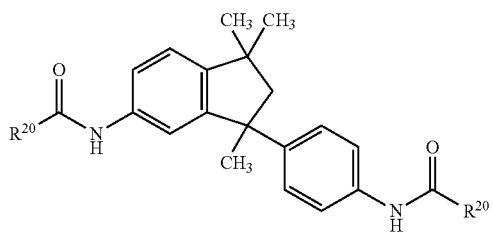

(XXIII.1)

c7.1) the diamide of the formula (XXIII.1) is subjected to a hydrolysis to give the compound 6-amino-1-(4'-aminophenyl)-1,3,3-trimethylindane.

Yet another aspect of the present invention relates to the intermediate compound 6-amino-1-(4'-aminophenyl)-1,3,3-trimethylindane containing less than 1% by weight regioisomeric impurities selected from 5-amino-1-(4'-aminophenyl)-1,3,3-trimethylindane, 4-amino-1-(4'-aminophenyl)-1,3,3-trimethylindane or 7-amino-1-(4'-aminophenyl)-1,3,3-trimethylindane.

These and other aspects of the invention are described in the following paragraphs.

DETAILED DESCRIPTION OF THE INVENTION

Figure 1:
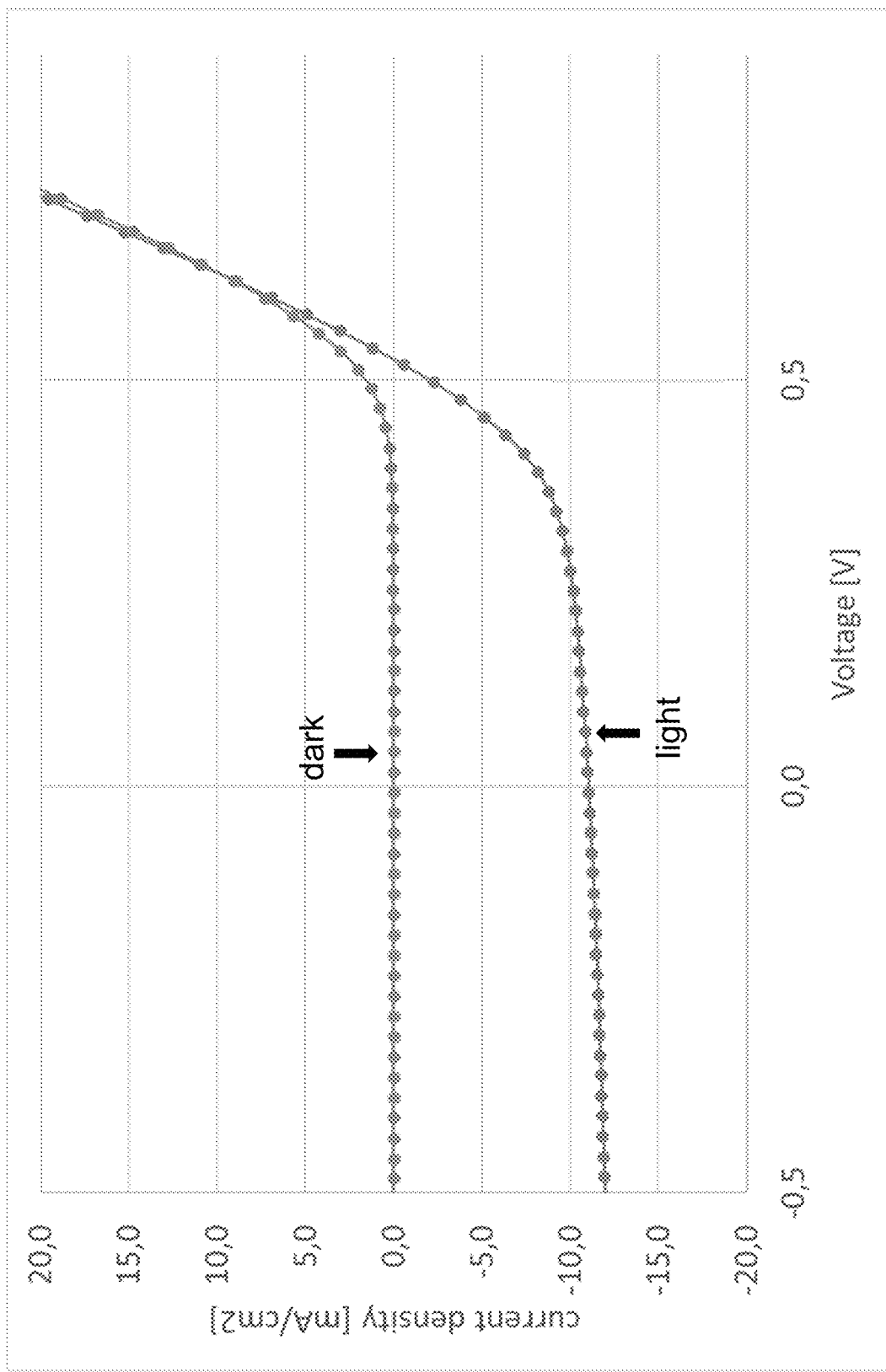
FIG. 1 illustrates current density-voltage characteristics of an organic photovoltaic cell (in the dark and under illumination) using an exemplary compound as provided herein.

The compounds of the general formula (I) and the methods for their preparation have at least one of the following advantages:

The compounds of the formula (I) are characterized by a good thermal stability and environmental stability. Most compounds (I) have a high glass transition temperature. They are usually sublimable, can be purified by fractional sublimation and allow the fabrication of devices by physical vapor deposition.

The compounds of the formula (I) are in particular suitable as organic semiconductors. They function generally as p-semiconductors. Preferred applications of the compounds (I) are as hole transport material (HTM) or electron blocking material (EBM).

OFETs, in particular OTFTs produced from the compounds of the formula (I) are characterized by at least one of the following properties: a high charge transport mobility, a high on/off ratio, low threshold voltages and air stability. The compounds of the invention allow the formation of well-ordered thin films. OTFTs usually show well-defined linear- and saturation-regime output characteristics.

The compounds of the formula (I) further have good properties in OPV applications. They allow that the excited states (excitons) generated by the absorbed photons can be passed on over very large distances, i.e. they have good exciton diffusion lengths. The invention further allows providing compounds of the formula (I)

where the size of the semiconductor band gap is adjusted to very effectively utilize the solar light.

The processes of the invention allow a very effective and economic synthesis of a great variety of compounds of the formula (I). Thus, it is possible to easily provide a compound (1) with optimized properties for the intended use.

Described herein are compounds of formula (I)

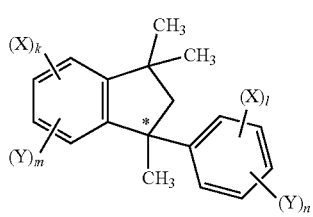

wherein $(X)_k$, $(X)_l$, $(Y)_m$ and $(Y)_n$ are as described in the Summary and below in the Detailed Description of the Invention. The asterisk (*) in formula (I) represents an asymmetric carbon atom. Thus, the invention provides both the pure enantiomer and the mixture of the enantiomers of the compound of formula (I). The invention also provides the use of the pure enantiomer of the compound of formula (I) and the mixture of the enantiomers. Depending on the substitution pattern, the compounds of formula (I) may have further centers of chirality, in which case they are present as mixtures of diastereomers. The compound of formula (I) can be obtained in enantiomerically enriched or pure form by standard methods known in the art, which includes e.g. chiral separation or by preparing the compounds of formula (I) by using an appropriate chiral 1,1,3-trimethyl-3-phenyl-indane compound as starting material. Suitable compounds of the formula (I) also include all possible regioisomers and mixtures thereof.

It is noted that in the formulae depicted herein, a methyl group may be indicated as a solid line. Thus, for example, the solid lines at positions 1 and 3 in formula (I) depicted below signify the methyl groups attached at positions 1 and 3 of the compound of formula (I) and the solid lines at position 9 of 9,9-dimethylfluorene depicted below signify the two methyl groups.

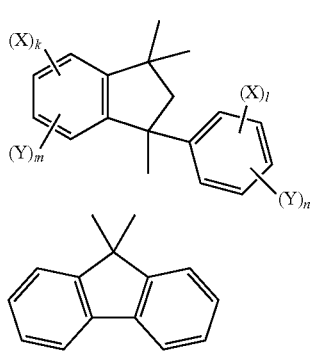

It is noted that in general hydrogen atoms are not depicted in a formula, unless the formula clearly dictates otherwise. In other words, in some specific formulae of this application the hydrogen atoms are explicitly shown but in most cases not, as is the usual practice.

As used in this specification and the claims, the singular form "a", "an", and "the" include plural forms unless the context clearly indicates otherwise.

The definitions of the variables specified in the above formulae use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine. Similarly, the term "halo" denotes in each case fluor, chloro, bromo or iodo.

The term "unbranched" as used herein is also referred to as linear or straight-chain.

The term "$C_n$-$C_m$-alkyl" as used herein refers to a branched or unbranched saturated hydrocarbon group having n to m carbon atoms, e.g., 1 to 2 ("$C_1$-$C_2$-alkyl"), 1 to 4 ("$C_1$-$C_4$-alkyl") or 1 to 6 ("$C_1$-$C_6$-alkyl"). $C_1$-$C_2$-Alkyl is methyl or ethyl. Examples for $C_1$-$C_4$-alkyl are, in addition to those mentioned for $C_1$-$C_2$-alkyl, propyl, isopropyl, butyl, 1-methylpropyl (sec-butyl), 2-methylpropyl (isobutyl) or 1,1-dimethylethyl (tert-butyl). Examples for $C_1$-$C_6$-alkyl are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethyl propyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$CH_2$—($C_6$-$C_{10}$-aryl)" as used herein denotes benzyl, 1-naphthylmethyl or 2-naphthylmethyl.

Similarly, the term "$C_n$-$C_m$-alkoxy" refers to straight-chain or branched alkyl groups having n to m carbon atoms, e.g. 1 to 2 carbon atoms or 1 to 4 carbon atoms or 1 to 6 carbon atoms (as mentioned above) attached via an oxygen atom at any bond in the alkyl group to the remainder of the molecule. $C_1$-$C_2$-Alkoxy is methoxy or ethoxy. Examples for $C_1$-$C_4$-alkoxy are, in addition to those mentioned for $C_1$-$C_2$-alkoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). Examples for $C_1$-$C_6$-alkoxy are, in addition to those mentioned for $C_1$-$C_4$-alkoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1, 2-tri methylpropoxy, 1,2,2-trimethylpropoxy, 1-ethyl-1-methylpropoxy or 1-ethyl-2-methylpropoxy.

The term "$C_n$-$C_m$-cycloalkyl" as used herein refers to a monocyclic n- to m-membered saturated cycloaliphatic radical having, e.g. 3 to 8 carbon atoms. Examples for $C_3$-$C_8$-cycloalkyl are cyclopropyl, cyclobutyl, cyclopentyl, cyclohexyl, cycloheptyl and cyclooctyl.

Similarly, the term "$C_n$-$C_m$-cycloalkoxy" refers to a monocyclic n- to m-membered saturated cycloaliphatic radical, e.g. $C_3$-$C_8$-cycloalkyl (as mentioned above) bonded through 0 linkage to the skeleton.

The term "aryl" as used herein refers to monocyclic, bicyclic, tricyclic and tetracyclic aromatic hydrocarbon radicals with 6 to 18 ring carbon atoms, in which the rings are all condensed (fused) or two of the aromatic rings may also be joined to one another by a chemical bond and a divalent radical selected from —CH$_2$—, —O—, —S— or —N(H)—. Examples include phenyl, naphthyl, anthracenyl, phenanthrenyl, fluorenyl, dibenzofuranyl (dibenzofuryl), dibenzothienyl, carbazolyl, 11H-benzo[b]fluorenyl, naphtho[2,3-b]benzofuryl, naphtho[2,3-b]benzothienyl and 5H-benzo[b]carbazolyl. Aryl may be substituted at one, two, three, four, more than four or all substitutable positions. Suitable substituents are in general C$_1$-C$_6$-alkyl, C$_1$-C$_6$-alkoxy, carbazol-9-yl (N-bound carbazolyl), which is unsubstituted or substituted by C$_1$-C$_4$-alkyl, C$_1$-C$_4$-alkoxy and phenyl, wherein phenyl on its part may be substituted by 1, 2, 3 or 4 different or identical substituents selected from C$_1$-C$_4$-alkyl and C$_1$-C$_4$-alkoxy. In addition, suitable substituents attached at aryl are in general also diphenylamino, C$_5$-C$_8$-cycloalkyl, phenyl, biphenylyl, terphenyl, naphthyl, anthracenyl and phenanthryl, wherein each of the cyclic rings in the 8 last-mentioned groups are unsubstituted or substituted by 1, 2, 3, 4 or 5 different or identical substituents selected from C$_1$-C$_4$-alkyl, C$_1$-C$_4$-alkoxy and carbazol-9-yl which is unsubstituted or substituted by C$_1$-C$_4$-alkyl, C$_1$-C$_4$-alkoxy and phenyl, wherein phenyl on its part may be substituted by 1, 2, 3 or 4 different or identical substituents selected from C$_1$-C$_4$-alkyl and C$_1$-C$_4$-alkoxy. In addition, two substituents bonded to the same carbon atom of fluorenyl or 11H-benzo[b]fluorenyl, together may form an alkylene group (CH$_2$)$_r$ with r being 4, 5, 6 or 7 thus forming a 5- to 8-membered saturated carbocycle, in which 1 or 2 hydrogen atoms in this group may be replaced by a group C$_1$-C$_4$-alkyl or C$_1$-C$_4$-alkoxy or two substituents bonded to the same carbon atom of fluorenyl or 11H-benzo[b]fluorenyl together may form an alkylene group (CH$_2$)$_r$ with r being 4, 5, 6 or 7 thus forming a 5- to 8-membered saturated carbocycle, which may be benz-annelated with one or two benzene groups, where the benzene ring(s) is (are) optionally substituted by 1, 2, 3 or 4 identical or different C$_1$-C$_4$-alkyl or C$_1$-C$_4$-alkoxy.

If a moiety is described as being "optionally substituted", the moiety may be either unsubstituted or substituted.

If a moiety is described as "substituted", a non-hydrogen radical is in the place of hydrogen radical of any substitutable atom of the moiety. If there are more than one substitution on a moiety, each non-hydrogen radical may be identical or different (unless otherwise stated).

The remarks made above and in the following with respect to preferred aspects of the invention, e.g. to preferred meanings of the variables X and Y and the indices n, m, l and k of compounds of formula (I), to preferred compounds of formula (I) and to the use according to the invention, apply in each case on their own or in particular to combinations thereof:

Preference is given to compounds of formula (I), wherein k is 1 and l is 1.

Likewise, preference is given to compounds of formula (I), wherein k is 2 and l is 2.

A more preferred embodiment of the present invention relates to compounds of formula (I), wherein k is 1 and l is 1.

Among these, preference is given to the compounds of formula (I.A), wherein m, n, Y, A and Ar are as defined hereinabove and herein below for compounds of formula (I).

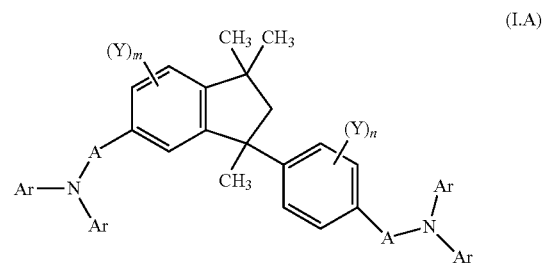

(I.A)

Among the compounds of formula (I), wherein k is 1 and l is 1, likewise preference is given to the compounds of formula (I.B), wherein m, n, Y, A and Ar are as defined hereinabove and hereinbelow for compounds of formula (I).

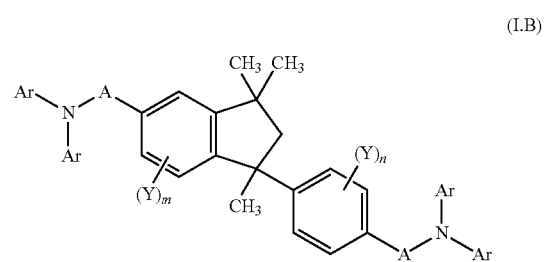

(I.B)

Among the compounds of formula (I), wherein k is 1 and l is 1, likewise preference is given to compound of formula (I.C), wherein m, n, Y, A and Ar are as defined hereinabove and hereinbelow for compounds of formula (I).

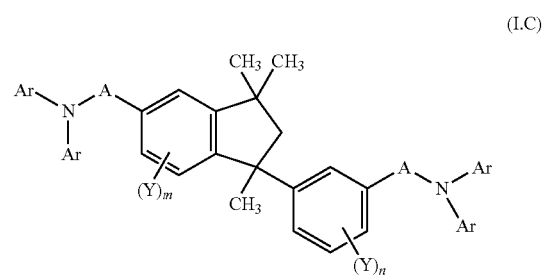

(I.C)

Among the compounds of formula (I), wherein k is 1 and l is 1, likewise preference is given to compound of formula (I.D), wherein m, n, Y, A and Ar are as defined hereinabove and hereinbelow for compounds of formula (I).

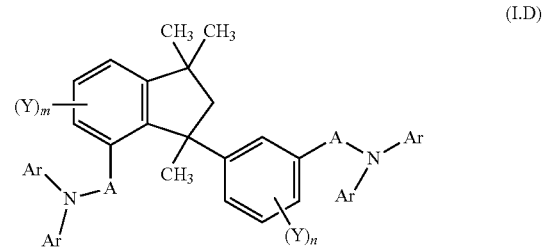

(I.D)

A further more preferred embodiment of the present invention relates to compounds of formula (I), wherein k is 2 and l is 2. Among these, preference is given to compounds of formula (I.E), wherein m, n, Y, A and Ar are as defined hereinabove and hereinbelow for compounds of formula (I).

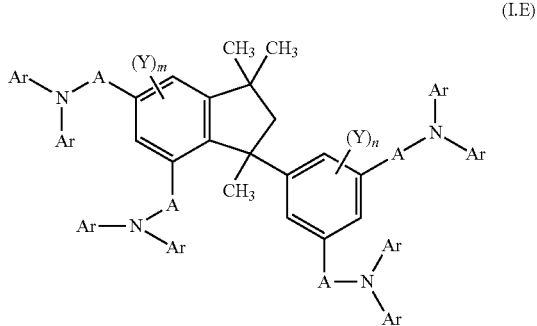

(I.E)

A skilled person will readily understand that the preferences given for X, i.e. -A-NAr$_2$, and Y in connection with compounds of formula (I) also apply for compounds of formulae (I.A), (I.B), (I.C), (I.D) and (I.E) as defined hereinafter.

In one embodiment, X indicates A-N(Ar)$_2$, wherein the group A is a divalent phenylene group. Irrespectively of its occurrence, A is preferably selected from the group consisting of the groups of the formulae (A1), (A2) and (A3),

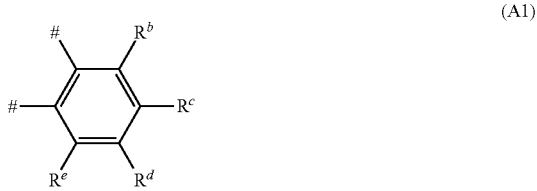

(A1)

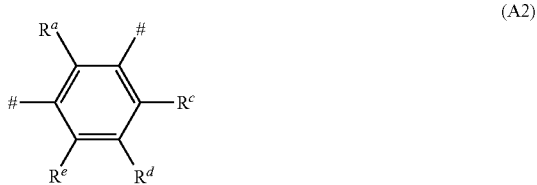

(A2)

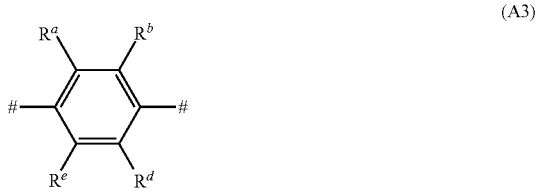

(A3)

wherein
# are the bonding sites to the benzene ring and the nitrogen atom, respectively; and $R^a$, $R^b$, $R^c$, $R^d$ and $R^e$ if present, are each independently selected from hydrogen, straight-chain and branched $C_1$-$C_4$-alkyl and straight-chain and branched $C_1$-$C_4$-alkoxy.

In a specific embodiment, each group A in formula (I) is a divalent phenylene group as defined above. In a more specific embodiment, each group A in formula (I) is a divalent phenylene group and all groups A have the same meaning. Preferably, $R^a$, $R^b$, $R^c$, $R^d$ and $R^e$, if present, are each hydrogen. Likewise preferably, at least one of the radicals $R^a$, $R^b$, $R^c$, $R^d$ and $R^e$, if present, is different from hydrogen and the remaining radicals $R^a$, $R^b$, $R^c$, $R^d$ and $R^e$, if present, are each hydrogen. More preferably, one of $R^a$, $R^b$, $R^c$, $R^d$ and $R^e$, if present, are methoxy or methyl and the remaining $R^a$, $R^b$, $R^c$, $R^d$ and $R^e$, if present, are each hydrogen.

In another embodiment of the invention, X is NAr$_2$, i.e., the group A is a chemical bond. Among the compounds of formula (I) however, more preference is given to those compounds of formula (I), wherein each group A is a single bond.

Thus, amongst the compounds of formula (I), wherein each group A is a single bond, preference is given to compounds of formula (I.A.a),

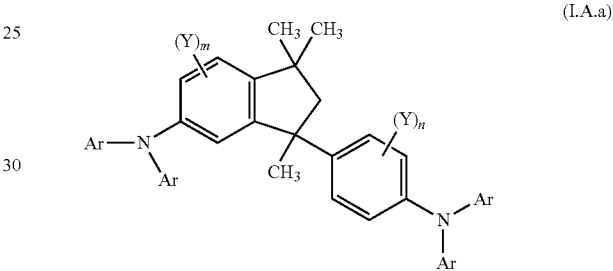

(I.A.a)

wherein m, n, Y and Ar are as defined hereinabove for compounds of formula (I).

A skilled person will readily understand that the preferences given for $(Y)_m$, $(Y)_n$ and Ar in connection with compounds of formulae (I) and (I.A) also apply for formula (I.A.a) as defined hereinafter.

Among the compounds of formula (I), wherein each group A is a single bond, likewise preference is given to compounds of formula (I.B.a), wherein m, n, Y and Ar are as defined hereinabove for compounds of formula (I).

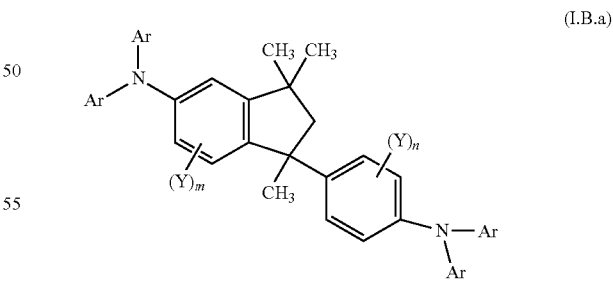

(I.B.a)

A skilled person will readily understand that the preferences given for $(Y)_m$, $(Y)_n$ and Ar in connection with compounds of formulae (I) and (I.B) also apply for formula (I.B.a) as defined hereinafter.

Among the compounds of formula (I), wherein each group A is a single bond, likewise preference is given to compounds of formula (I.C.a), wherein m, n, Y and Ar are as defined hereinabove for compounds of formula (I).

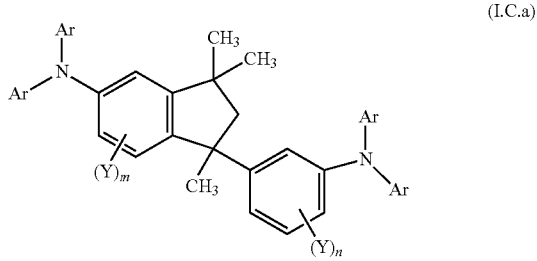

(I.C.a)

A skilled person will readily understand that the preferences given for $(Y)_m$, $(Y)_n$ and Ar in connection with compounds of formulae (I) and (I.C) also apply for formula (I.C.a) as defined hereinafter.

Among the compounds of formula (I), wherein each group A is a single bond, likewise preference is given to compounds of formula (I.D.a), wherein m, n, Y and Ar are as defined hereinabove for compounds of formula (I).

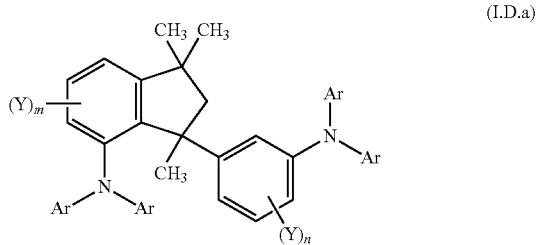

(I.D.a)

A skilled person will readily understand that the preferences given for $(Y)_m$, $(Y)_n$ and Ar in connection with compounds of formulae (I) and (I.D) also apply for formulae (I.D.a) as defined hereinafter.

Among the compounds of formula (I), wherein each group A is a single bond, likewise preference is given to compounds of formula (I.E.a), wherein m, n, Y and Ar are as defined hereinabove for compounds of formula (I).

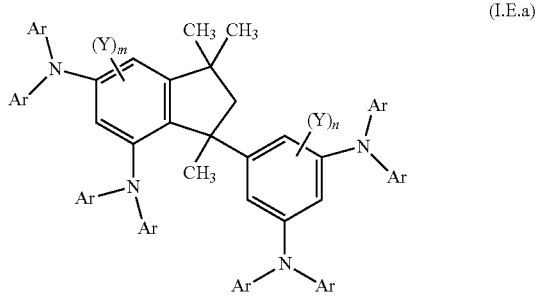

(I.E.a)

A skilled person will readily understand that the preferences given for $(Y)_m$, $(Y)_n$ and Ar in connection with compounds of formulae (I) and (I.E) also apply for formulae (I.E.a) as defined hereinafter.

Preference is given to compounds of the formulae (I), (I.A), (I.B), (I.C), (I.D), (I.E), (I.A.a), (I.B.a), (I.C.a), (I.D.a) and (I.E.a) in which the group Ar, irrespectively of its occurrence, is selected from unsubstituted or substituted phenyl, unsubstituted or substituted naphthyl, unsubstituted or substituted phenanthryl, unsubstituted or substituted anthracenyl, unsubstituted or substituted fluorenyl, unsubstituted or substituted C-bound carbazolyl, unsubstituted or substituted dibenzofuranyl, unsubstituted or substituted dibenzothiophenyl, or 2 groups Ar together with the nitrogen atom to which they are attached form an unsubstituted or substituted N-bound carbazolyl.

More preferably, each Ar, irrespectively of its occurrence, is selected from:
phenyl, biphenylyl, terphenyl, quaterphenyl, wherein phenyl, biphenylyl, terphenyl and quaterphenyl are unsubstituted or substituted by one or more, e.g. 1, 2, 3, 4 or more than 4, substituents $R^{Ar1}$;
naphthyl, anthracenyl, phenanthryl, fluorenyl, spirofluorenyl, C-bound carbazolyl, dibenzofuranyl and dibenzothiophenyl, wherein naphthyl, phenanthryl, fluorenyl, spirofluorenyl, C-bound carbazolyl, dibenzofuranyl and dibenzothiophenyl are unsubstituted or substituted by one or more, e.g. 1, 2, 3, 4 or more than 4, substituents $R^{Ar2}$; or
2 groups Ar together with the nitrogen atom to which they are attached may form an N-bound carbazolyl, which is unsubstituted or substituted by one or more substituents $R^{Ar3}$;
wherein
each $R^{Ar1}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy,
diphenylamino, $C_5$-$C_8$-cycloalkyl and naphthyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy;
each $R^{Ar2}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy,
diphenylamino, $C_5$-$C_8$-cycloalkyl and phenyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy and,
in addition, in the case of fluorenyl, two geminal radicals $R^{Ar2}$ may form an alkylene group $(CH_2)_r$ with r being 4, 5, 6 or 7, where 1 or 2 hydrogen atoms in this group may be replaced by a methyl group or a methoxy group; and each $R^{Ar3}$ is independently selected from
$C_1$-$C_6$ alkyl, $C_1$-$C_6$-alkoxy, diphenylamino and phenyl, wherein each of the cyclic rings in the two last-mentioned groups are unsubstituted or substituted by 1, 2, 3 or 4 different or identical substituents selected from $C_1$-$C_4$-alkyl and $C_1$-$C_4$-alkoxy.
Particular examples of the group Ar include the following radicals of the formulae (AR-I) to AR-XLIV)
(AR-I)
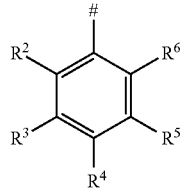
(AR-II)
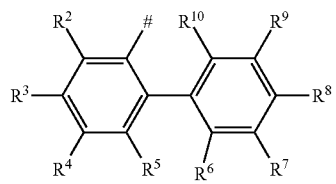
(AR-III)
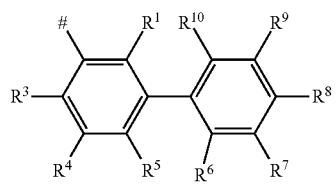
(AR-IV)
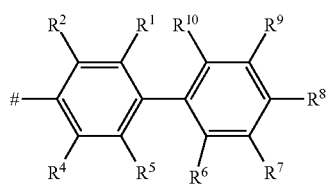
(AR-V)
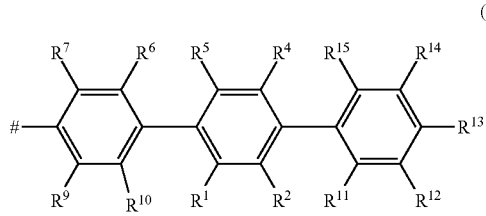
(AR-VI)
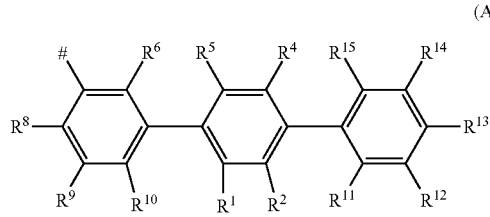
(AR-VII)
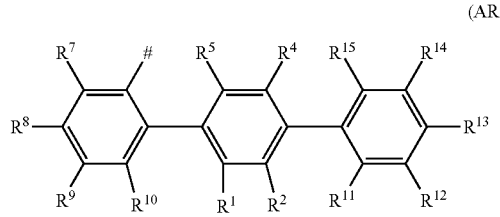
-continued
(AR-VIII)
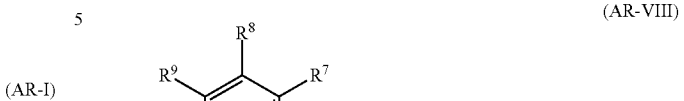
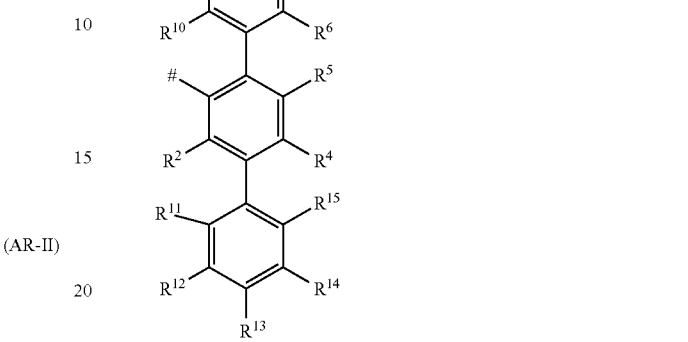
(AR-IX)
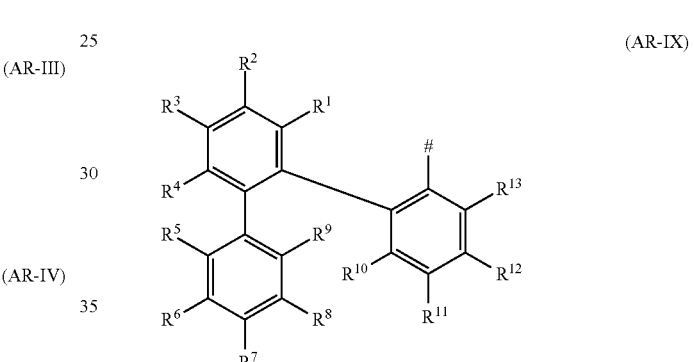
(AR-X)
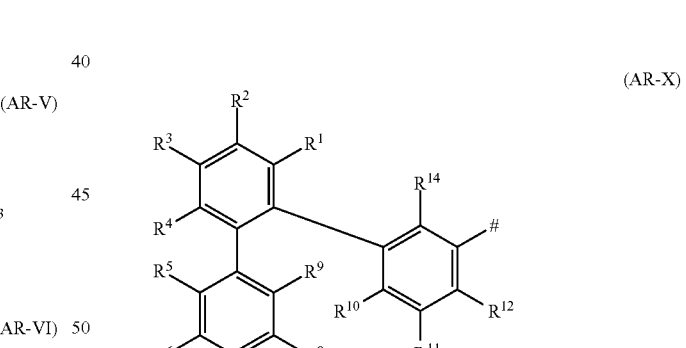
(AR-XI)
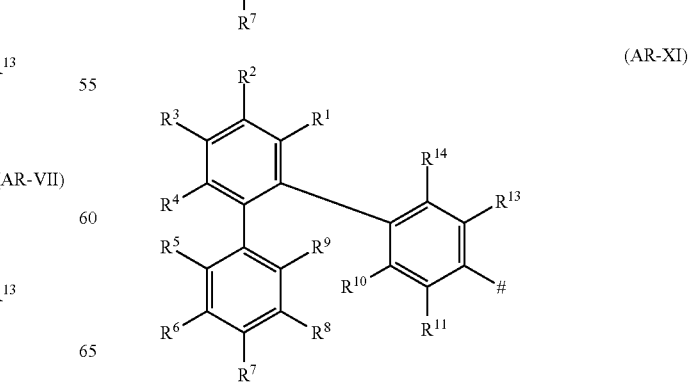

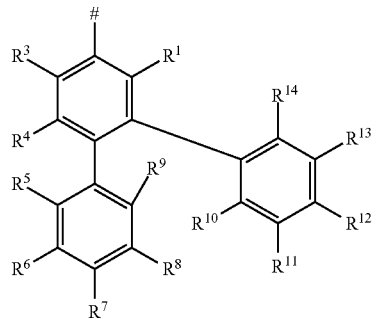
(AR-XII)
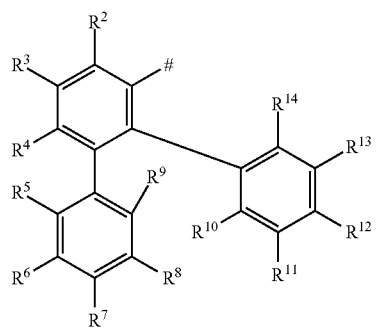
(AR-XIII)
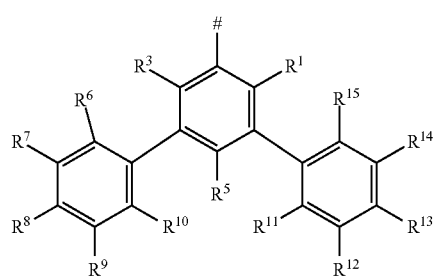
(AR-XIV)
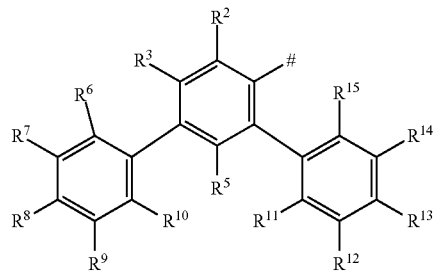
(AR-XV)
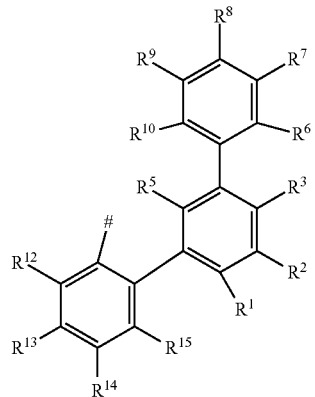
(XVI)
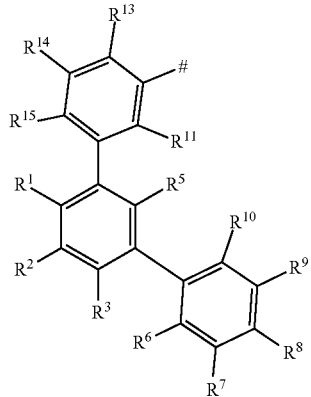
(AR-XVII)
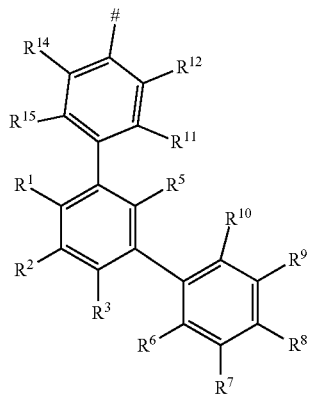
(AR-XVIII)
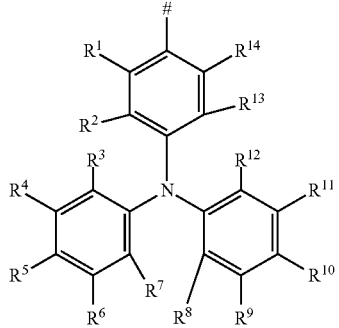
(AR-XIX)
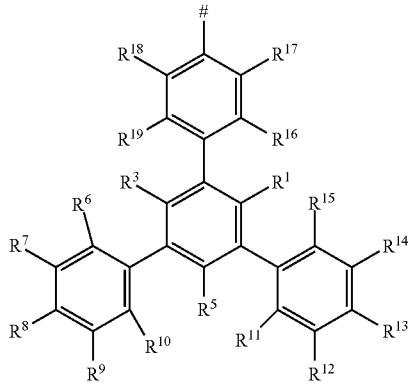
(AR-XX)

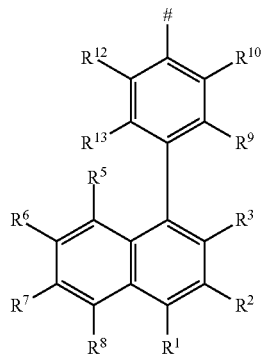 (AR-XXI)
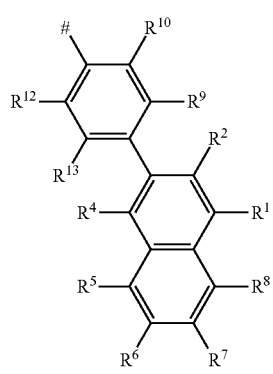 (AR-XXII)
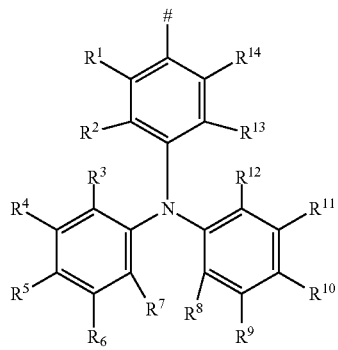 (AR-XXIII)
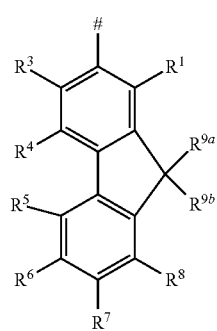 (AR-XXIV)
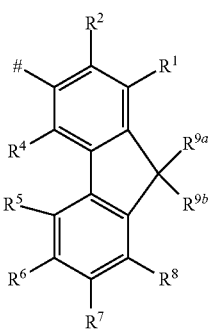 (AR-XXV)
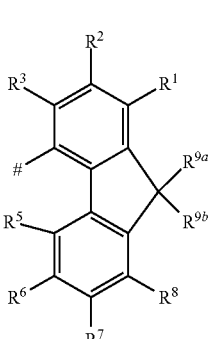 (AR-XXVI)
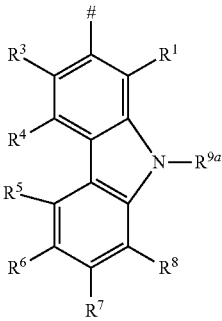 (AR-XXVII)
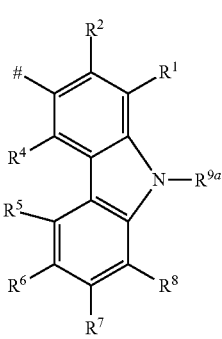 (AR-XXVIII)
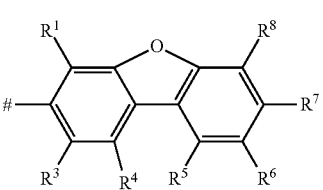 (AR-XXIX)

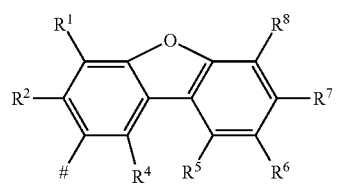
(AR-XXX)
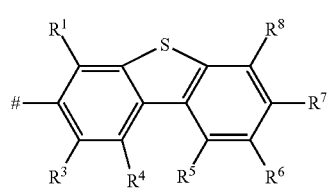
(AR-XXXI)
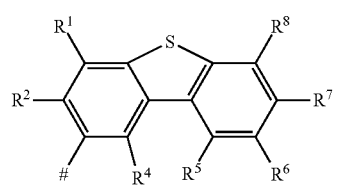
(AR-XXXII)
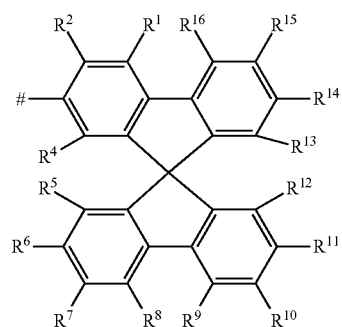
(AR-XXXIII)
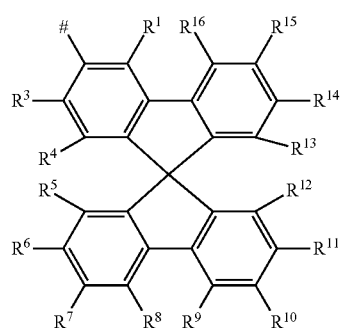
(AR-XXXIV)
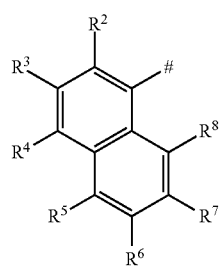
(AR-XXXV)
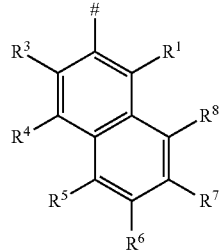
(AR-XXXVI)
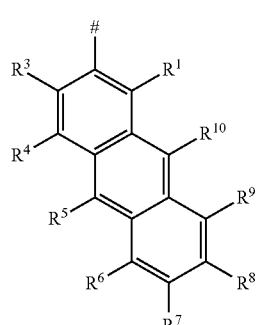
(AR-XXXVII)
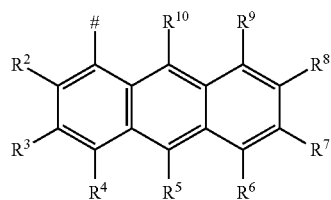
(AR-XXXVII)
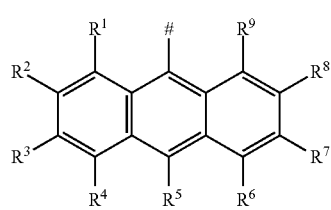
(AR-XXXIX)
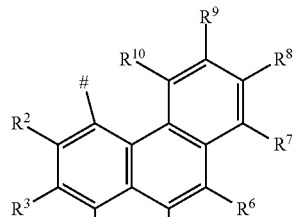
(AR-XL)
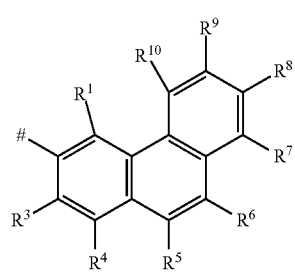
(AR-XLI)

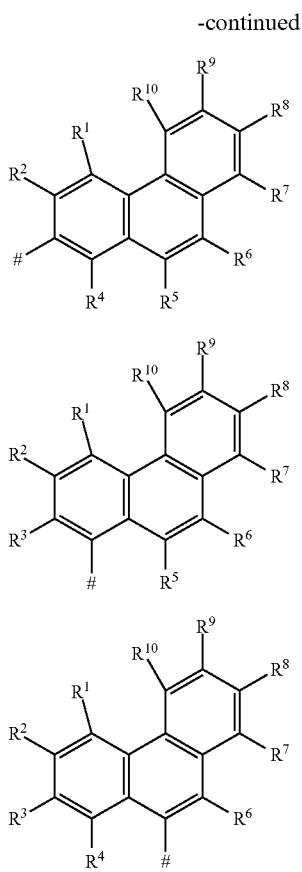

(AR-XLII)

(AR-XLIII)

(AR-XLIV)

wherein
in each case denotes the bonding site to the nitrogen atom;
in formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII and AR-XXIII:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present independently of one another, are selected from hydrogen, straight-chain or branched $C_1$-$C_4$-alkyl, straight-chain or branched $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy, phenyl, tolyl, xylyl, mesityl and anisyl;
in formulae AR-XXIV, AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII and AR-XLIV: $R^1$, $R^2$, $R^3$, $R^4$, $R^5$, $R^6$, $R^7$, $R^8$, $R^9$, $R^{9a}$, $R^{9b}$, $R^{10}$, $R^{11}$, $R^{12}$, $R^{13}$, $R^{14}$, $R^{15}$ and $R^{16}$, if present, independently of one another, are selected from hydrogen, straight-chain or branched $C_1$-$C_4$-alkyl, straight-chain or branched $C_1$-$C_4$-alkoxy, carbazol-9-yl and phenyl, wherein carbazol-9-yl and phenyl are unsubstituted or substituted by 1, 2 or 3 different or identical substituents selected from $C_1$-$C_4$-alkyl, $C_1$-$C_4$-alkoxy, phenyl, tolyl, xylyl, mesityl and anisyl; and,
in addition, $R^{9a}$ and $R^{9b}$ in formulae AR-XXIV, AR-XXV and AR-XXVI together may form an alkylene group $(CH_2)_r$ with r being 4, 5 or 6 where 1 or 2 hydrogen atoms in this group may be replaced by a methyl or methoxy group.
In formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII and AR-XXIII, each radical $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present, is preferably selected from hydrogen, $C_1$-$C_2$-alkyl, $C_1$-$C_2$-alkoxy and carbazol-9-yl which may be substituted by 1 or 2 substituents selected from $C_1$-$C_2$-alkyl, $C_1$-$C_2$-alkoxy, phenyl, tolyl, xylyl, mesityl and anisyl. Especially, each radical $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present, is selected from hydrogen, methyl, methoxy and carbazol-9-yl which is unsubstituted or substituted by 1 or 2 identical or different substituents selected from methyl, methoxy, phenyl, tolyl, xylyl, mesityl and anisyl.

In formulae AR-XXIV, AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII and AR-XLIV, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, if present, is usually selected from hydrogen, $C_1$-$C_2$-alkyl, $C_1$-$C_2$-alkoxy and carbazol-9-yl which may be substituted by 1 or 2 substituents selected from $C_1$-$C_2$-alkyl, $C_1$-$C_2$-alkoxy, phenyl, tolyl, xylyl, mesityl and anisyl; $R^{9a}$ and $R^{9b}$, if present, are, independently of one another usually hydrogen, $C_1$-$C_2$-alkyl, phenyl or form together a group —$(CH_2)_4$— or —$(CH_2)_5$—. Especially, each radical $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, if present, is selected from hydrogen, methyl, methoxy and carbazol-9-yl which may be substituted by 1 or 2 substituents selected from methyl, methoxy, phenyl, tolyl, xylyl, mesityl and anisyl. Especially, $R^{9a}$ and $R^{9b}$, if present, are independently of one another hydrogen, methyl, phenyl or form together a group —$(CH_2)_4$— or —$(CH_2)_5$—.

The groups Ar of the above-mentioned formulae (AR-I) to (AR-XLIV) which are bonded to the nitrogen atom can be combined with one another as desired. The groups of the formulae (AR-I), (AR-II), (AR-III), (AR-IV), (AR-V), (AR-VI), (AR-VIII), (AR-IX), (AR-X), (AR-XIV), (AR-XXIII), (AR-XXIV), (AR-XXV), (AR-XXIX), (AR-XXX), (AR-XXXI), (AR-XXXII), (AR-XXXIII), (AR-XXXIV), (AR-XXXV) and (AR-XXXVI) are particularly preferred here.

Particular examples of the group Ar include phenyl, 2-methylphenyl, 3-methylphenyl, 4-methylphenyl, 2,4-dimethylphenyl, 2,6-dimethyl phenyl, 3,5-dimethylphenyl, 2,4,6-trimethylphenyl, 2-methoxyphenyl, 3-methoxyphenyl, 4-methoxyphenyl, 2-phenylphenyl, 3-phenylphenyl, 4-phenylphenyl, 4-(o-tolyl)phenyl, 4-(m-tolyl)phenyl, 4-(p-tolyl)phenyl, 4-(2,6-dimethylphenyl)phenyl, 1-methyl-4-phenyl-phenyl, 2-methyl-4-phenyl-phenyl, 3-methyl-4-phenyl-phenyl, 2,6-dimethyl-4-phenyl-phenyl, 3-methyl-4-(o-tolyl)phenyl, 3-methyl-4-(m-tolyl)phenyl, 3-methyl-4-(p-tolyl)-phenyl, 3-methyl-4-(2,4,6-trimethylphenyl)phenyl, 3-methyl-4-(2,4-dimethylphenyl)-phenyl, 3-methyl-4-(2,6-dimethylphenyl)phenyl, 4-(4-methoxyphenyl)phenyl, 4-methoxy-3-phenyl-phenyl, 3-methoxy-4-phenyl-phenyl, 2-methoxy-5-phenyl-phenyl, 2-methoxy-4,5-diphenyl-phenyl, 3,4-diphenylphenyl, 3,5-diphenylphenyl, 3-(4-phenylphenyl)phenyl, 4-(4-phenylphenyl)phenyl, 3-(3,5-diphenylphenyl)phenyl, 4-diphenylaminophenyl, 1-naphthyl, 2-naphthyl, 1-phenanthryl, 2-phenanthryl, 3-phenanthryl, 4-phenanthryl, 9-phenanthryl, 9,9-dimethylfluoren-2-yl, 9-methyl-9-phenyl-fluoren-2-yl, 9,9-diphenylfluoren-2-yl, 9,9-dimethylfluoren-3-yl, 9-methyl-9-phenyl-fluoren-3-yl, 9,9-diphenylfluoren-3-yl, 9,9-dimethylfluoren-4-yl, 9-methyl-9-phenyl-fluoren-4-yl, 9,9-diphenylfluoren-4-yl, dibenzofuran-2-yl, dibenzothiophen-2-yl, dibenzofuran-3- yl, dibenzothiophen-3-yl, 9-methylcarbazol-2-yl, 9-phenylcarbazol-2-yl, 9-methylcarbazol-3-yl, 9-phenylcarbazol-3-yl, 4-(1-naphthyl)phenyl, 4-(2-naphthyl)phenyl, 4-(carbazol-9-yl)-phenyl, 4-(3,6-dimethoxycarbazol-9-yl)phenyl, 4-(3,6-dimethylcarbazol-9-yl)phenyl, 9,9'-spirobi(fluorene)-2-yl

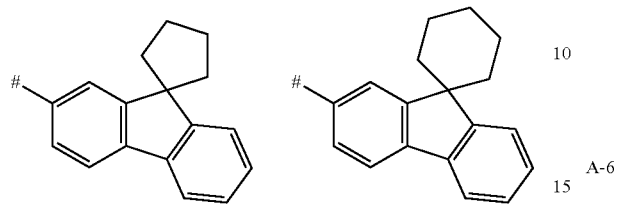

wherein # denotes the bonding site to the nitrogen atom

Likewise preferably, 2 groups Ar together with the nitrogen atom to which they are attached form a N-bound carbazolyl, which is unsubstituted or substituted by one or more, e.g. one, two, three, four or more than four substituents $R^{Ar3}$, wherein $R^{Ar3}$ is as defined above. In particular, irrespectively of its occurrence, $R^{Ar3}$ is phenyl, 2-methylphenyl, 3-methylphenyl, 4-methylphenyl. Particular examples include carbazol-9-yl, 3-phenylcarbazol-9-yl, 3-(o-tolyl)carbazol-9-yl, 3-(m-tolyl)carbazol-9-yl), 3-(p-tolyl)carbazol-9-yl, 3-(o-anisyl)carbazol-9-yl, 3-(m-anisyl)carbazol-9-yl, 3-(p-anisyl)carbazol-9-yl, 3,6-diphenylcarbazol-9-yl, 3,6-bis(o-tolyl)carbazol-9-yl, 3,6-bis(m-tolyl)carbazoyl-9-yl, 3,6-bis(p-tolyl)carbazol-9-yl, 3,6-bis(o-anisyl)carbazol-9-yl, 3,6-bis(m-anisyl)carbazoyl-9-yl, 3,6-bis(p-anisyl)carbazol-9-yl, 3,6-dimethylcarbazol-9-yl and 3,6-dimethoxycarbazol-9-yl.

In particular, the group $NAr_2$, irrespectively of its occurrence is selected from the formulae (A-1) to (A-83) listed in table A below.

Table A:

TABLE A-continued

| formula | NAr₂ |
|---|---|
| A-11 | |
| A-12 | |
| A-13 | |
| A-14 | |
| A-15 | |
| A-16 | |
| A-17 | |
| A-18 | |
| A-19 | |

TABLE A-continued
| formula | NAr₂ |
|---|---|
| A-20 | 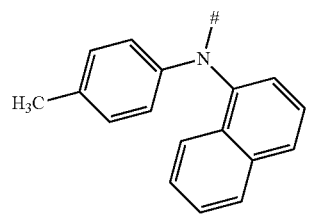 |
| A-21 | 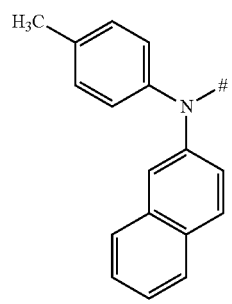 |
| A-22 | 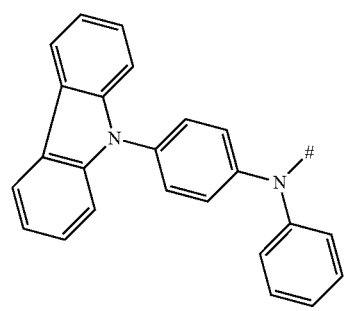 |
| A-23 | 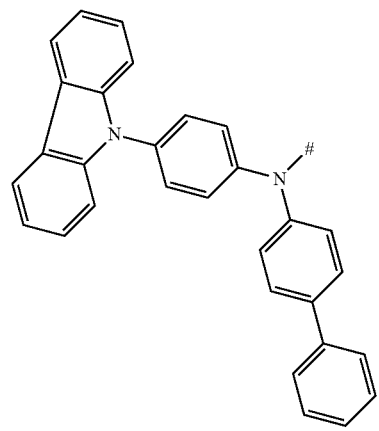 |
| A-24 | 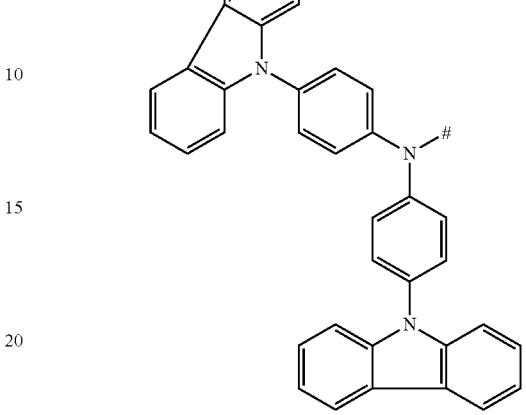 |
| A-25 | 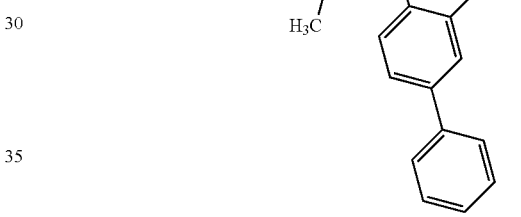 |
| A-26 | 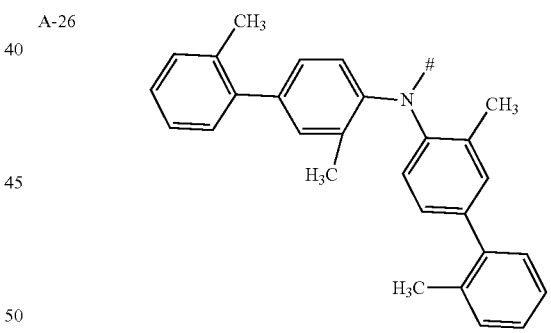 |
| A-27 | 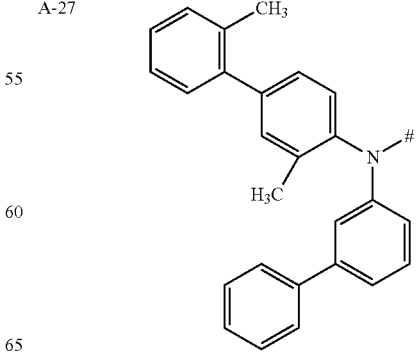 |

TABLE A-continued

| formula | NAr₂ |
| --- | --- |
| A-28 | |
| A-29 | |
| A-30 | |
| A-31 | |
| A-32 | |
| A-33 | |
| A-34 | |
| A-35 | |
| A-36 | |

TABLE A-continued
| formula | NAr₂ |
|---|---|
| A-37 | 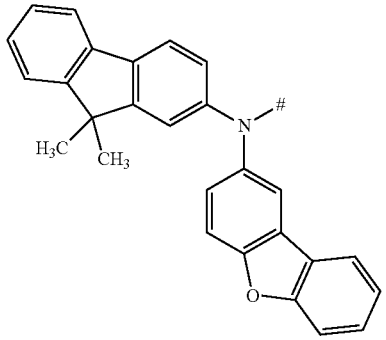 |
| A-38 | 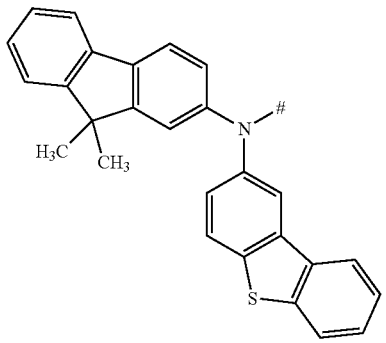 |
| A-39 | 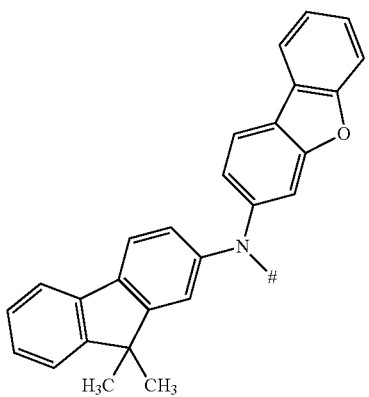 |
| A-40 | 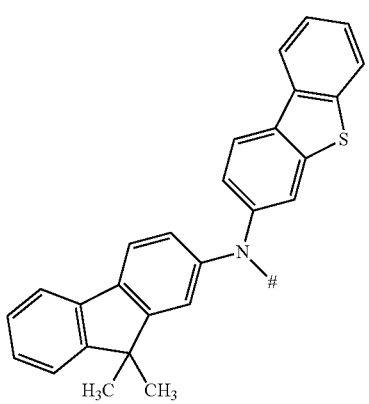 |
| A-41 | 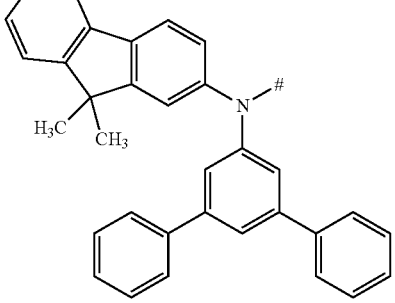 |
| A-42 | 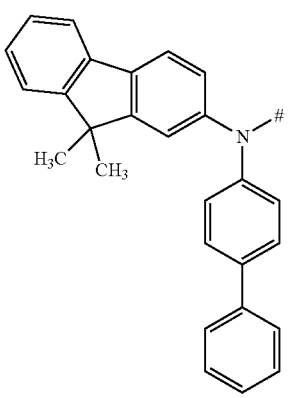 |
| A-43 | 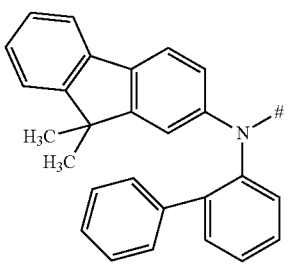 |
| A-44 | 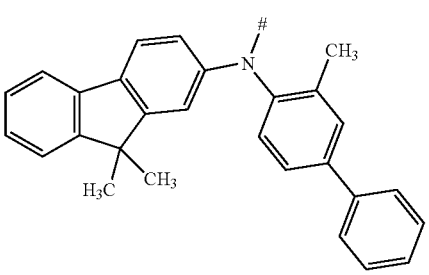 |
| A-45 | 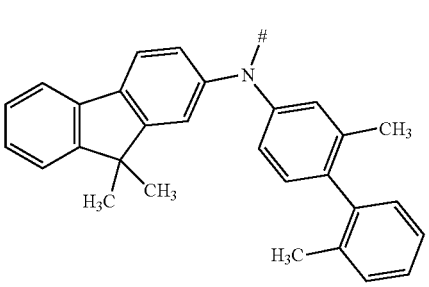 |

TABLE A-continued
| formula | NAr₂ |
|---|---|
| A-46 | 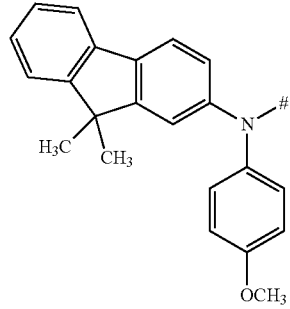 |
| A-47 | 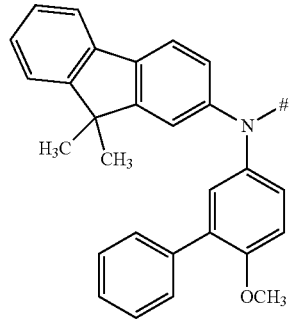 |
| A-48 | 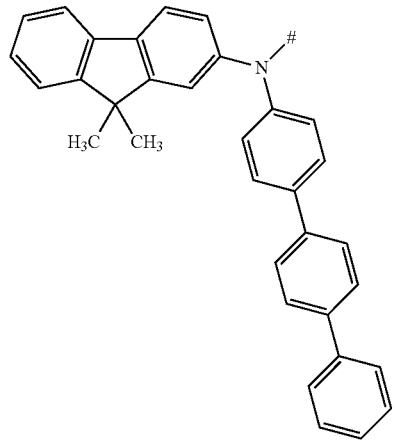 |
| A-49 | 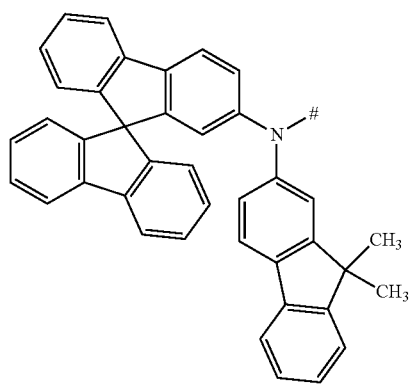 |
| A-50 | 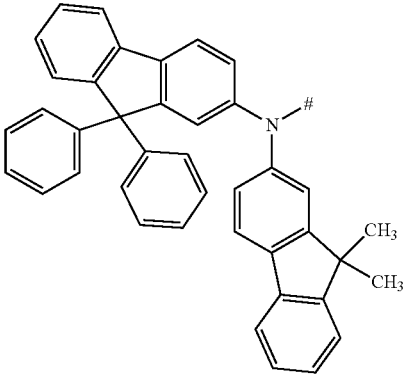 |
| A-51 | 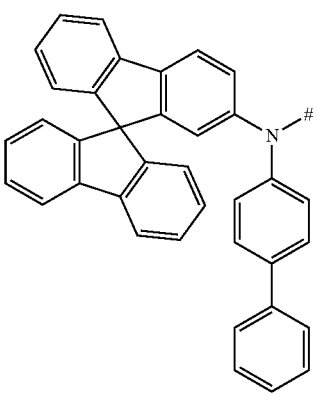 |
| A-52 | 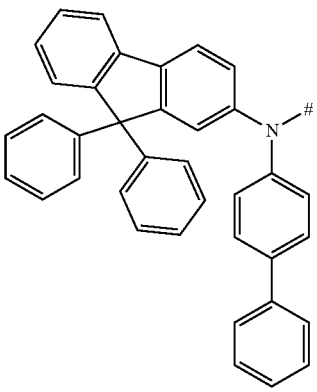 |
| A-53 | 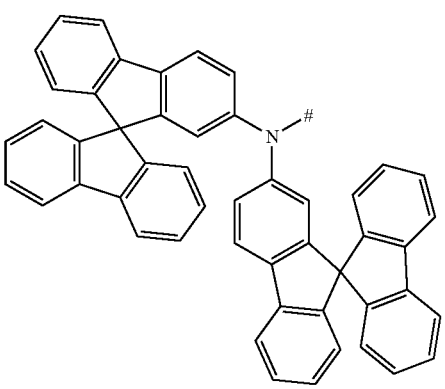 |

TABLE A-continued
| formula | NAr₂ |
|---|---|
| A-54 | 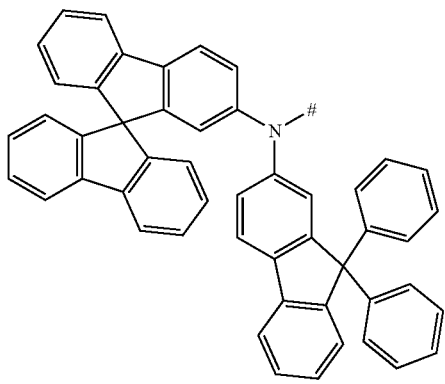 |
| A-55 | 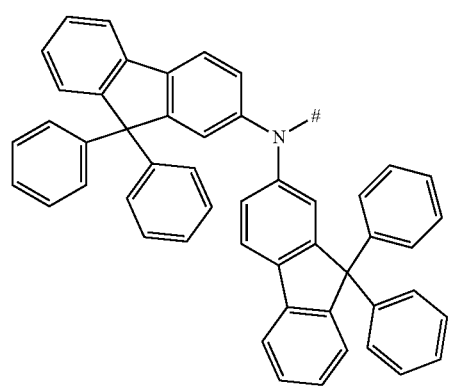 |
| A-56 | 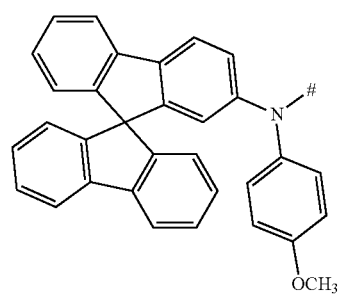 |
| A-57 | 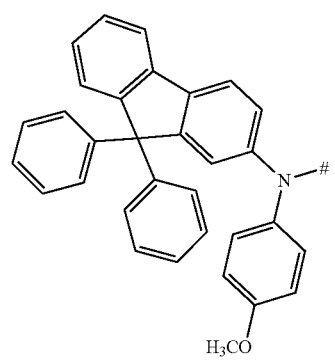 |
| A-58 | 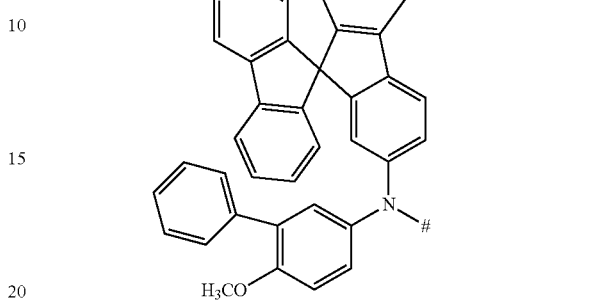 |
| A-59 | 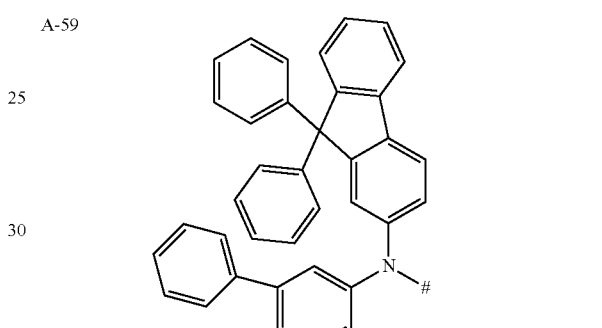 |
| A-60 | 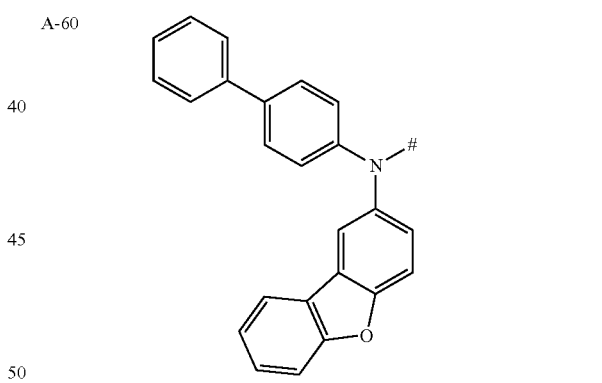 |
| A-61 | 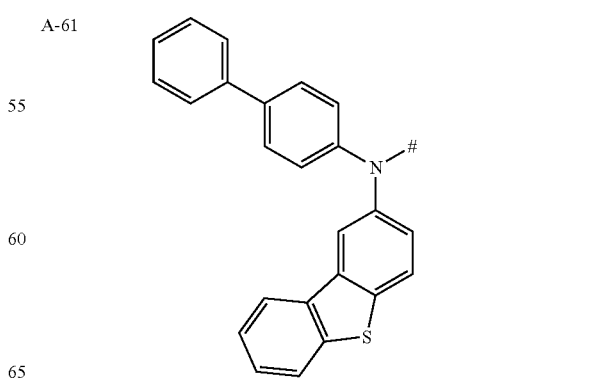 |

TABLE A-continued
| formula | NAr₂ |
|---|---|
| A-62 | 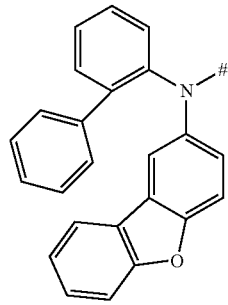 |
| A-63 | 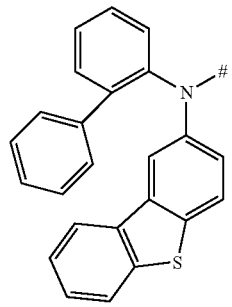 |
| A-64 | 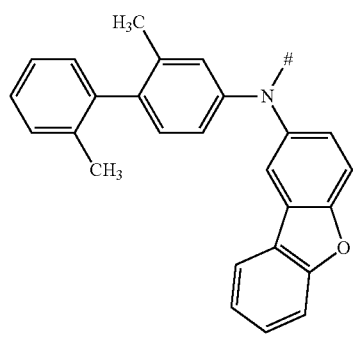 |
| A-65 | 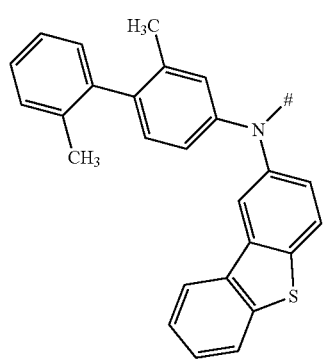 |
| A-66 | 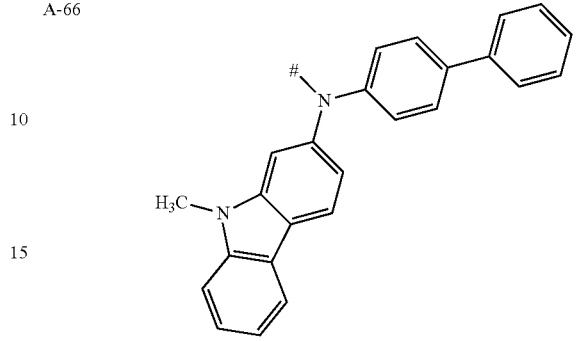 |
| A-67 | 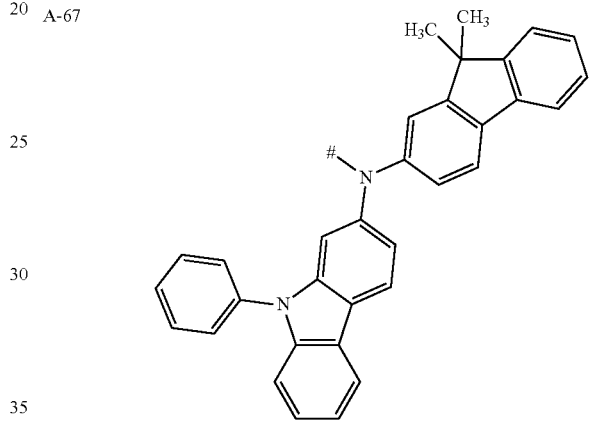 |
| A-68 | 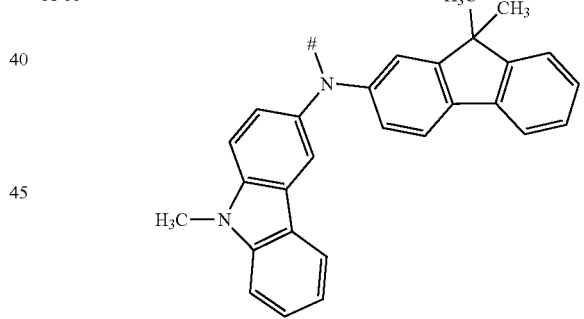 |
| A-69 | 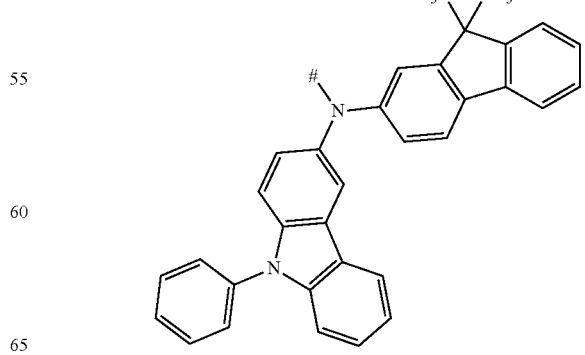 |

TABLE A-continued
| formula | NAr₂ |
|---|---|
| A-70 | 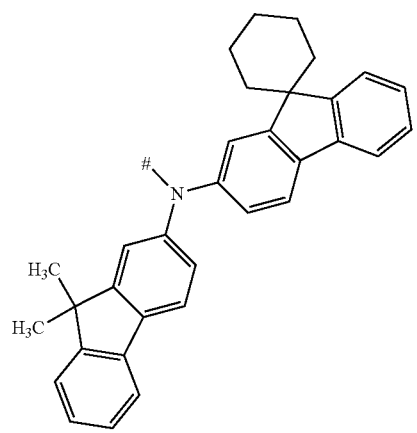 |
| A-71 | 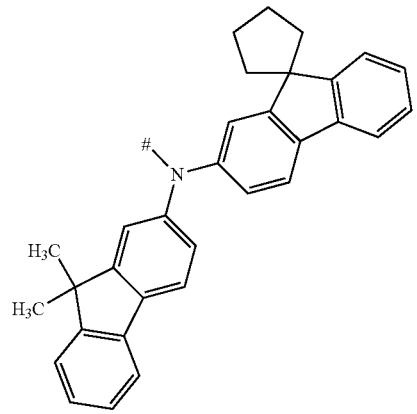 |
| A-72 | 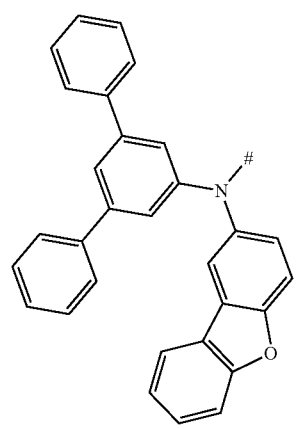 |
| A-73 | 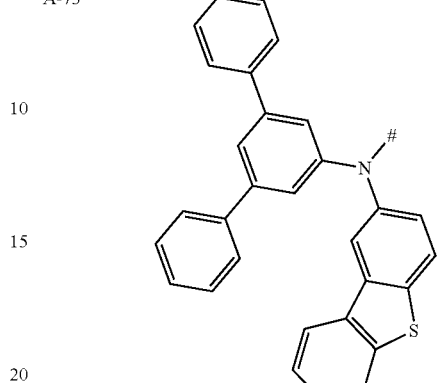 |
| A-74 | 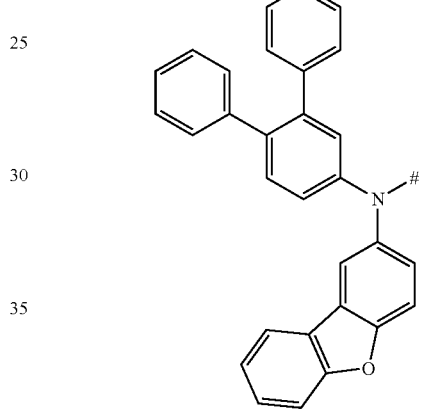 |
| A-75 | 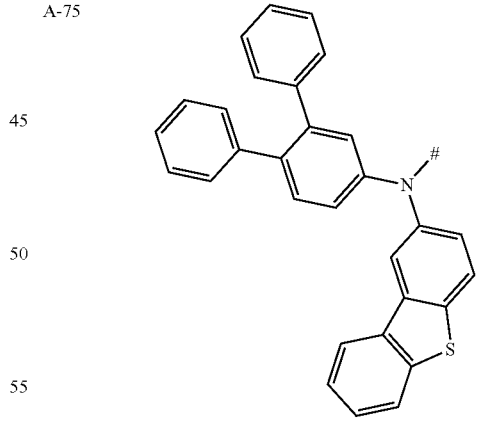 |
| A-76 | 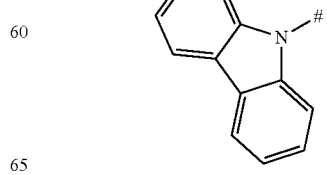 |

TABLE A-continued

| formula | NAr₂ |
|---|---|
| A-77 | (9-phenyl-carbazol-9-yl with 3-phenyl substituent) |
| A-78 | (carbazol-9-yl with 3-(2-methylphenyl) substituent) |
| A-79 | (carbazol-9-yl with 3-(4-methylphenyl) substituent) |
| A-80 | (carbazol-9-yl with 3,6-diphenyl substituents) |
| A-81 | (carbazol-9-yl with 3,6-bis(2-methylphenyl) substituents) |
| A-82 | (carbazol-9-yl with 3,6-bis(2-methoxyphenyl) substituents) |
| A-83 | (carbazol-9-yl with 3,6-bis(4-methylphenyl) substituents) | denotes the bonding site to the remainder of the molecule.

Especially, the group NAr₂, irrespectively of its occurrence, is selected from the groups of the formulae (1) to (38)

(1) N,N-bis(biphenyl-4-yl)amine (2) N-(biphenyl-4-yl)-N-(4-methoxyphenyl)amine

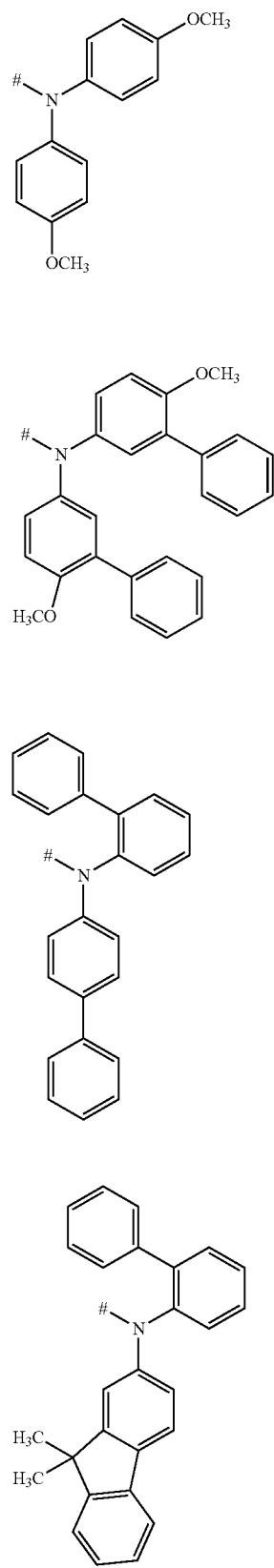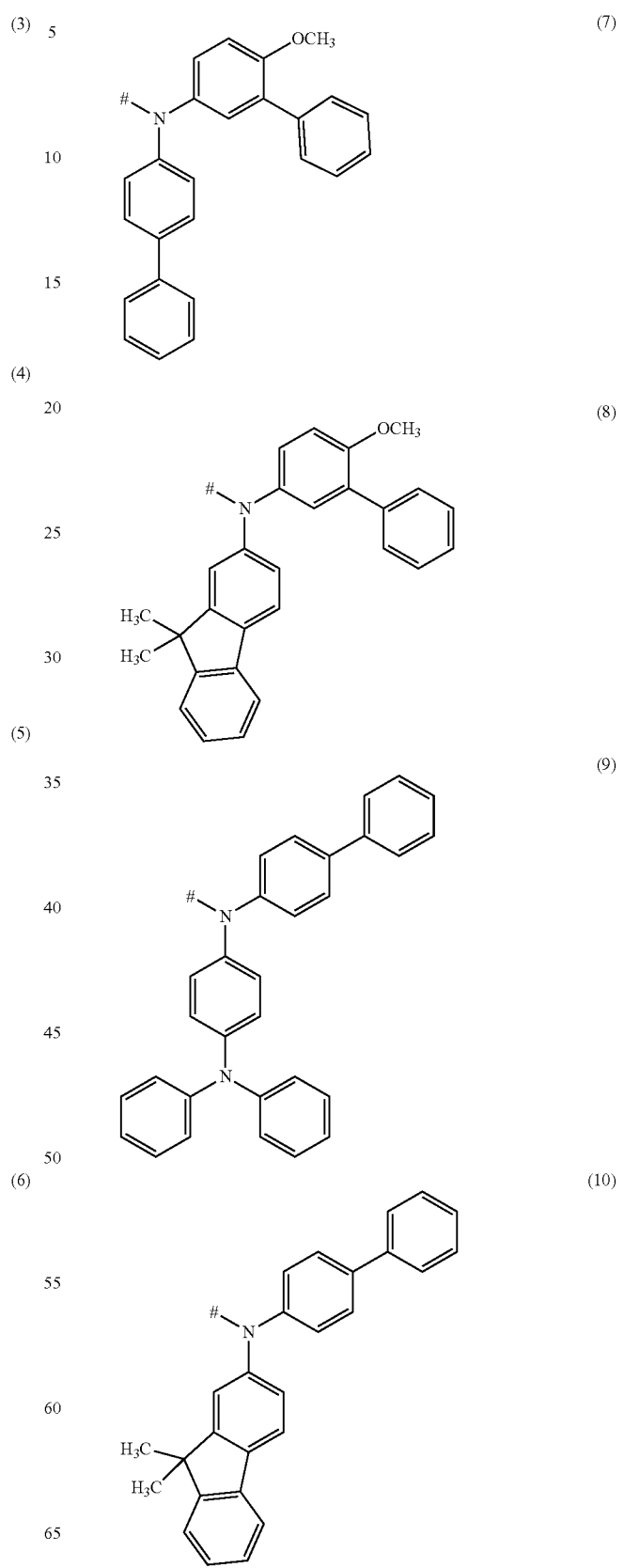

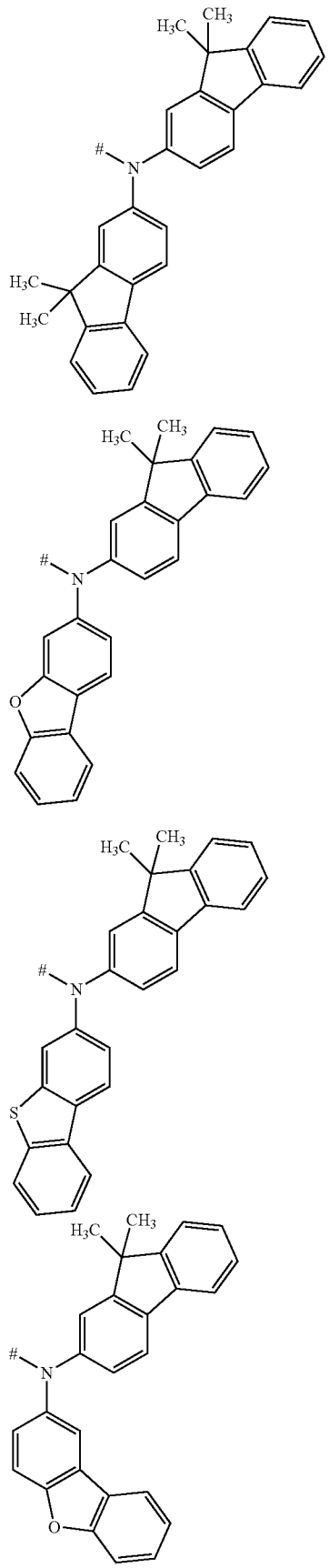
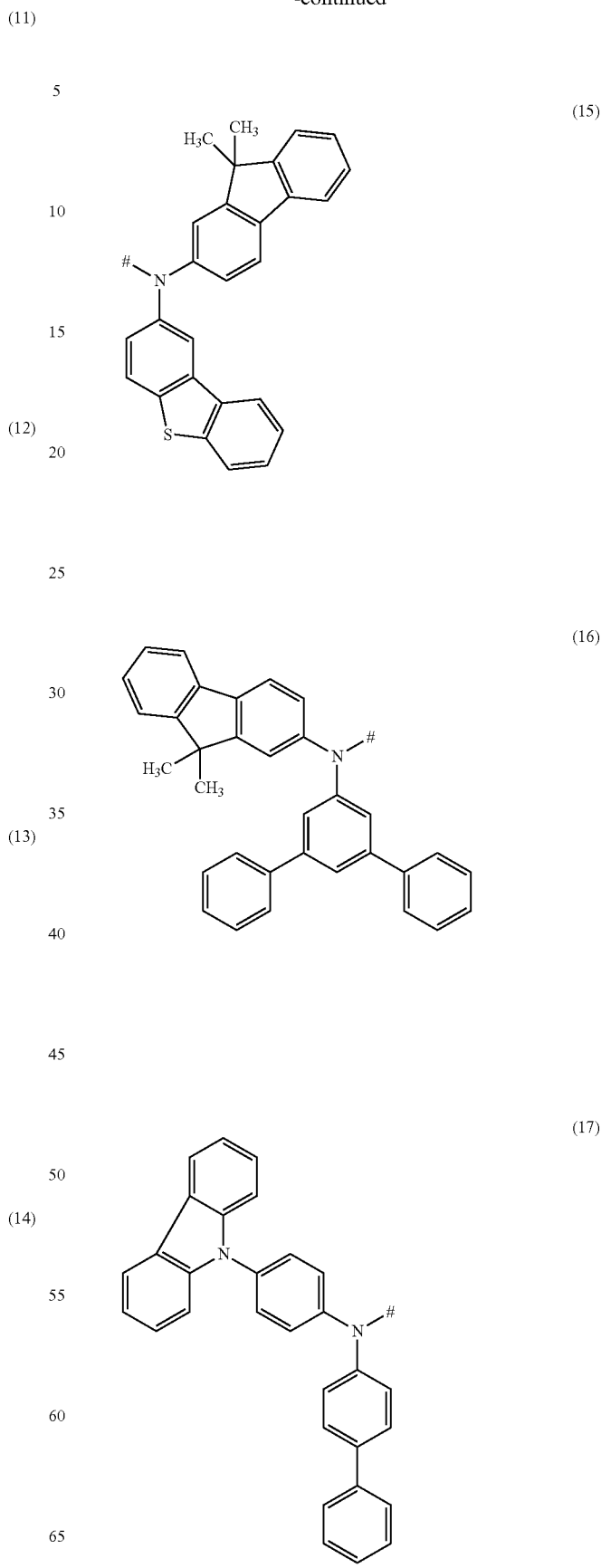

(18)
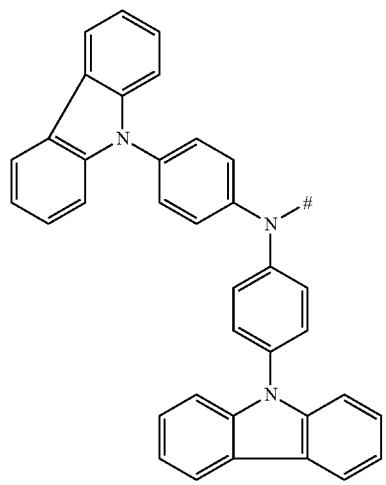
(19)
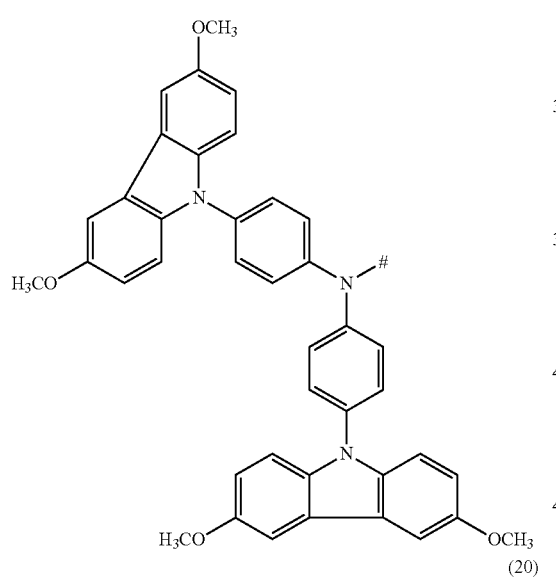
(20)
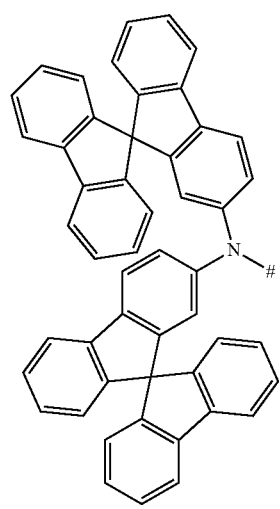
(21)
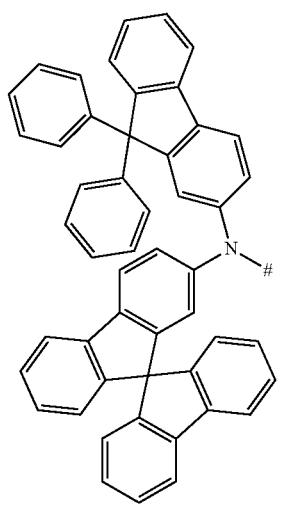
(22)
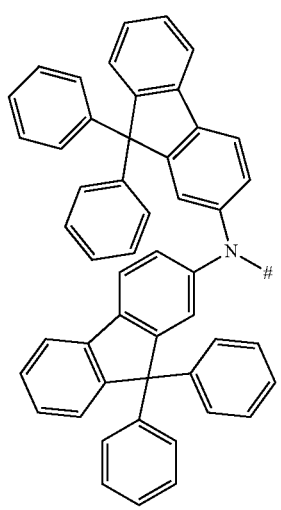
(23)
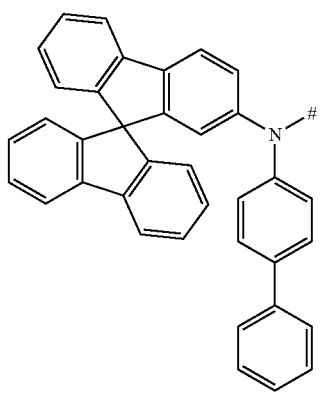

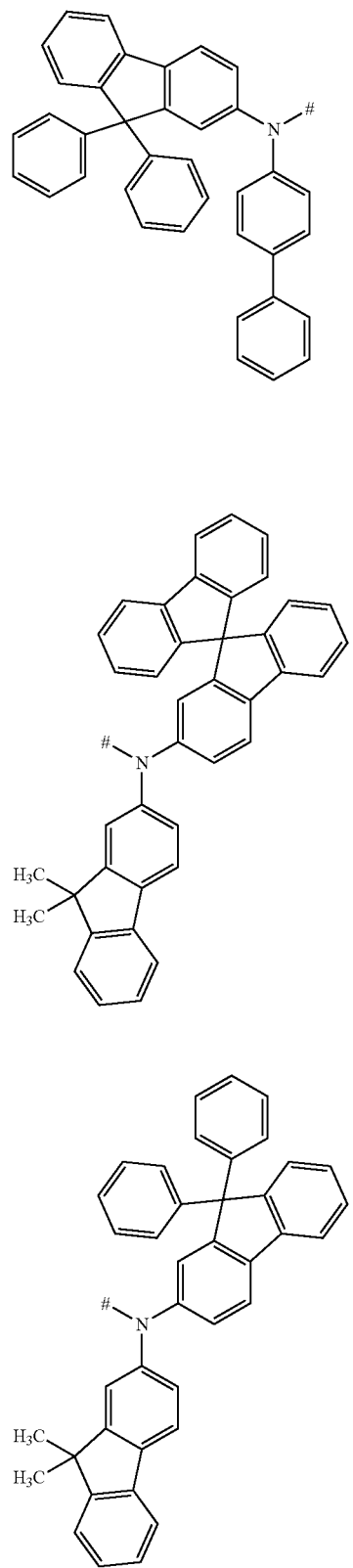
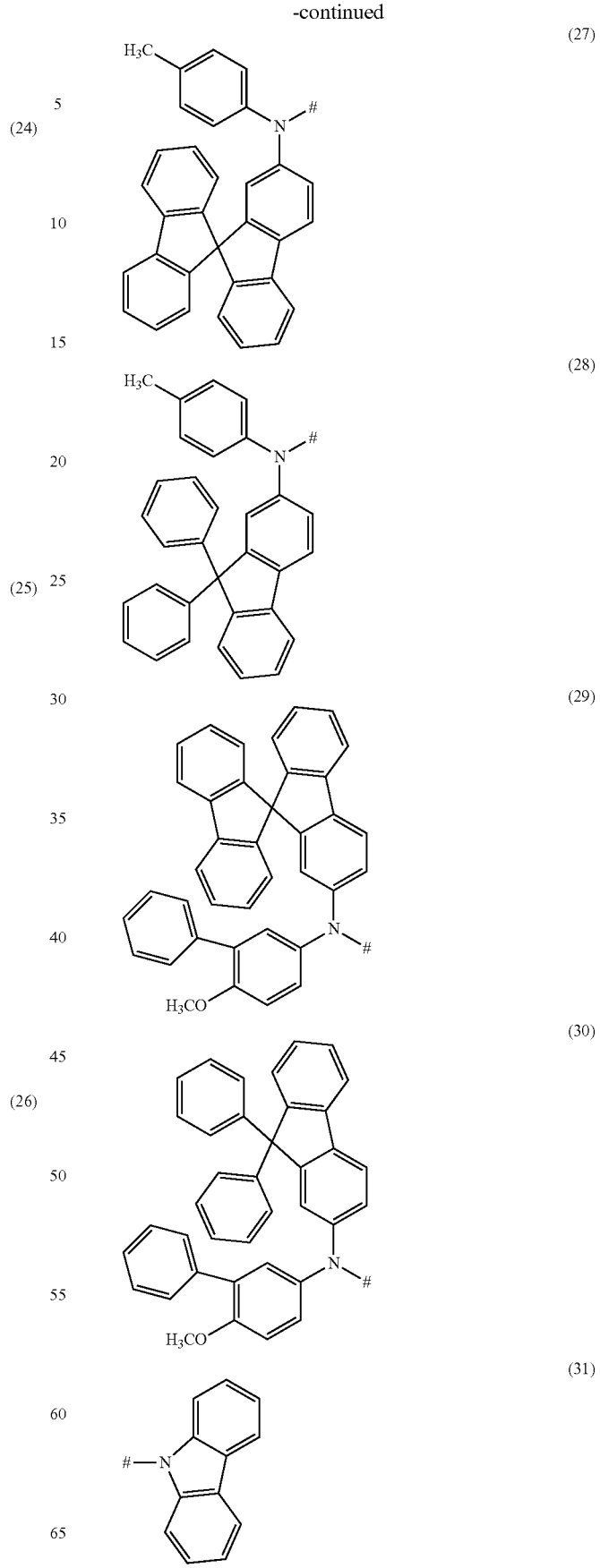

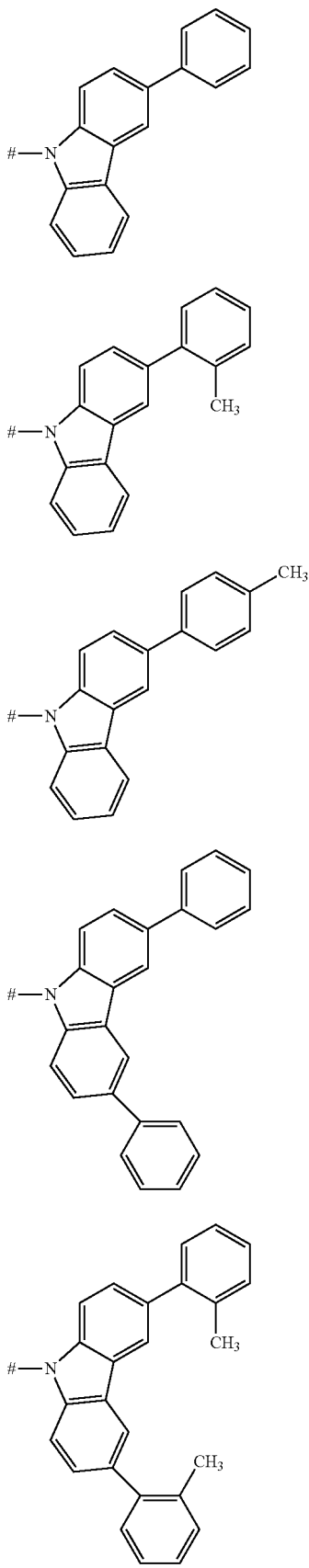

(32)

(33)

(34)

(35)

(36)

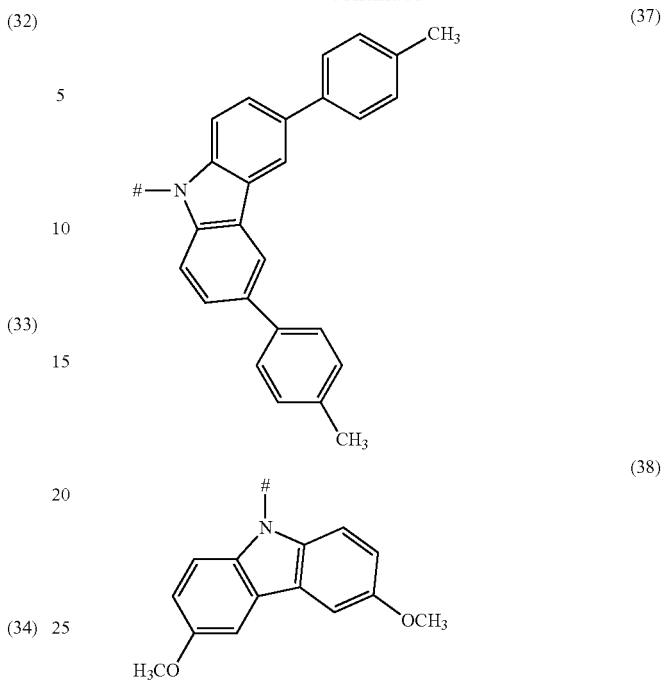

(37)

(38)

wherein # denotes the bonding side to the remainder of the compound.

Preference is given to compounds of the formulae (I), (I.A), (I.B), (I.C), (I.D), (I.E), (I.A.a), (I.B.a), (I.C.a), (I.D.a) and (I.E.a), wherein all groups $NAr_2$ have the same meaning and the two groups Ar bound to the same nitrogen atom have different meanings. Further preference is given to compounds of formulae (I), (I.A), (I.B), (I.C), (I.D), (I.E), (I.A.a), (I.B.a), (I.C.a), (I.D.a) and (I.E.a), wherein all groups Ar have the same meaning.

Preference is given to compounds of the formulae (I), (I.A), (I.B), (I.C), (I.D), (I.E), (I.A.a), (I.B.a), (I.C.a), (I.D.a) and (I.E.a), in which Y, irrespectively of its occurrence, is as defined above. Among these, those are preferred in which each $(Y)_m$, irrespectively of its occurrence, is selected from the group consisting of hydrogen, $C_1$-$C_4$-alkyl, $C_1$-$C_4$-alkoxy, phenyl, tolyl, xylyl, mesityl, phenoxy, O-tolyl, O-xylyl and O-mesityl, specifically hydrogen, methyl, methoxy and phenyl. Especially, 0 or 1 of the m Y groups is different from hydrogen.

One $(Y)_n$ bound in ortho-position on the phenyl ring relative to the phenylindane moiety mandatorily is hydrogen and the remaining $(Y)_n$ are independently of one another preferably selected from the group consisting of hydrogen, $C_1$-$C_4$-alkyl, $C_1$-$C_4$-alkoxy, phenyl, tolyl, xylyl, mesityl, phenoxy, O-tolyl, O-xylyl and O-mesityl, specifically hydrogen, methyl, methoxy and phenyl. Especially, both groups $(Y)_n$ bound in ortho positions on the phenyl ring relative to phenylindane moiety are hydrogen. Especially, the groups $(Y)_n$ bound in non-ortho positions on the phenyl ring relative to phenylindane moiety may be different from hydrogen. Especially, 0 or 1 of the n Y groups is different from hydrogen.

Examples of preferred compounds are the individual compounds of the following formulae (I.A.a.1), (I.A.1), (I.A.2), (I.A.3), (I.A.4), (I.B.a.1), (I.B.1), (I.B.2), (I.B.3), (I.B.4), (I.C.a.1), (I.C.a.2), (I.C.a.3), (I.C.a.4), (I.C.1), (I.C.2), (I.C.3), (I.C.4), (I.D.a.1), (I.D.1), (I.D.2), (I.D.3), (I.D.4) and (I.E.a.1), compiled in the tables 1 to 24 below.
-continued
(I.A.a.1)
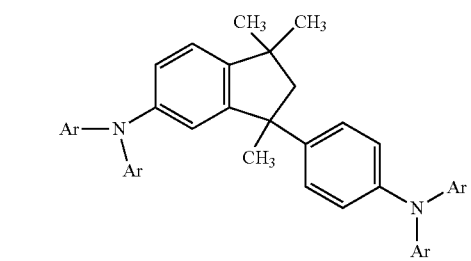
(I.B.a.1)
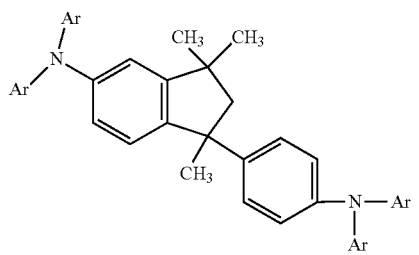
(I.A.1)
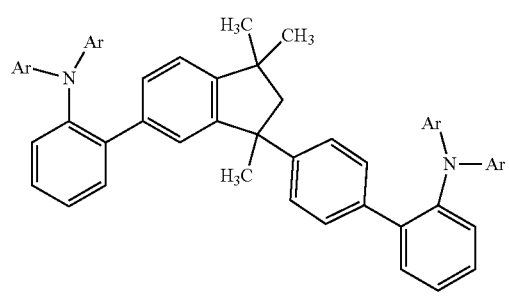
(I.B.1)
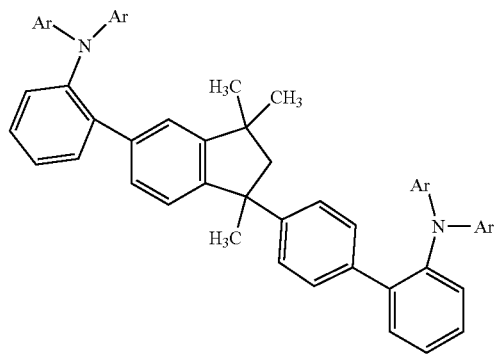
(I.A.2)
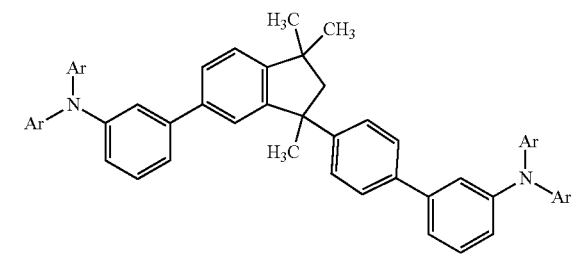
(I.B.2)
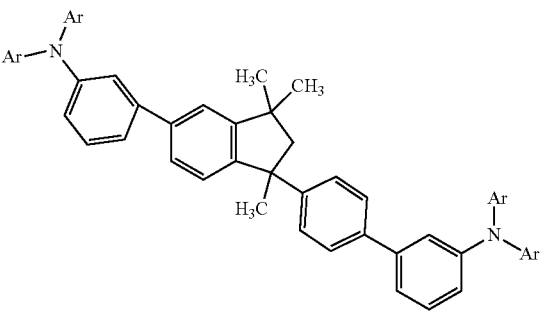
(I.A.3)
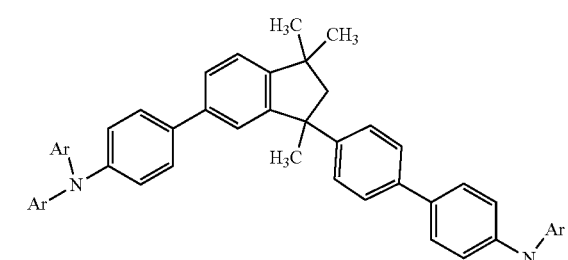
(I.B.3)
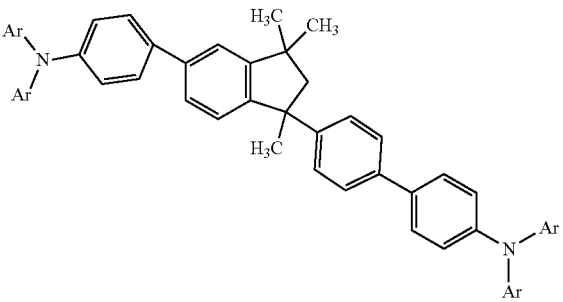
(I.A.4)
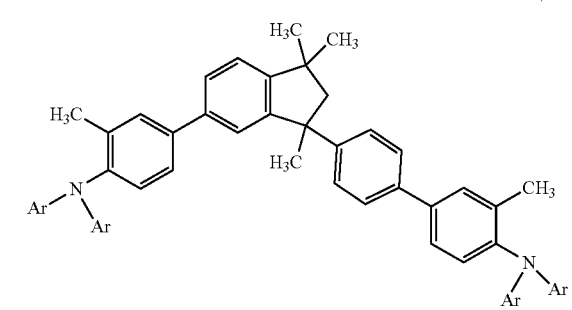
(I.B.4)
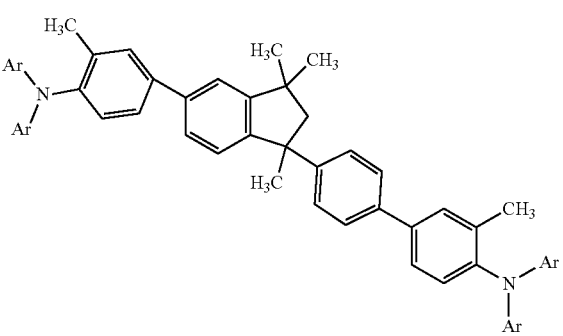

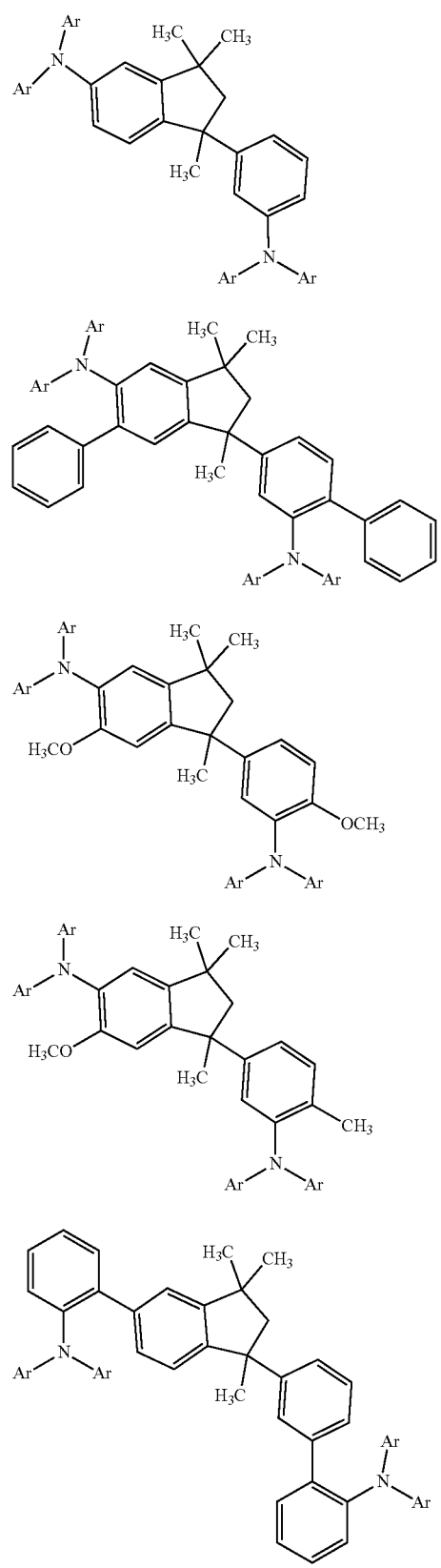
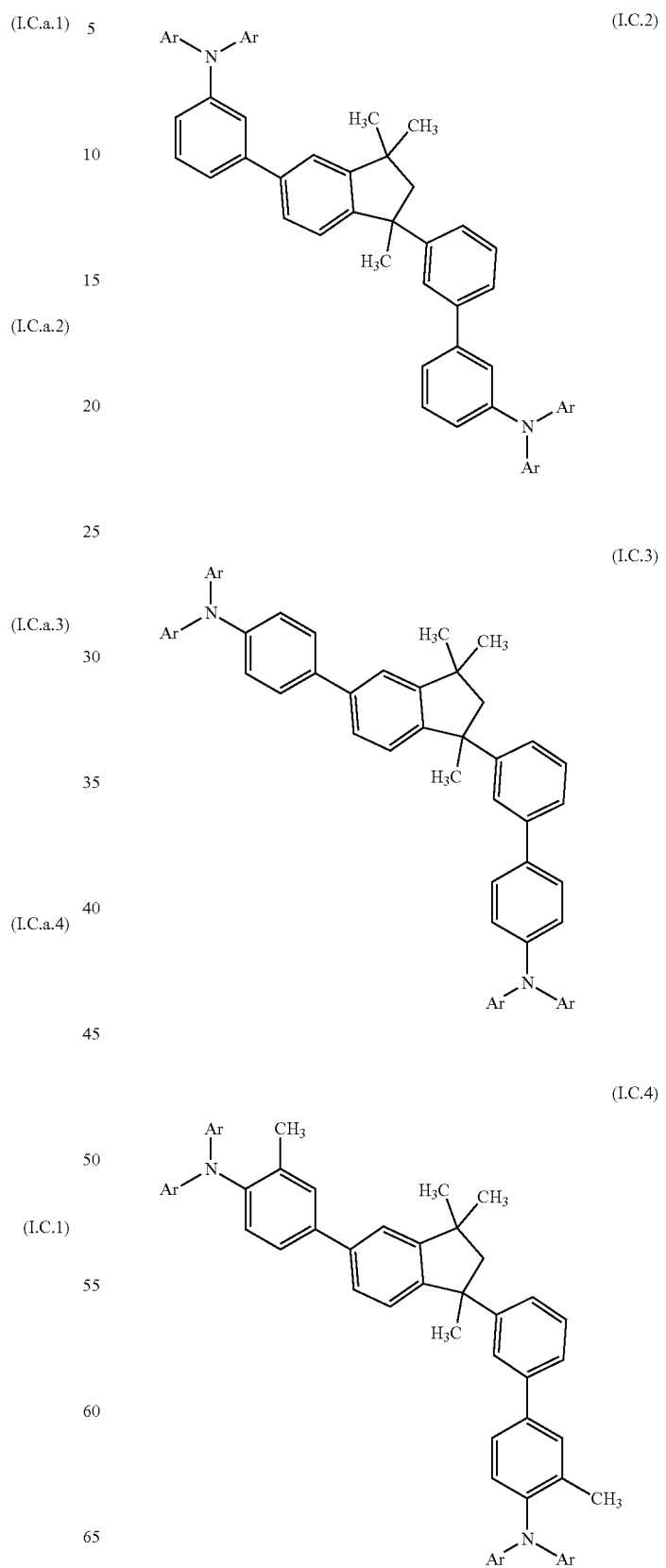

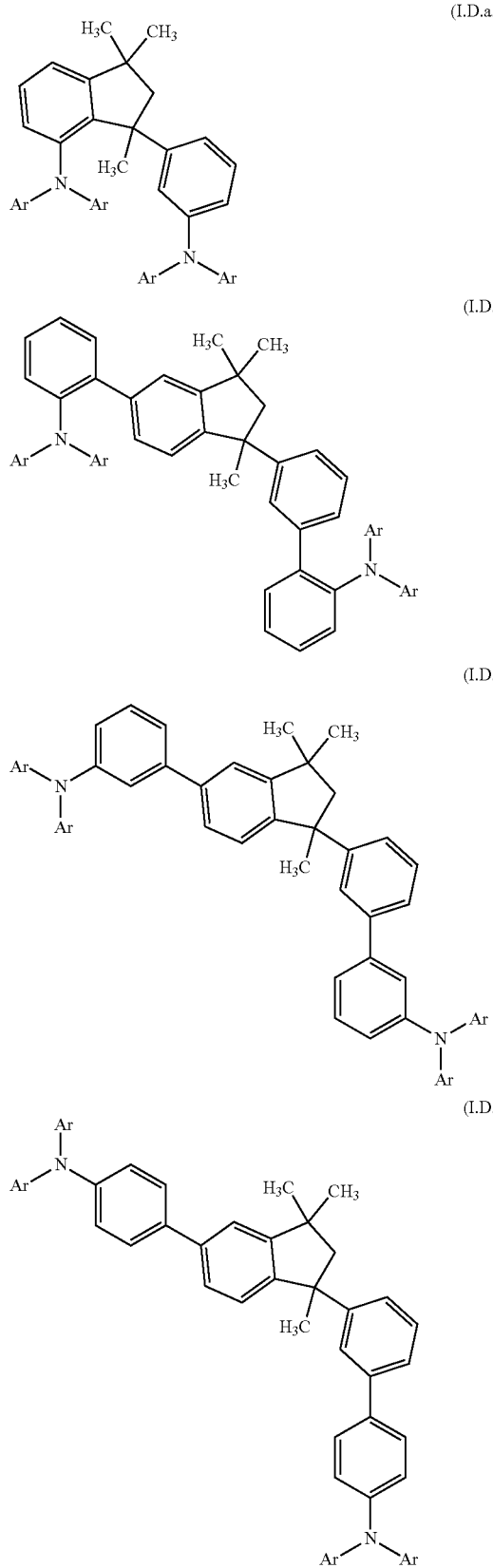

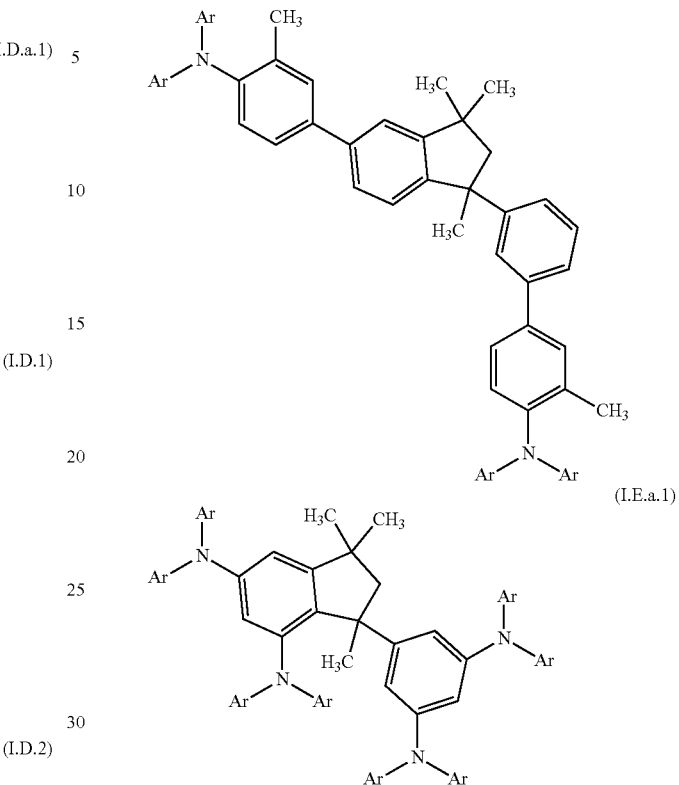

Table 1
Compounds of the formula I.A.a.1 in which the combination of the groups $NAr_2$ corresponds in each case to one row of Table B.

Table 2
Compounds of the formula I.A.1 in which the combination of the groups $NAr_2$ corresponds in each case to one row of Table B.

Table 3
Compounds of the formula I.A.2 in which the combination of the groups $NAr_2$ corresponds in each case to one row of Table B.

Table 4
Compounds of the formula I.A.3 in which the combination of the groups $NAr_2$ corresponds in each case to one row of Table B Table 5
Compounds of the formula I.A.4 in which the combination of the groups $NAr_2$ corresponds in each case to one row of Table B.

Table 6
Compounds of the formula I.B.a.1 in which the combination of the groups $NAr_2$ corresponds in each case to one row of Table B.

Table 7
Compounds of the formula I.B.1 in which the combination of the groups $NAr_2$ corresponds in each case to one row of Table B.

Table 8
Compounds of the formula I.B.2 in which the combination of the groups $NAr_2$ corresponds in each case to one row of Table B.

Table 9
Compounds of the formula I.B.3 in which the combination of the groups NAr$_2$ corresponds in each case to one row of Table B.

Table 10
Compounds of the formula I.B.4 in which the combination of the groups NAr$_2$ corresponds in each case to one row of Table B.

Table 11
Compounds of the formula I.C.a.1 in which the combination of the groups NAr$_2$ corresponds in each case to one row of Table B.

Table 12
Compounds of the formula I.C.a.2 in which the combination of the groups NAr$_2$ corresponds in each case to one row of Table B.

Table 13
Compounds of the formula I.C.a.3 in which the combination of the groups NAr$_2$ corresponds in each case to one row of Table B.

Table 14
Compounds of the formula I.C.a.4 in which the combination of the groups NAr$_2$ corresponds in each case to one row of Table B.

Table 15
Compounds of the formula I.C.1 in which the combination of the groups NAr$_2$ corresponds in each case to one row of Table B.

Table 16
Compounds of the formula I.C.2 in which the combination of the groups NAr$_2$ corresponds in each case to one row of Table B.

Table 17
Compounds of the formula I.C.3 in which the combination of the groups NAr$_2$ corresponds in each case to one row of Table B.

Table 18
Compounds of the formula I.C.4 in which the combination of the groups NAr$_2$ corresponds in each case to one row of Table B.

Table 19
Compounds of the formula I.D.a.1 in which the combination of the groups NAr$_2$ corresponds in each case to one row of Table B.

Table 20
Compounds of the formula I.D.1 in which the combination of the groups NAr$_2$ corresponds in each case to one row of Table B.

Table 21
Compounds of the formula I.D.2 in which the combination of the groups NAr$_2$ corresponds in each case to one row of Table B.

Table 22
Compounds of the formula I.D.3 in which the combination of the groups NAr$_2$ corresponds in each case to one row of Table B.

Table 23
Compounds of the formula I.D.4 in which the combination of the groups NAr$_2$ corresponds in each case to one row of Table B.

Table 24
Compounds of the formula I.E.a.1 in which the combination of the groups NAr$_2$ corresponds in each case to one row of Table B and the two groups NAr$_2$ attached to the phenylindane moiety have the same meaning and the two groups NAr$_2$ attached to the phenyl ring have the same meaning.

TABLE B

| Example No. | (NAr$_2$) attached to the phenylindane moiety | (NAr$_2$) attached to the phenyl ring |
| --- | --- | --- |
| B-1 | formula (A-1) | formula (A-1) |
| B-2 | formula (A-2) | formula (A-2) |
| B-3 | formula (A-3) | formula (A-3) |
| B-4 | formula (A-4) | formula (A-4) |
| B-5 | formula (A-5) | formula (A-5) |
| B-6 | formula (A-6) | formula (A-6) |
| B-7 | formula (A-7) | formula (A-7) |
| B-8 | formula (A-8) | formula (A-8) |
| B-9 | formula (A-9) | formula (A-9) |
| B-10 | formula (A-10) | formula (A-10) |
| B-11 | formula (A-11) | formula (A-11) |
| B-12 | formula (A-12) | formula (A-12) |
| B-13 | formula (A-13) | formula (A-13) |
| B-14 | formula (A-14) | formula (A-14) |
| B-15 | formula (A-15) | formula (A-15) |
| B-16 | formula (A-16) | formula (A-16) |
| B-17 | formula (A-17) | formula (A-17) |
| B-18 | formula (A-18) | formula (A-18) |
| B-19 | formula (A-19) | formula (A-19) |
| B-20 | formula (A-20) | formula (A-20) |
| B-21 | formula (A-21) | formula (A-21) |
| B-22 | formula (A-22) | formula (A-22) |
| B-23 | formula (A-23) | formula (A-23) |
| B-24 | formula (A-24) | formula (A-24) |
| B-25 | formula (A-25) | formula (A-25) |
| B-26 | formula (A-26) | formula (A-26) |
| B-27 | formula (A-27) | formula (A-27) |
| B-28 | formula (A-28) | formula (A-28) |
| B-29 | formula (A-29) | formula (A-29) |
| B-30 | formula (A-30) | formula (A-30) |
| B-31 | formula (A-31) | formula (A-31) |
| B-32 | formula (A-32) | formula (A-32) |
| B-33 | formula (A-33) | formula (A-33) |
| B-34 | formula (A-34) | formula (A-34) |
| B-35 | formula (A-35) | formula (A-35) |
| B-36 | formula (A-36) | formula (A-36) |
| B-37 | formula (A-37) | formula (A-37) |
| B-38 | formula (A-38) | formula (A-38) |
| B-39 | formula (A-39) | formula (A-39) |
| B-40 | formula (A-40) | formula (A-40) |
| B-41 | formula (A-41) | formula (A-41) |
| B-42 | formula (A-42) | formula (A-42) |
| B-43 | formula (A-43) | formula (A-43) |
| B-44 | formula (A-44) | formula (A-44) |
| B-45 | formula (A-45) | formula (A-45) |
| B-46 | formula (A-46) | formula (A-46) |
| B-47 | formula (A-47) | formula (A-47) |
| B-48 | formula (A-48) | formula (A-48) |
| B-49 | formula (A-49) | formula (A-49) |
| B-50 | formula (A-50) | formula (A-50) |
| B-51 | formula (A-51) | formula (A-51) |
| B-52 | formula (A-52) | formula (A-52) |
| B-53 | formula (A-53) | formula (A-53) |
| B-54 | formula (A-54) | formula (A-54) |
| B-55 | formula (A-55) | formula (A-55) |
| B-56 | formula (A-56) | formula (A-56) |
| B-57 | formula (A-57) | formula (A-57) |
| B-58 | formula (A-58) | formula (A-58) |
| B-59 | formula (A-59) | formula (A-59) |
| B-60 | formula (A-60) | formula (A-60) |
| B-61 | formula (A-61) | formula (A-61) |
| B-62 | formula (A-62) | formula (A-62) |
| B-63 | formula (A-63) | formula (A-63) |
| B-64 | formula (A-64) | formula (A-64) |
| B-65 | formula (A-65) | formula (A-65) |

TABLE B-continued

| Example No. | (NAr₂) attached to the phenylindane moiety | (NAr₂) attached to the phenyl ring |
|---|---|---|
| B-66 | formula (A-66) | formula (A-66) |
| B-67 | formula (A-67) | formula (A-67) |
| B-68 | formula (A-68) | formula (A-68) |
| B-69 | formula (A-69) | formula (A-69) |
| B-70 | formula (A-70) | formula (A-70) |
| B-71 | formula (A-71) | formula (A-71) |
| B-72 | formula (A-72) | formula (A-72) |
| B-73 | formula (A-73) | formula (A-73) |
| B-74 | formula (A-74) | formula (A-74) |
| B-75 | formula (A-75) | formula (A-75) |
| B-76 | formula (A-76) | formula (A-76) |
| B-77 | formula (A-77) | formula (A-77) |
| B-78 | formula (A-78) | formula (A-78) |
| B-79 | formula (A-79) | formula (A-79) |
| B-80 | formula (A-80) | formula (A-80) |
| B-81 | formula (A-81) | formula (A-81) |
| B-82 | formula (A-82) | formula (A-82) |
| B-83 | formula (A-83) | formula (A-83) |

Specially preferred embodiments of the invention relate to the compounds of formula I and their enantiomers depicted below.

2

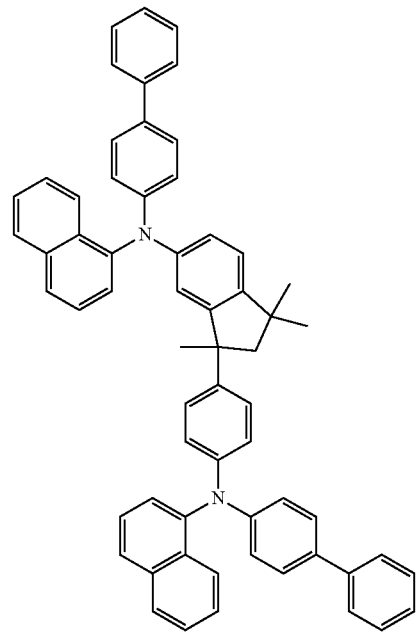

1

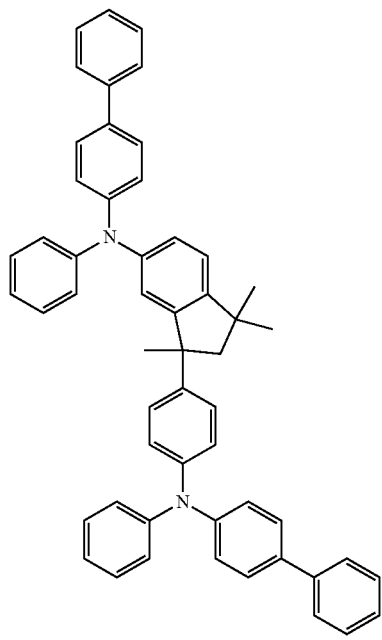

3

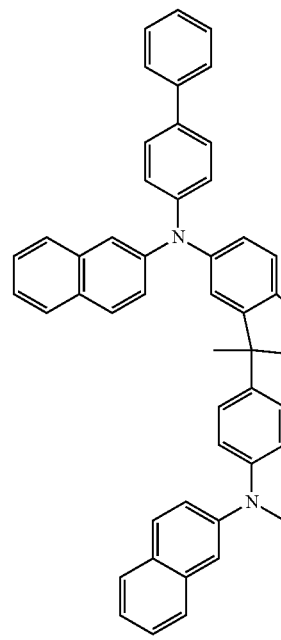

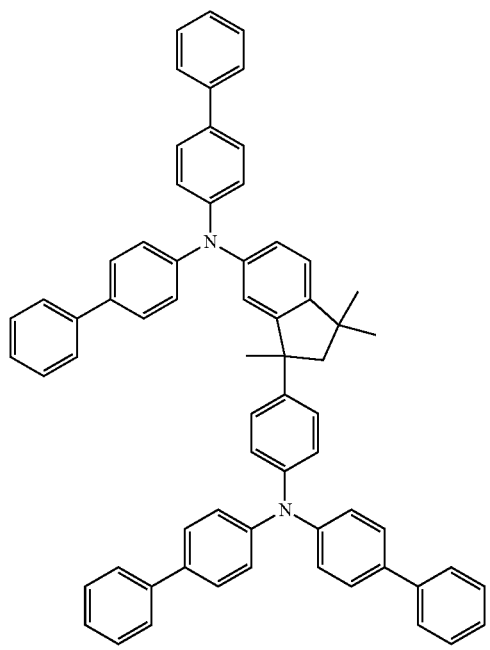
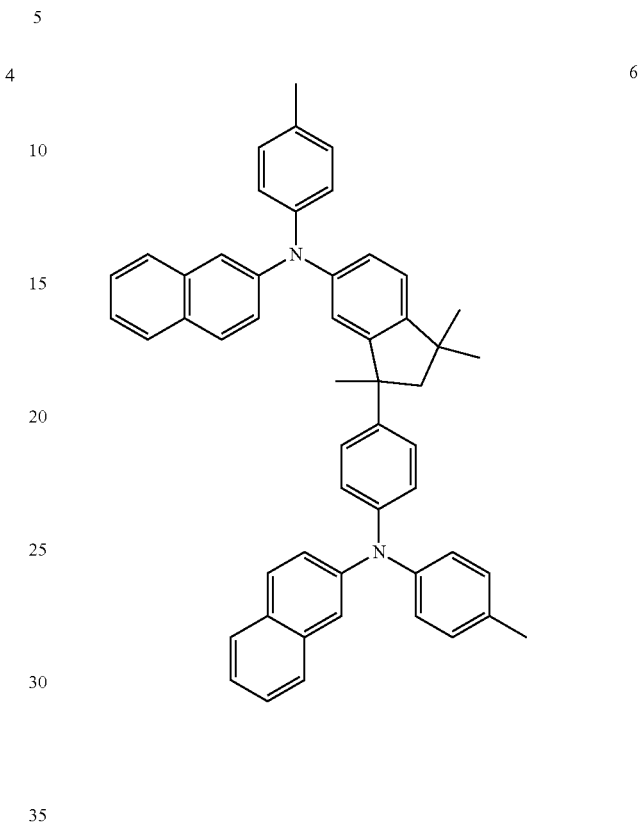
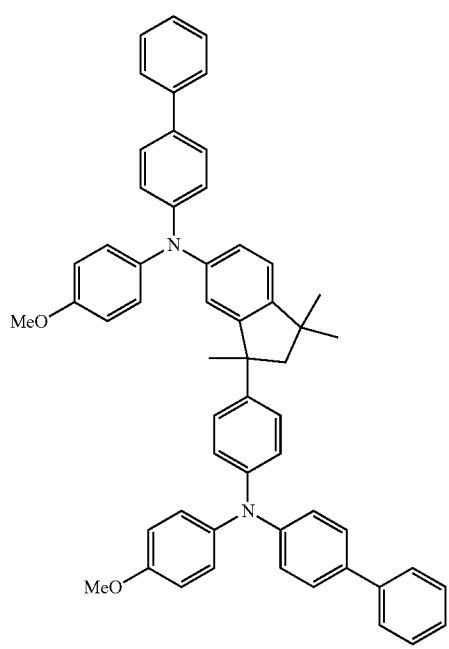
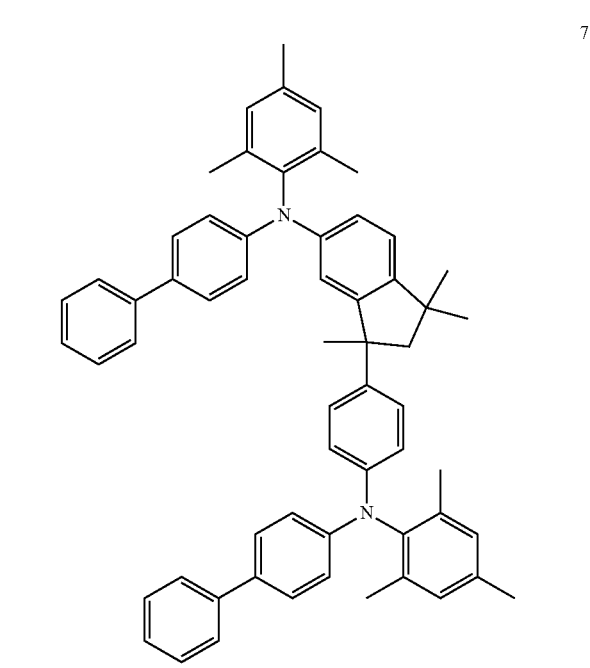

8
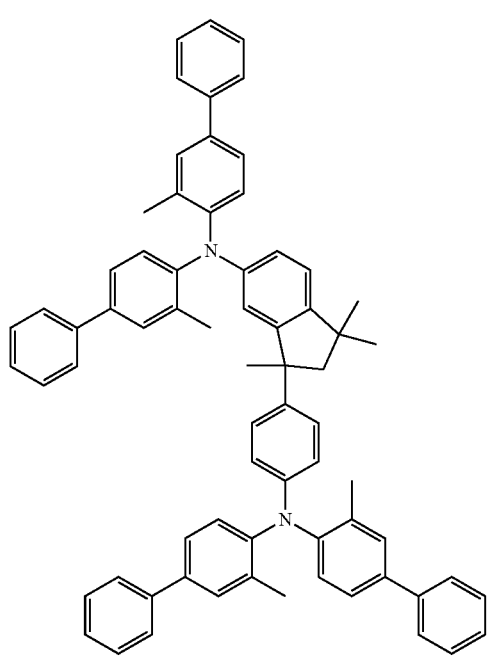
9
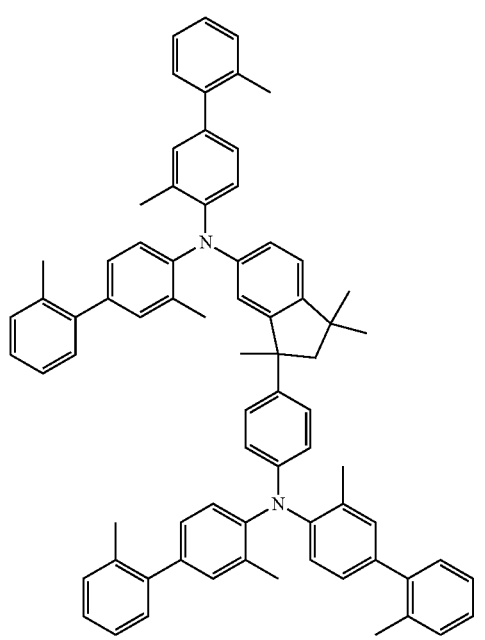
10
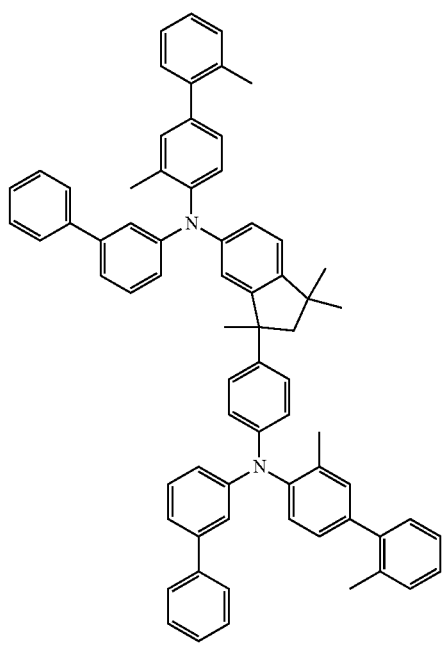
11
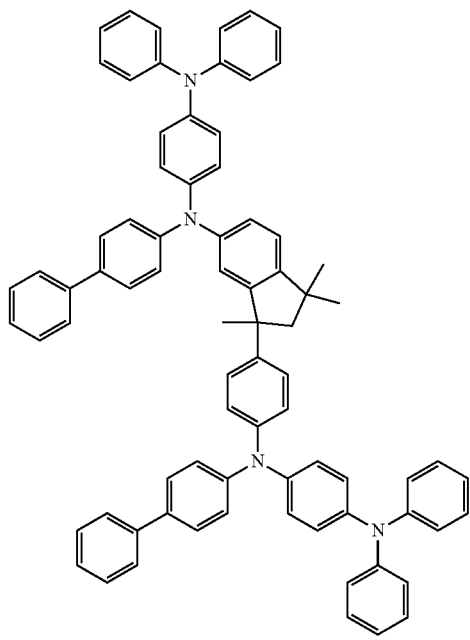

71
-continued
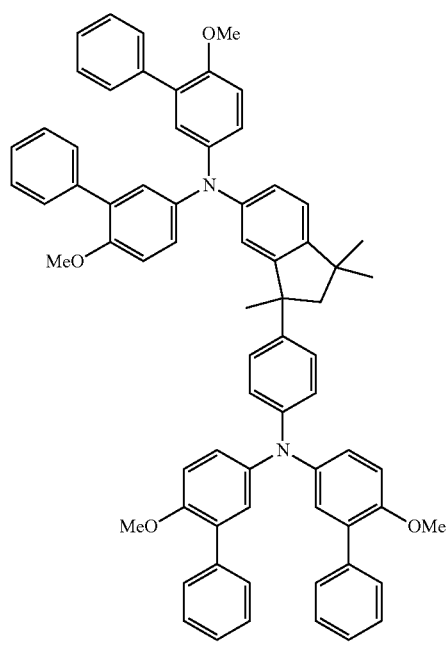
5
12
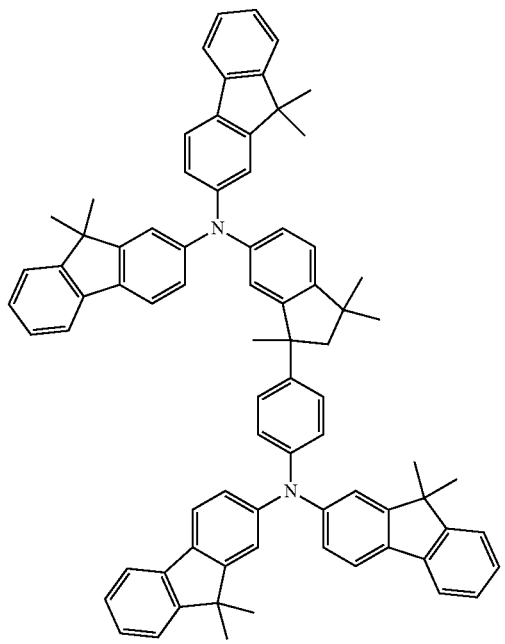
13
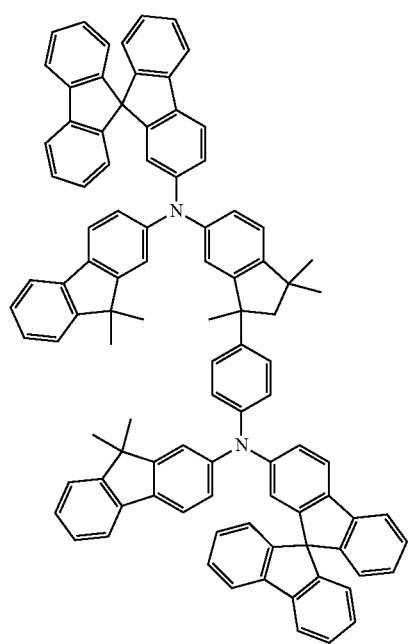
72
-continued
14
15
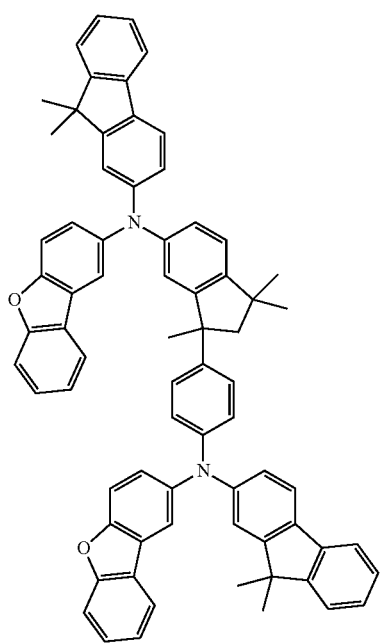

73
-continued
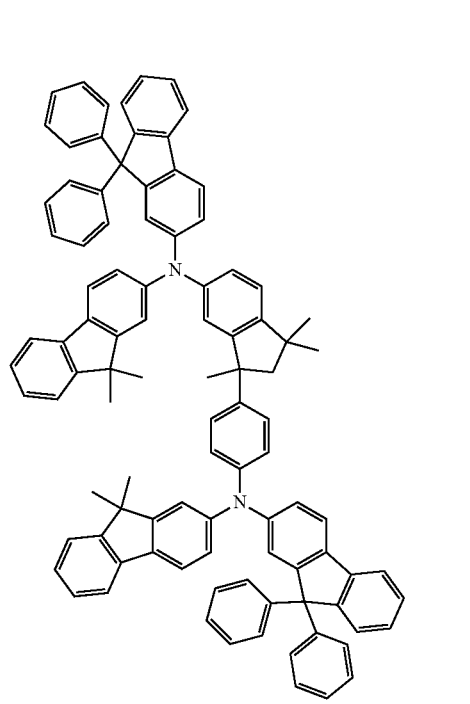
18
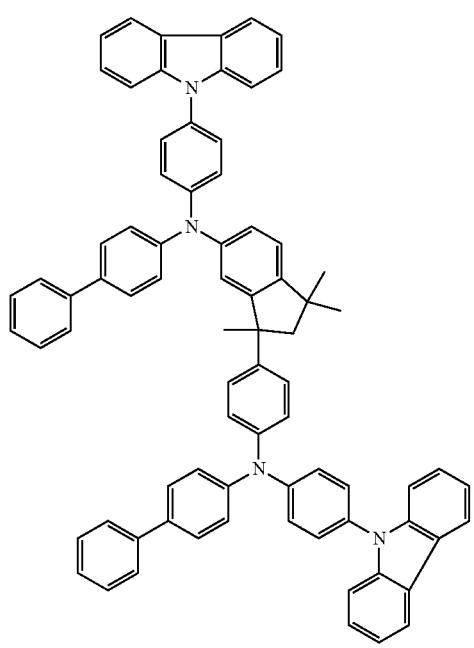
74
-continued
17
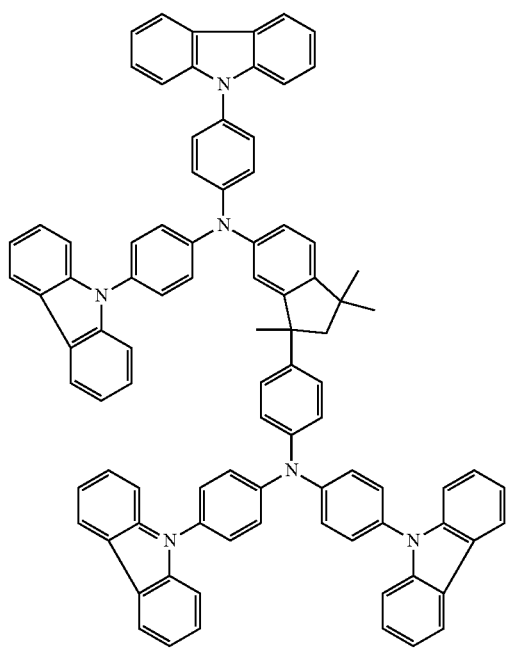
19
20
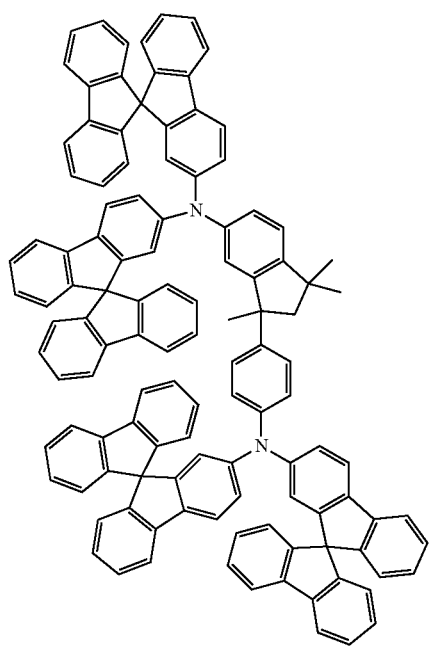

21
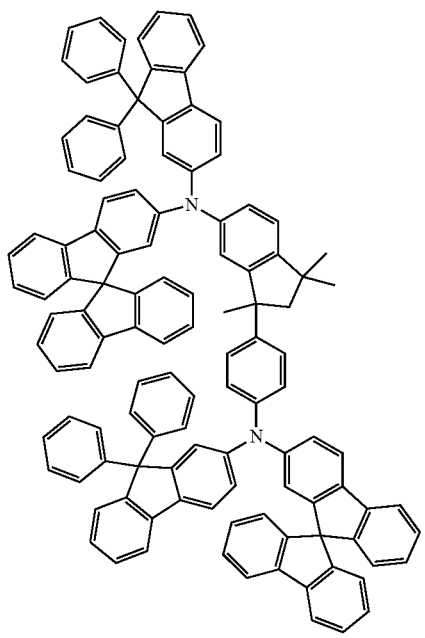
22
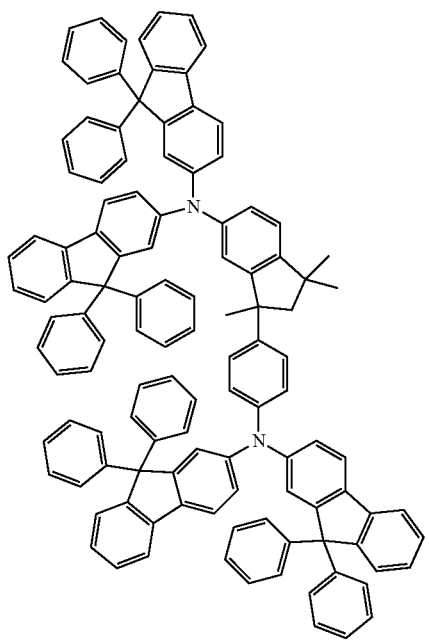
23
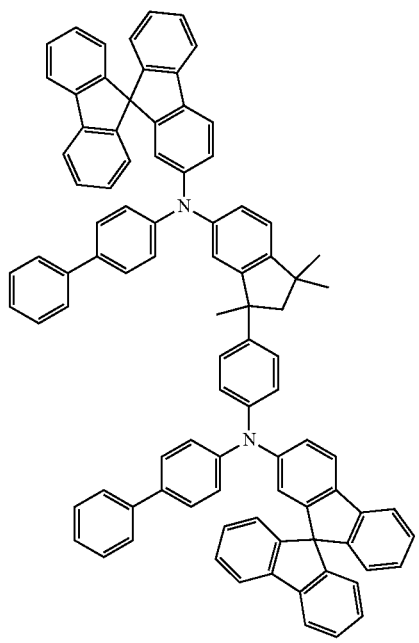
24
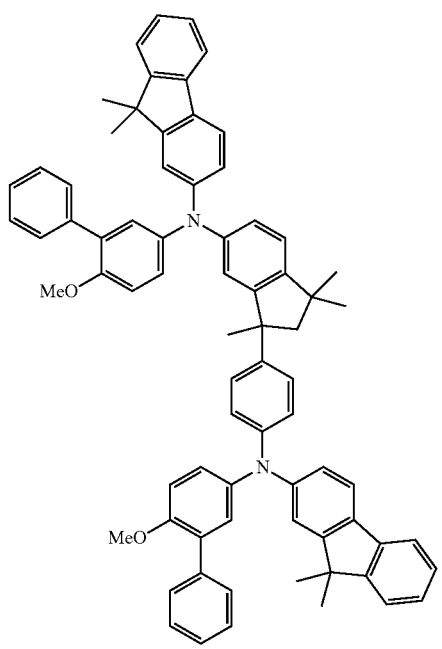

77
-continued
5
25
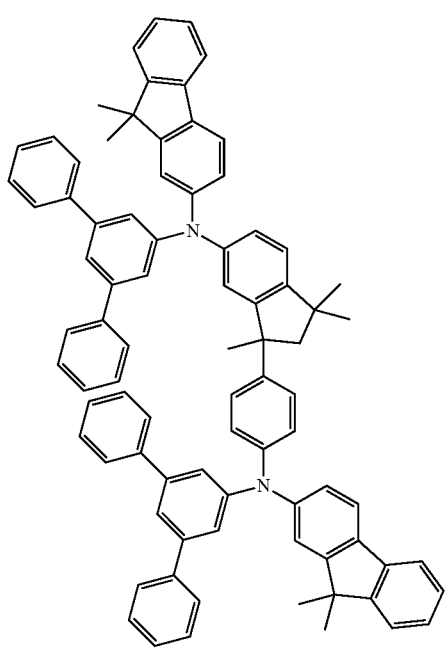
10
15
20
25
30
35
78
-continued
27
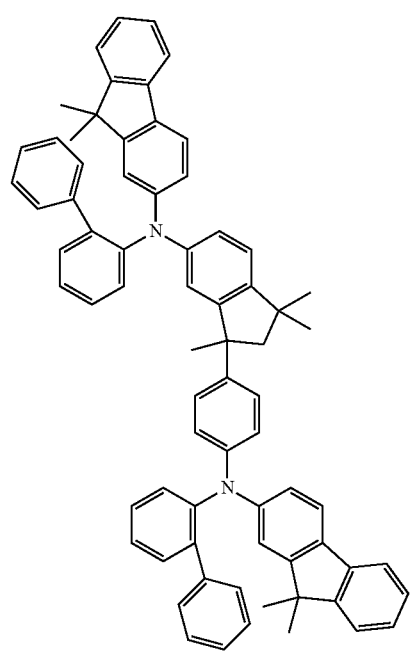
40
26
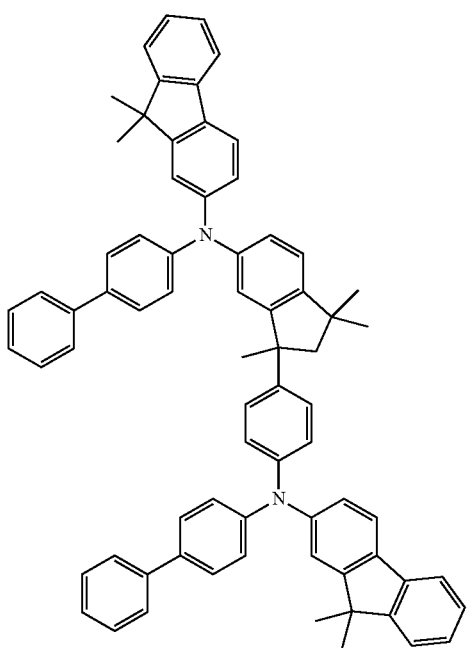
45
50
55
60
65
28
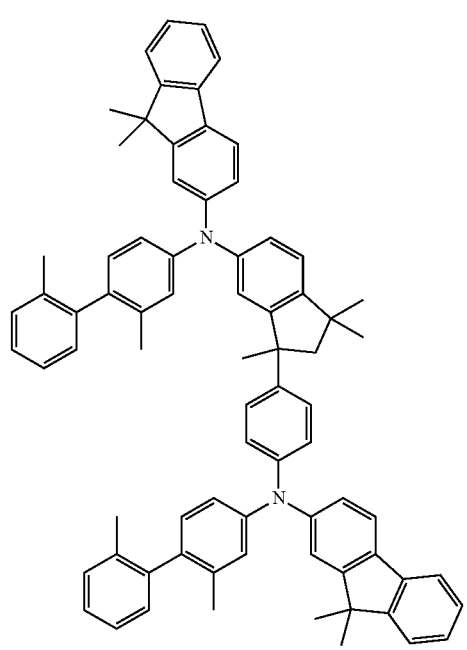

29
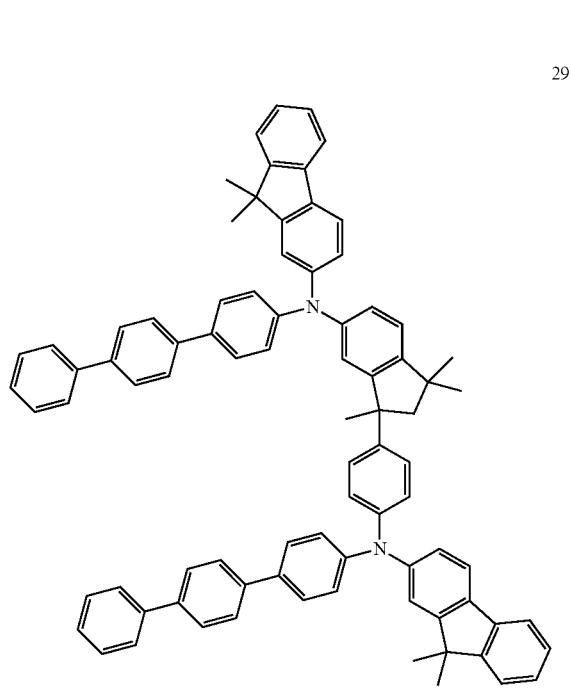
30
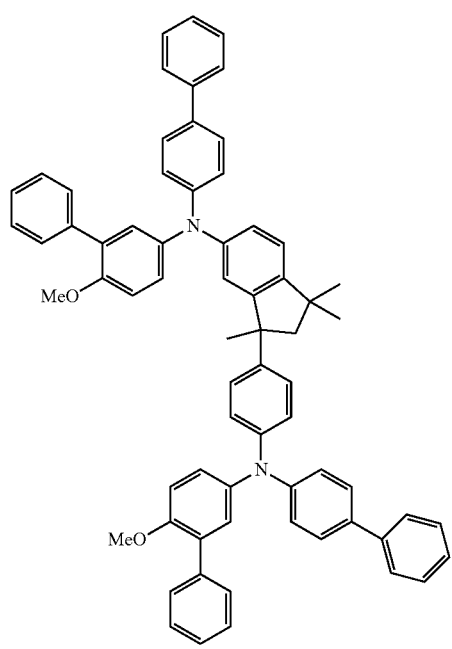
31
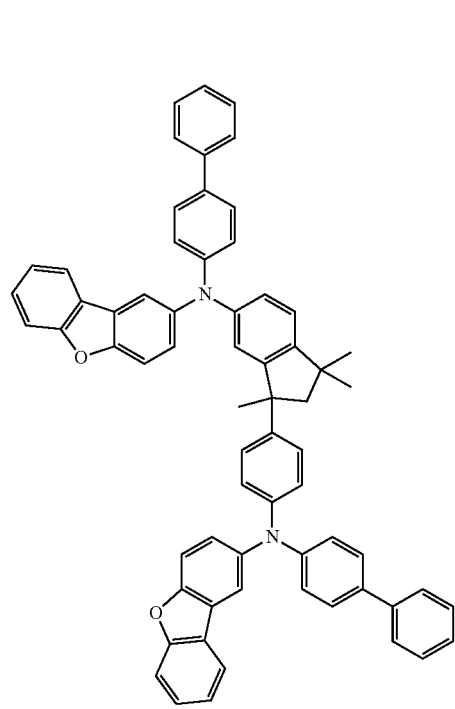
32
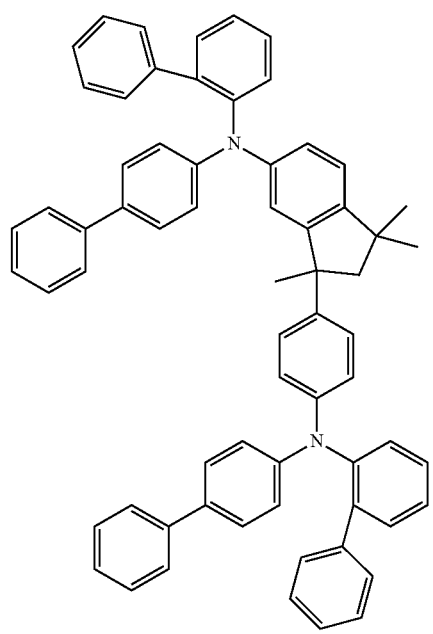

33
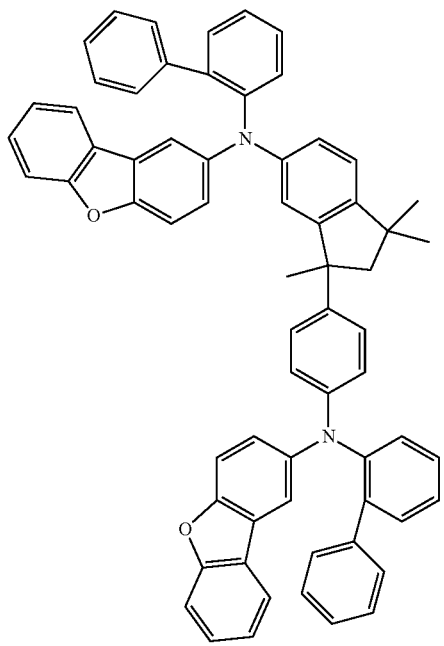
34
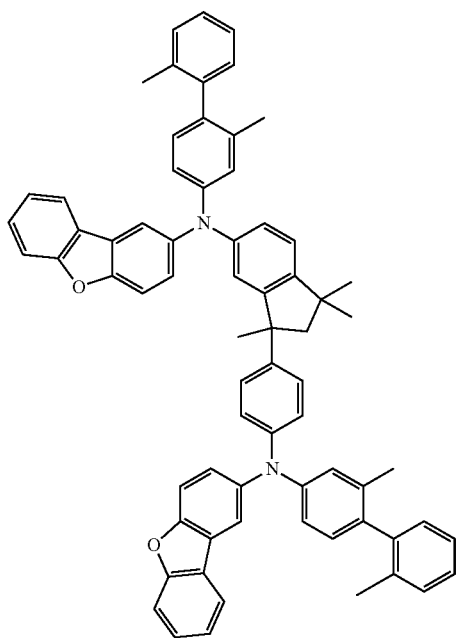
35
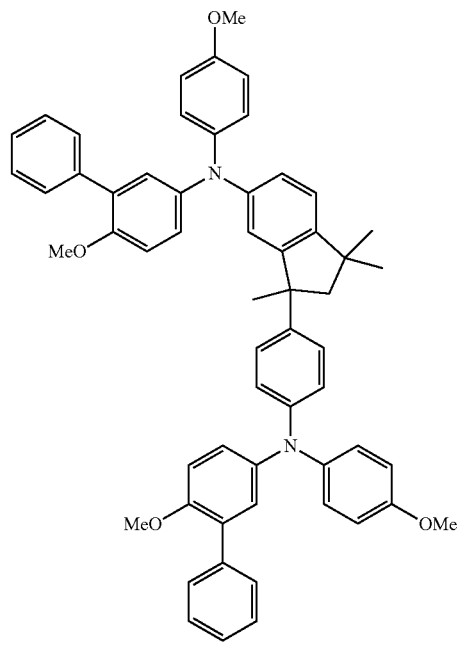
36
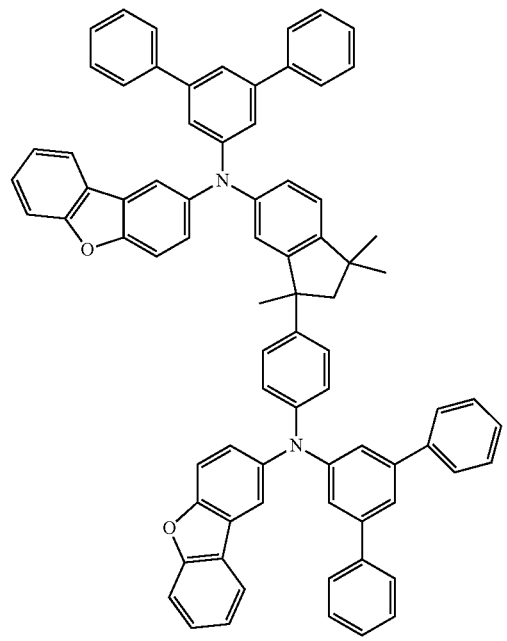

83
-continued
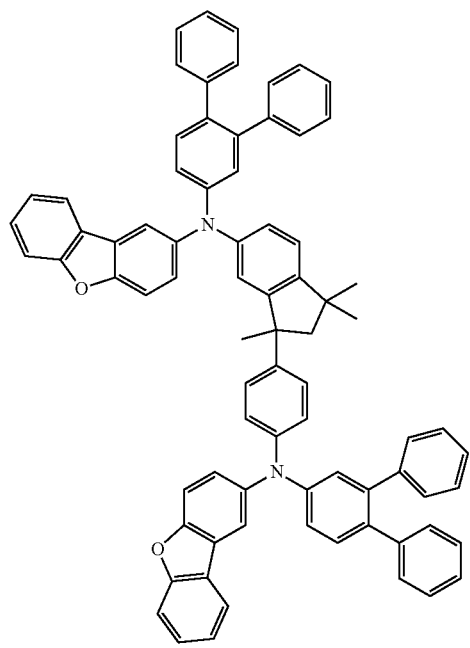
37
84
-continued
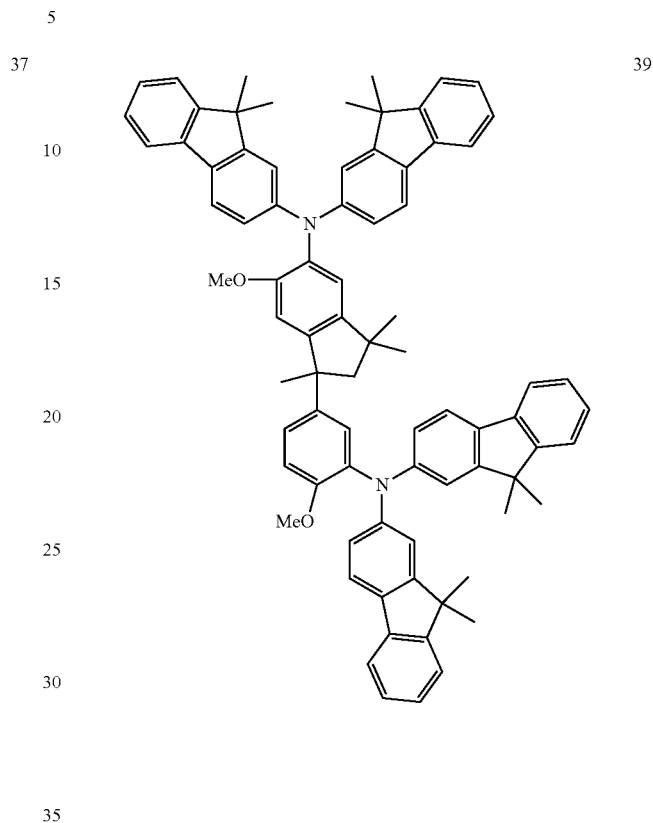
39
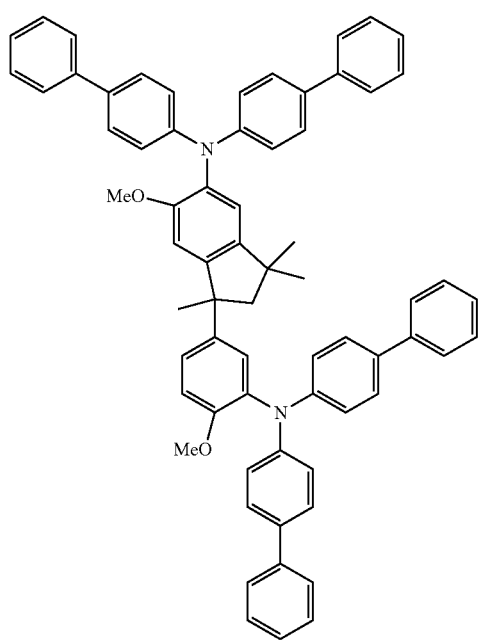
38
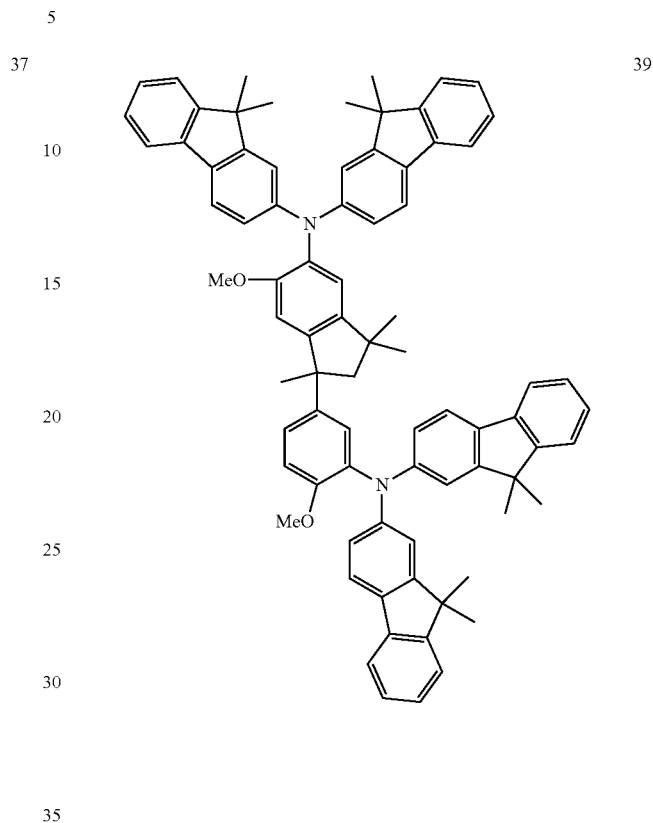
40

85
-continued
86
-continued
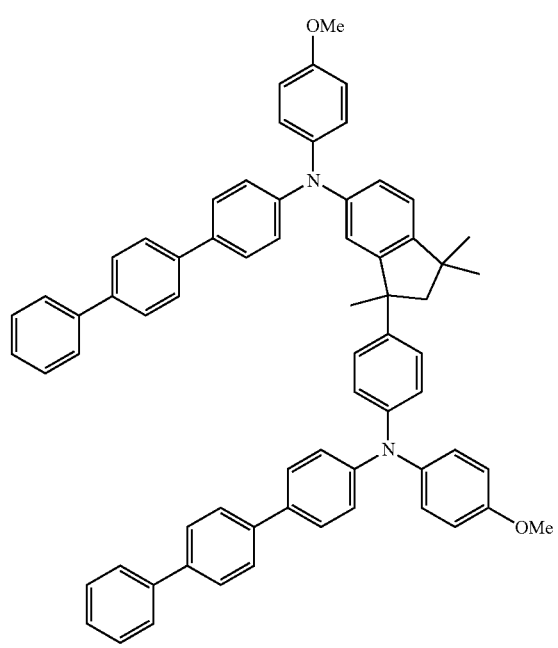
41
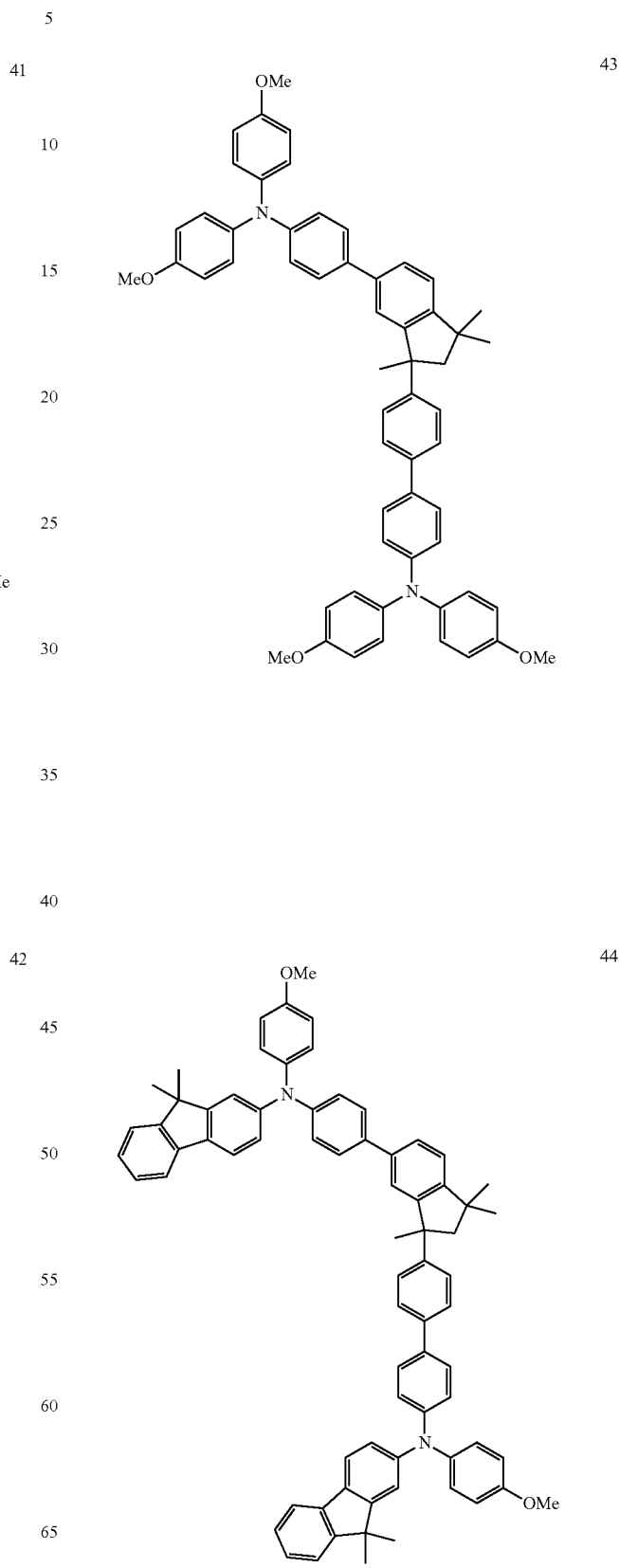
43
42
44

87
-continued
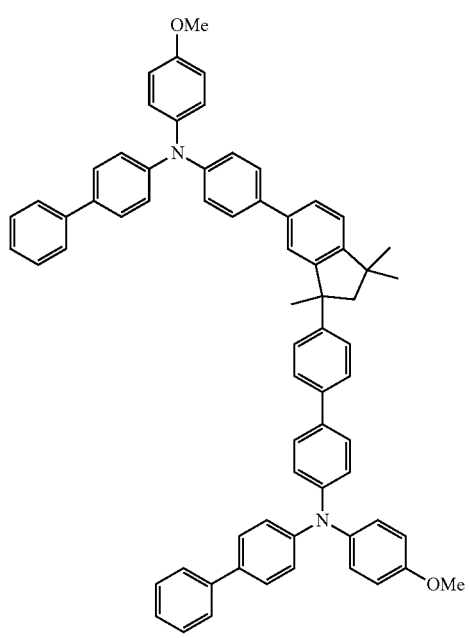
45
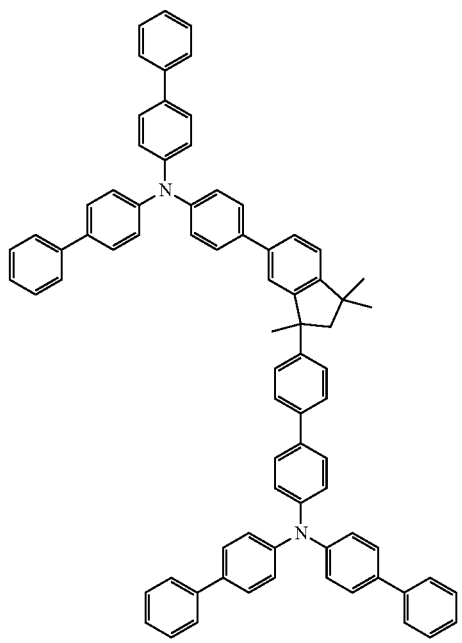
47
46
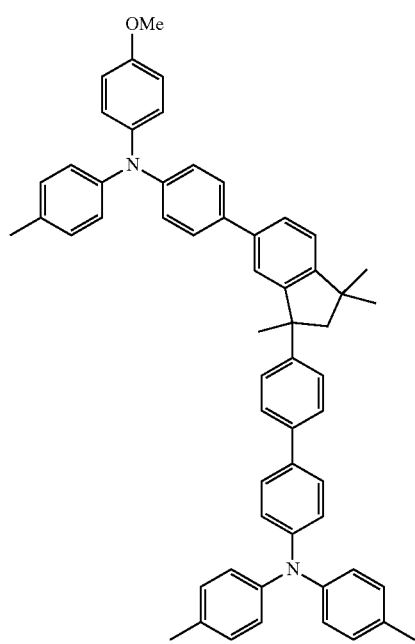
88
-continued
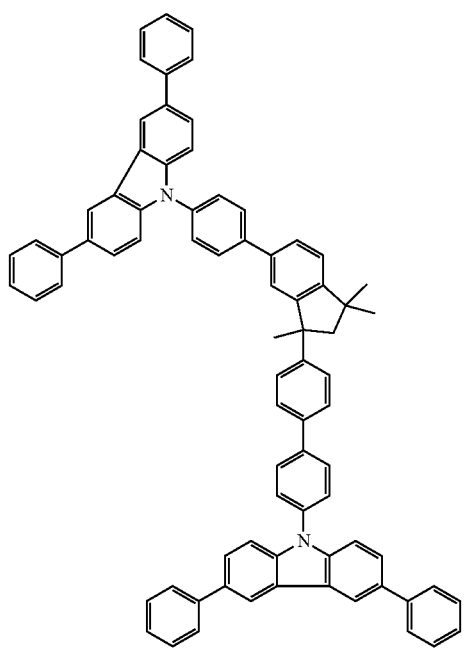
48

89
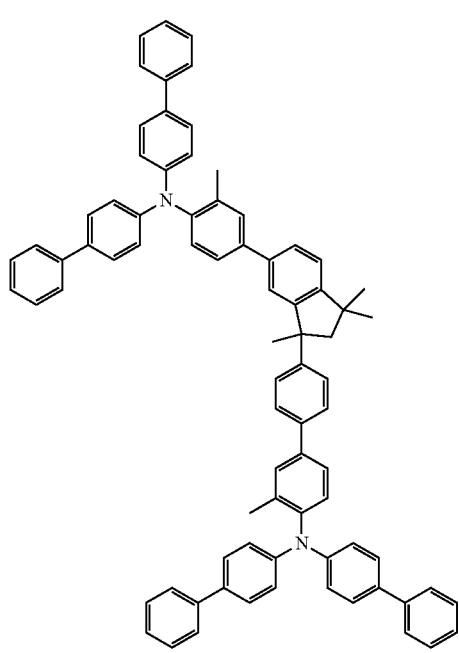
49
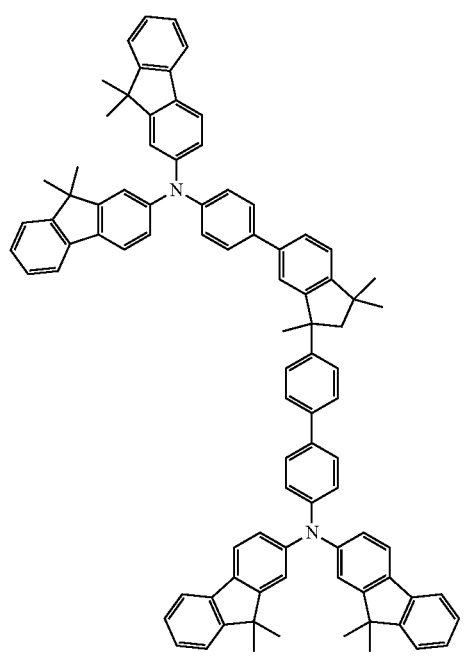
50
90
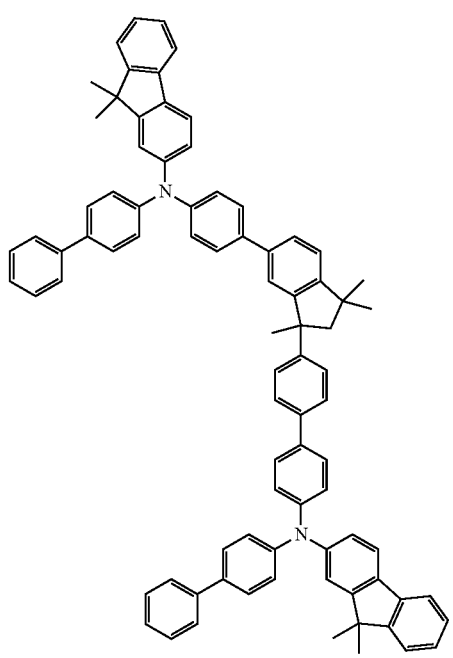
51
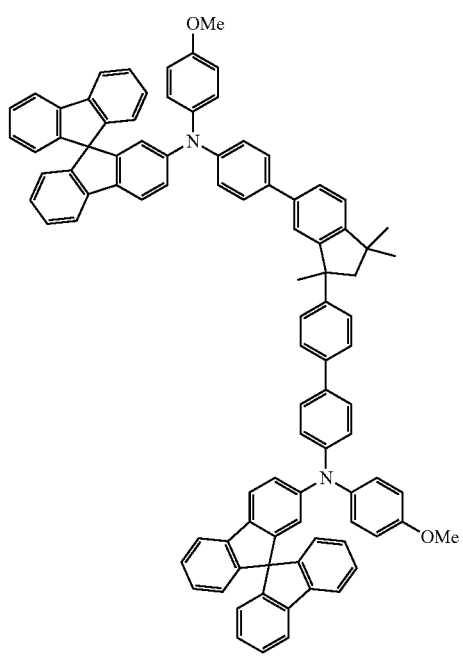
52

91
-continued
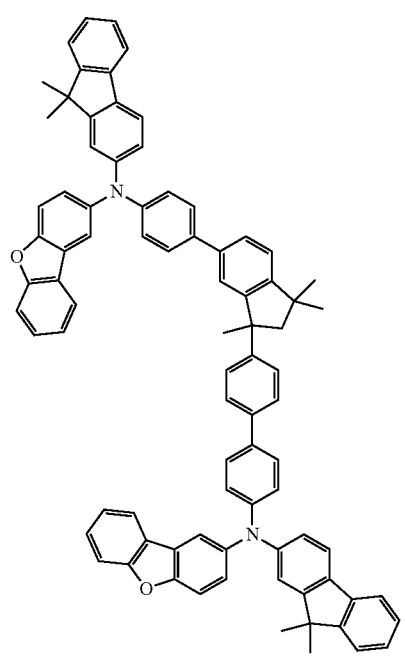
92
-continued
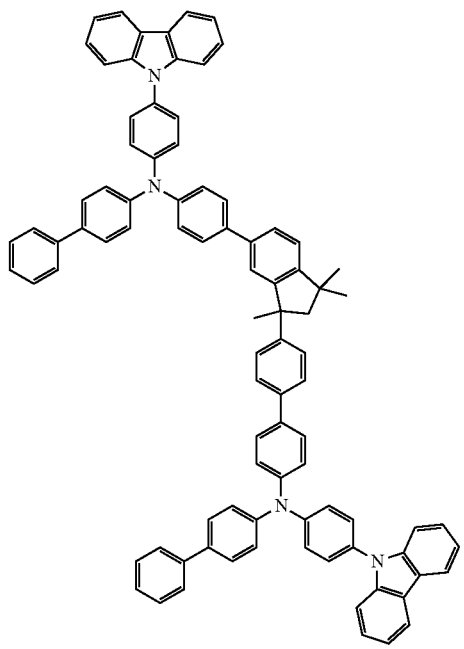
54
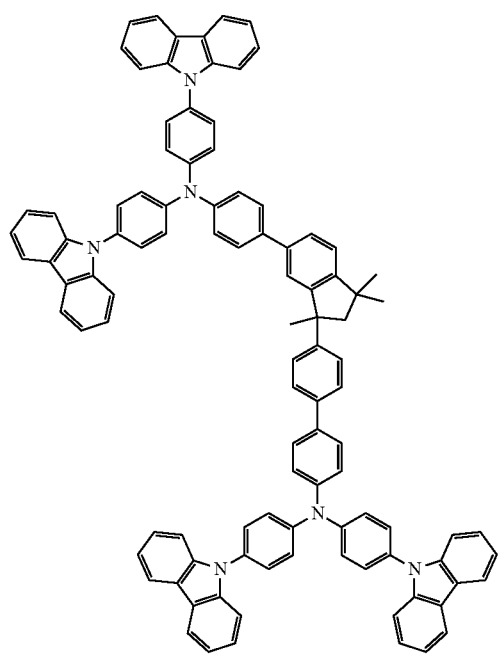
56
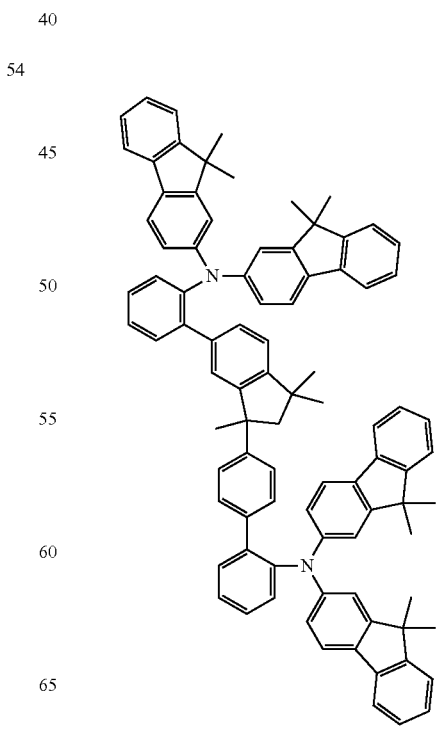

93
-continued
57
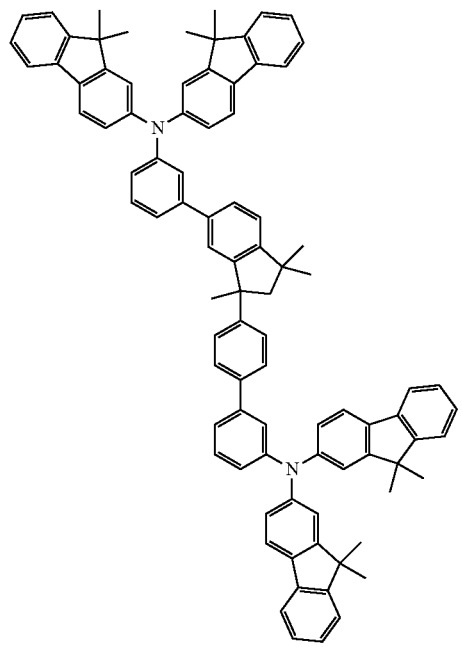
58
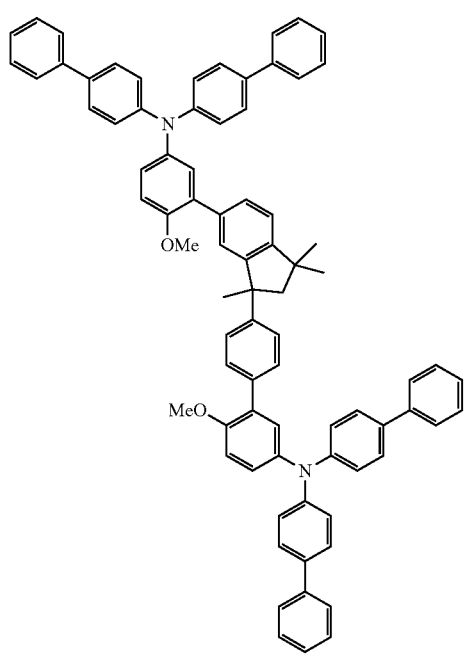
94
-continued
59
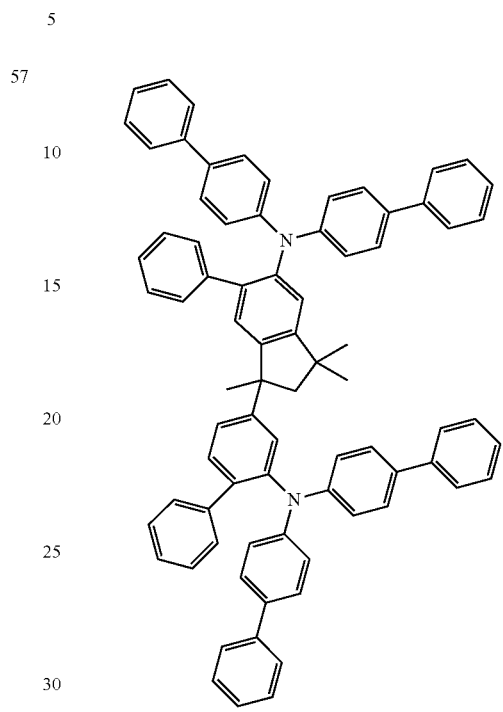
60

61
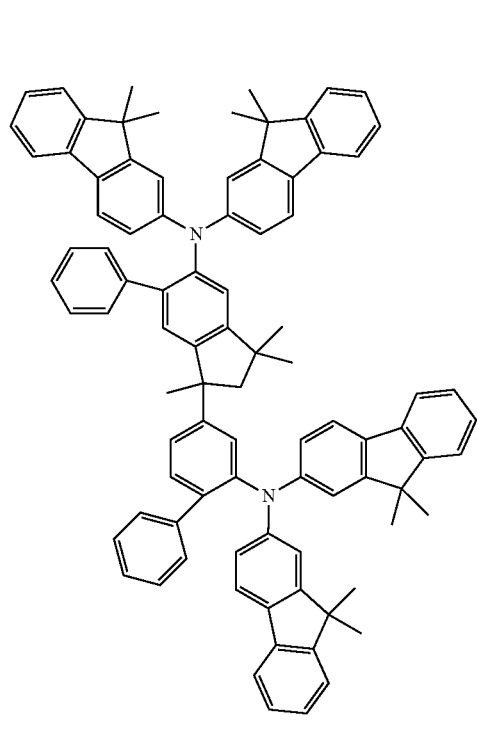
63
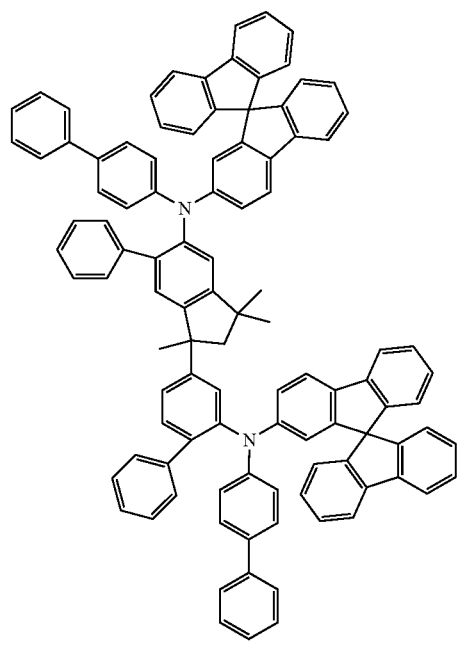
62
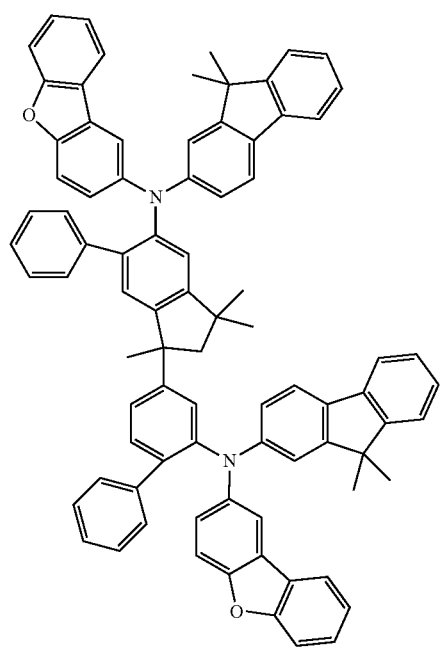
64
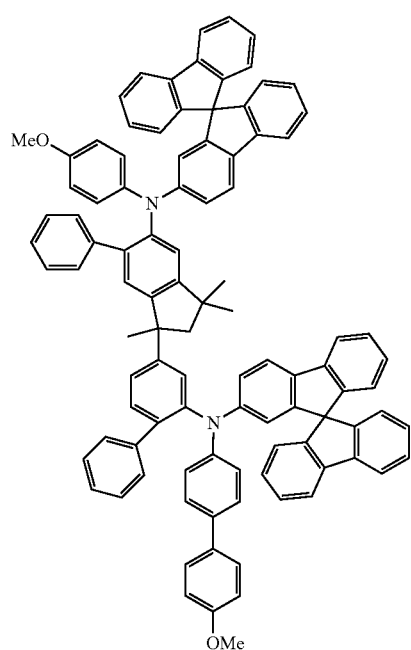

97
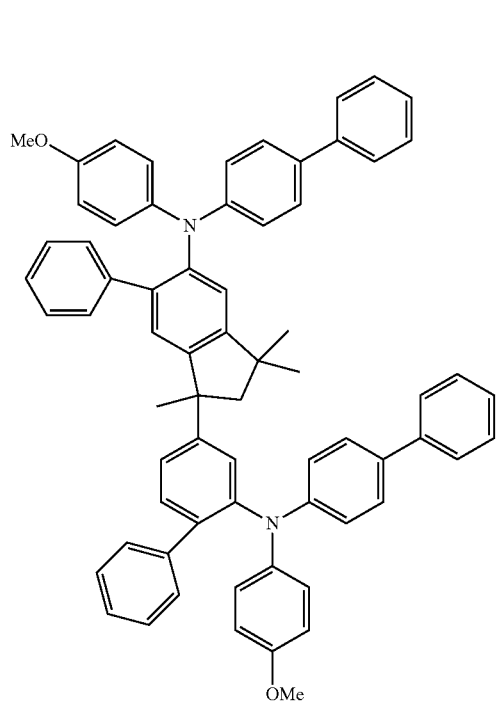
66
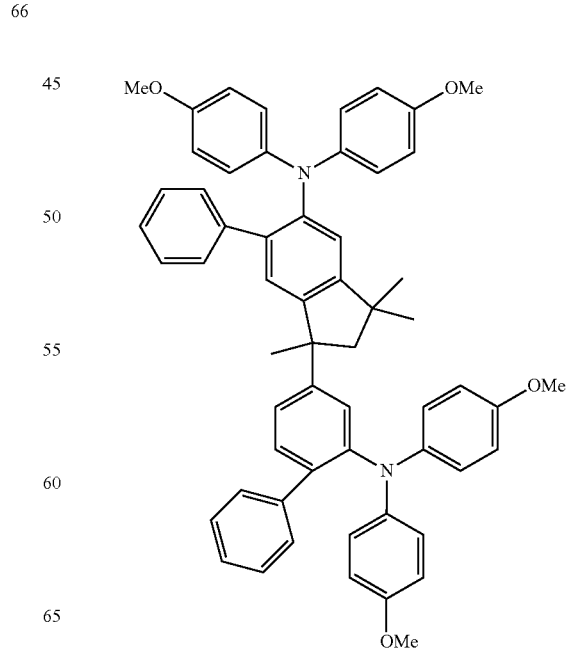
98
67
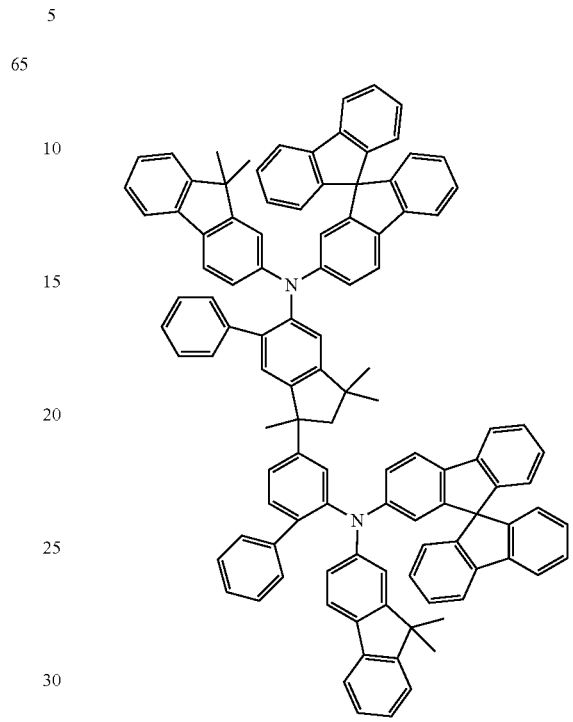
68

99
-continued
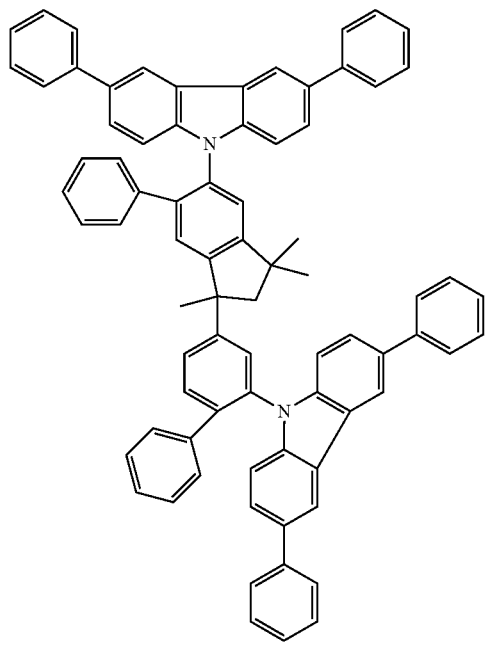
69
100
-continued
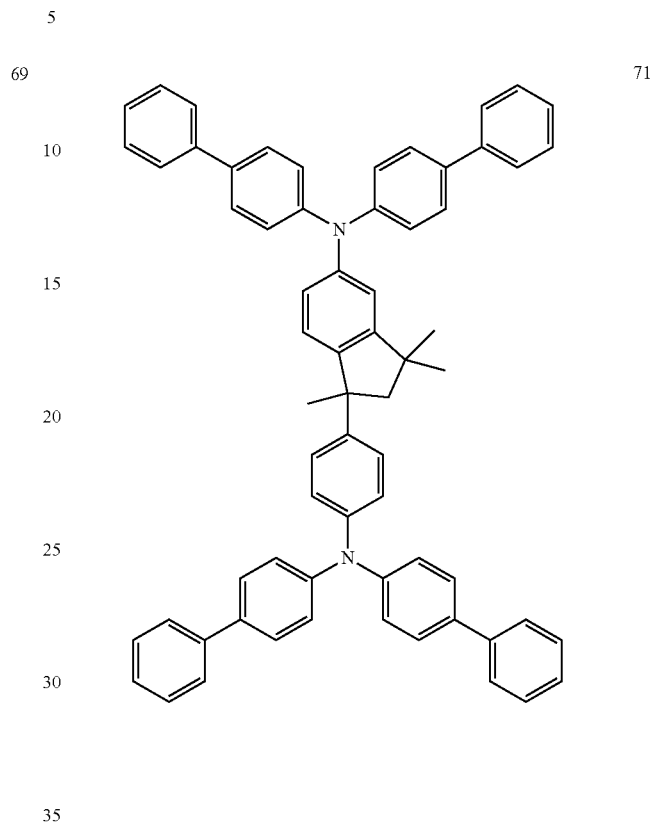
71
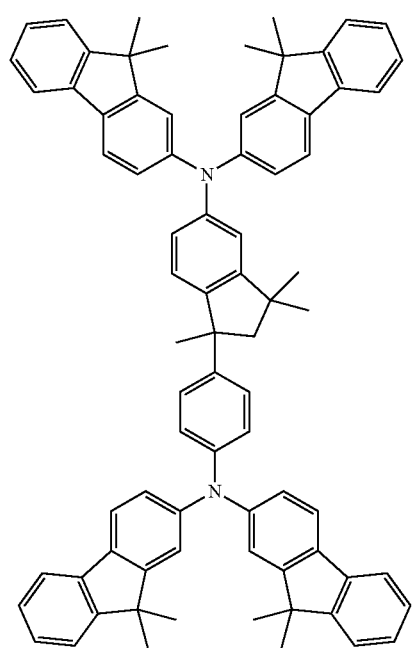
70
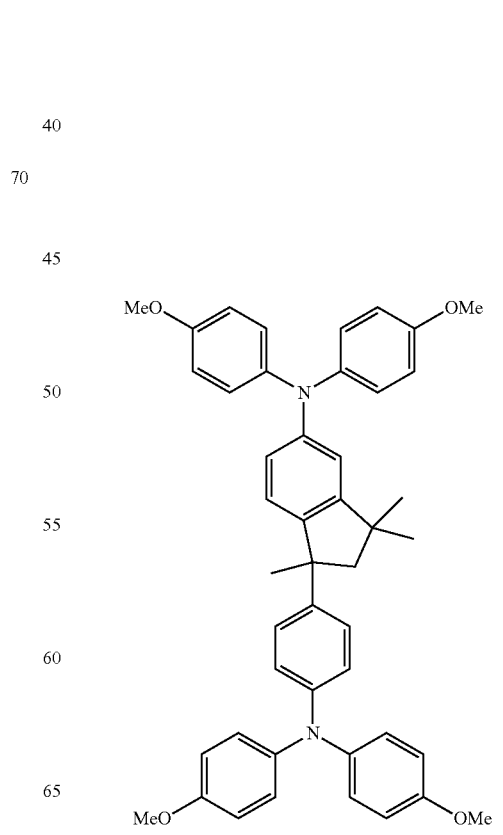
72

101
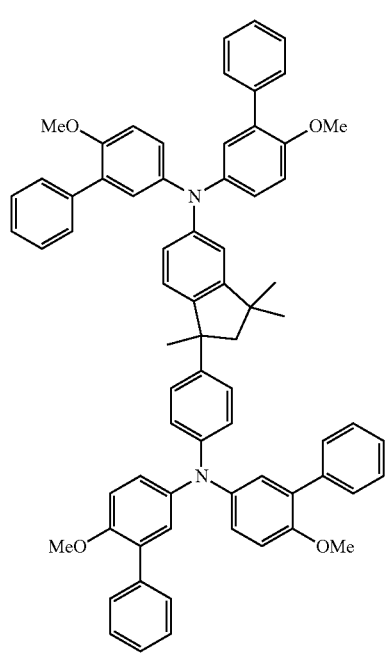
73
74
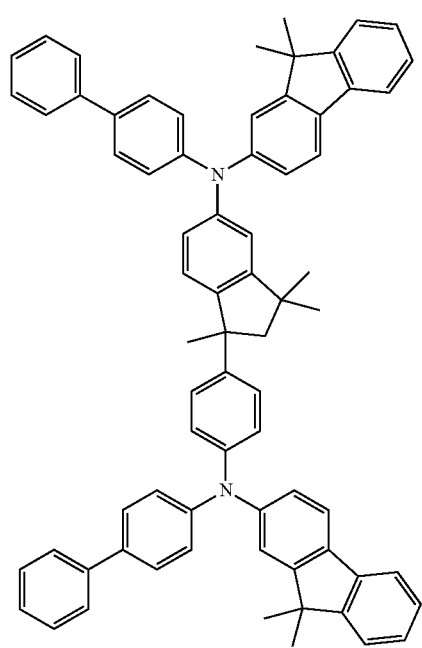
102
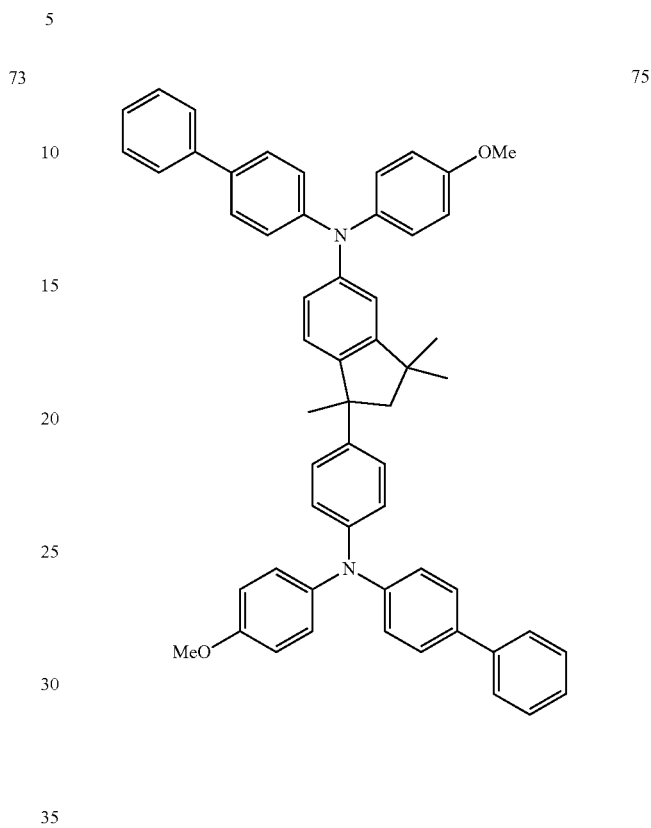
75
76
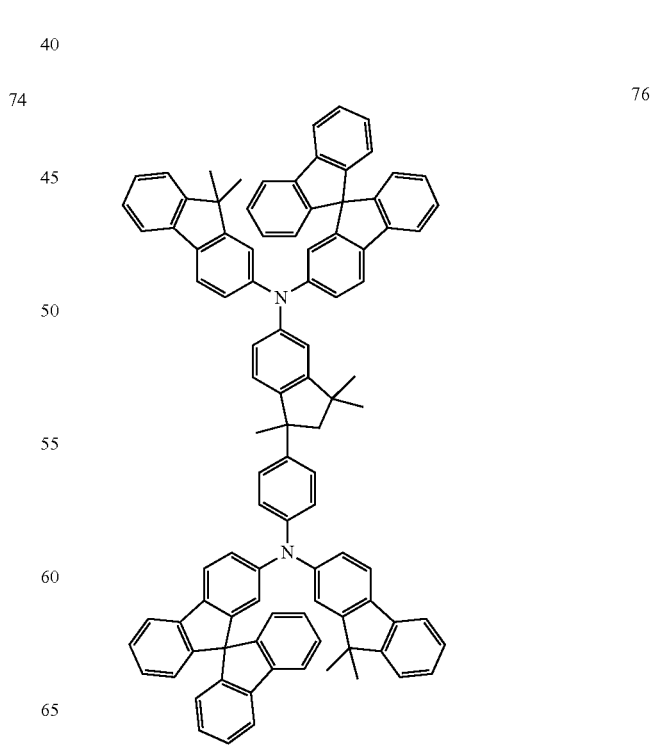

77
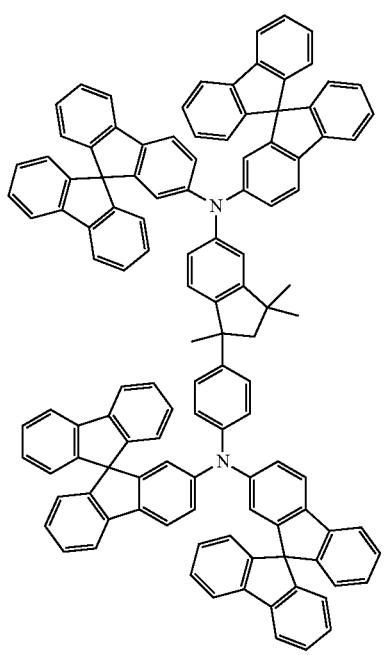
78
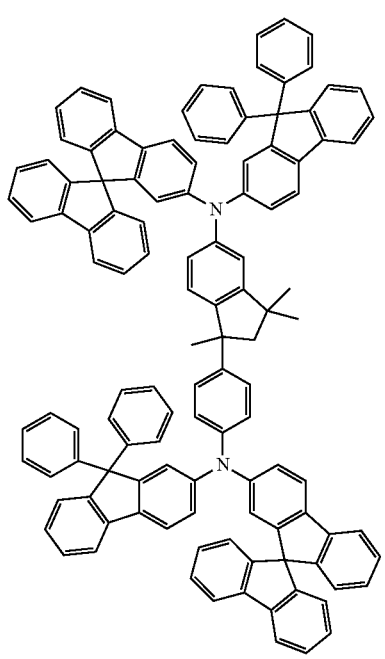
79
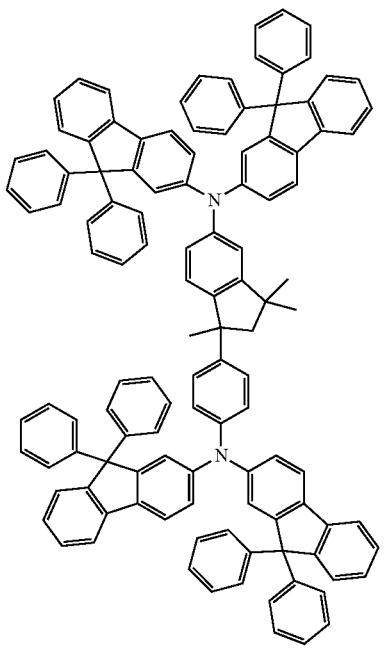
80
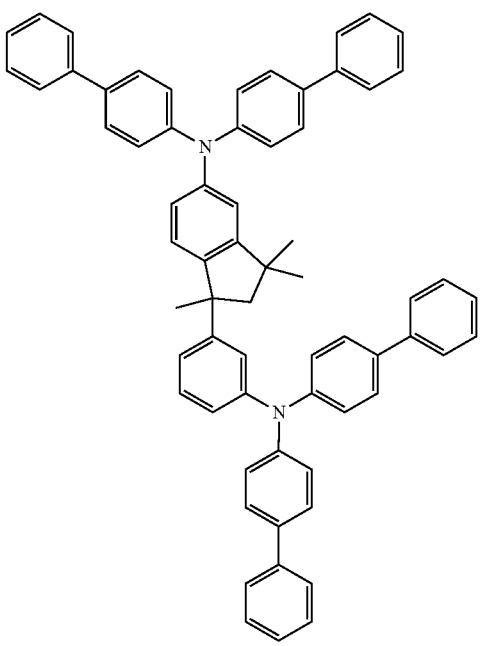

105
-continued
81
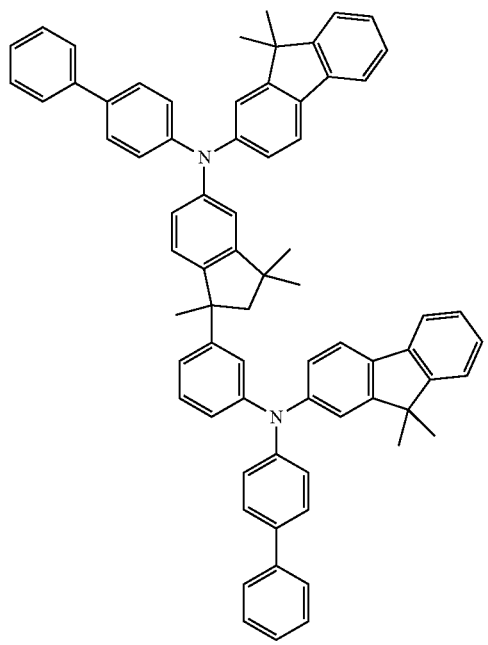
82
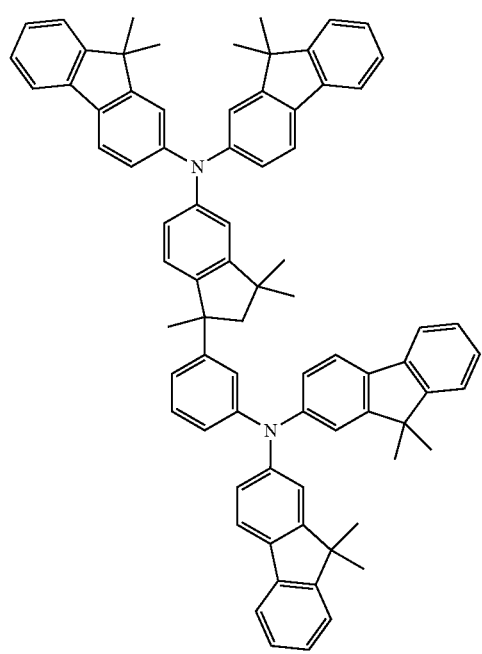
106
-continued
83
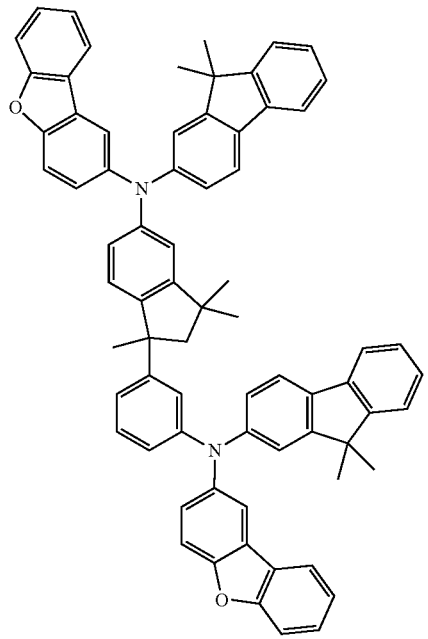
84
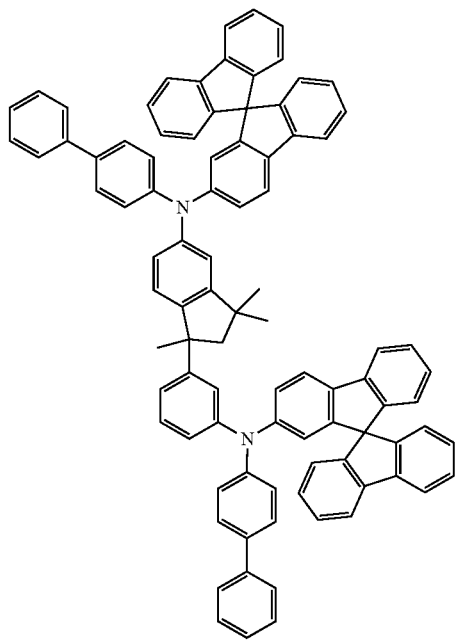

85
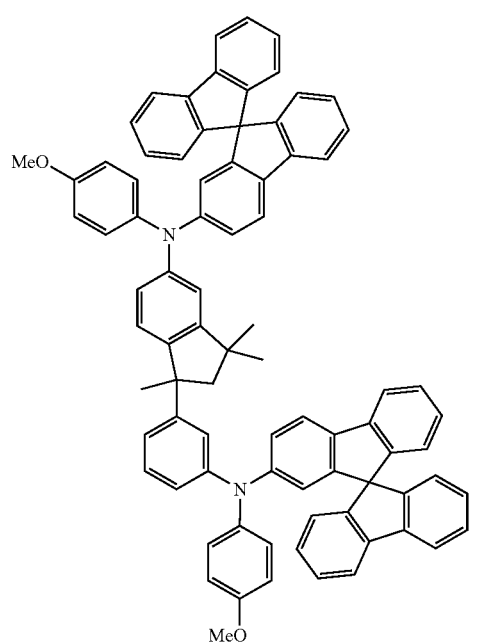
86
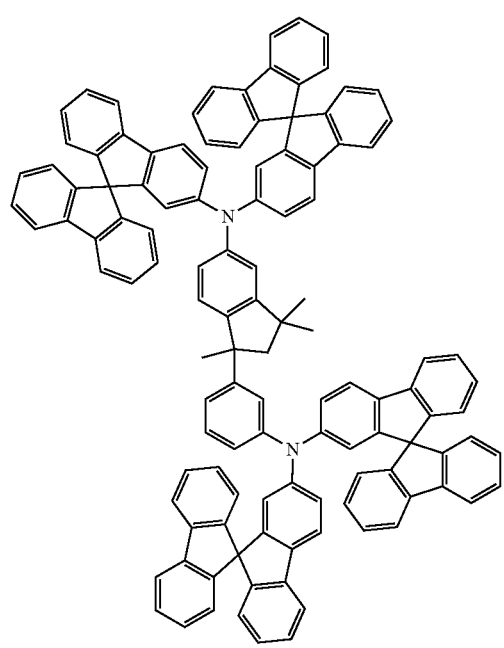
87
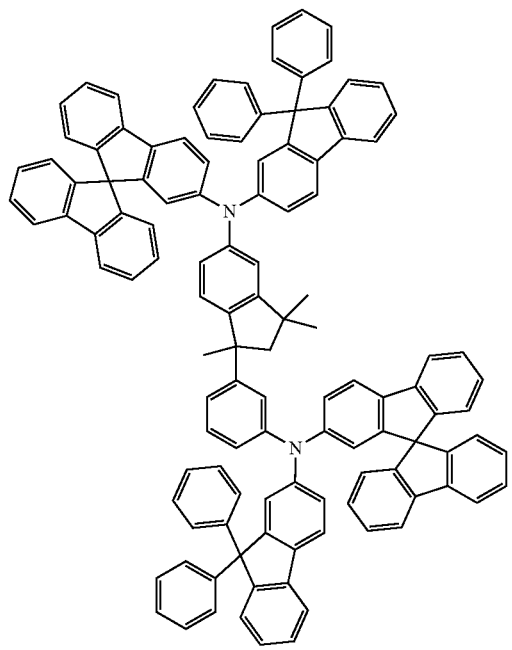
88
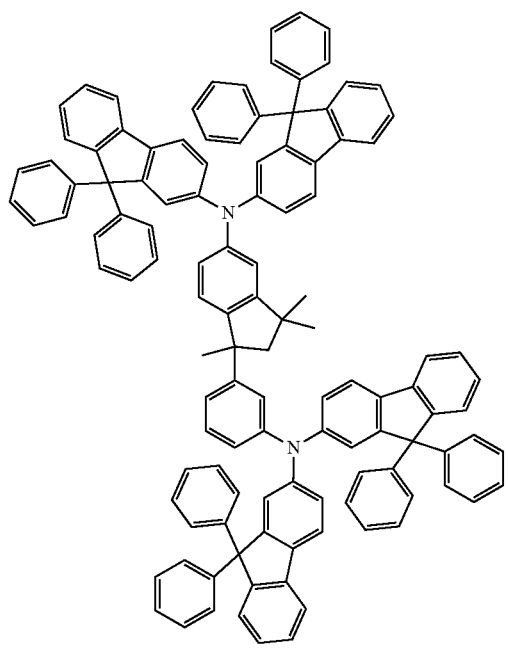

109
-continued
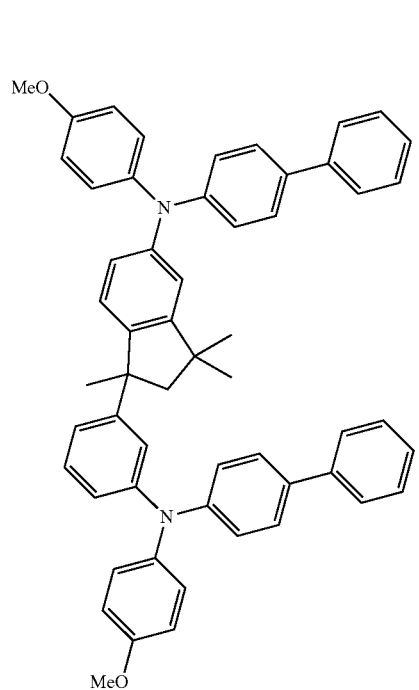
90
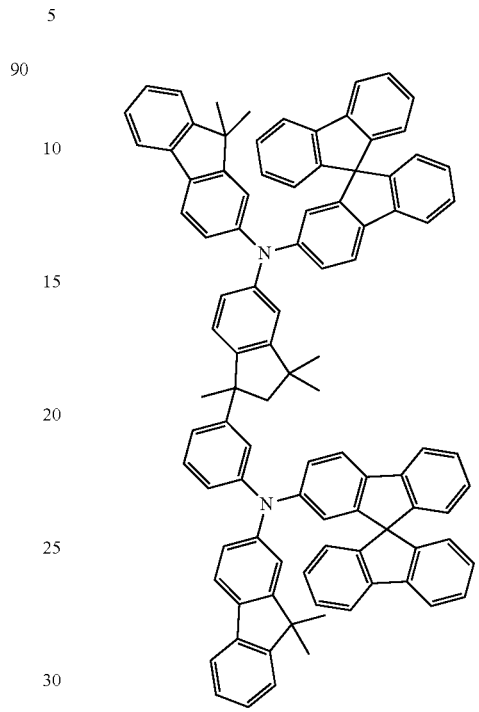
92
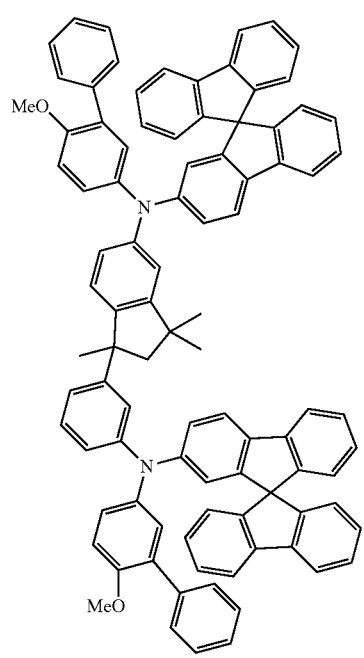
91
110
-continued
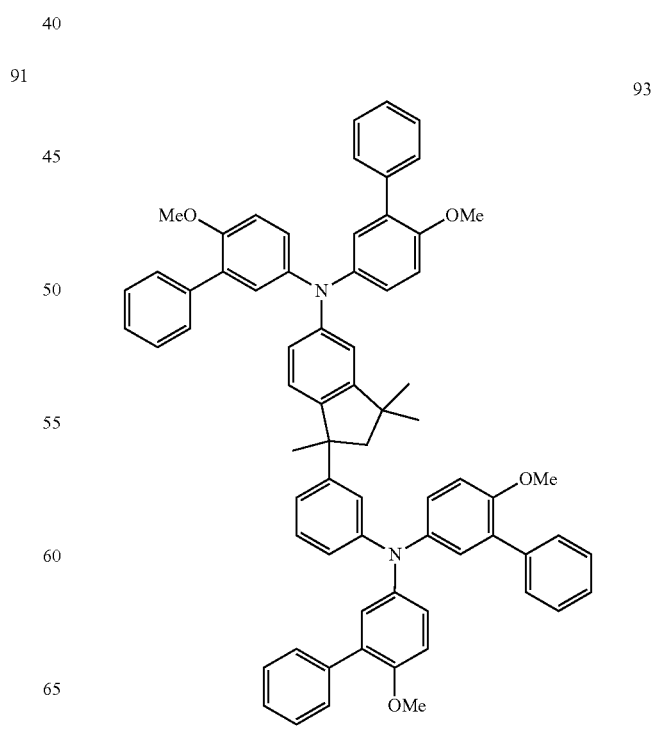
93

111
-continued
112
-continued
94
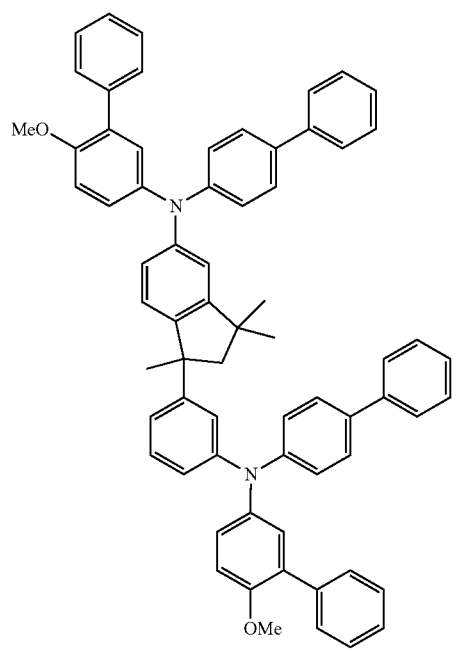
96
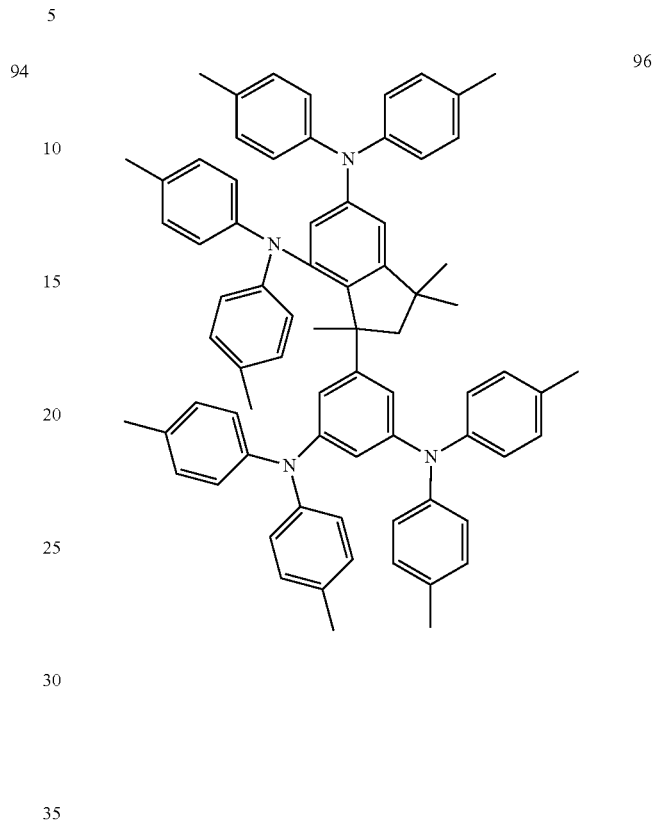
95
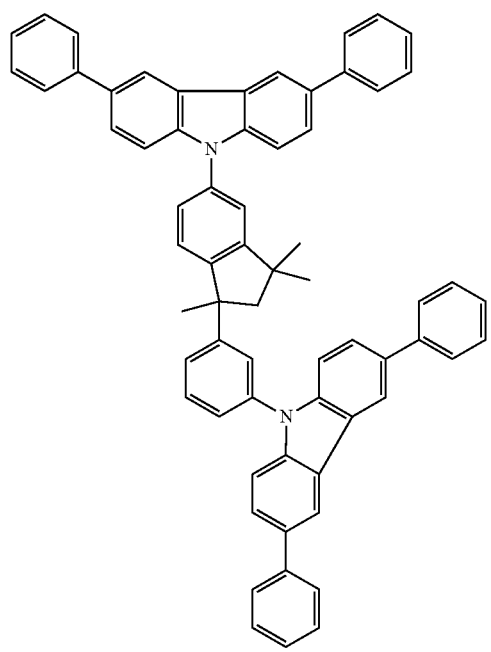
97
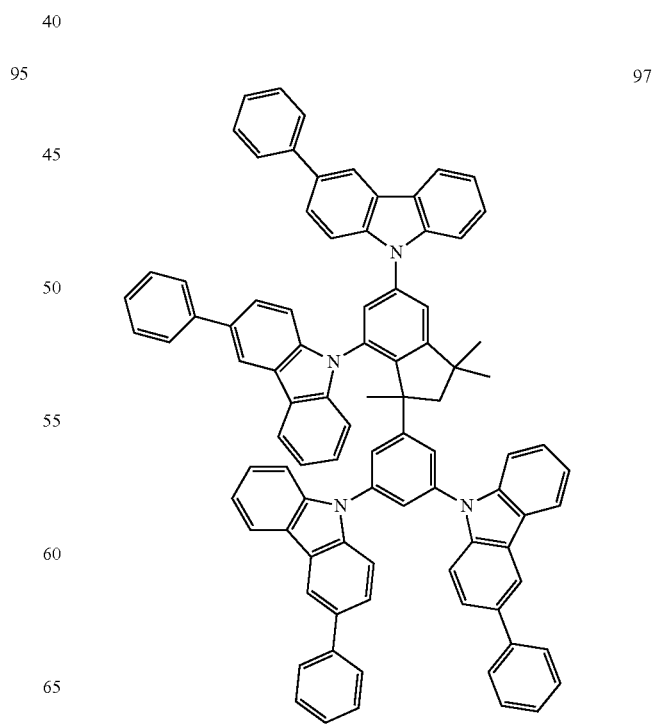

113
-continued
98
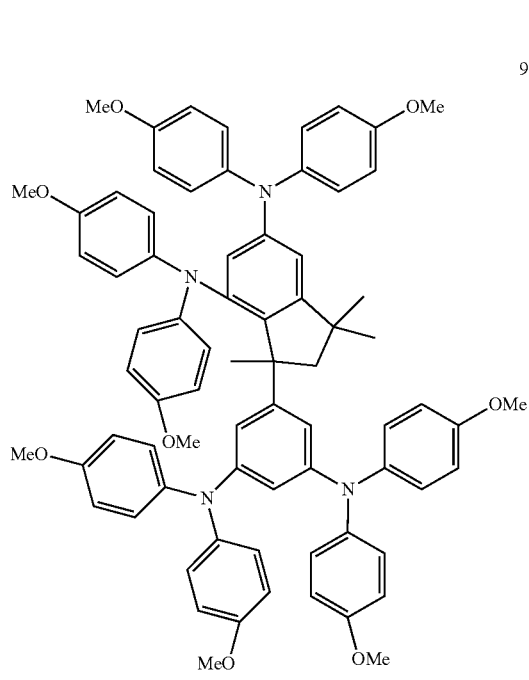
99
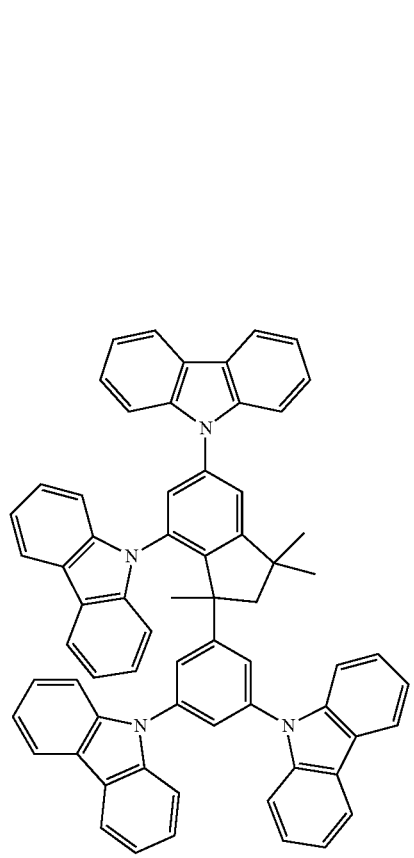
114
-continued
100
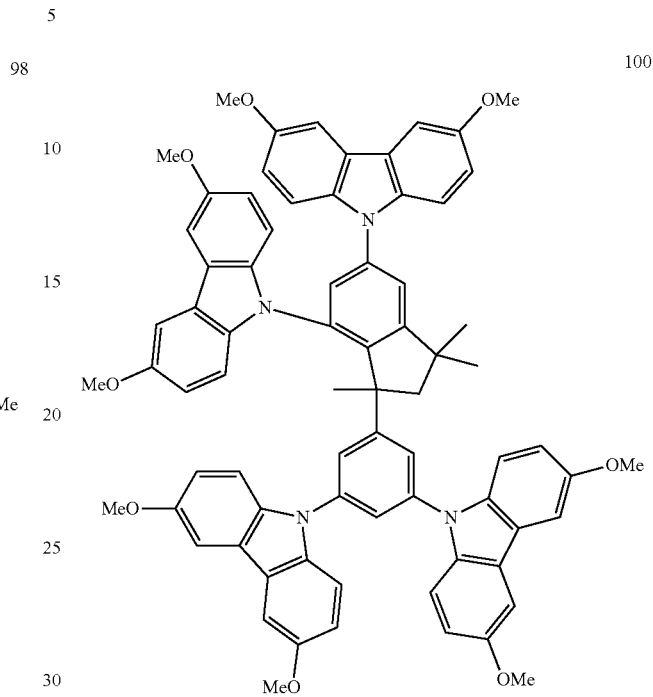
101
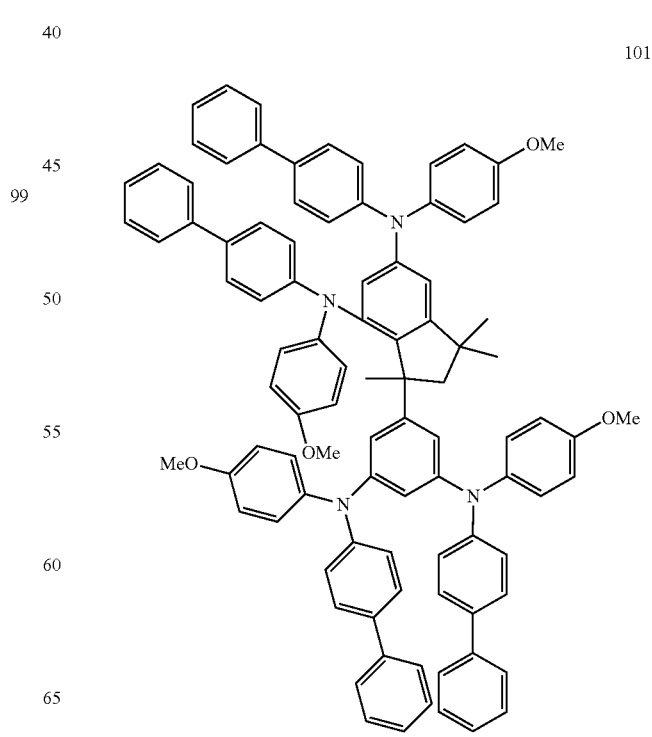

115
-continued
102
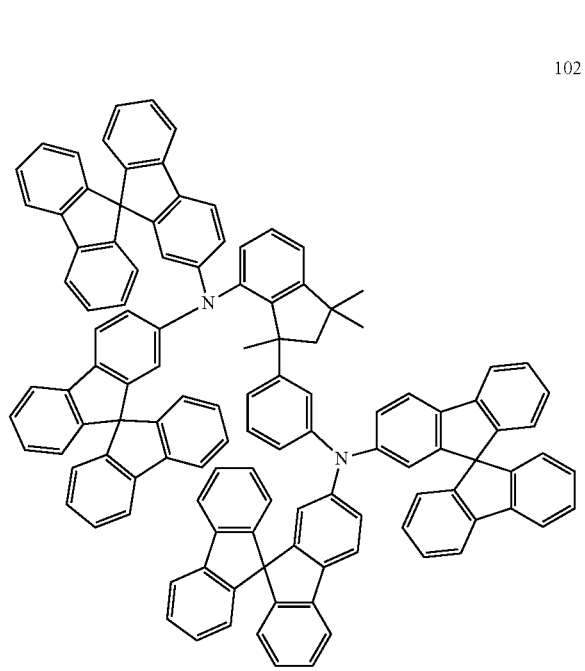
103
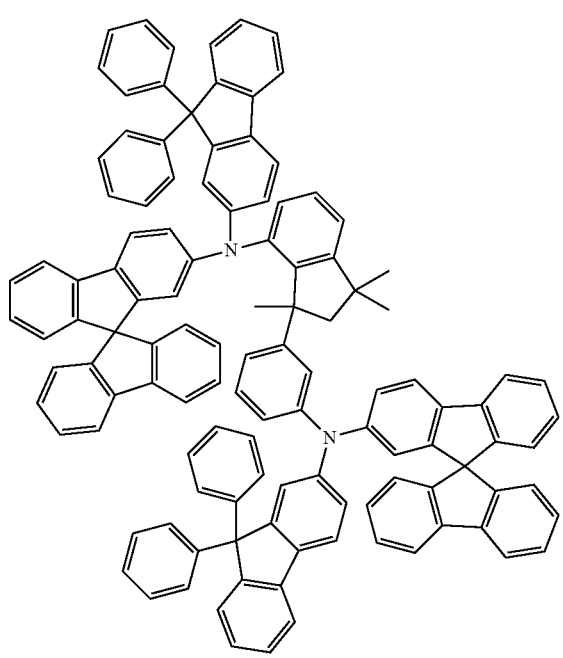
116
-continued
104
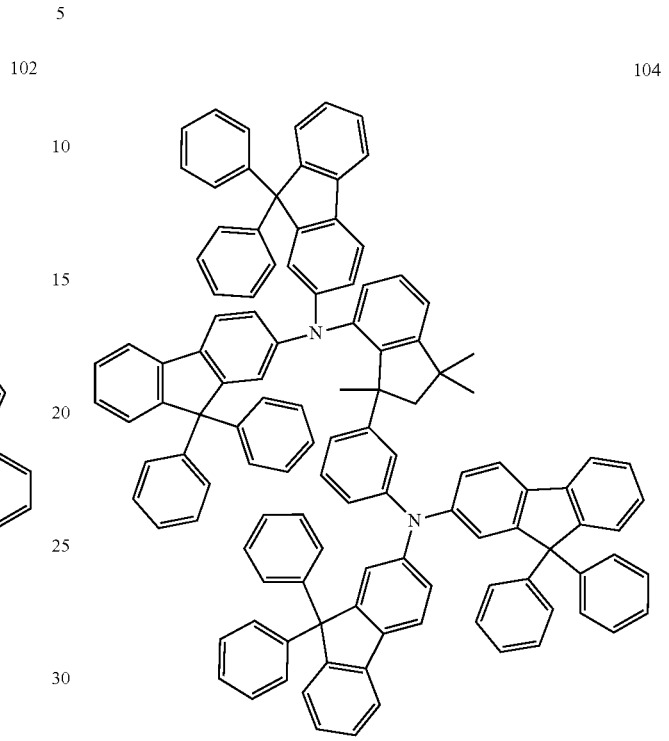
105
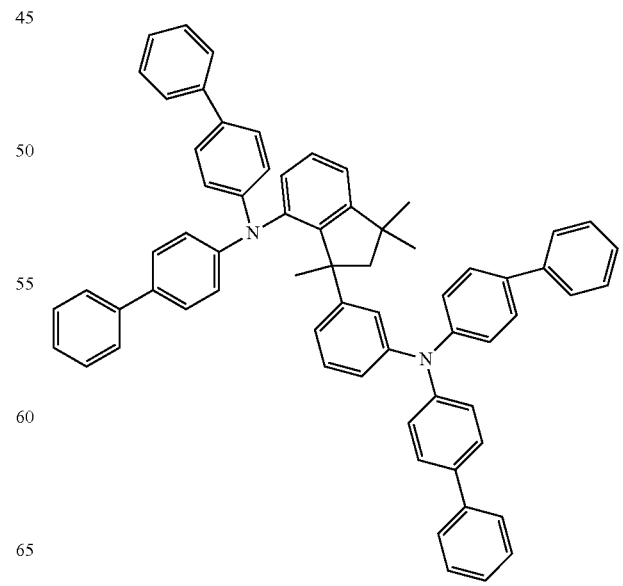

-continued

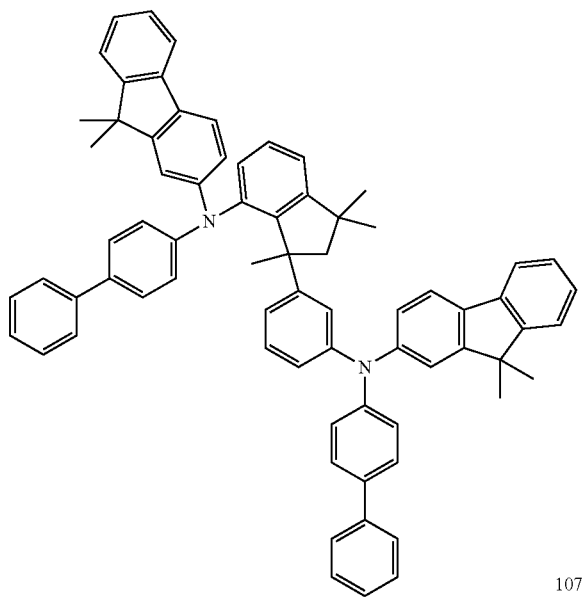
106

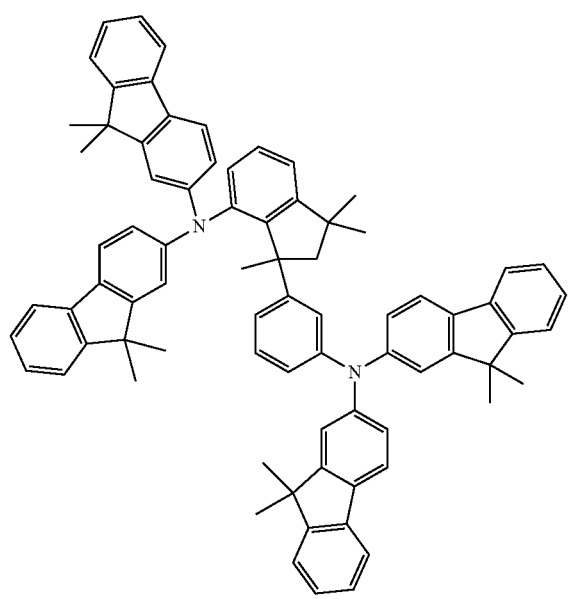
107

OMe means OCH₃.

Likewise, particular preference is given to a mixture (composition) of compounds of the formula (I), comprising the compounds of formulae (I.A.a) and (I.B.a)

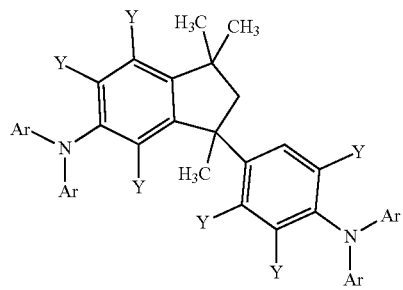
(I.A.a)

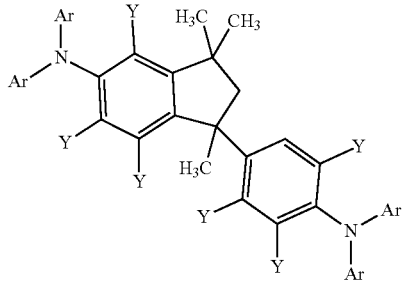
(I.B.a)

wherein
each Y is independently defined as above; and
each Ar is independently defined as above;
m is 3, wherein 0, 1, 2 or 3 of the m Y groups are different from hydrogen; and
n is 4, wherein 0, 1, 2 or 3 of the n Y groups are different from hydrogen.

In particular, the group NAr₂ attached to the phenylindane moiety of the compound of formula (I.A.a) has the same meaning as the group NAr₂ attached to the phenylindane moiety of the compound of formula (I.B.a) and the group NAr₂ attached to the phenyl ring in the compound of formula (I.A.a.) has the same meaning as that in the compound of formula (I.B.a).

Thus, a further aspect of the present invention relates to a mixture of compounds of the formula (I), comprising the compounds of formulae (I.A.a) and (I.B.a), wherein Y and Ar are as defined herein. Especially, each Y and each Ar has one of the meanings mentioned as preferred. In particular, the composition comprises the compounds of formulae (I.A.a.1) and (I.B.a.1).

Examples of preferred compositions of compounds of formulae (I.A.a.1) and (I.B.a.1) are compiled in table 25 below.

Table 25
Mixture of compounds of the formulae (I.A.a.1) and (I.B.a.1), wherein the group NAr₂ attached to the phenylindane moiety of the compound of formula (I.A.a.1) has the same meaning as the group NAr₂ attached to the phenylindane moiety of the compound of formula (I.B.a.1) and the group NAr₂ attached to the phenyl ring of the compound of formula (I.A.a.1) has the same meaning as the group NAr₂ attached to the ring of the compound of formula (I.B.a.1) and the groups NAr₂ in each case corresponds to one line of Table B.

Likewise preference is given to a mixture of compounds of the formula (I), comprising the compounds of formulae (I.C.a) and (I.D.a)

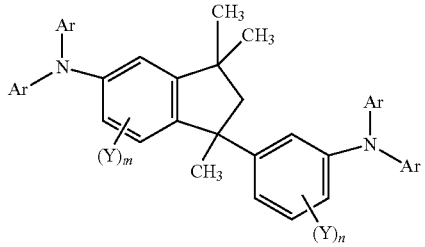
(I.C.a)

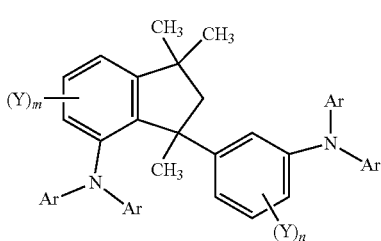

(I.D.a)

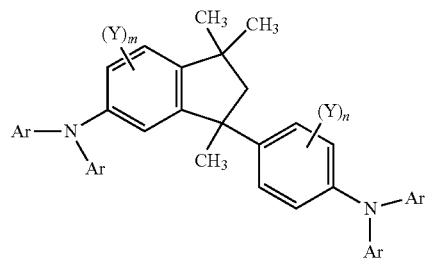

(I.A.a)

wherein
each Y is independently defined as above; and
each Ar is independently defined as above;
m is 3, wherein 0, 1, 2 or 3 of the m Y groups are different from hydrogen; and
n is 4, wherein 0, 1, 2 or 3 of the n Y groups are different from hydrogen.

In particular, the group $NAr_2$ attached to the phenylindane moiety of the compound of formula (I.C.a.) has the same meaning as the group $NAr_2$ attached to the phenylindane moiety of the compound of formula (I.D.a.) and the group $NAr_2$ attached to the phenyl ring in the compound of formula (I.C.a.) has the same meaning as that in the compound of formula (I.D.a).

Thus, a further aspect of the present invention relates to a mixture of compounds of the formula (I), comprising the compounds of formulae (I.C.a) and (I.D.a), wherein Y and Ar are as defined herein. Especially, each Y and each Ar has one of the meanings mentioned as preferred. In particular, the mixture comprises the compounds of formulae (I.C.a.1) and (I.D.a.1).

Examples of preferred mixtures of compounds of formulae (I.C.a.1) and (I.C.a.1) are compiled in table 26 below.

Table 26
Mixture of compounds of the formulae (I.C.a.1) and (I.D.a.1), wherein the group $NAr_2$ attached to the phenylindane moiety of the compound of formula (I.C.a.1) has the same meaning as the group $NAr_2$ attached to the phenylindane moiety of the compound of formula (I.D.a.1) and the group $NAr_2$ attached to the phenyl ring of the compound of formula (I.C.a.1) has the same meaning as the group $NAr_2$ attached to the ring of the compound of formula (I.D.a.1) and the groups $NAr_2$ in each case corresponds to one line of Table B.

In a specific embodiment, the compounds of the formula (I) are selected from the compounds specified in the examples, either in form of the pure enantiomer or the mixtures of both enantiomers.

The compounds of the invention of the formula (I) and the starting materials used to prepare them can be prepared in analogy to known processes of organic chemistry as are described in standard works of organic chemistry. The compounds of the formula (I) may be prepared by various routes.

The compounds of formula (I) can advantageously be prepared by the methods described below or and in the synthesis descriptions of the working examples, or by standard methods of organic chemistry. The substituents, variables and indices are as defined above for formula (I), if not otherwise specified.

Thus, a further aspect of the present invention is a process for the preparation of a compound (I.A.a)

wherein
each Ar is independently defined as above;
each Y is independently defined as above;
m is 3, wherein 0, 1, 2 or 3 of the m Y groups are different from hydrogen; and
n is 4, wherein 0, 1, 2 or 3 of the n Y groups are different from hydrogen;
in which
a1) an isopropenylbenzene compound of formula (II)

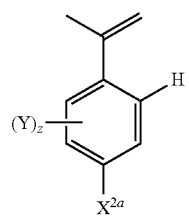

(II)

is provided, wherein
$X^{2a}$ is selected from F, Cl, Br, I, O-benzyl, $CH_3SO_3$ and $CF_3SO_3$;
each Y is independently selected from hydrogen and $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups; and
z is 3, wherein 0, 1, 2 or 3 of the z Y groups are different from hydrogen;
b1) the isopropenylbenzene compound of the formula (II) is subjected to a dimerization in the presence of an acidic catalyst resulting in the compound of the formula (III)

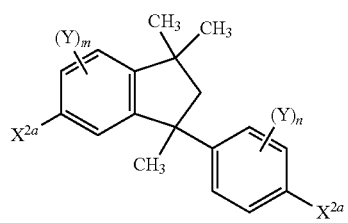

(III)

c1) the compound of the formula (III) is subjected to an amination reaction with at least one aromatic amine of formula (IV)

$Ar_2NH$     (IV)

in the presence of a palladium complex catalyst and a base to give the compound of the formula (I.A.a).

Step a1)
The compounds of formula (II) are either commercially available or can be prepared, for example by a one-pot process by reacting a corresponding acetophenone compound of formula (XIV) with a methylmagnesium halide of the formula (XV) by a Grignard reaction to give a corresponding 2-phenyl-propan-2-ol of formula (XVI). The acid catalyst dehydratisation of the alcohol of formula (XVI) gives the compound of formula (II) as outlined in scheme 1.

Scheme 1

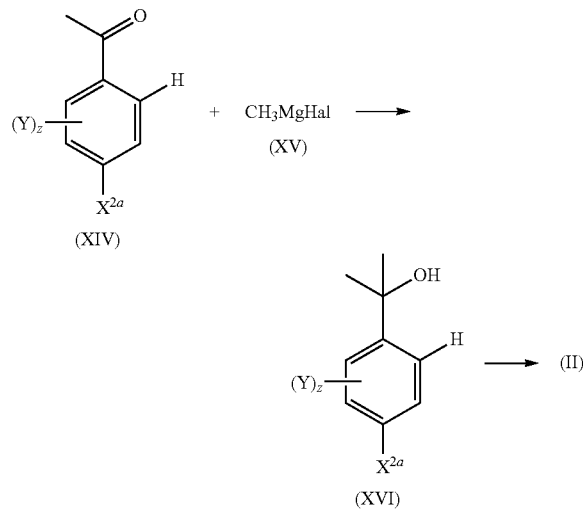

In Scheme 1, z, Y and $X^{2a}$ are defined as above and Hal means chlorine or bromine. The Grignard addition reaction is generally carried out at a temperature in the range of 0° to 60° C., preferably 10° to 40° C. The dehydration is generally carried out at the same temperature as the Grignard reaction. The quantity of Grignard reagent (XV) is 1.0 to 1.4 equivalents relative to the acetophenone compound XIV. Suitable acids for the dehydration are polyphosphoric acid sulfuric acid, hydrochloric acid, trifluoracetic acid, p-toluenesulfonic acid. Advantageously, the reaction can be performed as one-pot reaction. It is known that aryl Grignards undergo the same reactions as alkyl Grignards. Thus, the compound of formula (II) can also be prepared using acetone and an appropriate aryl Grignard reagent.

Step b1)
The dimerization can be carried out in the presence of an acidic catalyst. Suitable catalysts are for example polyphosphoric acid, sulfuric acid, hydrochloric acid, trifluoracetic acid, p-toluenesulfonic acid, acidic ion exchangers and acidic montmorillonite-containing earths, preferably trifluoroacetic acid. The acid catalyst is generally used as solvent so is present in large excess. The reaction is generally carried out at a temperature in the range of 40 to 120° C.

Step c1)
Compounds of the formula I.A.a can be obtained by a coupling reaction between the compound III and the corresponding diarylamine (IV) in the presence of a palladium catalyst in terms of a Buchwald-Hartwig reaction. Suitable palladium catalyst or catalyst precursors are for example palladium(0) bis(dibenzylideneacetone) (Pd(dba)$_2$), tris-(dibenzylideneacetone)dipalladium(0) (Pd$_2$(dba)$_3$), [1,1-bis(diphenylphosphino)-ferrocene]dichloropalladium(II) (PdCl$_2$(dppf)), palladium chloride (PdCl$_2$), bis(acetonitrile) palladium chloride (Pd(ACN)$_2$O$_2$), [1,3-bis(2,6-diisopropylphenyl)imidazol-2-ylidene](3-chloropyridyl)palladium dichloride (PEPPSI-iPr), dichloro[1,3-bis(2,6-di-3-pentylphenyl)imidazol-2-ylidene](3-chloro-pyridyl)palladium (PEPPSI-iPent), or palladium acetate (Pd(OAc)$_2$). Preferably, the catalyst is palladium acetate, Pd(dba)$_2$ or Pd$_2$(dba)$_3$. The reaction is usually carried out in the presence of a ligand. The ligand is any molecule capable of coordinating to the palladium precursor and facilitating the Buchwald-Hartwig reaction, preferably an dialkylbiarylphosphines or tri-tert-butyl phosphine. Examples of dialkylbiarylphosphine ligands include 2-dicyclohexylphosphino-2'-(N,N-dimethylamino)biphenyl (DavePhos), 2-dicyclohexylphosphino-2',4',6'-triisopropylbiphenyl (Xphos), 2-dicyclohexylphosphino-2',6'-dimethoxybiphenyl (Sphos), 2-di-tert-butylphosphino-2',4',6'-triisopropylbiphenyl (tBuXPhos), (2-biphenyl)dicyclohexylphosphine, 2-(dicyclohexylphosphino)biphenyl (CyJohnPhos), (2-biphenyl)di-tert-butylphosphine (JohnPhos), 2-dicyclohexylphosphino-2',6'-diisopropoxybiphenyl (RuPhos), 2-di-tert-butylphosphino-2'-methylbiphenyl (tBuMePhos), 2-di-tert-butylphosphino-3,4,5,6-tetramethyl-2',4',6'-triisopropyl-1,1-biphenyl 2-di-tert-butylphosphino-2'-methylbiphenyl (tBuMePhos), 2-di-tert-butylphosphino-3,4,5,6-tetramethyl-2',4',6'-triisopropyl-1,1-biphenyl (Tetramethyl tBuXPhos), and 2-(dicyclophexylphosphino)3,6-dimethoxy-2',4',6'-triisopropyl-1,1-biphenyl (BrettPhos). The palladium catalyst and phosphine ligand are preferably used in a molar ratio in the range of from about 0.5 to about 5 moles of ligand per mole of palladium catalyst.

Usually, the reaction is performed in the presence of a base such as an alkaline alkoxide, earth alkaline alkoxide, alkaline carbonate or earth alkaline carbonate, alkali metal amides or trialkyl amines. Preferably, the base is sodium tert-butoxide, cesium carbonate, lithium bis(trimethylsilyl)amide, sodium bis(trimethylsilyl)amide, potassium bis(trimethylsilyl)amide, lithium diisopropylamide or lithium dicyclohexylamide. More preferably, the base is sodium tert-butoxide.

The reaction is generally carried out in a solvent. Suitable solvents are for example aliphatic hydrocarbons, such as pentane, hexane, cyclohexane and petroleum ether, aromatic hydrocarbons, such as toluene, o-, m- and p-xylene, ethers, such as diisopropyl ether, tert-butyl methyl ether, dioxane, anisole and tetrahydrofuran and dimethoxyethane, amide such as dimethylformamide or N-methylpyrrolidone. The reaction temperature generally ranges between 50° and 130° C. The reactions generally are run under an inert atmosphere (e.g. under dry nitrogen or argon).

The compound of formula (I.A.a.) can also be prepared by a process in which
a2) an isopropenylbenzene compound (II)

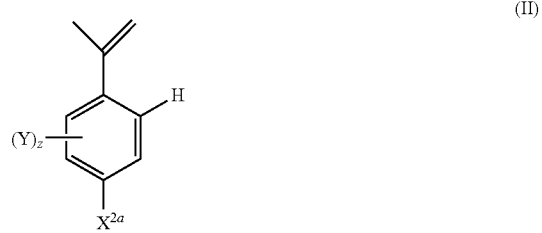

is provided, wherein
$X^{2a}$ is selected from F, Cl, Br, I, O-benzyl, $CH_3SO_3$ and $CF_3SO_3$;

each Y is independently selected from hydrogen, $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups; and z is 3, wherein 0, 1, 2 or 3 of the z Y groups are different from hydrogen;

b2) the isopropenylbenzene compound of the formula (II) is subjected to a dimerization in the presence of an acidic catalyst resulting in the compound of the formula (III)

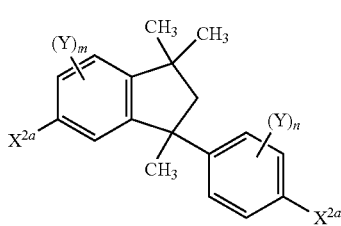

(III)

c2) the compound of formula (III) is subjected to an amination reaction with an alkali bis(trialkylsilyl) amide in the presence of a palladium complex catalyst followed by removal of the trialkylsilyl protecting group to give a compound of the formula (V)

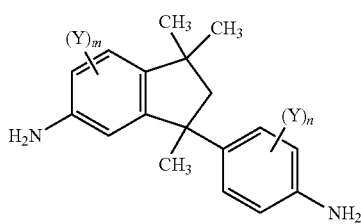

(V)

d2) the compound of the formula (V) is subjected to an arylation reaction with at least one aromatic compound of formula (VI)

Ar—$X^{2b}$ (VI)

wherein $X^{2b}$ is selected from F, Cl, Br, I, O-benzyl, $CH_3SO_3$ and $CF_3SO_3$, in the presence of a palladium complex catalyst and a base to give the compound of the formula (I.A.a).

Step a2) and step b2)
Suitable reaction conditions are described above in step a1) and step b1).

Step c2)
The diamino compound of the formula (V) can be prepared from the corresponding phenylindane compound of formula (III) having labile leaving groups $X^{2a}$ by reacting the compound of formula (III) with an alkali metal salt of a hexaalkyldisilazide of the formula M-N(Si(R')$_3$)$_2$, where M is an alkali metal and R' may be the same or a different $C_1$-$C_6$-alkyl, especially lithium bis(trimethylsilyl)amide in the presence of a palladium catalyst and subsequent hydrolysis. An example for a suitable palladium catalyst is tris(dibenzylideneacetone)dipalladium(0) or PdCl$_2$(dppf), optionally in the presence of a tri(substituted)phosphine, e.g. a triarylphosphine such as triphenylphosphine or tritolylphosphine, tri (cyclo)alkylphosphine such as tris-n-butylphosphine, tris (tert-butyl)phosphine, tris(cyclohexylphosphine) or 2-(dicyclohexylphosphino)biphenyl. The reaction of compound (III) with the alkalimetal hexaalkyldisilazide can be performed by analogy to a Buchwald-Hartig coupling. The alkalimetal hexaalkyldisilazide is commercially available or can be generated in-situ from the corresponding amine by a strong base such an alkalimetal alkoxide, e.g. potassium tert-butylate, or an alkalimetal hydride such as lithium hydride, sodium hydride and the like. Removal of the trialkylsilyl group is simply achieved by aqueous work-up, preferably under acidic conditions, such as aqueous hydrochloric acid, sulfuric acid etc, or using fluoride sources such as HF, KF, ammonium fluoride or HF-pyridine.

Step d2)
Suitable reaction conditions are described above in step c1). In some embodiments of the amination reaction in step d2), the reaction includes a first aromatic compound of the formula (VI) and a second aromatic compound of the formula (VI), in which the first aromatic compound of formula (VI) is different from the second aromatic compound of formula (VI). In a specific embodiment, only one aromatic compound of the formula (VI) is used in step d2) to give a compound of the formula (I.A.a), wherein all Ar groups have the same meaning.

Compounds of formula (V) are especially useful intermediate compounds, for example for preparing compounds of formula (I) according to the invention or for preparing triarylamine compounds different from those of the present invention.

U.S. Pat. No. 3,856,752 describes a process for preparing a mixture of 6-amino-1-(4'-aminophenyl)-1,3,3-trimethylindane of formula (B) and 5-amino-1-(4'-aminophenyl)-1,3,3-trimethylindane of formula (C)

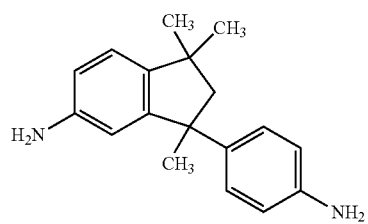

(B)

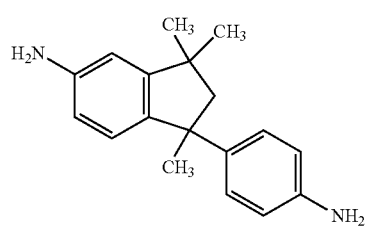

(C)

in a yield of 71%. The obtained diamine product was a mixture of 62% 6-amino- and 38% 5-amino-1-(4'-aminophenyl)-1,3,3-trimethylindane (as indicated by NMR analysis). The present inventors found that the reaction mixture may also comprise small amounts of regioisomeric impurities, namely 4-amino-1-(4'-aminophenyl)-1,3,3-trimethylindane and/or 7-amino-1-(4'-aminophenyl)-1,3,3-trimethylindane. The regioisomers different from the compounds of formulae (B) and (C), however, have different reaction properties that can be unwanted for certain uses. In particular, there exists a need for a process for preparing the intermediate compound 6-amino-1-(4'-aminophenyl)-1,3,3-trimethylindane of formula B which eliminates or reduces the formation of the regioisomers 5-amino-1-(4'-aminophenyl)-1,3,3-trimethylindane, 4-amino-1-(4'-aminophenyl)-1,3,3-trimethylindane and/or 7-amino-1-(4'-aminophenyl)-1,3,3-trimethylindane.

Thus, a further aspect of the present invention provides a process for preparing an intermediate compound of formula (V). In one embodiment of this aspect, the process comprises the steps a2), b2) and c2) as described above. In particular, the process comprising the steps a2), b2) and c2) described above is used for preparing the intermediate compound of formula (V), wherein zero of the m Y groups is different from hydrogen and zero of the n Y groups are different from hydrogen.

In another embodiment of this aspect, the invention provides a process for preparing an intermediate compounds of formula (V) comprising the steps:

a7) a halogenated 1,3,3-trimethylindane compound of the formula XXI is provided

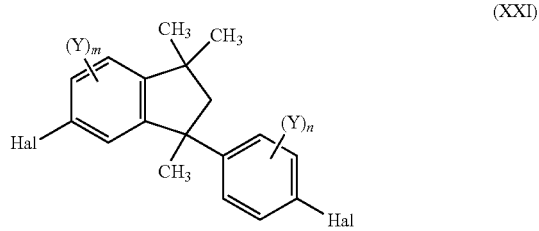

(XXI)

in which
Hal is chlorine, bromine or iodine;

b7) the compound of formula (XXI) is subjected to a copper promoted amidation with an amide of the formula (XXII)

(XXII)

in which
$R^{20}$ is hydrogen, $C_1$-$C_{10}$-alkyl, $C_3$-$C_8$-cycloalkyl or $CH_2$—($C_6$-$C_{10}$-aryl);
to give a diamide of the formula (XXXIII)

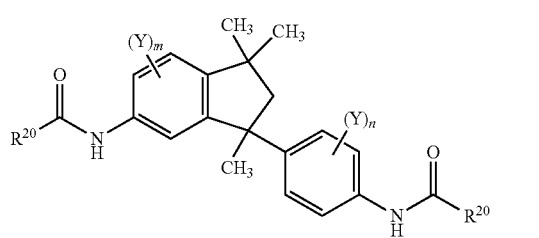

(XXIII)

c7) the diamide of the formula (XXIII) is subjected to a hydrolysis to give the compound of formula (V).

Step a7)
Compounds of formula (XXI) can be prepared as outlined in step b2) above.

Step b7)
In formula XXII, $R^{20}$ is preferably linear $C_1$-$C_{10}$-alkyl or branched $C_3$-$C_{10}$-alkyl. In a preferred embodiment, the amide of formula XXII is pivalamide. The amination process can be carried out in the sense of a Goldberg type reaction using a copper catalyst, such as a copper(I) compound. Suitable copper(I) compounds are copper(I) oxide, copper(I) bromide or copper(I) iodide, in particular copper (I) iodide. The amount of copper(I) compound is typically in the range from 5 to 20 mol %, based on the amount of compound of formula (XXI). The reaction usually is carried out in the presence of a ligand such as dimethylethylenediamine (dmeda) or 1,2-cyclohexanediamine. The ligand is typically present in the range from 0.01 to 300 mol %, based on the amount of the catalyst. In general, the reaction is carried out in an inert, aprotic solvent such as an ether, e.g. dimethoxyethane or dioxane or an amide, e.g. dimethylformamide or N-methylpyrrolidone, or an aromatic solvent, e.g. toluene. In general, the reaction is carried out in the presence of a base. Suitable bases are alkalimetal carbonates, in particular potassium carbonate, or alkalimetal phosphates such as potassium carbonate. Typically, the reaction is carried out under an inert atmosphere in the temperature range of 60–180° C.

Step c7)
The amide can be hydrolyzed under basic or acidic conditions. Suitable basic conditions are for example a treatment of the amide (XXIII) with an alkalimetal hydroxide such as KOH or NaOH in an alcohol followed by addition of water. Suitable alcohols are for example $C_1$-$C_4$-alkanols such as n-butanol. Suitable acidic conditions are for example a treatment of the amide (XXIII) with an aqueous acid such as a mineralic acid, e.g. sulfuric acid, hydrochloric acid, nitric acid or phosphoric acid, or with hydrobromic acid or hydroiodic acid.

In particular, the process described above comprising the steps a7), b7) and c7) is used for preparing the intermediate compound of formula (V), wherein zero of the m Y groups is different from hydrogen and zero of the n Y groups is different from hydrogen.

A further aspect of the present invention relates to the intermediate compound 6-amino-1-(4'-aminophenyl)-1,3,3-trimethylindane which is also referred to as 3-(4-aminophenyl)-1,1,3-trimethyl-indan-5-amine,

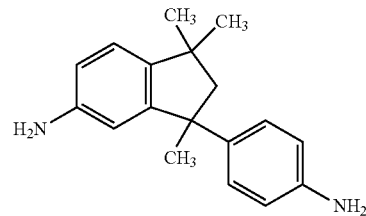 [SMILES: CC1(C)CC(C)(c2ccc(N)cc2)c2cc(N)ccc21]

obtainable by a process, in which
a2.1) an isopropenylbenzene compound (11.1)

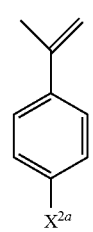

(II.1)

is provided, wherein $X^{2a}$ is selected from F, Cl, Br, I, O-benzyl, $CH_3SO_3$ and $CF_3SO_3$;

b2.1) the isopropenylbenzene compound of the formula (II.1) is subjected to a dimerization in the presence of an acidic catalyst resulting in the compound of the formula (III.1)

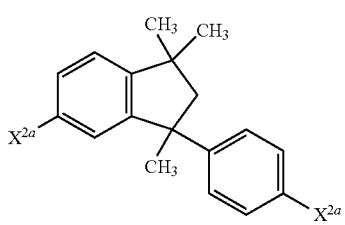
(III.1)

c2.1) the compound of formula (III.1) is subjected to an amination reaction with an alkali bis(trialkylsilyl) amide in the presence of a palladium complex catalyst followed by removal of the trialkylmethylsilyl protecting group to give 6-amino-1-(4'-aminophenyl)-1,3,3-trimethylindane;

Or a7.1) a halogenated 1,3,3-trimethylindane compound of the formula XXI.1 is provided

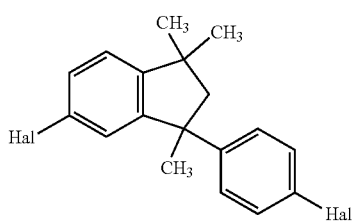
(XXI.1)

in which

Hal is chlorine, bromine or iodine;

b7.1) the compound of formula (XXI.1) is subjected to a copper promoted amidation with an amide of the formula XXII

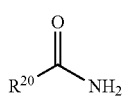
(XXII)

in which $R^{20}$ is hydrogen, $C_1$-$C_{10}$-alkyl, $C_3$-$C_8$-cycloalkyl or $CH_2$—($C_6$-$C_{10}$-aryl);

to give a diamide of the formula (XXIII.1)

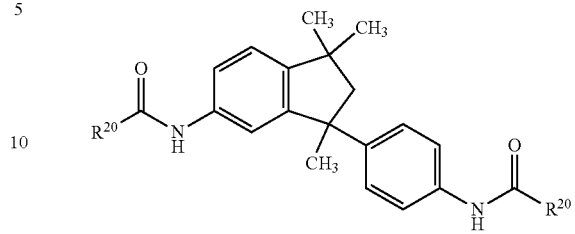
(XXIII.1)

c7.1) the diamide of the formula (XXIII.1) is subjected to a hydrolysis to give the compound 6-amino-1-(4'-aminophenyl)-1,3,3-trimethylindane.

Steps a2.1), b2.1), c2.1), a7.1), b7.1) and c7.1)

Suitable reaction conditions are described above in steps a2), b2), c2), a7), b7) and c7), respectively.

A further aspect of the present invention relates to the compound 6-amino-1-(4'-aminophenyl)-1,3,3-trimethylindane containing less than 1% by weight regioisomeric impurities selected from 5-amino-1-(4'-aminophenyl)-1,3,3-trimethylindane, 4-amino-1-(4'-aminophenyl)-1,3,3-trimethylindane or 7-amino-1-4'-aminophenyl)-1,3,3-trimethylindane. Preferably, 6-amino-1-(4'-aminophenyl)-1,3,3-trimethylindane has a LC (liquid chromatography) purity of equal to or more than 99.0%.

A further aspect of the present invention relates to a process for the preparation of a mixture of the compounds (I.A.a.1) and (I.B.a.1)

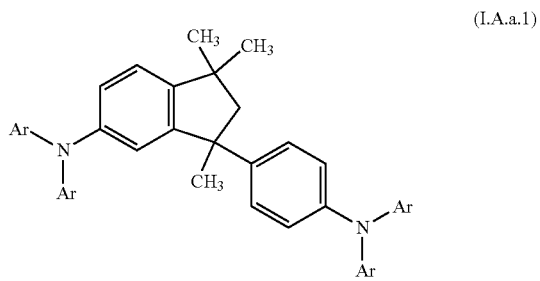
(I.A.a.1)

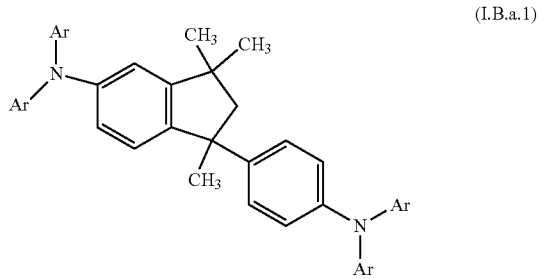
(I.B.a.1)

wherein each Ar is independently defined as in any of claims 1 and 4 to 8;

in which a3) a mixture of 5(6)-amino-1-(4'-aminphenyl)-1,3,3-trimethylindane compounds of formulae (VIIa) and (VIIb)

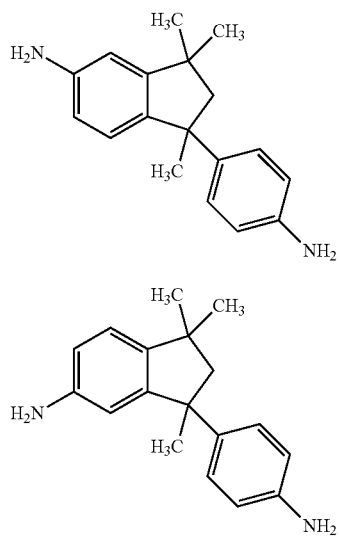

(VIIa)

(VIIb)

is provided;

b3) the mixture of compounds of formulae (VIIa) and (VIIb) is subjected to an arylation reaction with at least one aromatic compound of formula (VI)

$Ar—X^{2b}$ (VI)

wherein $X^2b$ is selected from F, Cl, Br, I, O-benzyl, $CH_3SO_3$ and $CF_3SO_3$;

in the presence of a palladium complex catalyst and a base to give a mixture of the compounds of the formulae (I.A.a1) and (I.B.a1).

Step a3)

The compounds of formulae (Vila) and (VIIb) can be prepared, for example, as described in U.S. Pat. No. 3,856,752, 3,983,092 or 4,026,876.

Step b3)

Suitable reaction conditions are described above in step c1). In some embodiments of the amination reaction in step b3), the reaction includes a first aromatic compound of the formula (VI) and a second aromatic compound of the formula (VI), in which the first aromatic compound of formula (VI) is different from the second aromatic compound of formula (VI). In a specific embodiment, only one aromatic compound of the formula (VI) is used in step b3) to give a mixture of compound of the formula (I.A.a.1) and (I.B.a.1), wherein all Ar groups have the same meaning.

Optionally, the obtained mixture of compounds of the formulae (I.A.a.1) and (I.B.a.1) are optionally subjected to at least one separation and/or purification step. The separation and/or purification step can be effected by customary processes known to those skilled in the art, such as recrystallization or separation on suitable stationary phases, and a combination of these measures.

A further aspect of the present invention relates to a process for the preparation of a mixture of the compounds of the formulae (I.C.a) and (I.D.a)

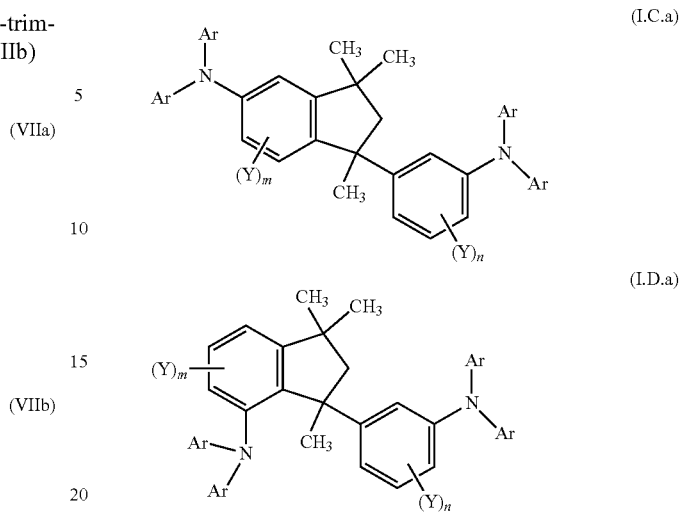

(I.C.a)

(I.D.a)

wherein each Ar is independently defined as above;

each Y is independently defined as above;

m is 3, wherein 0, 1, 2 or 3 of the m Y groups are different from hydrogen; and n is 4, wherein 0, 1, 2 or 3 of the n Y groups are different from hydrogen;

in which a4) an isopropenylbenzene compound of formula (IX)

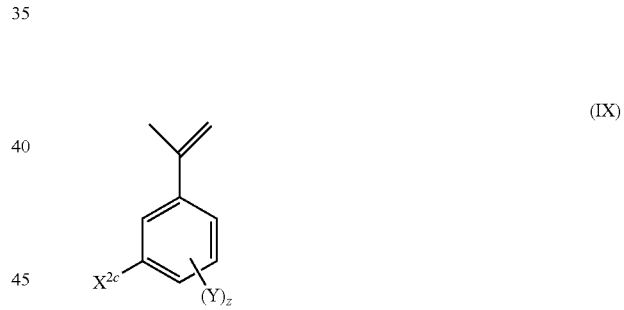

(IX)

is provided, wherein $X^{2c}$ is selected from F, Cl, Br, I, O-benzyl, $CH_3SO_3$ and $CF_3SO_3$;

each Y is independently selected from hydrogen, $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups and wherein one of the z Y groups in one of the ortho-positions on the phenyl ring relative to the isopropenyl group is hydrogen; and z is 4, wherein 0, 1, 2 or 3 of the z Y groups are different from hydrogen;

b4) the isopropenylbenzene compound of formula (IX) is subjected to a dimerization in the presence of an acidic catalyst resulting in the compound of the formulae (Xa) and (Xb)

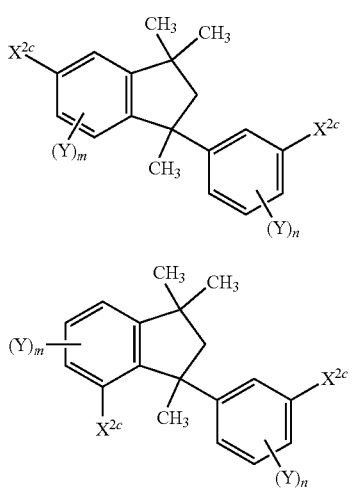

(Xa)

(Xb)

c4) the mixture of compounds of formulae (Xa) and (Xb) is subjected to an amination reaction with at least one aromatic amine of formula (IV)

Ar$_2$NH  (IV)

in the presence of a palladium complex catalyst and a base to give a mixture of compound of the formulae (I.C.a) and (I.D.a).

Step a4)
The compounds of formula (IX) are either commercially available or can be prepared, for example, in analogy to the process outlined in step a1)

Steps b4) and c4)
Suitable reaction conditions are described above in step b1) and c1), respectively.

Optionally, the obtained mixture of compounds of the formulae (I.C.a) and (I.D.a) are optionally subjected to at least one separation and/or purification step. The separation and/or purification step can be effected by customary processes known to those skilled in the art, such as recrystallization or separation on suitable stationary phases, and a combination of these measures.

A further aspect of the present invention relates a process for the preparation of a compound of the formula (I.E.a)

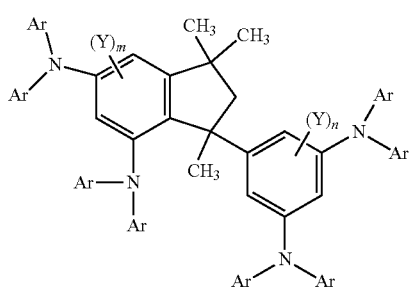

(I.E.a)

wherein
each Ar is independently defined as in any of claims 1 and 4 to 8;
each Y is independently defined as in claim 1;
m is 2, wherein 0, 1 or 2 of the m Y groups are different from hydrogen; and n is 3, wherein 0, 1 or 2 of the n Y groups are different from hydrogen;
in which
a5) an isopropenylbenzene compound of formula (XI)

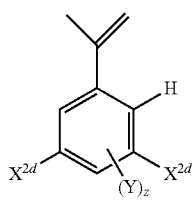

(XI)

wherein
each $X^{2d}$ is independently selected from F, Cl, Br, I, O-benzyl, CH$_3$SO$_3$ and CF$_3$SO$_3$;
each Y is independently selected from hydrogen, C$_1$-C$_6$-alkyl, C$_1$-C$_6$-alkoxy, C$_3$-C$_8$-cycloalkyl, C$_3$-C$_8$-cycloalkoxy, phenyl and phenyloxy, wherein each of the cyclic rings in the four last-mentioned groups are unsubstituted or substituted by 1, 2 or 3 C$_1$-C$_6$-alkyl groups; and
z is 2, wherein 0, 1 or 2 of the z Y groups are different from hydrogen;
is provided;
b5) the isopropenylbenzene compound of formula (XI) is subjected to a dimerization in the presence of an acidic catalyst resulting in the compound of the formulae (XII)

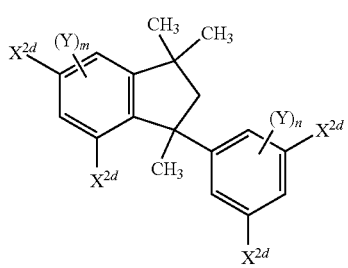

(XII)

c5) the compound (XII) is subjected to an amination reaction with an alkali bis(trialkylsilyl) amide in the presence of a palladium complex catalyst followed by removal of the trialkylsilyl protecting group to give a compound of the formula (XIII)

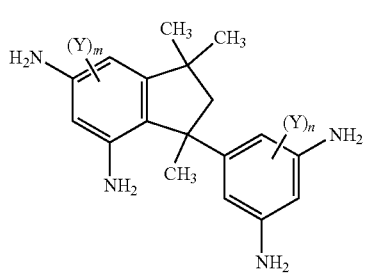

(XIII)

d5) the compound (XIII) is subjected to an arylation reaction with at least one aromatic compound of formula VI

wherein $X^{2b}$ is selected from F, Cl, Br, I, O-benzyl, $CH_3SO_3$ and $CF_3SO_3$;
in the presence of a palladium complex catalyst and a base to give the compound of the formula (I.E.a).
Step a5)
The compounds of formula (IX) are either commercially available or can be prepared, for example, in analogy to the process outlined in step a1) Steps b5), c5) and d5)
Suitable reaction conditions are described above in step b2), c2), and d2), respectively.

A further aspect of the present invention is a process for the preparation of a compound of the formula (I.E.a)

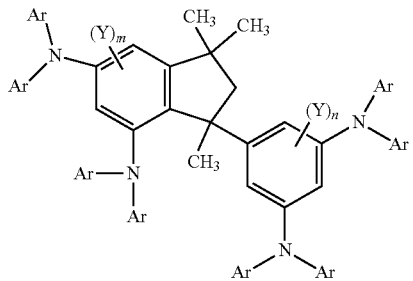

wherein
each Ar is independently defined as above;
each Y is independently defined as above;
in which
a6) a 1,1,3-trimethyl-3-phenylindane compound of formula (XII) is provided

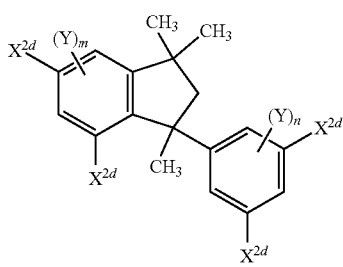

in which
$X^{2d}$ is selected from F, Cl, Br, I, O-benzyl, $CH_3SO_3$ and $CF_3SO_3$;
b6) the compound (XII) is subjected to an amination reaction with at least one aromatic amine of formula (IV)

in the presence of a palladium complex catalyst and a base to give compound of the formula (I.E.a).
Step a6)
The compounds of formula (IX) are either commercially available or can be prepared, for example, in analogy to the process outlined in step a1).
Step b6) and c6)
Suitable reaction conditions are described above in step b1) and c1), respectively.

Compounds of formula (I), in which X is phenylene-$NAr_2$ can for example be prepared by various C—C coupling reactions of the suitable A-$NAr_2$ derivative and the 1,1,3-trimethyl-3-phenyl-indane derivative. Suitable coupling reactions are for example the Suzuki reaction and the Stille reaction. For example, the compound of formula XVII

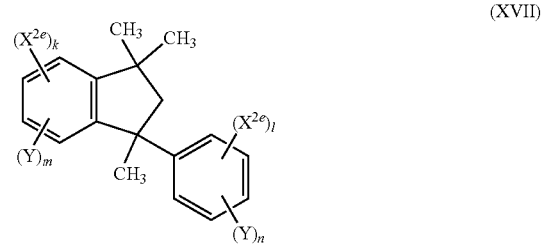

in which
each $X^{2e}$ is a $B(OR^{B1})(OR^{B2})$ radical or an $Sn(R^{Sn})_3$ radical, where $R^{B1}$ and $R^{B2}$ are, independently of each other, hydrogen or $C_1$-$C_4$-alkyl or $R^{B1}$ and $R^{B2}$ together form a $C_2$-$C_6$-alkanediyl moiety, e.g. ethan-1,2-diyl, propan-1,3-diyl or 1,1,2,2-tetramethylethan-1,2-diyl, and wherein $R^{Sn}$ is $C_1$-$C_6$-alkyl, $C_3$-$C_6$-cycloalkyl or phenyl,
Y is as defined above;
k is 1 or 2;
l is 1 or 2;
m is 2 or 3, wherein 0, 1, 2 or 3 of the m Y groups are different from hydrogen;
n is 3 or 4, wherein 0, 1, 2 or 3 of the n Y groups are different from hydrogen;
the sum of k and m is 4 and the sum of l and n is 5
can be reacted with a suitable compound of formula (XVIII),

where
A is as defined herein,
Ar is as defined herein
Hal is bromine or chlorine.
The reaction of the compound of formula (XVII) with the compound (XVIII) can be performed by analogy to known coupling reactions in the presence of suitable transition metal catalysts, in particular palladium catalysts. Typical reactions conditions are those of Stille coupling (see e.g. Stille et al. Angew. Chem. Int. Ed. Engl. 1986, 25,508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253). Borylated compound (XVII) can be prepared via a Miyaura borylation reaction, e.g. by treating the compound of formula (XIX)

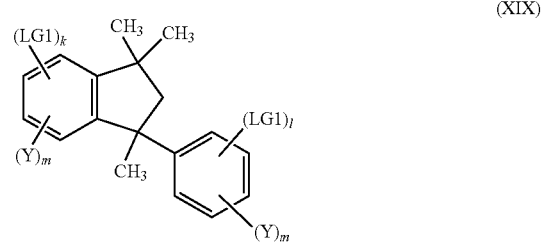

where each LG1 is selected from bromine, chlorine of triflate, Y is as defined above and k, l, m and n are as defined above,
with bisboronic acid or a boric ester.

Compounds of formula (I) with X being phenylene-NAr$_2$ can also be prepared under the reaction conditions of a Suzuki coupling as outlined in scheme 2 below.

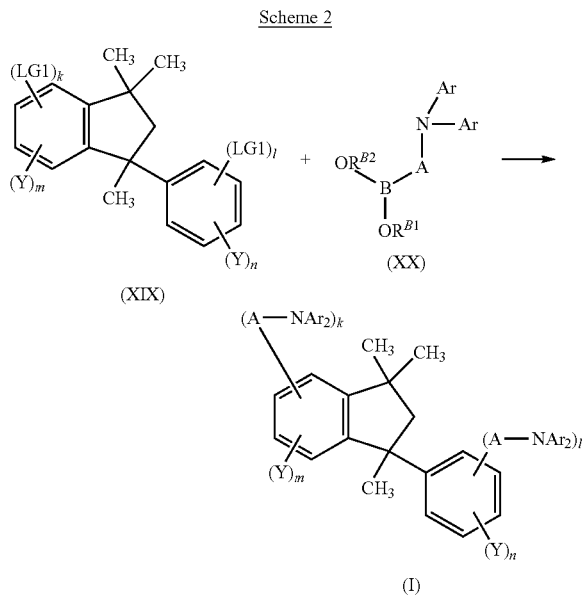

In scheme 2, m, n, k, l, LG1, $R^{B1}$, $R^{B2}$, Y, A and Ar are as defined above. The borylated compound (XX) can be prepared in analogy to the process described for the compound (XVII).

The compounds according to the invention are in particular suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds of formula (I), (I.A.a.1), (I.A.1), (I.A.2), (I.A.3), (I.A.4), (I.B.a.1), (I.B.1), (I.B.2), (I.B.3), (I.B.4), (I.C.a.1), (I.C.a.2), (I.C.a.3), (I.C.a.4), (I.C.1), (I.C.2), (I.C.3), (I.C.4), (I.D.a.1), (I.D.1), (I.D.2), (I.D.3), (I.D.4) and (I.E.a.1), respectively, or a mixture of compounds of formulae (I.A.a) and (I.B.a) or a mixture of compounds of formulae (I.C.a) and (I.D.a) or a mixture of at least different compounds of the general formula I
- as a hole transport material (HTM) in organic electronics,
- as an electron blocking material (EBM) in organic electronics,
- as a semiconductor material in organic field-effect transistors (OFETs), in particular in thin-film transistors (TFTs),
- in organic solar cells (OSCs), solid-state dye sensitized solar cells (DSSCs) or Perovskite solar cells, in particular as a hole transport material in organic solar cells, as replacement of the liquid electrolyte in dye sensitized solar cells, as a hole transport material in Perovskite solar cells,
- in organic light-emitting diodes (OLEDs), in particular for displays on electronic devices and lighting,
- for electrophotography, in particular as photoconductive material in an organic photoconductor (OPC),
- for organic optical detectors, organic photoreceptors, organic field-quench devices (O-FQDs), light-emitting electrochemical cells (LECs) and organic laser diodes.

The compounds according to the invention are especially suitable as a hole transport material (HTM) in organic electronics. HTMs are employed in a wide range of electronic devices and applications, such as in organic electroluminescent (EL) devices and in solar cells.

The compounds according to the invention may be employed as the sole HTM or in combination with at least one further HTM. Suitable further hole transport materials are well-known in the art. Preferred hole transport materials for combination are spiro-OMeTAD, 2,2',7,7'-tetrakis-(N, N'-di-4-methoxy-3,5-dimethylphenylamine)-9,9'-spirofluorene, tris(p-anisyl)amine, N,N,N',N'-tetrakis(4-methoxyphenyl)-1,1-biphenyl-4,4'-diamine, 2,7-bis[N,N-bis(4-methoxy-phenyl)amino]-9,9-spirobifluorene, poly(3-hexylthiophene) (P3HT), poly(3,4-ethylenedioxythiophene)-poly(styrenesulfonate) (PEDOT: PSS), poly[bis(4-phenyl)(2,4,6-trimethylphenyl)amine] (PTAA), NiO and V$_2$O$_5$.

Furthermore, the compounds according to the invention used as HTMs may be combined with at least one further additive. Suitable additives are pyridine compounds such as tert-butylpyridine, imidazoles as disclosed in WO2013/026563, claims 1 to 15 and disclosed on pages 15 to 17 or polymer additives such as poly(4-vinylpyridine) or its copolymer with e.g. vinylstyrene or alkylmethacrylate. A preferred pyridine compound is tert-butylpyridine.

The compounds according to the invention used as the HTMs may be combined with lithium salts as described in Phys. Chem., Chem. Phys, 2013, 15, 1572-2579.

The usefulness of a pyridine compound is described in Sol. Energy Mater. & Solar Cells, 2007, 91, 424-426.

Furthermore, the compounds according to the invention used as HTMs may be combined with a p-dopant such as N(C$_6$H$_5$Br)$_3$, SbCl$_6$, V$_2$O$_5$, MoO$_3$, WO$_3$, RuO$_4$, Re$_2$O$_3$, F$_4$-TCNQ (tetrafluoro-tetracyanoquinodimethane), HAT-CN (1,4,5,8,9,11-hexaazatri-phenylene-hexacarbonitrile) F6-TCNNQ (1,3,4,5,7,8-hexafluorotetracyanonaphtho-quinodimethane, obtainable from Novaled), NDP-9 (a p-dopant obtainable from Novaled) or Co complex salts. Suitable dopants are described in Chem. Mater., 2013, 25, 2986-2990 or J.Am. Chem. Soc, 2011, 133, 18042. Also suitable [3]-radialenes as described in EP 2 180 029 A1 can be applied.

The invention furthermore relates to an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I). The preferences stated above likewise apply to the substrate. Especially, the at least one compound of formula I), (I.A.a.1), (I.A.1), (I.A.2), (I.A.3), (I.A.4), (I.B.a.1), (I.B.1), (I.B.2), (I.B.3), (I.B.4), (I.C.a.1), (I.C.a.2), (I.C.a.3), (I.C.a.4), (I.C.1), (I.C.2), (I.C.3), (I.C.4), (I.D.a.1), (I.D.1), (I.D.2), (I.D.3), (I.D.4) and (I.E.a.1), respectively, is employed in a hole-transporting layer or electron blocking layer.

The invention furthermore relates to an electroluminescent arrangement in form of an organic light-emitting diode (OLED). In an organic light emitting device, an electron blocking layer is disposed adjacent to an emissive layer. Blocking layers may be used to reduce the number of charge carriers (electrons or holes) and/or excitons that leave the emissive layer. An electron blocking layer may be disposed between emissive layer and an hole transport layer, to block electrons from leaving emissive layer in the direction of hole transport layer. Similarly, a hole blocking layer may be disposed between emissive layer and electron transport layer, to block holes from leaving emissive layer in the direction of electron transport layer.

The OLEDs can be employed for various applications, for example for monochromatic or polychromatic displays, for lighting applications or for medical and/or cosmetic applications, for example in phototherapy.

The organic electroluminescent device, particularly in form of an OLED, comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be noted that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (I) or the preferred embodiments as hole-transport material in a hole-transport or hole-injection or electron-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (I) or the preferred embodiments is employed as hole-transport or hole-injection material in a hole-transport or hole-injection layer. The emitting layer here can be fluorescent or phosphorescent.

A hole-injection layer generally is a layer which facilitates electron injection from the anode to the organic layer. The hole-injection layer can be situated directly adjacent to the anode.

A hole-transport layer transports the holes from the anode to the emitting layer and is located between a hole-injection layer and an emitting layer.

To enhance the hole transport characteristics, doped hole transport layers can be employed. The architecture of actual OLEDs often improves quantum efficiency by using a graded heterojunction. In the graded heterojunction architecture, the composition of hole and electron-transport materials varies continuously within the emissive layer with a dopant emitter. The graded heterojunction architecture combines the benefits of both conventional architectures by improving charge injection while simultaneously balancing charge transport within the emissive region.

In still a further preferred embodiment of the invention, the compounds of the formula (I) or the preferred embodiments thereof are employed in an electron-blocking layer. An electron-blocking layer may be used to reduce the number of charge carriers (electrons) that leave the emissive layer. An electron-blocking layer usually is a layer which is directly adjacent to an emitting layer on the anode side. An electron blocking layer may be disposed between emissive layer and hole transport layer to block electrons from leaving the emissive layer in the direction of hole transport layer.

The compound of the formula (I) or the preferred embodiments thereof are particularly preferably employed in a hole-transport layer or electron blocking layer.

In a further preferred embodiment of the invention, the compound of the formula (I) or the preferred embodiments thereof are employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (I) or the preferred embodiments thereof are employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity >1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the compound of the formula (I) or the preferred embodiments and the emitting compound comprises between 99.9 and 1% by weight, preferably between 99 and 10% by weight, particularly preferably between 97 and 60% by weight, in particular between 95 and 80% by weight, of the compound of the formula (1) or the preferred embodiments, based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material. The limits indicated above apply, in particular, if the layer is applied from solution. If the layer is applied by vacuum evaporation, the same numerical values apply, with the percentage in this case being indicated in % by vol. in each case.

The present invention again furthermore relates to an organic field-effect transistor comprising a substrate having at least one gate structure, a source electrode and a drain electrode and at least one compound of the formula I above as a semiconductor material. The preferences stated above likewise apply to the organic field-effect transistor.

The present invention again furthermore relates to a substrate comprising a plurality of organic field-effect transistors, at least some of the field-effect transistors comprising at least one compound of the formula I. The preferences stated above likewise apply to the substrate.

The invention furthermore relates to a semiconductor unit comprising at least one substrate as defined above.

The compounds of the invention, i.e. at least one compound of formula (I), (I.A.a.1), (I.A.1), (I.A.2), (I.A.3), (I.A.4), (I.B.a.1), (I.B.1), (I.B.2), (I.B.3), (I.B.4), (I.C.a.1), (I.C.a.2), (I.C.a.3), (I.C.a.4), (I.C.1), (I.C.2), (I.C.3), (I.C.4), (I.D.a.1), (I.D.1), (I.D.2), (I.D.3), (I.D.4) and (I.E.a.1), respectively can be used advantageously as HTMs in perovskite solar cells. They can also be used to replace the liquid electrolyte of conventional DSSCs to provide solid-state DSSC devices.

The compounds of the invention are then preferably employed in a photosensitized nanoparticle layer comprising a sensitizing dye or a perovskite and at least one compound according to the invention.

In a first embodiment, the compounds of the invention are employed in a DSSC. The construction of a DSSC is generally based on a transparent substrate, which is coated with a transparent conductive layer, the working electrode. An n-conductive metal oxide is generally applied to this electrode or in the vicinity thereof, for example a nanoporous $TiO_2$ layer of approximately 2 to 20 μm thickness. On the surface thereof, in turn, a monolayer of a light-sensitive dye is typically adsorbed, which can be converted to an excited state by light absorption. This layer which carries the light-sensitive dye is generally referred to as the light absorbing layer of the DSSC. The counter electrode may optionally have a catalytic layer of a metal, for example platinum, with a thickness of a few μm.

Suitable are in principle all sensitizing dyes, as long as the LUMO energy state is marginally above the conduction bandedge of the photoelectrode to be sensitized. Examples of dyes are disclosed in Nanoenergy, de Souza, Flavio Leandro, Leite, Edson Roberto (Eds.), Springer, ISBN 978-3-642-31736-1, pages 58 to 74 or black dyes as described in U.S. Pat. No. 8,383,553. Preferred dyes are described in WO 2015049031 A1 which is incorporated herein by reference.

In a second embodiment, the compounds of the invention are employed in a Perovskite solar cell. Suitable Perovskites for Perovskite solar cells (PSCs) are known in the art. In principle, the perovskite material comprised in the devices according to the invention may be part of the charge transport layer but may also be part of another layer or scaffold within the device.

Suitable perovskite materials may comprise two halides corresponding to formula $Xa_{p-x}Xb(x)$, wherein Xa and Xb are each independently selected from Cl, Br, or I, and x is greater than 0 and less than 3. Suitable perovskite materials are also disclosed in WO 2013/171517, claims 52 to 71 and claims 72 to 79, which is entirely incorporated herein by reference. Suitable perovskite materials are $CsSnI_3$, $CH_3NH_3PbI_2Cl$, $CH_3NH_3PbI_3$, $CH_3NH_3Pb(I_{1-x}Br_x)_3$, $CH_3NH_3SnI_2Cl$, $CH_3NH_3SnI_3$ or $CH_3NH_3Sn(I_{1-x}Br_x)_3$, with $0<x<1$.

Preferred perovskite materials are disclosed in WO 2013/171517 on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The charge transport layer according to the invention as described before or the device according to the invention as described before or below may furthermore comprise an insulator such as alumina as described in Michael M. Lee et al, Science, 338, 643, 2012.

The charge transport layer according to the invention or the device according to the invention as described before or below may furthermore comprise semiconductor oxide nanoparticles. The charge transport layer according to the invention or the device according to the invention preferably comprises semiconductor oxide nanoparticles.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$.

Preferably, the charge transport layer according to the invention as described before is present on a glass support or plastic or metal foil, optionally together with a dense layer of $TiO_2$. Preferably, the support is conductive.

The present invention furthermore relates to a electronic device or optoelectronic device comprising a charge transport layer as described or preferably described before. Preferably, the invention relates furthermore to a solid-state dye-sensitized solar cell comprising a charge transport layer as described or preferably described before. Suitable device structures according to the invention comprising further a mixed halide perovskite are described in WO 2013/171517, claims 52 to 71 and claims 72 to 79, which is entirely incorporated herein by reference.

Suitable device structures according to the invention comprising further a dielectric scaffold together with perovskite material are described in WO 2013/171518, claims 1 to 90 or WO 2013/171520, claims 1 to 94 which are entirely incorporated herein by reference.

Suitable device structures according to the invention comprising further a semiconductor and a perovskite material are described in WO 2014/020499, claims 1 and 3 to 14, which is entirely incorporated herein by reference The surface-increasing scaffold structure described therein comprises nanoparticles which are applied and/or fixed on a support layer, e.g. porous $TIO_2$.

Suitable device structures according to the invention comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film. Additionally, the invention relates to a method of preparing an electrochemical device and/or optoelectronic device as described or preferably described before, the method comprising the steps of:

providing a first and a second electrode;
providing a charge transport layer according to the invention as described before. There are no restrictions per se with respect to the choice of the first and second electrode. The substrate may be rigid or flexible.

Abbreviations which have been Used in the Examples that Follow were:

a/a for area percentage; Al for aluminium; BPhen for 4,7-diphenyl-1,10-phenanthroline, can be purchased from Luminescence Technology Corp., Taiwan; C60 for fullerene, can be purchased from CreaPhys GmbH Dresden, Germany; EBL for electron blocking layer, EIL for electron injection layer; EML for emission layer; ETL for electron transport layer; $F_6TCNNQ$ for 2,2'-(perfluoronaphthalene-2,6-diylidene)dimalononitrile, can be purchased from Novaled AG, Germany; GC for gas chromatography; HAT-CN or $HAT(CN)_6$ for 1,4,5,8,9,11-hexaazatriphenylene-hexanitrile, can be purchased from Jilin OLED Material Tech Co., LTD, China; HBL for hole blocking layer; HIL for hole injection layer; HPLC for high-performance liquid chromatography; HTL for hole transport layer; iPrOH for isopropanol; Ir(MDQ)$_2$(acac) for bis(2-methyldibenzo[f,h]quinoxaline)(acetylacetonate)iridium(III), can be purchased from Luminescence Technology Corp., Taiwan; ITO for indium tin oxid; LiQ for 8-hydroxyquinolatolithium, can be purchased from Nichem Fine Technology Co. Ltd, Taiwan; NDP-9, NHT-18, Novaled n-dopant, can be purchased from Novaled AG, Germany; NPB for N,N'-bis(naphthalen-1-yl)-N,N'-bis(phenyl)benzidine, can be purchased from Sensient, Germany; OMe for methoxy; Pd(dba)$_2$ for palladium(0) bis(dibenzylideneacetone); Pd$_2$(dba)$_3$ for tris(dibenzylideneacetone)dipalladium(0); RuPhos for 2-dicyclohexylphosphino-2',6'-diisopropoxybiphenyl; SPhos for 2-dicyclohexyl-phosphino-2',6'-dimethoxybiphenyl; TDSF for 1,3,5-triazine,2,4-diphenyl-6-(9,9'-spiro-b[9H-fluoren]-2-yl, can be purchased from Nichem Fine Technology Co. Ltd., Taiwan; THF for tetrahydrofuran; v/v for volume/volume; ZnPc for zinc phthalocyanine, can be purchased from CreaPhys GmbH Dresden, Germany.

Preparation Examples

I. Preparation of Intermediates

The starting materials used in the examples were either commercially available or could be synthesized by the average skilled person trained in organic chemistry following routine laboratory practice as outlined, for example in the examples below.

a) 1,3,3-Trimethylindane Compounds a1)
5-chloro-3-(4-chlorophenyl)-1,1,3-trimethylindane To 51.8 g (155.4 mmol) of methylmagnesium chloride (3 M in THF) were added 20 g (129.5 mmol) of 4'-chloroacetophenone over a period of 1 h at room temperature under argon. After 1 h, the reaction mixture was poured on 40 mL of hydrochloric acid (strength 36% in water, as commercially available). The phases were separated and the organic phase was washed with saturated aqueous NaHCO$_3$ solution and saturated NaCl solution. The organic phase was separated and 0.5 g (2.6 mmol) of p-toluene-sulfonic acid monohydrate were added. The mixture was evaporated to dryness. The crude solid was dissolved in 40 mL of trifluoroacetic acid and heated at 85° C. for 3 h. The trifluroacetic acid was removed by distillation and the crude product was crystallised from 2-propanol to obtain the title compound as a white powder (12 g, 60%; purity according to GC: 99.0%).

a2)
5-fluoro-3-(4-fluorophenyl)-1,1,3-trimethylindane

The title compound was prepared in analogy to the process described for 5-chloro-3-(4-chlorophenyl)-1,1,3-trimethylindane. Yield: 73%; purity according to GC: 99.0%.

a3)
5-bromo-3-(4-bromophenyl)-1,1,3-trimethylindane

The title compound was prepared in analogy to the process described for 5-chloro-3-(4-chlorophenyl)-1,1,3-trimethylindane. Yield: 76%; purity according to GC: 98.5%.

a4) 3-[3,5-bis(bromanyl)phenyl]-4,6-bis(bromanyl)-1,1,3-trimethyl-2H-indene 30.0 g (95 mmol) of tribromobenzene were dissolved in 60 mL of anhydrous THF. 105 mL of isopropylmagnesium chloride lithium chloride complex (1.3 M in THF) was added dropwise under an argon atmosphere. The reaction mixture was stirred at room temperature for 2 h, then 15 mL (204 mmol) of acetone were added dropwise. After additional 4 h, 150 mL of saturated aqueous NH$_4$Cl solution were added. The mixture was subsequently extended with tert-butyl methyl ether and water. The organic phase was separated and washed twice with water, dried with MgSO$_4$ and evaporated to dryness.

The crude product was dissolved in 220 mL of toluene and 0.3 g (1.6 mmol) of p-toluene-sulfonic acid monohydrate were added. The mixture was heated to reflux for 2 h in a dean stark trap. After cooling, the mixture was washed three times with aqueous 5% NaHCO$_3$ solution, dried with MgSO$_4$ and evaporated to dryness. The crude product was dissolved in 50 mL of heptane and 5 mL of sulfuric acid were added. The reaction mixture was heated at 85° C. for 18 h. After cooling, the mixture was filtered through celite and evaporated to dryness. The crude product was crystallised from toluene/methanol. The product was obtained as a white solid (13.21 g, 50%; purity according to GC: 99%).

a5) 6-amino-1-(4'-aminophenyl)-1,3,3-trimethylindane 50.38 g (164 mmol) of 5-chloro-3-(4-chlorophenyl)-1,1,3-trimethylindane were dissolved in 50 mL of anhydrous THF. 1.50 g (1.6 mmol) of Pd$_2$(dba)$_3$ and 1.38 g (4 mmol) of 2-(dicyclohexylphosphino)biphenyl were added, and 400 mL (400 mmol) of lithium bis(trimethylsilyl)amide in THF (1 M in THF) were added to the reaction mixture. The reaction mixture was heated at 75° C. under an argon atmosphere for 18 h. After cooling, aqueous hydrochloric acid (32%) was added until pH 2 was reached and the mixture was stirred at room temperature for additional 2 h. The phases were separated and the aqueous phase was washed twice with tert-butyl methyl ether. The organic phase was separated and the pH of the aqueous phases was adjusted to pH 9 by addition of NaOH solution (33%) in water. The aqueous phase was extracted three times with tert-butyl methyl ether. The combined organic phases were washed with water, dried with MgSO$_4$ and evaporated to dryness. After column chromatography (dichloromethane/heptane) the crude product was crystallised from toluene/heptane. The title compound was obtained as an off-white powder (22.2 g, 50%; purity according to GC: 98% (a/a).

a6) 5(6)-amino-1-(4'-aminophenyl)-1,3,3-trimethyl-indane

The mixture was obtainable as described in example 3 of U.S. Pat. No. 3,856,752.

a7) [3-(4-boronophenyl)-1,1,3-trimethyl-indan-5-yl] boronic Acid 3.88 g (9.84 mmol) of 5-bromo-3-(4-bromophenyl)-1,1,3-trimethyl-indane were dissolved in 39 ml of THF under an argon atmosphere. This solution was cooled to −78° C. and 9.1 ml of n-Butyllithium solution (2.7 M in heptane, 24.6 mmol) is added. Stirring was continued for 1 h and 6.8 mL (29.5 mmol) of triisopropyl borate are added. The solution was allowed to warm to room temperature and is subsequently cooled to 0° C. 100 mL of 1 M HCl solution was added and the volatiles were evaporated under reduced pressure. The remaining aqueous suspension was basified to pH 10 with 1M NaOH solution and heated to 75° C. and filtered under vacuum. The solution was adjusted to pH 1 with 1 M HCl and 150 mL of CH$_2$Cl$_2$ were added. The organic phase was separated and the aqueous phase was washed twice with 100 ml CH$_2$Cl$_2$/iPrOH 10:1 v/v. The combined organic phases were evaporated to dryness. The title compound was obtained as a white foam (3.38 g, 99%).

a8) 3-(4-aminophenyl)-1,1,3-trimethyl-indan-5-amine 100 g (254 mmol) of 5-bromo-3-(4-bromophenyl)-1,1,3-trimethylindane from example a3, 64.2 g (634 mmol) of pivalamide, and 87.7 g K$_2$CO$_3$ (634 mmol) were suspended in 400 mL of dioxane. Under an argon atmosphere, 7.25 g (38.0 mmol) of CuI and 6.71 g (76.1 mmol) of dimethylenediamine were added. The suspension was heated to reflux for 16 h and allowed to cool to room temperature. The suspension was filtered and the filter cake was washed with 100 mL of dioxane and 250 mL of NH$_3$ in water. In addition, the filter cake was washed with 20 mL of NH$_3$ in water, and then with water again. The crude product was dried under vacuum. N-[4-[6-(2,2-dimethylpropanoylamino)-1,3,3-trimethyl-indan-1-yl]phenyl]-2,2-dimethyl-propanamide was obtained as a colorless solid (110 g, 99% of theory). 68.4 g (1.22 mol) of KOH was suspended in 200 mL of n-butanol. Under an argon atmosphere, 100 g (230 mmol) of N-[4-[6-(2,2-dimethylpropanoylamino)-1,3,3-trimethyl-indan-1-yl]phenyl]-2,2-dimethyl-propanamide were added in small portions. The resulting suspension was heated to reflux for 3 h and allowed to cool to 80° C. 200 mL of water were added. The lower aqueous phase was separated and the organic phase was washed with 200 mL of water. The aqueous phases were combined, allowed to cool to room temperature and extracted with 100 mL of methyl tert-butyl ether. All organic phases were combined and the volatiles were removed under heating. 200 mL of water were added and the water was removed under heating until all remaining n-butanol was removed. The residue was crystallized by addition of 200 mL of cyclohexane and cooling to room temperature. The suspension was filtered and the filter cake was washed with cyclohexane and water and the crude product was dried under vacuum. The title product was obtained as light-brown solid (55.2 g, 90% of theory).

b) Preparation of Aromatic Amines b1) N-(4-methoxyphenyl)-4-phenyl-aniline

To a suspension of 11.6 g (50.0 mmol) of 4-bromo-1,1'-biphenyl, 9.20 g (74.7 mmol) of 4-methoxyaniline, and 7.18 g (74.7 mmol) of sodium tert-butanolate in 150 mL of toluene were added 0.29 g (1.00 mmol) of tri-tert-butylphosphine tetrafluoroborate and 1.04 g (1.00 mmol) of Pd$_2$(dba)$_3$ under an argon atmosphere. The mixture was heated at 90° C. for 19 h. After cooling, the mixture was added to 100 mL of half saturated aqueous NH$_4$Cl solution. The mixture was extended with 100 mL of ethyl acetate and the organic phase was separated. The aqueous phase was washed with ethyl acetate and the combined organic phases were washed with saturated NaCl solution. The organic phase was separated, dried with MgSO$_4$, and evaporated to dryness. The product was purified with column chromatography (cyclohexane/dichloromethane) to give the title compound as an off-white solid (7.1 g, 51%).

b2) N'-(4-Biphenylyl)-N,N-diphenyl-1,4-benzenediamine

To a suspension of 17.8 g (55.0 mmol) of 4-bromo-N,N-diphenylaniline, 8.46 g (50.0 mmol) of [1,1'-biphenyl]-4-amine, and 7.18 g (74.7 mmol) of sodium tert-butanolate in 150 mL of toluene were added 0.29 g (1.00 mmol) of tri-tert-butylphosphine tetrafluoroborate and 1.04 g (1.00 mmol) of Pd$_2$(dba)$_3$ under an argon atmosphere. The mixture was heated at 90° C. for 19 h. After cooling, the mixture was added to 100 mL of half saturated aqueous NH$_4$Cl solution. The mixture was extended with 100 mL of ethyl acetate and the organic phase was separated. The aqueous phase was washed with ethyl acetate and the combined organic phases were washed with saturated NaCl solution. The organic phase was separated, dried with MgSO$_4$, and evaporated to dryness. The product was purified with column chromatography (cyclohexane/dichloromethane) to give the title compound as an off-white solid (12.4 g, 60%).

b3) N-(9,9-dimethylfluoren-2-yl)-9,9-dimethyl-fluoren-2-amine

To a suspension of 22.6 g (82.7 mmol) of 2-bromo-9,9-dimethyl-9H-fluorene, 17.3 g (82.7 mmol) of 9,9-dimethyl-9H-fluoren-2-amine, and 23.8 g (248.1 mmol) of sodium tert-butanolate in 300 mL of toluene were added 0.96 g (3.31 mmol) of tri-tert-butylphosphine tetrafluoroborate and 3.03 g (3.31 mmol) of Pd$_2$(dba)$_3$ under an argon atmosphere. The mixture was heated at 90° C. for 19 h. After cooling, 40 mL of saturated aqueous NH$_4$Cl solution were added. After 30 minutes, the combined phases were filtered through celite and extended with 500 mL of dichloromethane and 250 mL of water. The organic phase was separated and the aqueous phase was washed with 200 mL of dichloromethane. The combined organic phases were washed with saturated NaCl solution, dried with MgSO$_4$, and evaporated to dryness. The crude solid was crystallised from toluene to give the title compound as a white solid (20.0 g, 60%).

b4) N-(9,9-dimethylfluoren-2-yl)dibenzofuran-2-amine

To a suspension of 9.0 g (36.4 mmol) of 2-bromodibenzo[b,d]furan, 11.4 g (54.6 mmol) of 9,9-dimethyl-9H-fluoren-2-amine, and 10.5 g (109.2 mmol) of sodium tert-butanolate in 200 mL of toluene were added 0.42 g (1.46 mmol) of tri-tert-butylphosphine tetrafluoroborate and 1.33 g (1.46 mmol) of Pd$_2$(dba)$_3$ under an argon atmosphere. The mixture was heated at 90° C. for 15 h. After cooling, 100 mL of saturated aqueous NH$_4$Cl solution were added. After 30 minutes, the combined phases were filtered through celite and extended with 100 mL of toluene. The organic phase was separated, and the aqueous phase was washed with 100 mL of toluene. The combined organic phases were dried with MgSO$_4$ and evaporated to dryness. The crude solid was crystallised from toluene/cyclohexane. The crude solid was purified with column chromatography (heptane/dichloromethane) to give the title compound as a white solid (6.9 g, 51%).

II. Preparation of Compounds of Formula (I)

Example 1

N-(4-methoxyphenyl)-3-[4-(N-(4-methoxyphenyl)-4-phenyl-anilino)phenyl]-1,1,3-trimethyl-N-(4-phenylphenyl)indan-5-amine

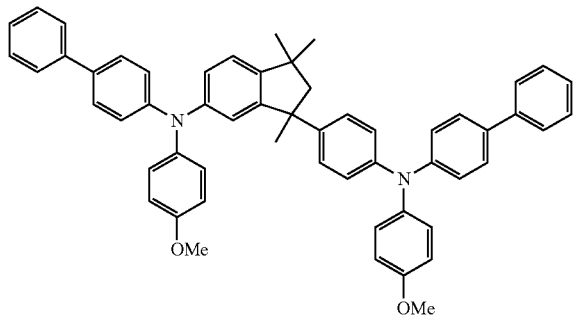 [SMILES: COc1ccc(N(c2ccc(-c3ccccc3)cc2)c2ccc(C3(C)CC(C)(C)c4ccc(N(c5ccc(OC)cc5)c5ccc(-c6ccccc6)cc5)cc43)cc2)cc1]

6.86 g (22.4 mmol) of N-(4-methoxyphenyl)-4-phenyl-aniline, 2.81 g (10.0 mmol) of 5-chloro-3-(4-chlorophenyl)-1,1,3-trimethylindane, and 2.88 g (30.0 mmol) of sodium tert-butanolate were suspended in 140 mL of toluene under an argon atmosphere. To this suspension, 0.23 g (0.50 mmol) of RuPhos, and 0.061 g (0.25 mmol) of palladium(II) acetate were added. The mixture was heated at 110° C. for 17 h. After cooling, the reaction mixture was poured on 300 mL of half saturated aqueous NH₄Cl solution. The organic phase was separated and the aqueous phase was extracted with ethyl acetate. The combined organic phases were washed with saturated NaCl solution and dried with MgSO₄ and evaporated to dryness. The solid crude title compound was purified with column chromatography (cyclohexane/dichloromethane) twice to give the title compound as a yellowish solid (7.5 g, 95%).

Example 2

N-[4-[6-[bis(9,9-dimethylfluoren-2-yl)amino]-1,3,3-trimethyl-indan-1-yl]phenyl]-N-(9,9-dimethylfluoren-2-yl)-9,9-dimethyl-fluoren-2-amine Route a)

20.0 g (49.8 mmol) bis(9,9-dimethyl-9H-fluoren-2-yl) amine, 6.90 g (22.6 mmol) of 5-chloro-3-(4-chlorophenyl)-1,1,3-trimethylindane, and 6.53 g (67.8 mmol) sodium tert-butanolate were suspended in 250 mL of toluene under an argon atmosphere. To this suspension, 0.53 g (1.13 mmol) of RuPhos, and 0.26 g (0.29 mmol) of Pd₂(dba)₃ were added. The mixture was heated at 110° C. for 17 h. After cooling, 100 mL of saturated aqueous NH₄Cl solution was added. After 30 minutes, 100 mL of ethyl acetate were added, the combined phases were filtered through celite and extended with 50 mL of ethyl acetate and 50 mL of water. The organic phases was separated, washed with saturated NaCl solution, dried with MgSO₄ and evaporated to dryness. The solid crude title compound was suspended in 300 mL of a 1:1 v/v mixture of acetone and isopropanol and heated to reflux. After cooling, the solid was filtrated off with suction, purified with column chromatography (pentane/dichloromethane) twice and crystallised from acetone/isopropanol to give the crude title compound as a white solid (15.6 g, 67%). 14.3 g of the crude title compound were purified further by vacuum zone sublimation (10⁻⁶-10⁻⁷ mbar, 240-300° C.) to give the title compound as a yellowish solid (10.7 g, purity >99.9% according to HPLC).

Route b)

9.32 g (35 mmol) of 6-amino-1-(4'-aminophenyl)-1,3,3-trimethylindane from example a8) were dissolved in 200 mL of toluene. 57.51 g (210.5 mmol) of 2-bromo-9,9-dimethylfluorene and 20.23 g (210.5 mmol) of sodium tert-butoxide were added under an argon atmosphere. 0.8 g (0.9 mmol) of tris(dibenzylideneacetone)dipalladium(0) and 1.63 g (3.5 mmol) of 2-dicyclohexylphosphino-2',6'-diisopropoxybiphenyl were subsequently added. The reaction mixture was heated at 110° C. for 24 h. After cooling, 40 mL of saturated aqueous NH₄Cl solution were added. The phases were separated and the aqueous phase was extracted twice with ethyl acetate. The combined organic phases were dried with MgSO₄ and evaporated to dryness. After column chromatography (dichloromethane/heptane) the crude product was crystallised from acetone/2-propanol. The title product was obtained as a white solid (18.9 g, 51% of theory). Of this product, 14.0 g are purified further by vacuum zone sublimation. The product is obtained as a yellowish solid (13.7 g, purity >99.9% according to HPLC).

Example 3

1,1,3-trimethyl-N,N-bis(4-phenylphenyl)-3-[4-(4-phenyl-N-(4-phenylphenyl)-anilino)phenyl]indan-5-amine

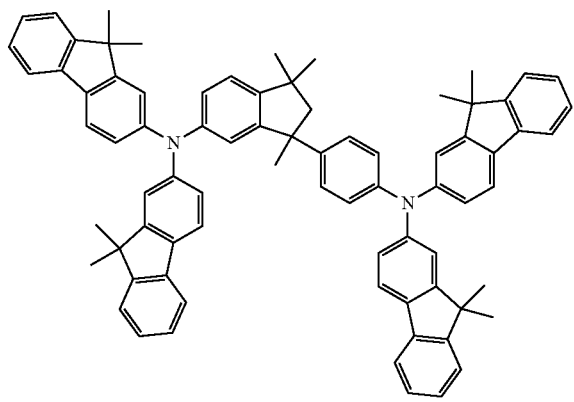 [SMILES: CC1(C)CC(C)(c2ccc(N(c3ccc4c(c3)C(C)(C)c3ccccc3-4)c3ccc4c(c3)C(C)(C)c3ccccc3-4)cc2)c2cc(N(c3ccc4c(c3)C(C)(C)c3ccccc3-4)c3ccc4c(c3)C(C)(C)c3ccccc3-4)ccc21]

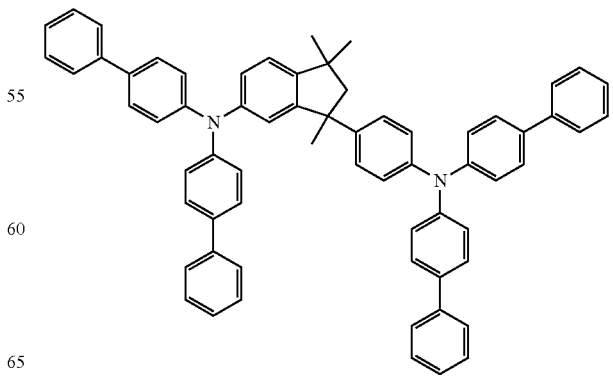

22.0 g (68.4 mmol) of di([1,1-biphenyl]-4-yl)amine, 9.50 g (31.1 mmol) of 5-chloro-3-(4-chlorophenyl)-1,1,3-trimethylindane, and 9.0 g (93.3 mmol) of sodium tert-butanolate were suspended in 190 mL of toluene under an argon atmosphere. To this suspension, 0.73 g (1.56 mmol) of RuPhos, and 0.36 g (0.39 mmol) Pd$_2$(dba)$_3$ were added. The mixture was heated at 110° C. for 20 h. After cooling, 20 mL of saturated aqueous NH$_4$Cl solution was added. After 30 minutes, 200 mL of half saturated aqueous NH$_4$Cl solution was added and the combined phases were filtered through celite and extended with 200 mL of toluene. The organic phase was separated and the aqueous phase was extracted with 200 mL of toluene. The combined organic phases were dried with Na$_2$SO$_4$ and evaporated to dryness. The crude solid was suspended in 280 mL of a 3:1 v/v mixture of acetone and isopropanol and heated under reflux for 1 h. After cooling, the solid was filtrated off with suction and then suspended in 250 mL of acetone. The suspension was heated under reflux for 1 h. After cooling, the solid was filtered off under suction, purified with column chromatography (heptane/dichloromethane) and crystallised from isopropanol/acetone/dichloromethane to give the crude title compound as a yellowish solid (17.2 g, 63%). 11.98 g of the crude title compound were purified further by vacuum zone sublimation ($10^{-6}$-$10^{-7}$ mbar, 240-310° C.) to give a yellowish solid (11.5 g, purity >99.9% according to HPLC 329 nm).

Example 4

N-[4-[6-(N-(9,9-dimethylfluoren-2-yl)-4-phenylanilino)-1,3,3-trimethyl-indan-1-yl]-phenyl]-9,9-dimethyl-N-(4-phenylphenyl)fluoren-2-amine

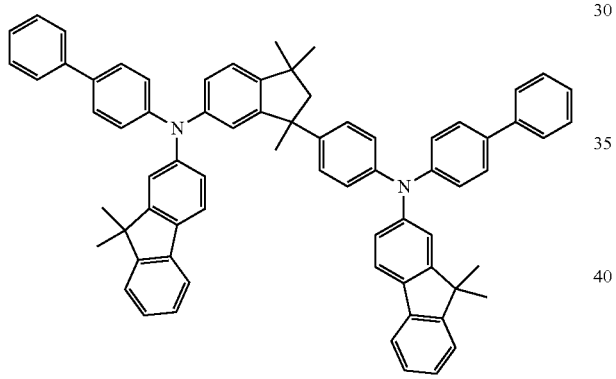

16.8 g (46.3 mmol) N-([1,1'-biphenyl]-4-yl)-9,9-dimethyl-9H-fluoren-2-amine, 6.43 g (21.1 mmol) of 5-chloro-3-(4-chlorophenyl)-1,1,3-trimethylindane, and 6.1 g (63.3 mmol) of sodium tert-butanolate were suspended in 200 mL of toluene under an argon atmosphere. To this suspension, 0.49 g (1.06 mmol) of RuPhos, and 0.24 g (0.26 mmol) Pd$_2$(dba)$_3$ were added. The mixture was heated at 110° C. for 18 h. After cooling, 20 mL of saturated aqueous NH$_4$Cl solution were added. After 30 minutes, 200 mL of half saturated aqueous NH$_4$Cl solution was added. The combined phases were filtered through celite and extended with 200 mL of toluene. The organic phase was separated and the aqueous phase was extracted with 200 mL of toluene. The combined organic phases were dried with MgSO$_4$ and evaporated to dryness. The crude solid was suspended in 200 mL of a 1:1 v/v mixture of acetone and isopropanol and heated to reflux. After cooling, the solid was filtrated off with suction and purified with column chromatography (hexane/dichloromethane) three times. The solid crude title compound was crystallised from isopropanol/acetone to give the title compound as a white solid (6.5 g, 32%). 3.23 g of the title compound were purified further by vacuum zone sublimation ($10^{-6}$-$10^{-7}$ mbar, 240-300° C.) to give the title compound as a yellowish solid (2.73 g, purity >99.9% according to HPLC).

Example 5

N4,N4-diphenyl-N1-(4-phenylphenyl)-N1-[4-[1,3,3-trimethyl-6-(4-phenyl-N-[4-(N-phenylanilino)phenyl]anilino)indan-1-yl]phenyl]benzene-1,4-diamine

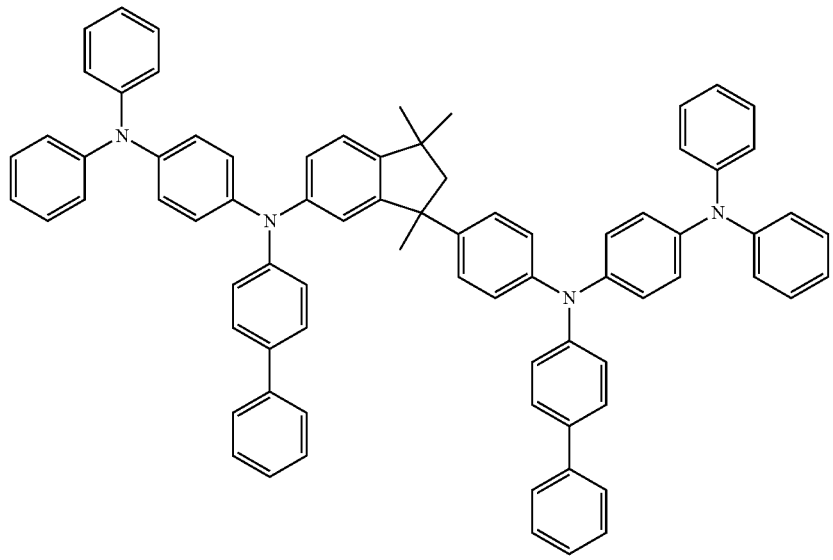 [SMILES: CC1(C)CC(C)(c2ccc(N(c3ccc(-c4ccccc4)cc3)c3ccc(N(c4ccccc4)c4ccccc4)cc3)cc2)c2cc(N(c3ccc(-c4ccccc4)cc3)c3ccc(N(c4ccccc4)c4ccccc4)cc3)ccc21]

11.37 g (27.6 mmol) of N'-(4-biphenylyl)-N,N-diphenyl-1,4-benzenediamine, 3.82 g (12.5 mmol) of 5-chloro-3-(4-chlorophenyl)-1,1,3-trimethylindane, and 3.62 g (37.6 mmol) of sodium tert-butanolate were suspended in 150 mL of toluene under an argon atmosphere. To this suspension, 0.29 g (0.63 mmol) of RuPhos and 0.077 g (0.31 mmol) of palladium(II) acetate were added. The mixture was heated at 110° C. for 16 h. After cooling, the reaction mixture was poured on 300 mL of half saturated aqueous NH$_4$Cl solution. The organic phase was separated and the aqueous phase was extracted with ethyl acetate. The combined organic phases were washed with saturated NaCl solution, dried with MgSO$_4$ and evaporated to dryness. The crude solid was purified with column chromatography (cyclohexane/dichloromethane) twice to give the title compound as a yellowish solid (10.9 g, 82%). 1.98 g of the title compound were purified further by vacuum zone sublimation ($10^{-6}$-$10^{-7}$ mbar, 270-320° C.) to give a yellowish solid (1.67 g, purity >99.9% according to HPLC).

Example 6

N-[4-[6-[dibenzofuran-2-yl-(9,9-dimethylfluoren-2-yl)amino]-1,3,3-trimethyl-indan-1-yl]phenyl]-N-(9,9-dimethylfluoren-2-yl)dibenzofuran-2-amine

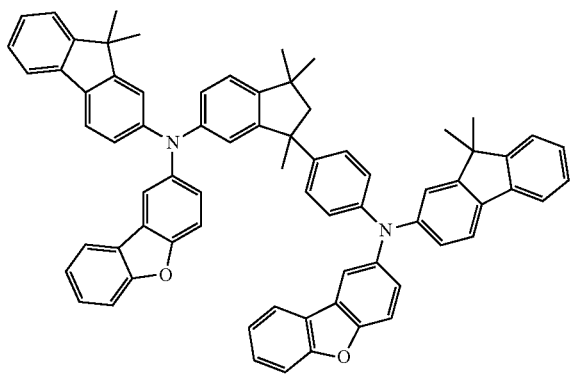 [SMILES: CC1(C)CC(C)(c2ccc(N(c3ccc4c(c3)C(C)(C)c3ccccc3-4)c3ccc4oc5ccccc5c4c3)cc2)c2cc(N(c3ccc4c(c3)C(C)(C)c3ccccc3-4)c3ccc4oc5ccccc5c4c3)ccc21]

6.8 g (18.0 mmol) N-(9,9-dimethyl-9H-fluoren-2-yl)dibenzo[b,d]furan-2-amine, 2.50 g (8.2 mmol) of 5-chloro-3-(4-chlorophenyl)-1,1,3-trimethylindane, and 2.36 g (24.5 mmol) sodium tert-butanolate were suspended in 81 mL of toluene under an argon atmosphere. To this suspension, 0.19 g (0.41 mmol) RuPhos, and 0.094 g (0.10 mmol) Pd$_2$(dba)$_3$ were added. The mixture was heated at 110° C. for 20 h. After cooling, 20 mL of saturated aqueous NH$_4$Cl solution was added. After 30 minutes, additional 100 mL of saturated aqueous NH$_4$Cl solution and 50 mL of toluene were added and the combined phases were filtered through celite. The organic phase was separated, dried with MgSO$_4$ and evaporated to dryness. The product was purified with column chromatography (hexane/dichloromethane) and crystallised from tert-butylmethyl ether/methanol. The solid was purified with column chromatography (pentane/dichloromethane) to give the title compound as a white solid (4.6 g, 57%). Of this product, 1.87 g were purified further by vacuum zone sublimation ($10^{-6}$-$10^{-7}$ mbar, 250-310° C.) to give the title compound as a yellowish solid (1.65 g, purity >99.9% according to HPLC).

Example 7

9-[3-(4-carbazol-9-ylphenyl)-1,1,3-trimethyl-indan-5-yl]carbazole

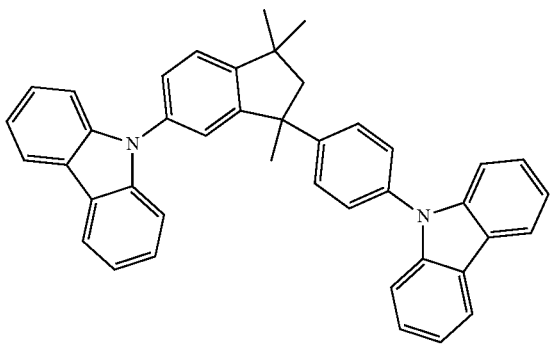 [SMILES: CC1(C)CC(C)(c2ccc(-n3c4ccccc4c4ccccc43)cc2)c2cc(-n3c4ccccc4c4ccccc43)ccc21]

2.4 g (14.4 mmol) carbazole, 2.0 g (6.6 mmol) of 5-chloro-3-(4-chlorophenyl)-1,1,3-trimethylindane and 1.38 g (14.4 mmol) of sodium tert-butanolate were suspended in 58 mL of toluene under an argon atmosphere. To this suspension, 0.19 g (0.66 mmol) tri-tert-butylphosphine tetrafluoroborate and 0.60 g (0.66 mmol) Pd$_2$(dba)$_3$ were added. The mixture was heated at 110° C. for 19 h. After cooling, 20 mL of saturated aqueous NH$_4$Cl solution was added. After 30 minutes, 100 mL of water and 100 mL of toluene were added. The organic phase was separated and the aqueous phase was washed with 150 mL of toluene. The combined organic phases were dried with MgSO$_4$ and evaporated to dryness. The product was purified with column chromatography (heptane/dichloromethane) to give the title compound as a white solid (2.5 g, 67%).

Example 8

N-[4-[5(6)-[bis(9,9-dimethylfluoren-2-yl)amino]-1,3,3-trimethyl-indan-1-yl]phenyl]-N-(9,9-dimethyl-fluoren-2-yl)-9,9-dimethyl-fluoren-2-amine

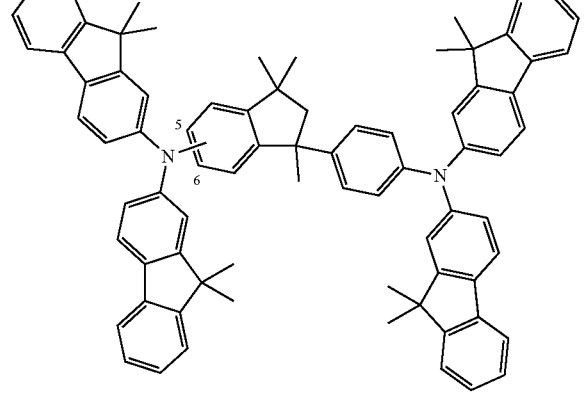

The mixture of N-[4-[5-[bis(9,9-dimethylfluoren-2-yl)amino]-1,3,3-trimethyl-indan-1-yl]-phenyl]-N-(9,9-dimethylfluoren-2-yl)-9,9-dimethyl-fluoren-2-amine and N-[4-[6-[bis(9,9-dimethylfluoren-2-yl)amino]-1,3,3-trimethylindan-1-yl]phenyl]-N-(9,9-dimethylfluoren-2-yl)-9,9-dimethyl-fluoren-2-amine was prepared in analogy to the process described in example 2, route b) but using 5(6)-amino-1-(4'-aminophenyl)-1,3,3-trimethylindane instead of 6-amino-1-(4'-aminophenyl)-1,3,3-trimethylindane as starting material. Yield: 82%, purity >99.9% according to HPLC. Examples 9-11 were prepared in analogy to the processes described above.

| Example | Compound |
|---------|----------|
| 9 | |
| 10 | |
| 11 | |

Example 12

4-phenyl-N-(4-phenylphenyl)-N-[4-[4-[1,3,3-trimethyl-6-[4-(4-phenyl-N-(4-phenyl-phenyl)anilino)phenyl]indan-1-yl]phenyl]phenyl]aniline

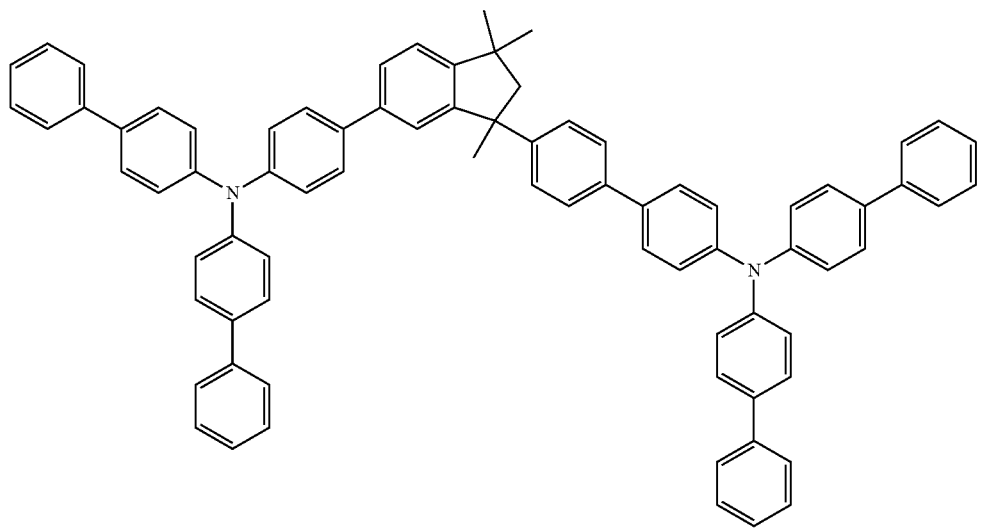 [SMILES: CC1(C)CC(C)(c2ccc(-c3ccc(N(c4ccc(-c5ccccc5)cc4)c4ccc(-c5ccccc5)cc4)cc3)cc2)c2cc(-c3ccc(N(c4ccc(-c5ccccc5)cc4)c4ccc(-c5ccccc5)cc4)cc3)ccc21]

2.00 g (6.17 mmol) of the compound from example a7), 5.88 g (12.3 mmol) of N-(4-bromophenyl)-4-phenyl-N-(4-phenylphenyl)aniline, 69.3 mg (0.31 mmol) of Pd(OAc)$_2$, 126 mg (0.309 mmol) of SPhos and 5.24 g (24.7 mmol) K$_3$PO$_4$ were suspended in 20 mL of toluene/n-butanol 1:1 v/v under an argon atmosphere. The resulting suspension was heated at 100° C. for 22 h and allowed to cool to room temperature. The suspension was filtered through celite and evaporated to dryness. The product was purified with column chromatography (heptane/dichloromethane). The title product was obtained as a white solid (3.6 g, 57%).

III. Use Examples

Compounds of formula (I) were tested and characterized by use of different types of stack architectures, in particular injection type devices and p-i-n type (positive-intrinsic-negative) devices.

Use Example 1: Production of an OLED 1 Using a Compound of the Invention Als Hole Transport Material in an Injection Type Stack Architecture A clean glass substrate was vacuum-deposited with indium tin oxide (ITO) through a mask to form a pattern of transparent electrodes. The ITO surface was treated with a plasma oxygen. Next, the ITO substrate was placed into a vacuum coating machine and when the pressure was $10^{-6}$ mbar, the materials listed in table I and finally a cathode were in turn evaporated onto the ITO layer. The ITO layer was correspondingly encapsulated by cavity glass after cathode evaporation. Table I also includes the thickness of the layers.

TABLE I

| Material | | Thickness [nm] | Remarks |
|---|---|---|---|
| Cathode | Al | 100 | |
| EIL | LiQ | 1 | |
| ETL | TDSF:LiQ | 60 | 1:1 |
| HBL | TDSF | 10 | |
| EML | NPB:Ir(MDQ)$_2$acac | 20 | 10% Ir(MDQ)$_2$acac |
| HTL | compound of formula (I) | 200 | |
| HIL | HAT(CN)$_6$ | 10 | |
| Anode | ITO | 155 | |

The OLEDs are characterized by standard methods. For this purpose, the electroluminescence spectra, the current density, the current efficiency, the luminous efficiency and the external quantum efficiency are determined from current density-voltage-luminance characteristic lines. The electroluminescence spectra were recorded at a luminous density of 1000 cd/m$^2$ and the CIE 1931 x and y coordinates were then calculated from the electroluminescence spectra.

The following values were obtained for the electrical parameters using the compound from example 11. The reproducibility was evaluated on the basis of results obtained with 16 samples. The results were then averaged to produce the median value.

Voltage=4.5 V
Current Density (CD)=3.7 mA/cm$^2$
Current efficiency (CE)=27.1 cd/A
Luminous efficiency=18.9 lm/W
External quantum efficiency (EQE)=18.2%
C.I.E.x=0.620
C.I.E.y=0.377
Driving voltage @ 1 mA/cm$^2$=3.7 V
Driving voltage @ 10 mA/cm$^2$=5.5 V
Reverse current density j(V_rev, max)=4.5E−05 mA/cm$^2$ Use Example 2: Production of an OLED 2 Using One and the Same Compound of the Invention Als Hole Transport Material as Well as Electron Blocking Material in a p-i-n Type Stack Architecture The procedure of use example 1 was repeated except that the materials listed in table II below were used.

TABLE II

| | Material | Thickness [nm] | Remarks |
|---|---|---|---|
| Cathode | Al | 100 | |
| EIL | LiQ | 1 | |
| ETL | TDSF:LiQ | 60 | 1:1 |
| HBL | TDSF | 10 | |
| EML | NPB:Ir(MDQ)$_2$acac | 20 | 10% Ir(MDQ)$_2$acac |
| EBL | compound of formula (I) | 10 | |
| HTL | compound of formula (I):NDP-9 | 200 | 5% NDP-9 |
| Anode | ITO | 155 | |

The following values were obtained for the electrical parameters using the compound from example 8. The reproducibility was evaluated on the basis of results obtained with 16 samples. The results were then averaged to produce the median value.

Voltage=3.4 V
Current Density (CD)=4.5 mA/cm$^2$
Current efficiency (CE)=22.1 cd/A
Luminous efficiency=20.4 lm/W
External quantum efficiency (EQE)=15.6%
C.I.E.x=0.624
C.I.E.y=0.373
Driving voltage @ 1 mA/cm$^2$=2.9 V
Driving voltage @ 10 mA/cm$^2$=3.8 V
Reverse current density j(V_rev, max)=2.5E-02 mA/cm$^2$ Use Example 3: Production of an OLED 3 Using Two Different Compounds of the Invention, One as Hole Transport Material an a Different One as Electron Blocking Material in a p-i-n Type Stack Architecture The procedure of use example 1 was repeated except that the materials listed in table III below were used.

TABLE III

| | Material | Thickness [nm] | Remarks |
|---|---|---|---|
| Cathode | Al | 100 | |
| EIL | LiQ | 1 | |
| ETL | TDSF:LiQ | 60 | 1:1 |
| HBL | TDSF | 10 | |
| EML | NPB:Ir(MDQ)$_2$acac | 20 | 10% Ir(MDQ)$_2$acac |
| EBL | compound of formula (I) | 10 | |
| HTL | compound of formula (I):NDP-9 | 200 | 5% NDP-9 |
| Anode | ITO | 155 | |

The following values were obtained for the electrical parameters using the compound from example 1 (use example 3a) and example 6 (use example 3b) respectively for the electron blocking layer and the compound from example 2 for the hole transport layer. The reproducibility was evaluated on the basis of results obtained with 8 samples. The results were then averaged to produce the median value.

Use example 3a:
EBL: compound from example 1
HTL: compound from example 2
Voltage=3.3 V
Current Density (CD)=4.1 mA/cm$^2$
Current efficiency (CE)=24.7 cd/A
Luminous efficiency=23.3 lm/W
External quantum efficiency (EQE)=17.4%
C.I.E.x=0.625
C.I.E.y=0.372
Driving voltage @ 1 mA/cm$^2$=2.8 V
Driving voltage @ 10 mA/cm$^2$=3.8 V
Reverse current density j(V_rev, max)=2.2E-02 mA/cm$^2$ Use example 3b:
EBL: compound from example 6
HTL: compound from example 2
Voltage=3.7 V
Current Density (CD)=4.7 mA/cm$^2$
Current efficiency (CE)=21.5 cd/A
Luminous efficiency=18.4 lm/W
External quantum efficiency (EQE)=15.7%
C.I.E.x=0.627
C.I.E.y=0.370
Driving voltage @ 1 mA/cm$^2$=3.1 V
Driving voltage @ 10 mA/cm$^2$=4.1 V
Reverse current density j(V_rev, max)=1.9E-02 mA/cm$^2$ Use Example 4: Production of an Organic Solar Cell Using a Compound of the Invention as Hole Transport Material The solar cell was produced in analogy to the procedure according to Hermenau et al., Solar Energy Materials & Solar Cells 95, 1268 (2011). The layer stack was as listed in table IV below.

TABLE IV

| Material | Thickness [nm] | Remarks |
|---|---|---|
| Al | 100 | |
| BPhen | 6 | |
| C60 | 30 | |
| ZnPc:C60 (1:1) | 30 | |
| compound of formula (I):NDP-9 | 30 | 5% NDP-9 |
| ITO | 155 | |

The solar cell was produced with the compound from example 8 and tested by use of an irradiation of AM1.5. The following values were obtained from the current density-voltage curve. The results are compiled in table V.

TABLE V

| | Compound from example 8 |
|---|---|
| P$_{max}$ | 3.18 mW/cm$^2$ |
| Short Circuit Current I$_{SC}$ | 11.0 mA/cm$^2$ |
| Open circuit Voltage V$_{OC}$ | 0.539 V |
| Fill factor FF | 53.6% |
| AM1.5 | 100 mW/cm$^2$ |
| efficiency eta | 3.18% |

P$_{max}$ = product of Maximum Power Point Voltage (V$_{mpp}$) and Maximum Power Point Current (I$_{mmp}$)

The current density-voltage characteristics of the organic photovoltaic cell (in the dark and under illumination) using the compound from example 8 is shown in FIG. 1. As illustrated in FIG. 1, the compound of formula (I) has a significant influence on device performance, in particular, the efficiency is remarkably increased in comparison to solar cells from prior art.

Use Example 5: Production of a Tandem Cell Using a Compound of the Invention as Hole Transport Layer and as Hole Transport Material in a Pn-Junction The tandem solar cell was produced in analogy to the procedure according to Rottinger et al., Solar Energy Materials & Solar Cells 154, 35 (2016). The layer stack was as listed in table VI below.

TABLE VI

| Material | Thickness [nm] | Remarks |
|---|---|---|
| Ag | 50 | |
| NHT-18:NDP-9 | 40 | NDP-9 (10%) |
| ZnPc:C60 | 30 | (1:1) |
| C60 | 10 | |
| C60:Novaled n-dopant | 10 | Novaled n-dopant (20%) |
| compound of formula (I):NDP-9 | 120 | NDP-9 (10%) |
| ZnPc:C60 | 30 | 1:1 |
| C60 | 10 | |
| C60:Novaled n-dopant | 10 | Novaled n-dopant (20%) |
| compound of formula (I):NDP-9 | 50 | NDP-9 (10%) |
| ITO | 155 | |

The solar cell was produced with the compound from example 2 and tested by use of an irradiation of AM1,5. The following values were obtained from the current density-voltage curve and are compiled in table VII:

TABLE VII

| | Compound from example 2 |
|---|---|
| $P_{max}$ | 3.58 mW/cm$^2$ |
| Short Circuit Current $I_{SC}$ | 6.2 mA/cm$^2$ |
| Open circuit Voltage $V_{OC}$ | 0.985 V |
| Fill factor FF | 58.2% |
| AM1.5 | 100 mW/cm$^2$ |
| efficiency eta | 3.58% |

$P_{max}$ = product of Maximum Power Point Voltage ($V_{mpp}$) and Maximum Power Point Current ($I_{mpp}$)

Figure 2:
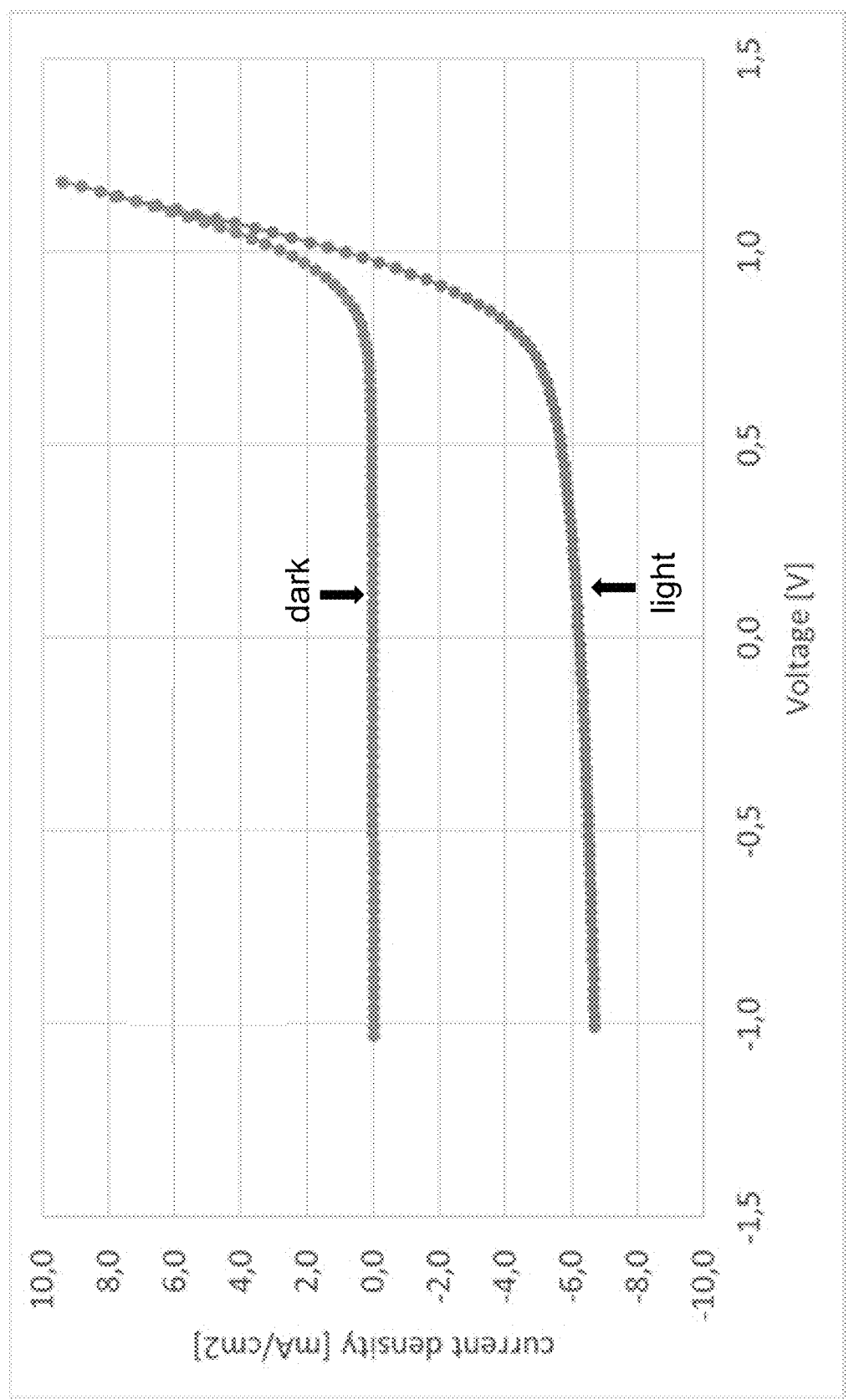
FIG. 2 illustrates current density-voltage characteristics of a tandem organic photovoltaic cell (in the dark and under illumination) using an exemplary compound as provided herein.

The current density-voltage characteristics of a tandem organic photovoltaic cell (in the dark and under illumination) using the compound from example 2 is shown in FIG. 2.

The results shown in FIG. 2 indicate that the compound of formula (I) has a significant influence on device performance, in particular, the efficiency is remarkably increased in comparison to solar cells from prior art.

Use Example 6: Conductivity Measurement Using F6TCNNQ as p-Dopant

General procedure: Glass substrates (35 mm×50 mm) were thoroughly cleaned and then coated with a 155-nm-thick layer of indium tin oxide (ITO) having trenches with a width of 20 μm, i.e. a trench separated two ITO sections. The trench was filled with a compound of formula (I) and F$_6$TCNNQ as p-dopant material by co-evaporation of the compound of formula (I) and the p-dopant material. Each doped layer had a thickness of 50 nm. After applying a voltage from 10 V between two ITO stripes, the conductivity was determined.

For each doping ratio (0% per volume, 1% per volume, 3% by volume, 5% by volume and 10% by volume), conductivity was determined for two different sample geometries (sample geometry A having a length of trench of 188 mm; sample geometry B having a length of trench of 146 mm), whereby the sample to be tested contained both geometries.

Example 6a: Conductivity of the Compound from Example 3 Doped with 2,2'-(perfluoronaphthalene-2,6-diylidene)dimalononitrile (F6TCNNQ) at Various Ratios The results are compiled in table VIII.

TABLE VIII

| | Conductivity of the hole transport material from example 3 at variant doping ratios | | |
|---|---|---|---|
| Sample Geometry | doping ratio [% by volume] | I [μA] | sigma [S/cm] |
| A | 0 | —[1)] | — |
| | 1% | 0.064 | 1.4E−07 |
| | 3% | 0.305 | 6.5E−07 |
| | 5% | 0.829 | 1.8E−06 |
| | 10% | 2.809 | 6.0E−06 |
| B | 0 | —[1)] | — |
| | 1% | 0.048 | 1.3E−07 |
| | 3% | 0.253 | 6.9E−07 |
| | 5% | 0.622 | 1.7E−06 |
| | 10% | 2.047 | 5.6E−06 |

[1)]too low to be measured

Example 6b: Conductivity of the Compound from Example 2 Doped with 2,2'-(perfluoronaphthalene-2,6-diylidene)dimalononitrile (F6TCNNQ) at Various Ratios The results are compiled in table IX.

TABLE IX

| | Conductivity of the hole transport material from example 2 at variant doping ratios | | |
|---|---|---|---|
| Sample Geometry | doping ratio [% by volume] | I [μA] | sigma [S/cm] |
| A | 0 | —[1)] | — |
| | 1% | 1.294 | 2.8E−06 |
| | 3% | 6.11 | 1.3E−05 |
| | 5% | 17.3 | 3.7E−05 |
| | 10% | 135 | 2.9E−04 |
| B | 0 | —[1)] | — |
| | 1% | 0.71 | 1.9E−06 |
| | 3% | 5.01 | 1.4E−05 |
| | 5% | 13.36 | 3.7E−05 |
| | 10% | 104 | 2.8E−04 |

[1)]too low to be measured

Use Example 7: Conductivity Measurement Using NDP-9 as p-Dopant Material

An evaporation pot was filled with 1.00 g of the mixture of regioisomers from example 8 and a first set of samples was prepared by coevaporation of the mixture of regioisomers from example 8 and NDP-9 (in an amount as indicated in table X) at a rate of 1 Angstrom per second. Evaporation of the mixture of regioisomers from example 8 was continued for 80 min at a rate of 1 Angstrom per second. Then, a second set of samples was prepared by coevaporation the mixture of regioisomers from example 8 and NDP-9 (in an amount as indicated in table X) at a rate of 1 Angstrom per second. After completion of the evaporation, the pot still contained 0.30 g of the mixture of regioisomers from example 8.

Glass substrates (35 mm×50 mm) were thoroughly cleaned and then coated with a 155-nm-thick layer of indium tin oxide (ITO) having trenches with a width of 20 μm, i.e. a trench separated two ITO sections. The trench was filled by evaporating the samples obtained above. Each layer had a thickness of 50 nm. After applying a voltage from 10 V between two ITO stripes, the conductivity was determined.

For each doping ratio, conductivity was determined for two different sample geometries (sample geometry A having a length of trench of 188 mm; sample geometry B having a length of trench of 146 mm), whereby the sample to be tested contained both geometries.

TABLE X

Conductivity of the hole transport material from the mixture of regioisomers from example 8 at variant doping ratios

| Sample Geometry | doping ratio [% by volume] | sigma [S/cm]# | sigma [S/cm]## |
|---|---|---|---|
| A | 0 | — | |
| | 1% | 4.8E−05 | 4.6E−05 |
| | 3% | 1.1E−04 | 1.2E−04 |
| | 5% | 2.6E−04 | 2.2E−04 |
| B | 0 | — | — |
| | 1% | 4.7E−05 | 4.8E−05 |
| | 3% | 1.2E−04 | 1.3E−04 |
| | 5% | 2.7E−04 | 2.2E−04 |

1) too low to be measured
first set of samples
second set of samples

As can be seen from table X, the conductivity of the mixture of regioisomers of the first set of samples is comparable to that of the second set of samples. The performance as shown above indicates a high conductivity of the regioisomeric mixture from example 8 regardless of the regioisomeric ratio, namely the ratio of the 5-isomer to the 6-isomer.

Use Example 8: Conductivity Measurement Using NDP-9 as p-Dopant Material

Glass substrates (35 mm×50 mm) were thoroughly cleaned and then coated with a 155-nm-thick layer of indium tin oxide (ITO) having trenches with a width of 20 μm, i.e. a trench separated two ITO sections. The trench was filled with the compound of formula I and NDP-9 as p-dopant material by co-evaporation of the compound from example 6 and the p-dopant material. Each doped layer had a thickness of 50 nm. After applying a voltage from 10 V between two ITO stripes, the conductivity was determined.

For each doping ratio (0% per volume, 1% per volume, 3% by volume, 5% by volume and 10% by volume), conductivity was determined for two different sample geometries (sample geometry A having a length of trench of 188 mm; sample geometry B having a length of trench of 146 mm), whereby the sample to be tested contained both geometries.

Example 8a: Conductivity of the Compound from Example 6 Doped with NDP-9 at Various Ratios The results are compiled in table XI.

TABLE XI

Conductivity of the hole transport material from example 6 at variant doping ratios.

| Sample Geometry | doping ratio [% by volume] | sigma [S/cm] |
|---|---|---|
| A | 0 | 2.1E−10 |
| | 1% | 1.5E−05 |
| | 3% | 4.1E−05 |
| | 5% | 7.2E−05 |
| | 10% | — |
| B | 0 | — |
| | 1% | 2.7E−10 |
| | 3% | 1.4E−05 |
| | 5% | 4.1E−05 |
| | 10% | 7.2E−05 |

Example 8b: Conductivity of the Compound from Example 11 Doped with NDP-9 at Various Ratios The results are compiled in table XI.

TABLE XI

Conductivity of the hole transport material from example 11 at variant doping ratios

| Sample Geometry | doping ratio [% by volume] | sigma [S/cm] |
|---|---|---|
| A | 0 | 2.1E−10 |
| | 1% | 3.4E−05 |
| | 3% | 7.3E−05 |
| | 5% | 1.1E−04 |
| | 10% | — |
| B | 0 | — |
| | 1% | 2.7E−10 |
| | 3% | 3.2E−05 |
| | 5% | 7.4E−05 |
| | 10% | 1.2E−04 |

The invention claimed is:

1. A compound of the general formula (I)

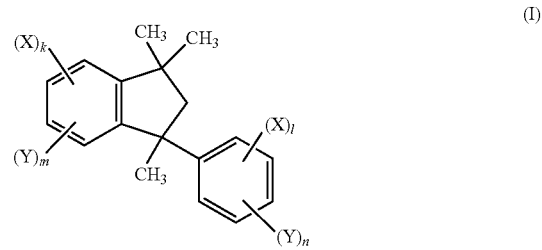

and mixtures thereof, wherein
X is independently on each occurrence selected from groups of the formula -A-(NAr$_2$), wherein
A is independently on each occurrence a chemical bond or phenylene which is unsubstituted or substituted by 1, 2 or 3 substituents independently selected from the group consisting of $C_1$-$C_6$ alkyl and $C_1$-$C_6$-alkoxy;
Ar is independently on each occurrence selected from in each case unsubstituted or substituted aryl, wherein two groups Ar bound to the same nitrogen atom may together with the nitrogen atom also form a fused ring system having 3 or more than 3 unsubstituted or substituted rings;

Y is independently on each occurrence selected from hydrogen, $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups and wherein the phenyl ring bound by a single bond to the phenylindane moiety bears at least one Y group in one of the ortho-positions on the phenyl ring relative to the phenylindane moiety that is hydrogen;

k is 1 or 2;
l is 1 or 2;
m is 2 or 3, wherein 0, 1, 2 or 3 of the m Y groups are different from hydrogen;
n is 3 or 4, wherein 0, 1, 2 or 3 of the n Y groups are different from hydrogen;
the sum of k and m is 4 and the sum of l and n is 5.

2. A compound of the formula (I) according to claim 1, which is selected from compounds (I.A), (I.B), (I.C), (I.D) and (I.E)

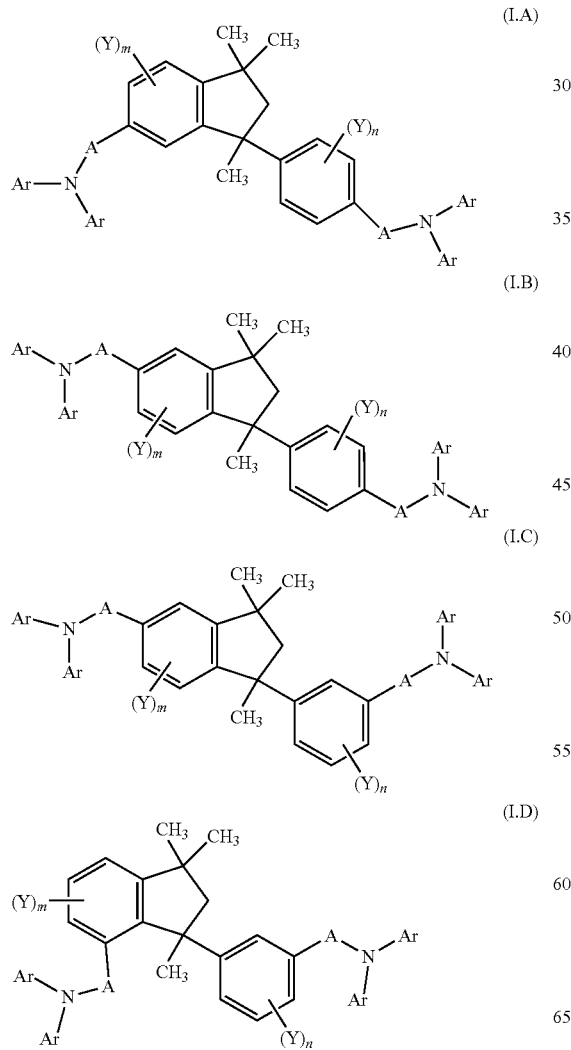

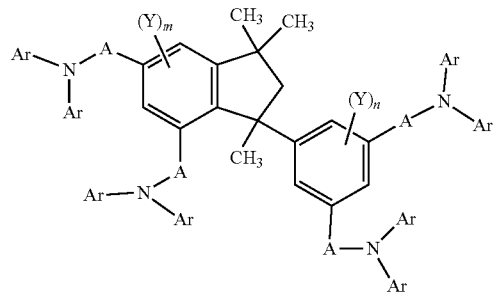

wherein Y, A and Ar are defined as in claim 1;
where in formulae (I.A), (I.B), (I.C) and (I.D):
m is 3, wherein 0, 1, 2 or 3 of the m Y groups are different from hydrogen; and
n is 4, wherein 0, 1, 2 or 3 of the n Y groups are different from hydrogen;
where in formula (I.E):
m is 2, wherein 0, 1 or 2 of the m Y groups are different from hydrogen; and
n is 3, wherein 0, 1 or 2 of the n Y groups are different from hydrogen.

3. A compound according to claim 1,
wherein the groups Ar are independently on each occurrence selected from phenyl, biphenylyl, terphenyl, quaterphenyl, wherein phenyl, biphenylyl, terphenyl and quaterphenyl are unsubstituted or substituted by one or more substituents $R^{Ar1}$;
naphthyl, anthracenyl, phenanthryl, fluorenyl, spirofluorenyl, C-bound carbazolyl, dibenzofuranyl and dibenzothiophenyl, wherein naphthyl, phenanthryl, fluorenyl, spirofluorenyl, C-bound carbazolyl, dibenzofuranyl and dibenzothiophenyl are unsubstituted or substituted by one or more substituents $R^{Ar2}$; or
2 groups Ar together with the nitrogen atom to which they are attached may form an N-bound carbazolyl, which is unsubstituted or substituted by one or more substituents $R^{Ar3}$;
wherein
each $R^{Ar1}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy,
diphenylamino, $C_5$-$C_8$-cycloalkyl and naphthyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy;
each $R^{Ar2}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy, diphenylamino, $C_5$-$C_8$-cycloalkyl and phenyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy and, in addition, in the case of fluorenyl, two geminal radicals $R^{Ar2}$ may form an alkylene group $(CH_2)_r$ with r being 4, 5, 6 or 7, where 1 or 2 hydrogen atoms in this group may be replaced by a methyl group or a methoxy group; and each $R^{Ar3}$ is independently selected from $C_1$-$C_6$-alkyl, $C_1$-$C_6$-alkoxy, diphenylamino and phenyl, wherein each of the cyclic rings in the two last-mentioned groups are unsubstituted or substituted by 1, 2, 3 or 4 different or identical substituents selected from $C_1$-$C_4$-alkyl and $C_1$-$C_4$-alkoxy.

4. A compound according to claim 1, wherein the groups Ar are independently on each occurrence selected from groups of the formulae (AR-I) to (AR-XLIV)

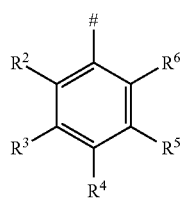
(AR-I)

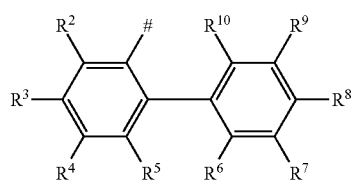
(AR-II)

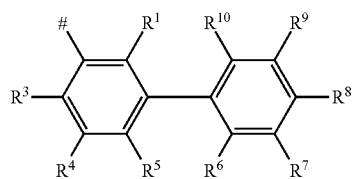
(AR-III)

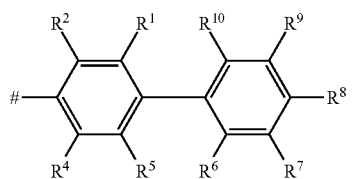
(AR-IV)

-continued

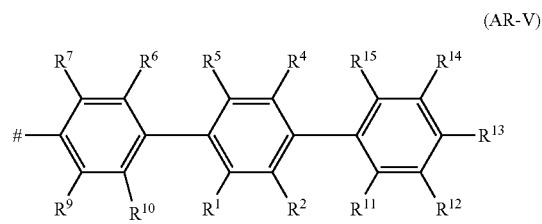
(AR-V)

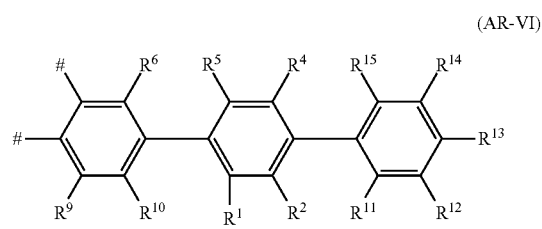
(AR-VI)

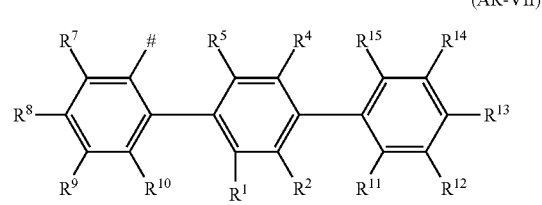
(AR-VII)

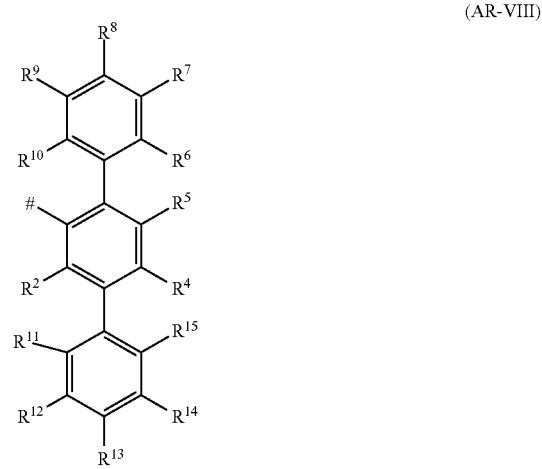
(AR-VIII)

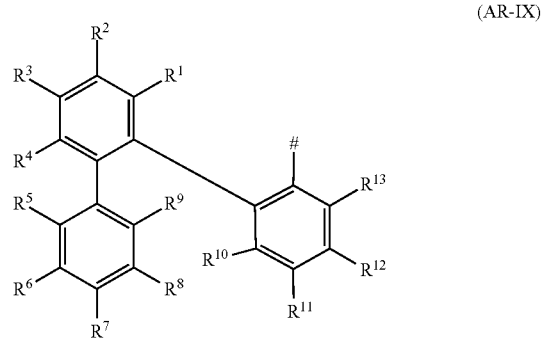
(AR-IX)

(AR-X)
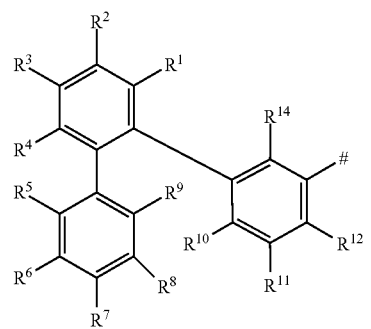
(AR-XI)
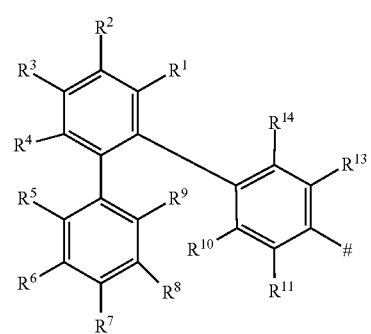
(AR-XII)
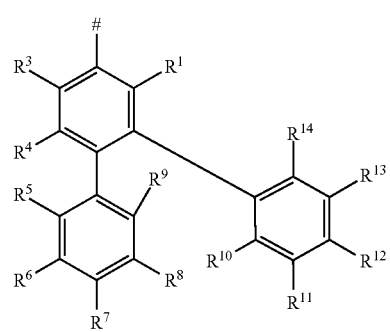
(AR-XIII)
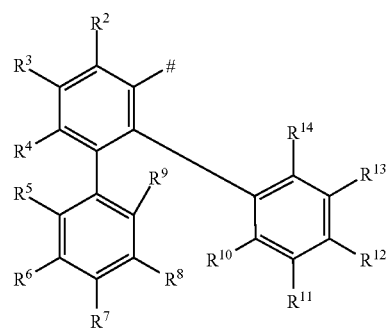
(AR-XIV)
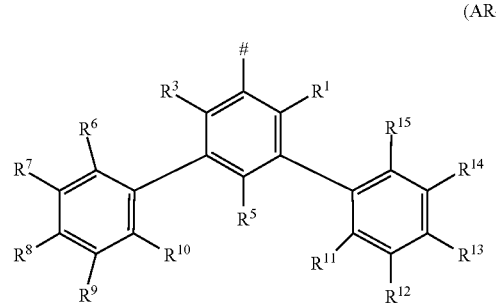
(AR-XV)
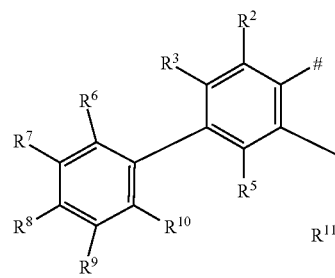
(AR-XVI)
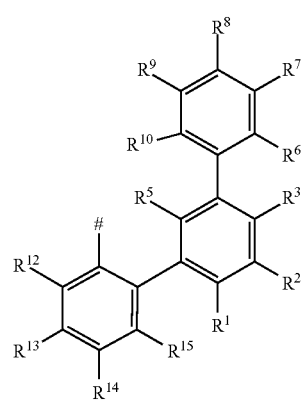
(AR-XVII)
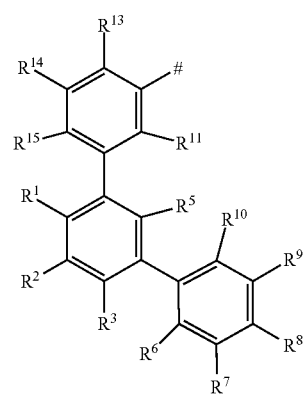
(AR-XVIII)
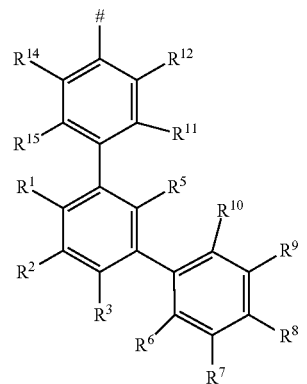

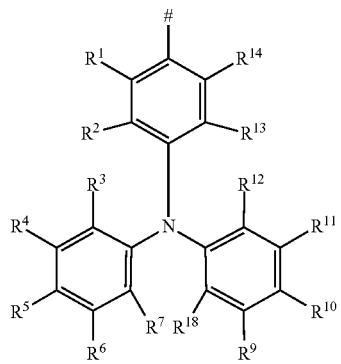 (AR-XIX)
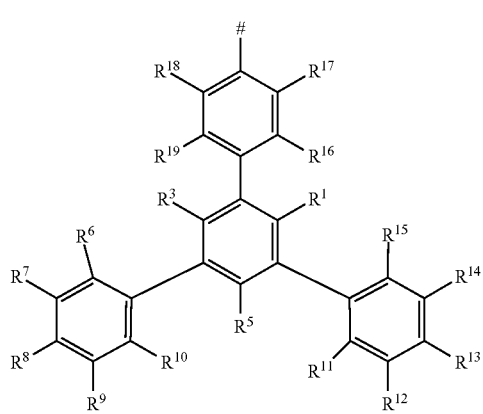 (AR-XX)
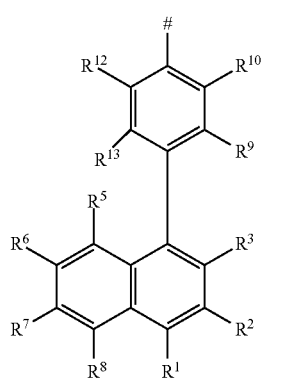 (AR-XXI)
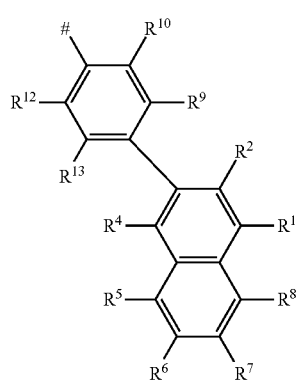 (AR-XXII)
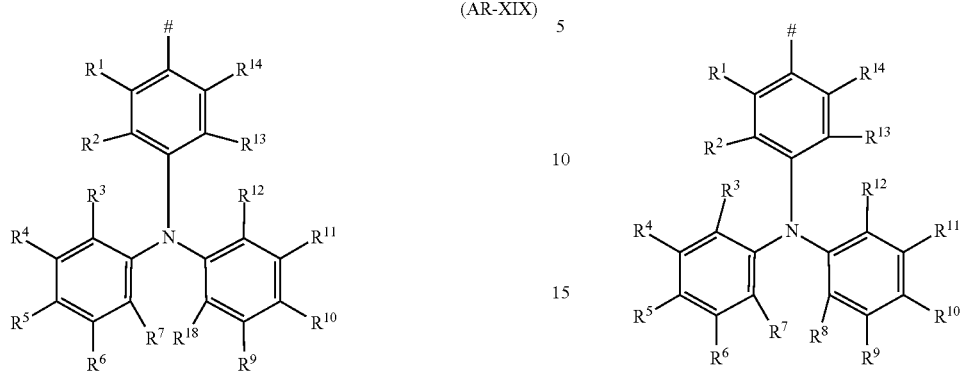 (AR-XXIII)
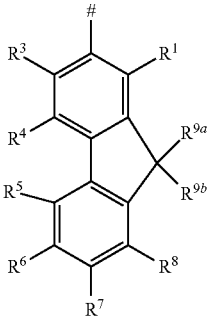 (AR-XXIV)
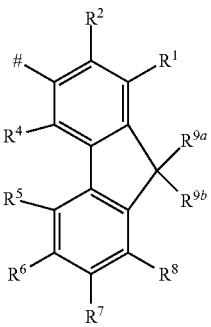 (AR-XXV)
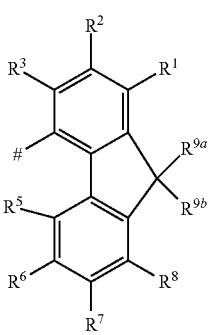 (AR-XXVI)

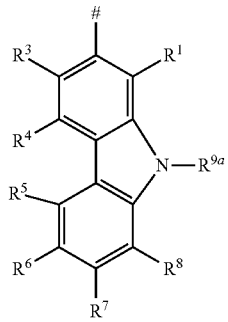
(AR-XXVII)
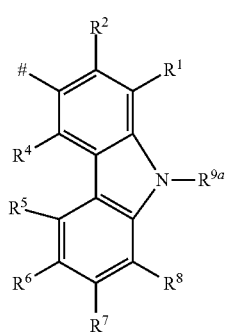
(AR-XXVIII)
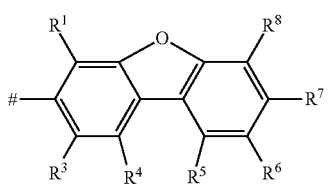
(AR-XXIX)
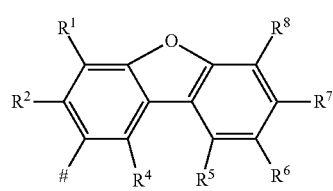
(AR-XXX)
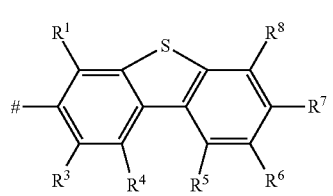
(AR-XXXI)
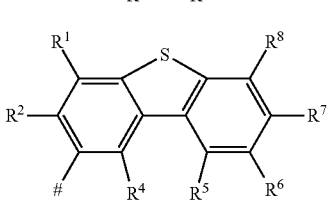
(AR-XXXII)
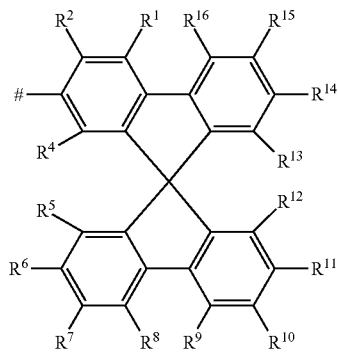
(AR-XXXIII)
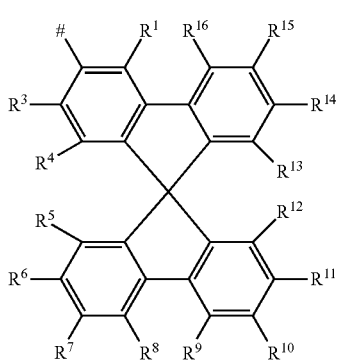
(AR-XXXIV)
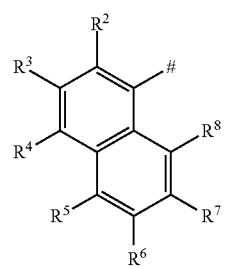
(AR-XXXV)
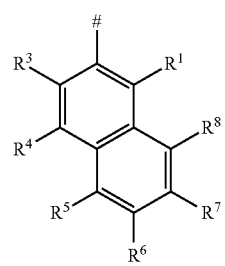
(AR-XXXVI)
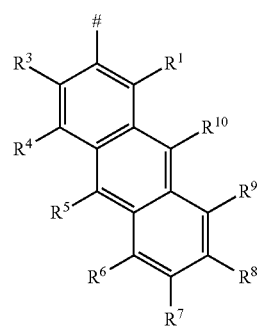
(AR-XXXVII)

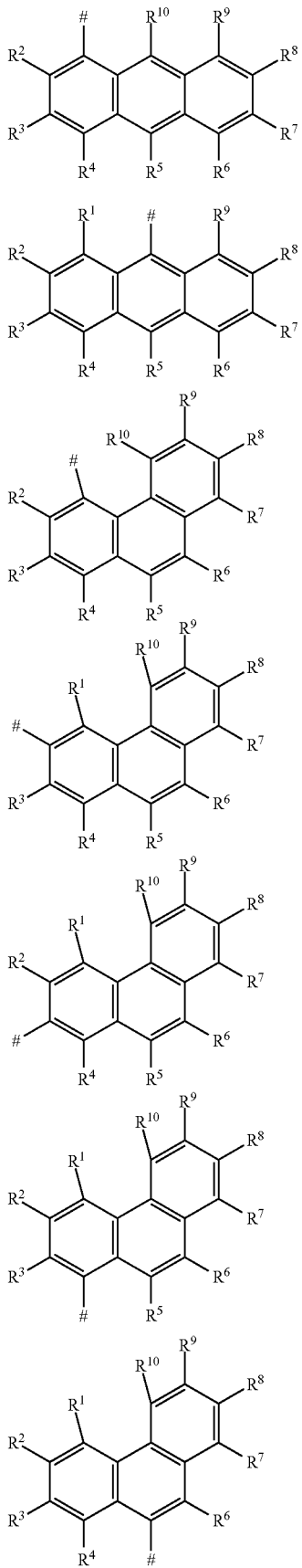

(AR-XXXVIII)

(AR-XXXIX)

(AR-XL)

(AR-XLI)

(AR-XLII)

(AR-XLIII)

(AR-XLIV)

wherein in each case denotes the bonding site to the nitrogen atom;

in formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII and AR-XXIII:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present, independently of one another, are selected from hydrogen, straight-chain or branched $C_1$-$C_4$-alkyl, straight-chain or branched $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy, phenyl, tolyl, xylyl, mesityl and anisyl;

in formulae AR-XXIV, AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII and AR-XLIV:

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, if present, independently of one another, are selected from hydrogen, straight-chain or branched $C_1$-$C_4$-alkyl, straight-chain or branched $C_1$-$C_4$-alkoxy, carbazol-9-yl and phenyl, wherein carbazol-9-yl and phenyl are unsubstituted or substituted by 1, 2 or 3 different or identical substituents selected from $C_1$-$C_4$-alkyl, $C_1$-$C_4$-alkoxy, phenyl, tolyl, xylyl and mesityl and, in addition, $R^{9a}$ and $R^{9b}$ in formulae AR-XXIV, AR-XXV and AR-XXVI together may form an alkylene group $(CH_2)_r$ with r being 4, 5 or 6 where 1 or 2 hydrogen atoms in this group may be replaced by a methyl or methoxy group.

5. A compound according to claim 1, wherein the groups ($NAr_2$) are independently on each occurrence selected from groups of the formulae (1)-(38)

(1)

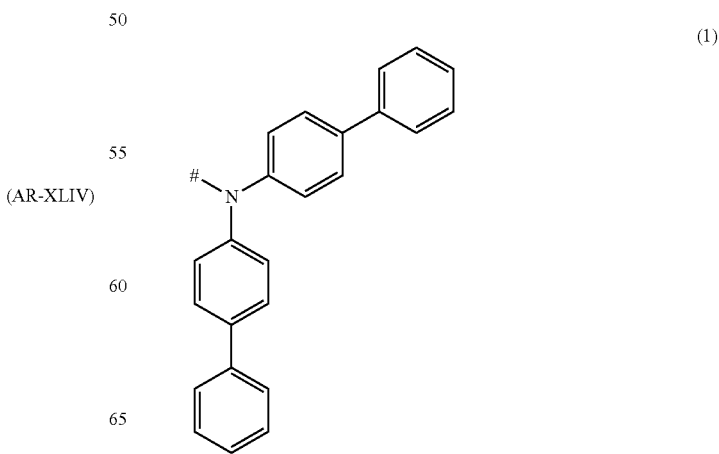

(2)
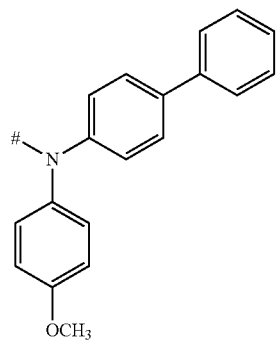
(3)
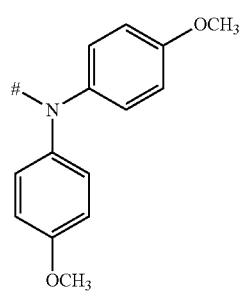
(4)
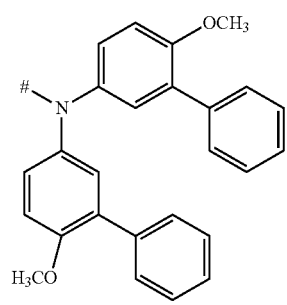
(5)
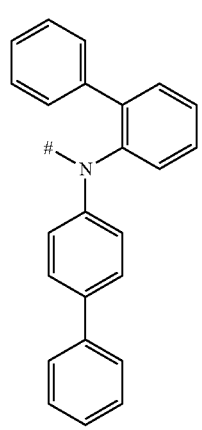
(6)
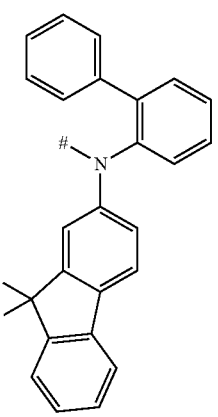
(7)
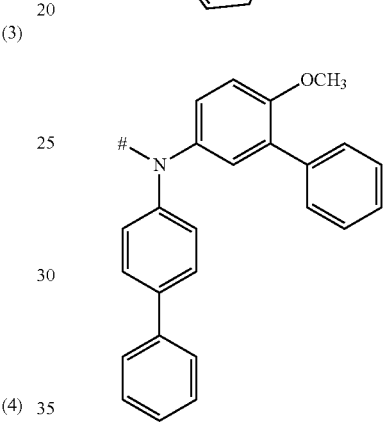
(8)
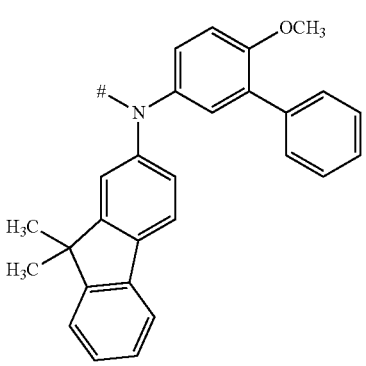
(9)
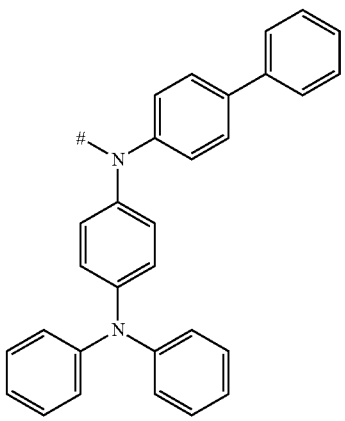

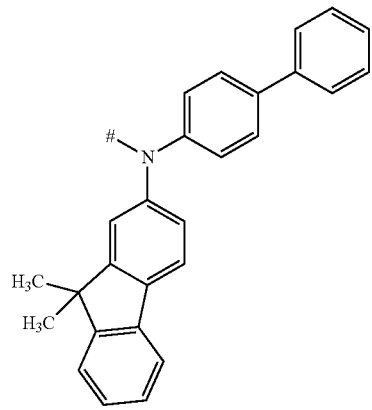
(10)
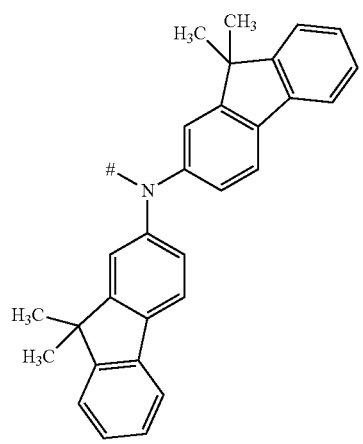
(11)
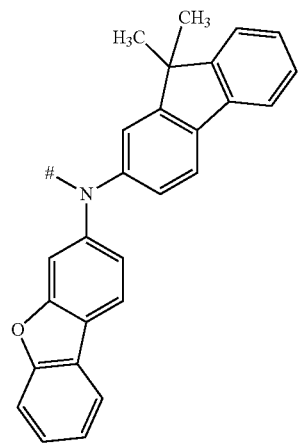
(12)
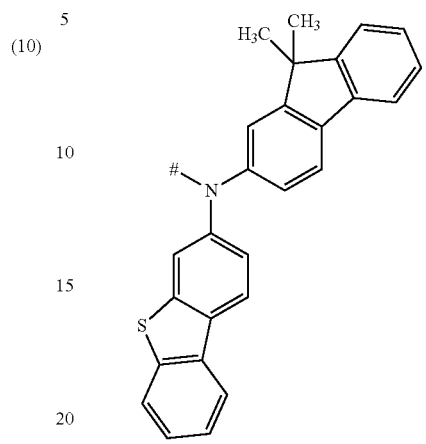
(13)
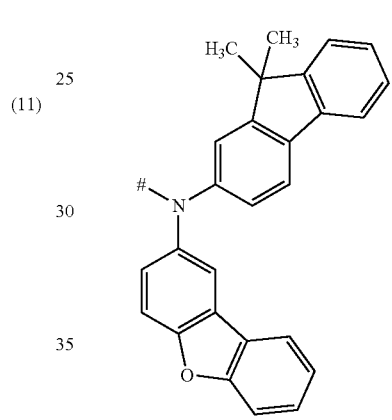
(14)
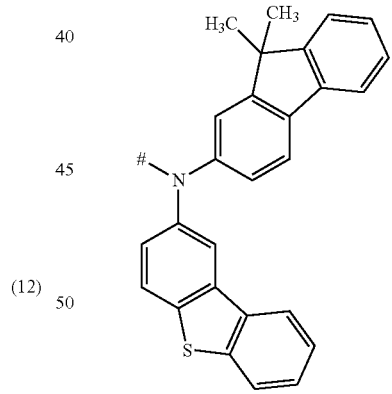
(15)
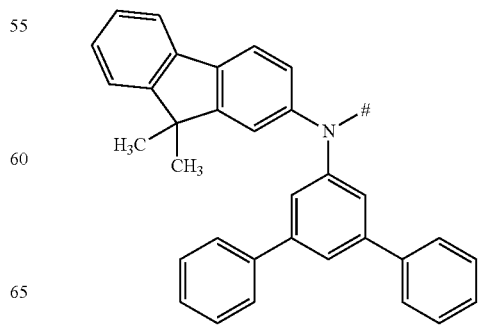
(16)

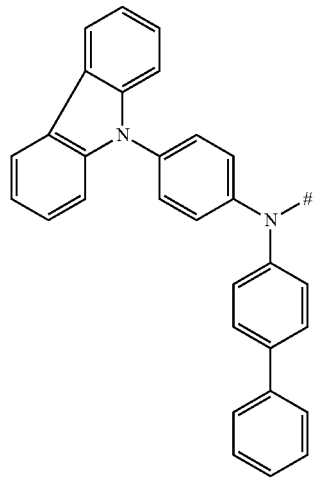
(17)
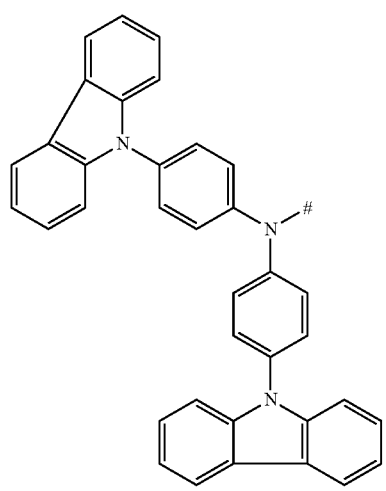
(18)
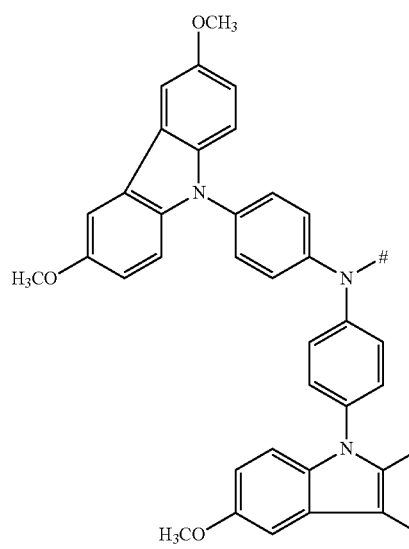
(19)
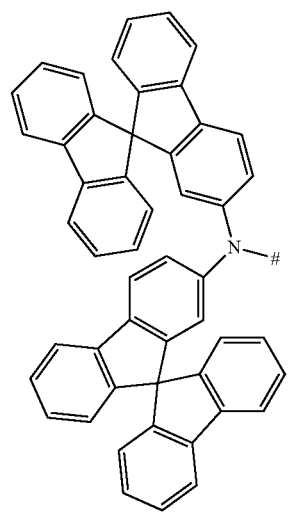
(20)
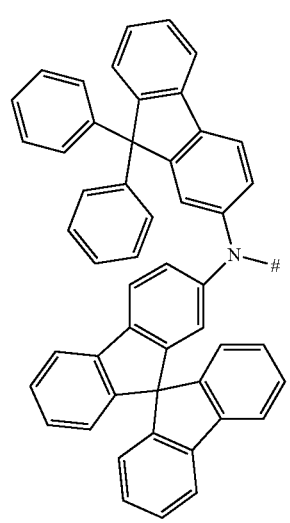
(21)
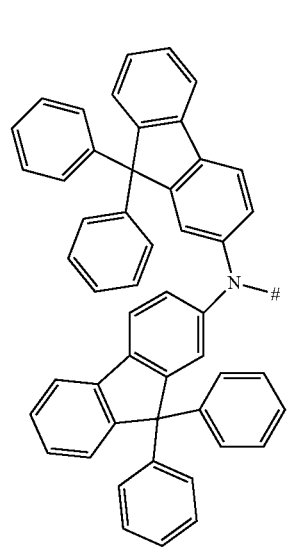
(22)

(23) 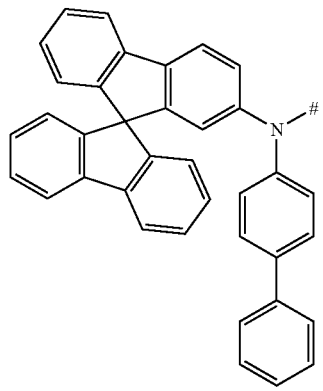
(24) 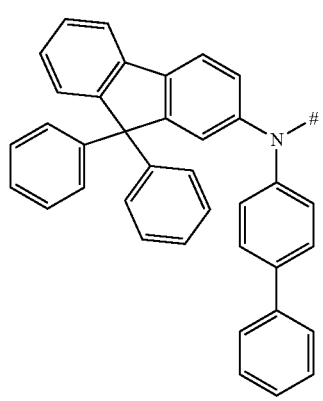
(25) 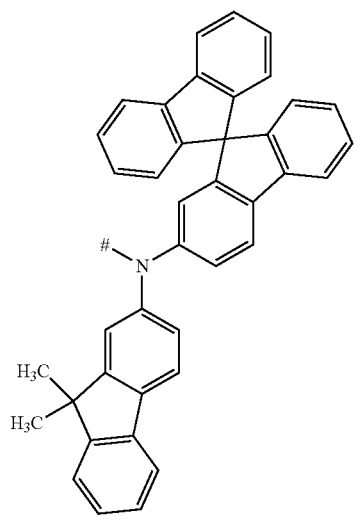
(26) 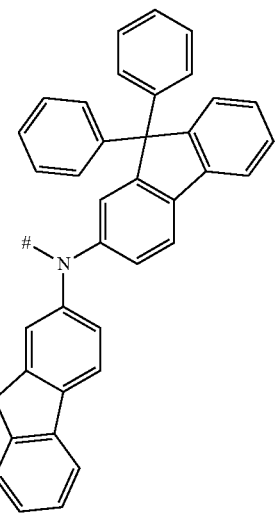
(27) 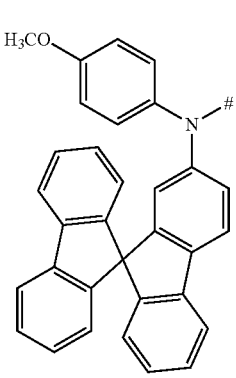
(28) 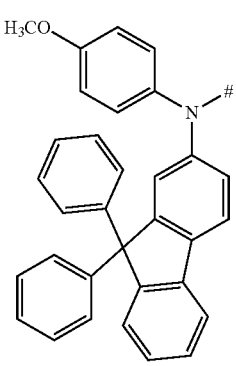
(29) 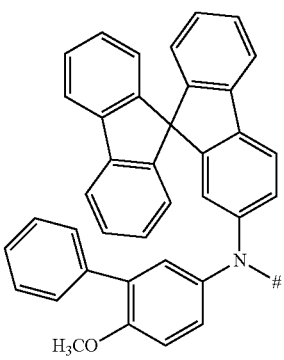

(30) 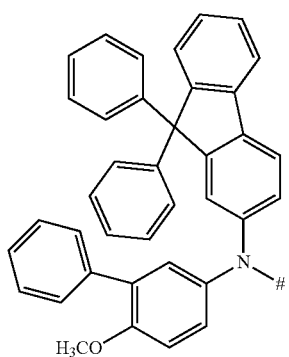
(31) 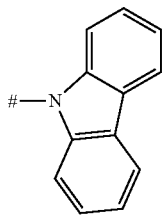
(32) 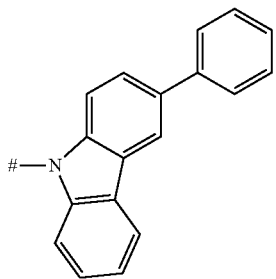
(33) 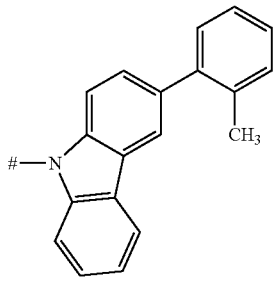
(34) 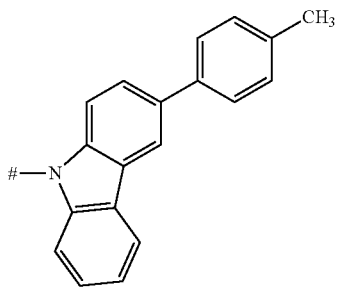
(35) 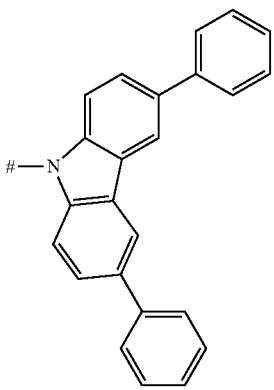
(36) 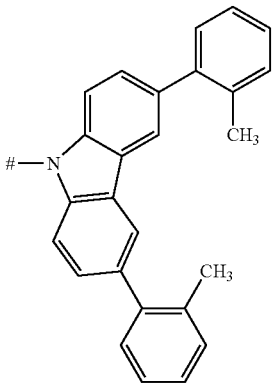
(37) 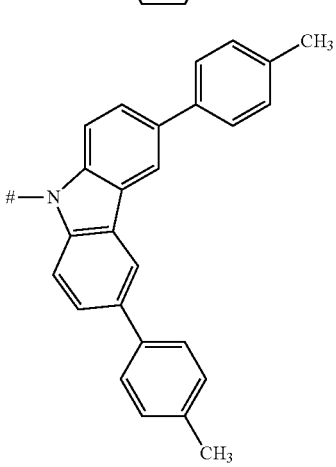
(38) 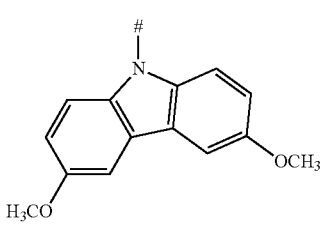
wherein
denotes the bonding side to the remainder of the compound.
6. A compound according to claim 1, wherein all groups (NAr$_2$) have the same meaning and the two groups Ar bound to the same nitrogen atom have different meanings.
7. A compound according to claim 1, wherein all groups Ar have the same meaning.

8. A compound according to claim 1, wherein said mixture comprises the compounds of formulae (I.A.a) and (I.B.a)

(I.A.a)

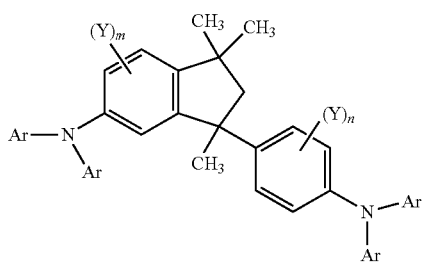

(I.B.a)

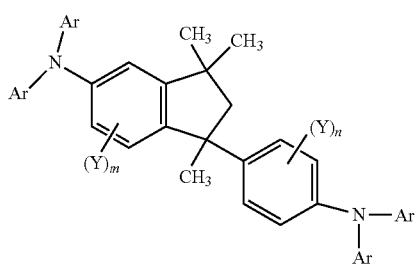

wherein each Y is independently defined as in claim 1; and each Ar is independently defined as in claim 1;

m is 3, wherein 0, 1, 2 or 3 of the m Y groups are different from hydrogen; and n is 4, wherein 0, 1, 2 or 3 of the n Y groups are different from hydrogen.

9. An electroluminescent arrangement comprising an upper electrode, a lower electrode, wherein at least one of said electrodes is transparent, an electroluminescent layer and optionally an auxiliary layer, wherein the electroluminescent arrangement comprises a mixture of compounds of formula (I) as defined in claim 8.

10. An electroluminescent arrangement as claimed in claim 9 comprising a mixture of compounds of formula (I) in a hole-transporting layer or electron blocking layer.

11. A compound according to claim 1, wherein said mixture comprises the compounds of formulae (I.C.a) and (I.D.a)

(I.C.a)

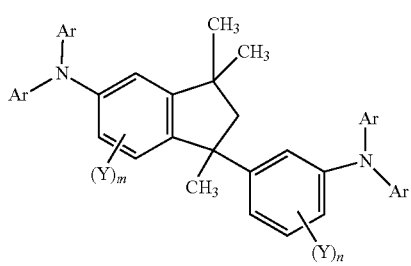

(I.D.a)

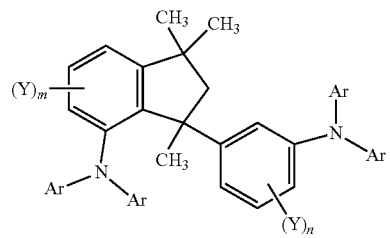

wherein each Y is independently defined as in claim 1;

each Ar is independently defined as in claim 1;

m is 3, wherein 0, 1 or 2 of the m Y groups are different from hydrogen; and n is 4, wherein 0, 1 or 2 of the n Y groups are different from hydrogen.

12. A process for the preparation of a compound of the formula (I.A.a), (I.A.a)

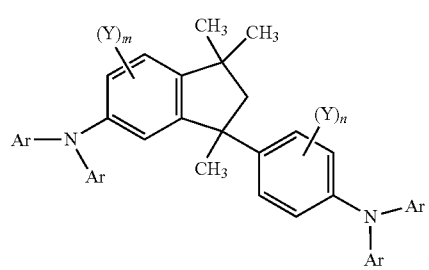

wherein each Ar is independently defined as in claim 1;

each Y is independently defined as in claim 1;

m is 3, wherein 0, 1, 2 or 3 of the m Y groups are different from hydrogen; and n is 4, wherein 0, 1, 2 or 3 of the n Y groups are different from hydrogen;

in which a1) an isopropenylbenzene compound of formula (II)

(II)

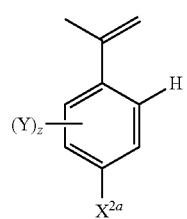

is provided, wherein $X^{2a}$ is selected from F, Cl, Br, I, O-benzyl, $CH_3SO_3$ and $CF_3SO_3$;

each Y is independently selected from hydrogen and $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups; and z is 3, wherein 0, 1, 2 or 3 of the z Y groups are different from hydrogen;

b1) the isopropenylbenzene compound of the formula (II) is subjected to a dimerization in the presence of an acidic catalyst resulting in the compound of the formula (III)

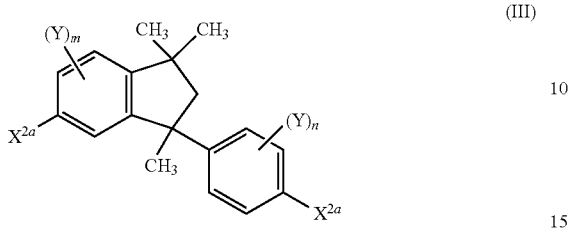
(III)

c1) the compound of the formula (III) is subjected to an amination reaction with at least one aromatic amine of formula (IV)

Ar$_2$NH     (IV)

in the presence of a palladium complex catalyst and a base to give the compound of the formula (I.A.a).

13. A process for the preparation of a compound of the formula (I.A.a),

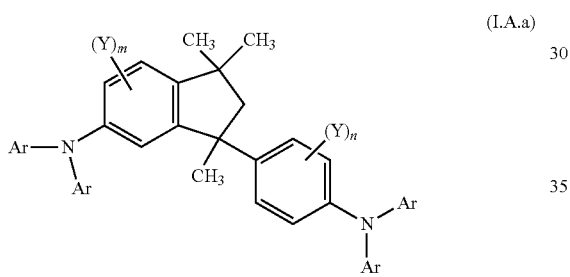
(I.A.a)

wherein
each Ar is independently defined as in claim 1;
each Y is independently defined as in claim 1;
m is 3, wherein 0, 1, 2 or 3 of the m Y groups are different from hydrogen; and
n is 4, wherein 0, 1, 2 or 3 of the n Y groups are different from hydrogen;
in which
a2) an isopropenylbenzene compound (II)

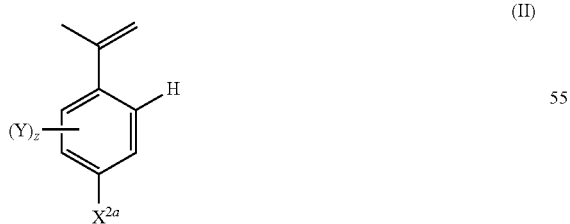
(II)

is provided, wherein
$X^{2a}$ is selected from F, Cl, Br, I, O-benzyl, CH$_3$SO$_3$ and CF$_3$SO$_3$;
each Y is independently selected from hydrogen, C$_1$-C$_6$-alkyl, C$_1$-C$_6$-alkoxy, C$_3$-C$_8$-cycloalkyl, C$_3$-C$_8$-cycloalkoxy, phenyl and phenyloxy, wherein each of the cyclic rings in the four last-mentioned groups are unsubstituted or substituted by 1, 2 or 3 C$_1$-C$_6$-alkyl groups; and
z is 3, wherein 0, 1, 2 or 3 of the z Y groups are different from hydrogen;

b2) the isopropenylbenzene compound of the formula (II) is subjected to a dimerization in the presence of an acidic catalyst resulting in the compound of the formula (III)

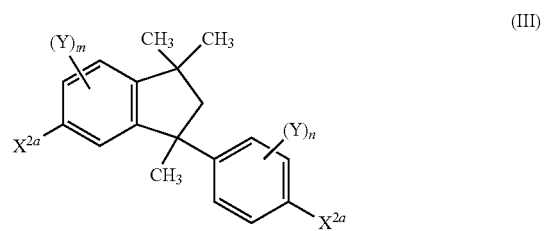
(III)

c2) the compound of formula (III) is subjected to an amination reaction with an alkali bis(trialkylsilyl) amide in the presence of a palladium complex catalyst followed by removal of the trialkylsilyl protecting group to give a compound of the formula (V)

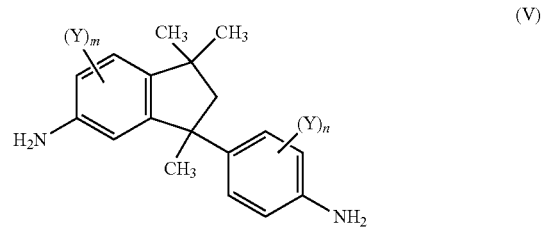
(V)

d2) the compound of the formula (V) is subjected to an arylation reaction with at least one aromatic compound of formula (VI)

Ar—$X^{2b}$     (VI)

wherein $X^{2b}$ is selected from F, Cl, Br, I, O-benzyl, CH$_3$SO$_3$ and CF$_3$SO$_3$,
in the presence of a palladium complex catalyst and a base to give the compound of the formula (I.A.a).

14. A process for the preparation of a mixture of the compounds (I.A.a.1) and (I.B.a.1)

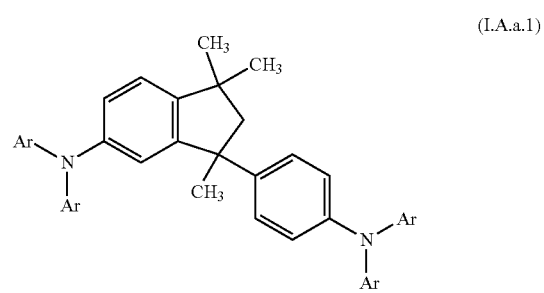
(I.A.a.1)

-continued

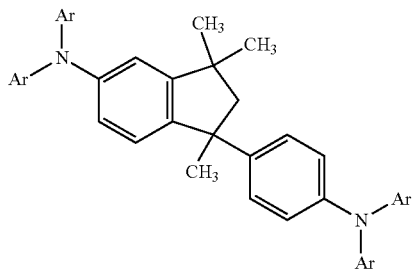
(I.B.a.1)

wherein
each Ar is independently defined as in claim 1;
in which
a3) a mixture of 5(6)-amino-1-(4'-aminphenyl)-1,3,3-trimethylindane compounds of formulae (VIIa) and (VIIb)

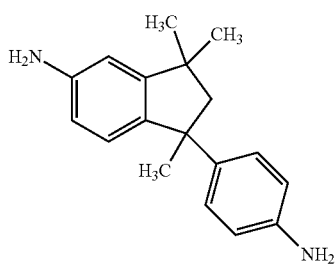
(VIIa)

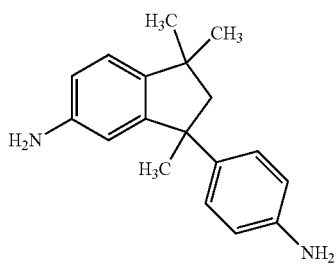
(VIIb)

is provided;
b3) the mixture of compounds of formulae (VIIa) and (VIIb) is subjected to an arylation reaction with at least one aromatic compound of formula (VI)

Ar—$X^{2b}$ (VI)

wherein $X^{2b}$ is selected from F, Cl, Br, I, O-benzyl, $CH_3SO_3$ and $CF_3SO_3$;
in the presence of a palladium complex catalyst and a base to give a mixture of the compounds of the formulae (I.A.a.1) and (I.B.a.1).

15. An organic field-effect transistor comprising a substrate having at least one gate structure, a source electrode and a drain electrode and at least one compound of the formula I as defined claim 1 or of a composition comprising at least two different compounds of the general formula I as defined in claim 1 as a semiconductor material.

16. An electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined in claim 1 or of a composition comprising at least two different compounds of the general formula I as defined in claim 1.

17. An electroluminescent arrangement as claimed in claim 16 comprising at least one compound of the formula I as defined in claim 1 or of a composition comprising at least two different compounds of the general formula I as defined in claim 1 in a hole-transporting layer or electron blocking layer.

18. A process for the preparation of a compound of formula (V)

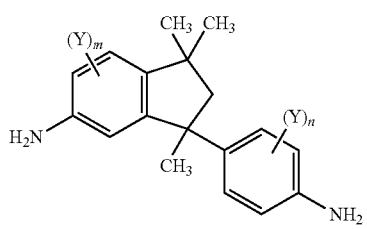
(V)

in which
each Y is independently defined as claim 1;
m is 3, wherein 0, 1, 2 or 3 of the m Y groups are different from hydrogen; and
n is 4, wherein 0, 1, 2 or 3 of the n Y groups are different from hydrogen;
in which
a2) an isopropenylbenzene compound (II)

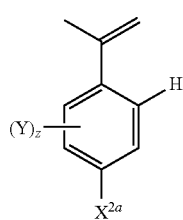
(II)

is provided, wherein
$X^{2a}$ is selected from F, Cl, Br, I, O-benzyl, $CH_3SO_3$ and $CF_3SO_3$;
each Y is independently selected from hydrogen, $C_1$-$C_6$-alkyl, $C_1$-$C_6$-alkoxy, $C_3$-$C_8$-cycloalkyl, $C_3$-$C_8$-cycloalkoxy, phenyl and phenyloxy, wherein each of the cyclic rings in the four last-mentioned groups are unsubstituted or substituted by 1, 2 or 3 $C_1$-$C_6$-alkyl groups and
z is 3, wherein 0, 1, 2 or 3 of the z Y groups are different from hydrogen;
b2) the isopropenylbenzene compound of the formula (II) is subjected to a dimerization in the presence of an acidic catalyst resulting in the compound of the formula (III)

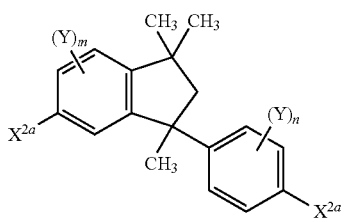
(III)

c2) the compound of formula (III) is subjected to an amination reaction with an alkali bis(trialkylsilyl)amide in the presence of a palladium complex catalyst followed by removal of the trialkylmethylsilyl protecting group to give a compound of the formula (V).

19. A process for the preparation of a compound of formula (V)

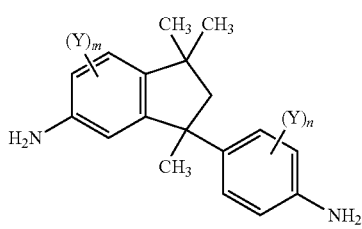
(V)

in which each Y is independently defined as claim 1;

m is 3, wherein 0, 1, 2 or 3 of the m Y groups are different from hydrogen; and n is 4, wherein 0, 1, 2 or 3 of the n Y groups are different from hydrogen;

in which a7) a halogenated 1,3,3-trimethylindane compound of the formula XXI is provided

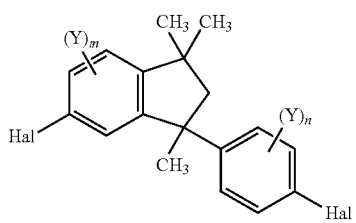
(XXI)

in which

Hal is chlorine, bromine or iodine;

b7) the compound of formula (XXI) is subjected to a copper promoted amidation with an amide of the formula XXII

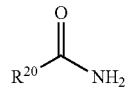
(XXII)

in which $R^{20}$ is hydrogen, $C_1$-$C_{10}$-alkyl, $C_3$-$C_8$-cycloalkyl or $CH_2$—($C_6$-$C_{10}$-aryl);

to give a diamide of the formula (XXIII)

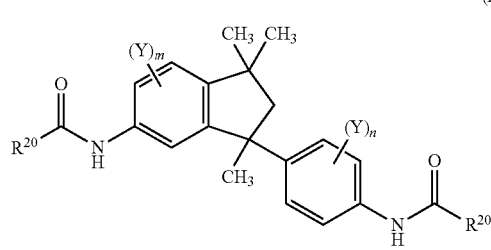
(XXIII)

c7) the diamide of the formula (XXIII) is subjected to a hydrolysis to give the compound of formula (V).

20. A compound of the formula

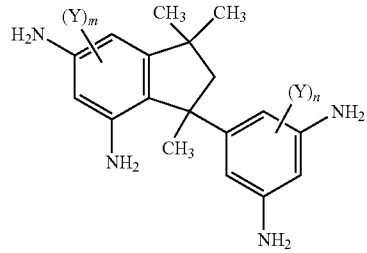
(XIII)

wherein each Y is independently defined as in claim 1;

m is 2, wherein 0, 1 or 2 of the m Y groups are different from hydrogen; and n is 3, wherein 0, 1 or 2 of the n Y groups are different from hydrogen.

21. A solar cell selected from an organic solar cell, a solid solid-state dye sensitized solar cell or a Perovskite solar cell comprising a compound of formula (I) as defined in claim 1.

* * * * *